United States Patent
Dong et al.

(10) Patent No.: US 12,319,966 B2
(45) Date of Patent: *Jun. 3, 2025

(54) COMBINATIONS OF CELL FREE NUCLEIC ACIDS

(71) Applicants: Yafeng Dong, Overland Park, KS (US); Carl Weiner, Mission Hills, KS (US)

(72) Inventors: Yafeng Dong, Overland Park, KS (US); Carl Weiner, Mission Hills, KS (US)

(73) Assignee: ROSETTA SIGNALING LABORATORIES, LLC, Phoenix, AZ (US)

( * ) Notice: Subject to any disclaimer, the term of this patent is extended or adjusted under 35 U.S.C. 154(b) by 156 days.

This patent is subject to a terminal disclaimer.

(21) Appl. No.: 17/118,322

(22) Filed: Dec. 10, 2020

(65) Prior Publication Data

US 2021/0095347 A1 Apr. 1, 2021

Related U.S. Application Data

(60) Continuation-in-part of application No. 15/991,725, filed on May 29, 2018, now Pat. No. 10,954,564, which is a continuation-in-part of application No. 14/851,809, filed on Sep. 11, 2015, now abandoned, which is a division of application No. 13/990,495, filed as application No. PCT/US2011/062661 on Nov. 30, 2011, now abandoned.

(60) Provisional application No. 61/418,368, filed on Nov. 30, 2010, provisional application No. 61/418,375, filed on Nov. 30, 2010.

(51) Int. Cl.
C12Q 1/6883 (2018.01)
C12Q 1/6876 (2018.01)

(52) U.S. Cl.
CPC ......... *C12Q 1/6883* (2013.01); *C12Q 1/6876* (2013.01); *C12Q 2600/158* (2013.01); *C12Q 2600/178* (2013.01); *G01N 2800/368* (2013.01)

(58) Field of Classification Search
None
See application file for complete search history.

(56) References Cited

U.S. PATENT DOCUMENTS

| | | | |
|---|---|---|---|
| 7,807,366 B2 | 10/2010 | Strauss et al. | |
| 10,954,564 B2 | 3/2021 | Dong et al. | |
| 2007/0037165 A1 | 2/2007 | Venter et al. | |
| 2007/0083334 A1 | 4/2007 | Mintz et al. | |
| 2008/0090759 A1 | 4/2008 | Kokenyesi et al. | |
| 2008/0254454 A1 | 10/2008 | Strauss et al. | |
| 2009/0117107 A1 | 5/2009 | Xavier Brys et al. | |
| 2010/0029006 A1* | 2/2010 | Rosenblatt | G01N 33/689 436/86 |
| 2010/0112581 A1 | 5/2010 | Lao et al. | |
| 2011/0098192 A1 | 4/2011 | Lo et al. | |

FOREIGN PATENT DOCUMENTS

WO 2009093254 A2 7/2009

OTHER PUBLICATIONS

Maron (The Journal of Clinical Investigation Oct. 2007 vol. 117 No. 10 pp. 3007-3019).*
Gardina (BMC Genomics 2006 7:325 pp. 1-18).*
Yang (Proc SPIE vol. 4266 Jun. 2001).*
Purwosunu (American Journal of Obstetrics and Gynecology Apr. 2009 200:386 ).*
Chappell (The Lancet vol. 354 Sep. 4, 1999 pp. 810-816).*
Sammour (The Journal of Steroid Biochemistry & Molecular Biology 97 (2005) 439-440).*
Ascher-Walsh (Preinduction, Labor, and Delivery vol. 5 No. 4 1998 p. 183).*
Miura (Prenatl Diagnosis Prenat Diagn 2010 vol. 30 pp. 849-861).*
Tanaka et al. "Down-Regulation of miR-92 in Human Plasma Is a Novel Marker for Acute Leukemia Patients" (PloS One May 2009 vol. 4 Issue 5 e5532 pp. 1-5).
Mehurg et al. "Abstract 3472: Relationship Between the Temporal Profile of Plasma microRNA and Left Ventricular Remodeling in Patients Following Myocardial Infarction" (circulation Nov. 3, 2009 vol. 120 Suppl Issue 18 S806).
GenBank Accession NR_029660 Oct. 29, 2009).
GenBank (Accession NR_004394.1 Nov. 27, 2007).
Weiner et al. "Human effector/initiator gene sets that regulate myometrial contractility during term and preterm labor", American journal of obstetrics and gynecology 202.5 (2010): 474-e1-e20.
International Search Report and Written Opinion mailed Jun. 21, 2012 in International Application No. PCT/US2011/062661.
European Search Report and Written Opinion mailed in European Application No. 11845889.
Mayor-Lynn K et al. "Expression Profile of MicroRNAs and mRNAs in Human Placentas From Pregnancies Complicated by Preeclampsia and Preterm Labor", Reproductive Sciences 2011 Sage Publications Inc. USA, vol. 18, No. 1, Nov. 15, 2010, pp. 46-56, XP002729181, ISSN: 1933-7191.
Yogev Y et al. "110: Spontaneous preterm labor—a possible role for micro-RNA", American Journal of Obstetrics & Gynecology, Mosby, St Louis, MO, US, vol. 197, No. 6, Dec. 1, 2007, p. S44, XP022591296, ISSN: 0002-9378, DOI: 10.1016/J.AJOG.2007.10.121.

(Continued)

*Primary Examiner* — Amanda Haney
(74) *Attorney, Agent, or Firm* — MASCHOFF BRENNAN

(57) ABSTRACT

A method of detecting a combination of nucleic acid biomarkers in a human subject can include: obtaining a nucleic acid sample from the human subject; selecting the combination of nucleic acid biomarkers; analyzing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from a transcription standard.

3 Claims, 6 Drawing Sheets
Specification includes a Sequence Listing.

(56) References Cited

OTHER PUBLICATIONS

Yogev Y et al. "459: Mircro RNA: A central new player in post-transcriptional regulation pathway in preeclampsia", American Journal of Obstetrics & Gynecology, Mosby, St Louis, MO, US, vol. 197, No. 6, Dec. 1, 2007, p. S135, XP022591645, ISSN: 0002-9378; DOI: 10.1016/J.AJOG.2007.10.478.

Chim Stepehn S C et al. "Detection and characterization of placental microRNAs in maternal plasma", Clinical Chemistry, American Assocition for Clinical Chemistry, Washington, DC, vol. 54, No. 3, Mar. 1, 2008, pp. 482-490, XP002518104, ISSN: 0009-0147, DOI: 10.1373/CLINCHEM.2007.097972.

Farina et al. "High levels of fetal cell-free DNA in maternal serum: A risk factor for spontaneous preterm delivery", American Journal of Obstetrics & Gynecology, Mosby, St Louis, MO, US, vol. 193, No. 2, Aug. 1, 2005, pp. 421-425, XP005079561, ISSN: 0002.9378, DOI: 10.1016/J.AJOG.2004.12.023.

Litton C et al. "Noninvasive prenatal diagnosis: Past, present, and future", Mount Sinai Journal of Medicine 2009 John Wiley and Sons Inc. USA, vol. 76, No. 6, Dec. 2009, pp. 521-528, XP002729182, ISSN: 0027.2507.

Wright C F et al. "The use of cell-free fetal nucleic acids in maternal blood for non-invasive prenatal diagnosis", Human Reproduction Update, Oxford University Press, Oxford, GB, vol. 15, No. 1, Jan. 1, 2009, pp. 139-151, XP002613058, ISSN: 1355-4786, DOI: 10.1093/HUMUPD/DMN047.

Tani et al., "Circulating Cell-free mRNA in Plasma as a Tumor Marker for Patients with Primary and Recurrent Gastric Cancer", Anticancer Reasearch, 2007, vol. 27, pp. 1207-1212.

ABS (Applied Biosystems Application Note—TaqMan Gene Expression Assays), "Using TaqMan Endogenous Control Assays to select an endogenous control for experimental studies", Pub Jan. 2006, accessed online at https://assets.thermofisher.com/TFS-Assets/LSG/Application-Notes/cms_042279.pdf on Jun. 12, 2018.

Purwosunu et al., "Cell-free mRNA concentrations of CRH, PLAC1, and selectin-P are increased in the plasma of pregnant women with preeclampsia", Prenatal Diagnosis, 2007, vol. 27, pp. 772-777, DOI: 10.1002/pd.1780.

Final Office Action mailed on Jun. 18, 2018 in U.S. Appl. No. 14/851,809.

Pradervand et al.; "Affymetrix Whole-Transcript Human Gene 1.0 ST array is highly concordant with standard 3" expression arrays"; Biotechniques vol. 44, May 2008; doi: 10.2144/000112751; pp. 759-762.

Weiner, C.P.; Weiss, M.L.; Zhou, H.; Syngelaki, A.; Nicolaides, K.H.; Dong, Y.; "Detection of Embryonic Trisomy 21 in the First Trimester Using Maternal Plasma Cell-Free RNA"; Diagnostics 2022; 12, 1410; https://doi.org/10.3390/diagnostics12061410.

Kabakchiev et al.—Gastroenterology vol. 136, Issue 5 1-172, May 2009.

* cited by examiner

SEQUENCE LISTING

```
<160> NUMBER OF SEQ ID NOS: 307

<210> SEQ ID NO 1
<211> LENGTH: 2276
<212> TYPE: DNA
<213> ORGANISM: Homo sapiens

<400> SEQUENCE: 1
gaacgtggta taaaagggc gggaggccag gctcgtgccg ttttgcagac gccaccgccg      60
aggaaaaccg tgtactatta gccatggtca accccaccgt gttcttcgac attgccgtcg     120
acggcgagcc cttgggccgc gtctcctttg agctgtttgc agacaaggtc ccaaagacag     180
cagaaaattt tcgtgctctg agcactggag agaaaggatt tggttataag ggttcctgct     240
ttcacagaat tattccaggg tttatgtgtc agggtggtga cttcacacgc cataatggca     300
ctggtggcaa gtccatctat ggggagaaat ttgaagatga gaacttcatc ctaaagcata     360
cgggtcctgg catcttgtcc atggcaaatg ctggacccaa cacaaatggt tcccagtttt     420
tcatctgcac tgccaagact gagtggttgg atggcaagca tgtggtgttt ggcaaagtga     480
aagaaggcat gaatattgtg gaggccatgg agcgctttgg gtccaggaat ggcaagacca     540
gcaagaagat caccattgct gactgtggac aactcgaata agtttgactt gtgttttatc     600
ttaaccacca gatcattcct tctgtagctc aggagagcac ccctccaccc catttgctcg     660
cagtatccta gaatctttgt gctctcgctg cagttccctt tgggttccat gttttccttg     720
ttccctccca tgcctagctg gattgcagag ttaagtttat gattatgaaa taaaaactaa     780
ataacaattg tcctcgtttg agttaagagt gttgatgtag gctttatttt aagcagtaat     840
gggttacttc tgaaacatca cttgtttgct taattctaca cagtacttag atttttttta     900
ctttccagtc ccaggaagtg tcaatgtttg ttgagtggaa tattgaaaat gtaggcagca     960
actgggcatg gtggctcact gtctgtaatg tattacctga ggcagaagac cacctgaggg    1020
taggagtcaa gatcagcctg ggcaacatag tgagacgctg tctctacaaa aaataattag    1080
cctggcctgg tggtgcatgc ctagtcctag ctgatctgga ggctgacgtg ggaggattgc    1140
ttgagcctag agtgagctat tatcatgcca ctgtacagcc tgggtgttca cagatcttgt    1200
gtctcaaagg taggcagagg caggaaaagc aaggagccag aattaagagg ttgggtcagt    1260
ctgcagtgag ttcatgcatt tagaggtgtt cttcaagatg actaatgtca aaaattgaga    1320
catctgttgc ggttttttttt tttttttttt ccctggaat gcagtggcgt gatctcagct    1380
cactgcagcc tccgcctcct gggttcaagt gattctagtg cctcagcctc ctgagtagct    1440
gggataatgg gcgtgtgcca ccatgcccag ctaattttg tattttttagt atagatgggg    1500 tttcatcatt ttgaccaggc tggtctcaaa ctcttgacct cagctgatgc gcctgccttg    1560
gcctcccaaa ctgctgagat tacagatgtg agccaccgca ccctacctca tttttctgtaa   1620 caaagctaag cttgaacact gttgatgttc ttgagggaag catattgggc tttaggctgt    1680
```

```
aggtcaagtt tatacatctt aattatggtg gaattcctat gtagagtcta aaaagccagg    1740
tacttggtgc tacagtcagt ctccctgcag agggttaagg cgcagactac ctgcagtgag    1800
gaggtactgc ttgtagcata tagagcctct ccctagcttt ggttatggag gctttgaggt    1860
tttgcaaacc tgaccaattt aagccataag atctggtcaa agggatacccc ttcccactaa   1920 ggacttggtt tctcaggaaa ttatatgtac agtgcttgct ggcagttaga tgtcaggaca    1980
atctaagctg agaaaacccc ttctctgccc accttaacag acctctaggg ttcttaaccc    2040
agcaatcaag tttgcctatc ctagaggtgg cggatttgat catttggtgt gttgggcaat    2100
ttttgtttta ctgtctggtt ccttctgcgt gaattaccac caccaccact tgtgcatctc    2160
agtcttgtgt gttgtctggt tacgtattcc ctgggtgata ccattcaatg tcttaatgta    2220
cttgtggctc agacctgagt gcaaggtgga aataaacatc aaacatcttt tcatta        2276

<210> SEQ ID NO 2
<211> LENGTH: 107
<212> TYPE: DNA
<213> ORGANISM: Drosophila melanogaster

<400> SEQUENCE: 2
gttcttgctt cggcagaaca tatactaaaa ttggaacgat acagagaaga ttagcatggc     60
ccctgcgcaa ggatgacacg caaaatcgtg aagcgttcca catttttt                 107

<210> SEQ ID NO 3
<211> LENGTH: 107
<212> TYPE: DNA
<213> ORGANISM: Drosophila melanogaster

<400> SEQUENCE: 3
gttcttgctt cggcagaaca tatactaaaa ttggaacgat acagagaaga ttagcatggc     60
ccctgcgcaa ggatgacacg caaaatcgtg aagcgttcca catttttt                 107

<210> SEQ ID NO 4
<211> LENGTH: 107
<212> TYPE: DNA
<213> ORGANISM: Drosophila melanogaster

<400> SEQUENCE: 4
gttcttgctt cggcagaaca tatactaaaa ttggaacgat acagagaaga ttagcatggc     60
ccctgcgcaa ggatgacacg caaaatcgtg aagcgttcca catttttt                 107

<210> SEQ ID NO 5
<211> LENGTH: 86
<212> TYPE: DNA
<213> ORGANISM: Homo sapiens

<400> SEQUENCE: 5
tattaggttg gtgcaaaagt atttgcgggt tttgtcgtag aaagtaatgg caaaaactgc     60
agttacttgt gcaccaacca aatgct                                          86

<210> SEQ ID NO 6
<211> LENGTH: 81
<212> TYPE: DNA
<213> ORGANISM: Homo sapiens

<400> SEQUENCE: 6
cccattggca taaacccgta gatccgatct tgtggtgaag tggaccgcac aagctcgctt     60
```

```
ctatgggtct gtgtcagtgt g                                          81

<210> SEQ ID NO 7
<211> LENGTH: 70
<212> TYPE: DNA
<213> ORGANISM: Homo sapiens

<400> SEQUENCE: 7
ggcacccacc cgtagaaccg accttgcggg gccttcgccg cacacaagct cgtgtctgtg  60
ggtccgtgtc                                                         70

<210> SEQ ID NO 8
<211> LENGTH: 76
<212> TYPE: DNA
<213> ORGANISM: Homo sapiens

<400> SEQUENCE: 8
tacttgaaga gaagttgttc gtggtggatt cgctttactt atgacgaatc attcacggac  60 aacactttt tcagta                                                   76

<210> SEQ ID NO 9
<211> LENGTH: 84
<212> TYPE: DNA
<213> ORGANISM: Homo sapiens

<400> SEQUENCE: 9
ttgacttagc tgggtagtgg ggaacccttc catgaggagt agaacactcc ttatgcaaga  60
ttcccttcta cctggctggg ttgg                                         84

<210> SEQ ID NO 10
<211> LENGTH: 110
<212> TYPE: DNA
<213> ORGANISM: Homo sapiens

<400> SEQUENCE: 10
ggcctggctg gacagagttg tcatgtgtct gcctgtctac acttgctgtg cagaacatcc  60
gctcacctgt acagcaggca cagacaggca gtcacatgac aacccagcct             110

<210> SEQ ID NO 11
<211> LENGTH: 71
<212> TYPE: DNA
<213> ORGANISM: Homo sapiens

<400> SEQUENCE: 11
ggagaggagg caagatgctg gcatagctgt tgaactggga acctgctatg ccaacatatt  60
gccatctttc c                                                       71

<210> SEQ ID NO 12
<211> LENGTH: 99
<212> TYPE: DNA
<213> ORGANISM: Homo sapiens

<400> SEQUENCE: 12
gaaactgggc tcaaggtgag gggtgctatc tgtgattgag ggacatggtt aatggaattg  60
tctcacacag aaatcgcacc cgtcaccttg gcctactta                         99

<210> SEQ ID NO 13
<211> LENGTH: 84
<212> TYPE: DNA
```

<400> SEQUENCE: 13
aggctgaggt agtagtttgt acagtttgag ggtctatgat accacccggt acaggagata    60
actgtacagg ccactgcctt gcca    84

<210> SEQ ID NO 14
<211> LENGTH: 85
<212> TYPE: DNA
<213> ORGANISM: Homo sapiens

<400> SEQUENCE: 14
atggtgttat caagtgtaac agcaactcca tgtggactgt gtaccaattt ccagtggaga    60
tgctgttact tttgatggtt accaa    85

<210> SEQ ID NO 15
<211> LENGTH: 85
<212> TYPE: DNA
<213> ORGANISM: Homo sapiens

<400> SEQUENCE: 15
tggttcccgc ccctgtaac agcaactcca tgtggaagtg cccactggtt ccagtggggc    60
tgctgttatc tggggcgagg gccag    85

<210> SEQ ID NO 16
<211> LENGTH: 96
<212> TYPE: DNA
<213> ORGANISM: Homo sapiens

<400> SEQUENCE: 16
cgggccccgg gcgggcggga gggacgggac gcggtgcagt gttgtttttt cccccgccaa    60
tattgcactc gtcccggcct ccggcccccc cggccc    96

<210> SEQ ID NO 17
<211> LENGTH: 79
<212> TYPE: DNA
<213> ORGANISM: Homo sapiens

<400> SEQUENCE: 17
aattaatccc tctctttcta gttcttccta gagtgaggaa aagctgggtt gagagggcaa    60
acaaattaac taattaatt    79

<210> SEQ ID NO 18
<211> LENGTH: 138
<212> TYPE: DNA
<213> ORGANISM: Homo sapiens

<400> SEQUENCE: 18
tgttattttt tgtcttctac ctaagaattc tgtctcttag gctttctctt cccagatttc    60
ccaaagttgg gaaagctggg gttgagaggg caaaaggaaa aaaaaagaat tctgtctctg    120
acataattag atagggaa    138

<210> SEQ ID NO 19
<211> LENGTH: 2368
<212> TYPE: DNA
<213> ORGANISM: Homo sapiens

<400> SEQUENCE: 19
gggtgactac ttccggtgca gtgaaggctc ggggctgaag cggggtaatt cctctcctgc    60

-continued

```
aattactttt ggatggaagt atgccccttt ctcagtagaa gatggtaatc ttggagaatg    120
accatggaga aggggatgag ttctggagaa gggctgcctt ccagatcatc tcaggtttcg    180
gctggtaaaa taacagccaa agagttggaa acaaagcagt cctataaaga gaaacgagga    240
ggctttgtgt tggtgcatgc aggtgcaggt tatcattctg aatccaaagc caaggagtat    300
aaacatgtat gcaaacgagc ttgtcagaag gcaattgaaa agctgcaggc cggtgctctt    360
gcaactgacg cagtcactgc agcactggtg gaacttgagg attctccttt tacaaatgca    420
ggaatgggat ctaatctaaa tctgttaggt gaaattgagt gtgatgccag cataatggat    480
ggaaaatcct taaattttgg agcagttgga gcactgagtg gaatcaagaa cccagtctcg    540
gttgccaaca gactcttatg tgaagggcag aagggcaagc tctcggctgg cagaattcct    600
ccctgctttt tagttggaga aggagcctac agatgggcag tagatcatgg aatacccttt    660
tgccctccta acatcatgac cacaagattc agtttagctg catttaaaag aaacaagagg    720
aaactagagc tggcagaaag ggtggacaca gattttatgc aactaaagaa agaagacaa    780 tcaagtgaga aggaaaatga ctcaggcact ttggacacgg taggcgctgt ggttgtggac    840
cacgaaggga atgttgctgc tgctgtctcc agtggaggct tggccttgaa acatccgggg    900
agagttgggc aggctgctct ttatggatgt ggctgctggg ctgaaaatac tggagctcat    960 aaccccctact ccacagctgt gagtacctca ggatgtggag agcatcttgt gcgcaccata   1020
ctggctagag aatgttcaca tgctttacaa gctgaggatg ctcaccaagc cctgttggag   1080
actatgcaaa acaagtttat cagttcacct ttccttgcca gtgaagatgg cgtgcttggc   1140
ggagtgattg tcctccgttc atgcagatgt tctgccgagc ctgactcctc ccaaaataag   1200
cagacacttc tagtggaatt tctgtggagc cacacgacgg agagcatgtg tgtcggatat   1260
atgtcagccc aggatgggaa agccaagact cacatttcaa gacttcctcc tggtgcggtg   1320
gcaggacagt ctgtggcaat cgaaggtggg gtgtgccgcc tggagagccc agtgaactga   1380
cccttcaggc tgagtgtgaa gcgtctcaga ggcatttcag aacctgagct ttggggggtt   1440
tttaactgaa gttggttgtt ttatctttct tgttttataa ttcctattgc aacctcgtgc   1500
actgctcgag acacaagtgc tgctgtagtt agcgcttagt gacacgcggg cctttggtgg   1560
gtgagcggga ctgtgtgtga gtgtgtgcgc gtatgtgcgc acatatgtgt atgtgtggag   1620
tatgtgtgtt tgcttctccg tggatgaaat agaaactcct cattgtgtga ccaggaatgg   1680
ttaaatcatc tttacaaaat gtgtgcttta actgtttaca agtaaaacct aaagttgcag   1740
gaaacatttt ttatttcgta aagaggtacc aactgtcgct gatgtgatat gtcagaactg   1800
aagagtaaat ctacttgttt aaatgacttg acagtggtag tgctccattt aataacagta   1860
ataagtaata aagtgttttt atttgttaac cagtttaagt ggatcctgtg gtaacttaaa   1920
ctgttgttct catcccttat atggggcatt tttctttaac aaagaatggt ttcagtgaaa   1980
caatctagca gagaattaat gtcagaacct ttttaaataa tagtctgatt gatacagttt   2040
gtacttattt catcaagctt ttctaagctt aaatattgca tagcttcgag ctgtatggac   2100
tatattatga agaatatgt aaagagaaca tacagtaatg cacagtcctt aatttgtgta    2160
taatggaaag ttatttacaa tataacactg taaataagaa agcaaagttt atgggaaaat   2220
tcaatattat ctttgttttt gtttaaatat attttttaaga taaaggcaca aaaataaaag   2280
aagcgtatta ctgggtatag tatgtgactc ctcttctcag actaataaat tatcttttga   2340
atccttggtt aaaaaaaaaa aaaaaaaa                                      2368
```

```
<210> SEQ ID NO 20
<211> LENGTH: 3111
<212> TYPE: DNA
<213> ORGANISM: Homo sapiens

<400> SEQUENCE: 20
atgtcttttt ggtctgaaaa atgtacaaga cttattctgt atgatttaaa aatagcactc      60
aaaaatggat cgttgacatt ttgggatgtg accatagaat tcgctctgga ggagtggcaa     120
tgcctggaca tggctcagca gaatttatat aggaatgtta tgttagagaa ctacagaaac     180
ctggtcttcc tgggtatcgc tgtctctaag ctagacttga taacttgtct gaagcaaggg     240
aaagagcctt ggaatatgaa gagacatgag atggtaacta accccccagt tattagttct     300
cattttacac aagacttttg gccagatcag agcataaaag attctttcca agaaataata     360
ttgagaacat atgcaagatg tggacataag aatttacgat taagaaaaga ttgtgaaagt     420
gtcaatgagg gtaagatgca cgaagaagct tataataaac ttaaccaatg ttggacaact     480
acccagggaa aaatatttca gtgtaacaaa tatgtgaaag tctttcataa atattcaaat     540
tcaaatagat ataagataat tcatactggg aagaaaccat ataaatgtga agaatgtggc     600
aaagctttta gcaatcctc acaccttact agacataaag caattcatac tggagagaaa     660
ccctacaaat gcgaagaatg tggcaaagct tttaaccatt tctcagccct tagaaaacat     720
cagataattc atactggaaa gaaaccctac aaatgtgaag aatgtggcaa agcttttagc     780
cagtcctcaa cccttagaaa acatgagata attcatactg aagagaaacc ctacaaatat     840
gaagaatgcg gcaaagcttt tagcaatttg tcagcccctta gaaaacatga gataattcat     900
actggacaga acccctacaa atgtgaagaa tgtggtaaag cttttaagtg gtcctcaaaa     960
cttactgtac ataaggtaat tcatactgca gagaaaccct gcaaatgtga agaatgtggc    1020
aaagctttta gcgtttctc agcccttaga aaacataaga taattcatac tggaaagcaa    1080
ccctacaaat gtgaagaatg cagcaaagct tttagcaatt tttcagccct tagaaaacat    1140
gagataattc atactggaga gaaaccctac aaatgtgaag aatgtggtaa agcttttaag    1200
tggtcctcaa aacttactgt acataaggta attcatatgg aagagaaacc ttgcaaatgt    1260
gaagaatgtg gcaaagcttt taagcatttc tcagccctta gaaaacataa gataattcat    1320
actggaaaga acccctacaa atgtgaagaa tgtggcaaag ctttttaacaa ttcctcaacc    1380 cttatgaaac ataagataat tcatactggg aagaaaccat acaaatgtga agaatgtggc    1440
aaagctttta gcaatccttc acatcttact agacataaag caattcatac tggggagaaa    1500
ccctacaaat gtgaagaatg tggcaaagct tttaaccact tctcagccct tagaaaacat    1560
cagataattc atactggaaa gaaaccctac aaatgtgaag aatgtggcaa agcttttagc    1620
cagtcctcaa cccttagaaa acatgagata attcatactg gagagaaacc ctacaaatgt    1680
gaagaatgtg gtaaagcttt taagtggtcc tcacacctta ctagacataa agtaattcat    1740
actgaagaga acccctacaa atgtgaagaa tgtggcaagg cttttaacca tttctcagcc    1800
cttaggaaac ataagataat tcatactgga agaaaccct acaaatgtga agaatgtggc    1860
aaagctttta gccagtcctc aactcttaga aacatgaga taattcatac tggagagaaa    1920
ccctacaaat gtgaagaatg tggtaaagct tttaagtggt cctcaaaact tactgtacat    1980
aaggtaattc atactgcaga gaaaccctgc aaatgtgaag aatgtggcaa agcttttaag    2040
catttctcag cccttagaaa acataagata attcatactg gaaagaaacc ctataaatgt    2100
gaagaatgtg gcaaagcttt taacaattcc tcaacccctta gaaaacatga gataattcat    2160
```

```
actggagaga aatcctacaa atgtgaagaa tgtgccctta gaaaacatga gataattcat    2220
actggaaaga aaccctacaa atgtgaagaa tgtggcaaag cttttaacaa ttcctcaacc    2280
cttaggaaac ataagataat ttatactggg aagaaaccat acaaatgtga agaatgtggc    2340
aaagctttta agcagtcctc acaccttact agacataaag cagttcatac tggggagaag    2400
ccctacaaat gtggagaatg tggaaaagct tttaacaatt cctcaaccct aagaaacat     2460 aagctaattc atactaggga gaaatcgtac aaatgtgaag aatgtggcaa agcttttagc    2520
aatttctcag cccttaggaa acataagata attcatactg gggagaaacc atacaaatgt    2580
gaagaatgtg aatgtggcaa agcttttaac aattcctcaa cccttatgaa acataagata    2640
attcatactg gggagaaacc gtacaaatgt gaagaatgtg gcaaaggttt taacaatttc    2700 tcgacccctta tgaaacataa gataattcat actggggaga aaccgtacaa atgtgaagaa    2760
tgtggcaaag cttttaagca atcctcacac cttactaaac ataaatcaat tcatactgga    2820
gagaaaccct acaaatgtga gaacgtggc aaagctttta gccatttctc acgccttact     2880
aaacatagga taattcatac tggaaagaaa ccctacaaat gtgaagagtg tgagaaaccc    2940
tacaaatgtg aagaatgtgg caaagccttt aaccagtcct cacaccttac tcaacataaa    3000
acaattcata ctggagggaa aacctacaaa tgtgaagaat gtggcaaagc ttttaaccat    3060 cttttcagccc ttactaaaca taagataatt catactgggg agaagcccta a            3111
```

<210> SEQ ID NO 21
<211> LENGTH: 2142
<212> TYPE: DNA
<213> ORGANISM: Homo sapiens

<400> SEQUENCE: 21

```
taactctcca aactcccatg agctgtaacc tagcttccct atgcagcaaa gttcttgaac      60
aaggtgctta ccatcctatc ctcattccct caccctctc tcctccctgg acccactgtg     120
cccaacatct gcgcccttgt acctgcaaag gctcatctca ctatggggac caacaacctc     180
gctcacaagt gttaaaactcc aagatgctcc tttctgcttc tgtccttgac cttccagtg    240 ttgacagtga tgccttttgaa atcctcctct ccttggcttc catagcaata cgcactccta    300
gagtttgtca ccctctttttg cccctccact tcattcttct tcacaagggc cagccttcac    360
atgttgaggt tctttgggat gctgcctggc tgttcttcat tgtggacttg atgttttcct    420
ctatcctgtt gtgcacattc ttacggcttc aatactttgt ctaagctgtt gatttcaaag    480
ttggcatttc atcccagctc tctcctgagt ttcagactgc cttttcaaaa gcctactggg    540
catctctatc cagtggtcac ccaggcacat caactcattc caaactggtg actctccagg    600
tatttctatc tcacccaccc caagatgctc aagcagaaca cctggcatct ccttgggtca    660
tcttttcccc atctttatac ttattctcca tctaatccca tctacccatt acatgttttt    720
taaatccatc caccttttttt caaccccact gctcattccc tacatcatta acatctttct    780
cgtagactcc tgacctccct ccaaattctt gctgtggtct gaagaatttt tctaaagtgt    840
aaatctggcc aagtcagtcc cctgtgtaag gctcttcat ggtttctcat tgcttttagg     900
ataagttcaa gtccttatca aggatcttaa gacctacctt gcctggcccc aggttaccct    960
ccccaaccta actcatacca ctcccaaaca catattccaa gttctgacca tacagcactg    1020
ttttcaaatc cttgaacaag ccaagggtga cttgcctctg gggcttttc ctgccattct     1080 tcttcctgga acactttctc agaatcctgt ttctccacta attcctattt gtctttctga    1140
tgctactcca caggtcccct cctccaggaa gccctccgtg ttctcccagg ctagatgaga    1200
```

```
gcccctcctc tgtatcctat atttcttggg cacacaataa ttctgtacat ttgaagctca    1260
ttctactctt tctacttcct ctgtcccagc acttagtaca ggtgattgta gcagcctctt    1320
tatgggtcag agccgcctac aggaccagaa gcttcatgaa gccagcaccc caacttccaa    1380
caccagcgtc cgcaatgccc aacagagatc ccaggtgagg aagctgaact gactttggtg    1440
acatatattc cccaagatct gacagctgat gagtgacaga gcacgtattc aaacccagag    1500
atgtgaattc gctatgctgc ctaggctggt cttgaactcc tgacttcaag taatcctccc    1560
accttcgctt gccaaagtgc tgggattata ggcgtgaact actgctccca gctgagagct    1620
cacttttgtt tgctagtggt gttcttagta tcttttcata tttgaggttt tggtggtagt    1680
gctgaagtat tgtactcacc atccaaggtt tacaggactt ttgtttttact atggaacaga    1740 tggaattgtt tagttctgca tctttgcaaa tatacaaaat gtgcctacca ggactctgct    1800
ttatatccat tgaaagcaag aagtaataca gtaaaacttt gcctggctag aggctttgaa    1860
agaatggact attctgattt aattgtatta acttggaagt atgaaggtga aaaaaattaa    1920
aaacttaaat ttcctgttga atgcaatttg aaaatatagc cattgattcc acttttattc    1980
tccagtaagt ctggacattc tgatatacct ggtgttttat tatagaactc ctagtgtgcc    2040
tgaagatcat tttctacaac tttaggtgta agaggatgta aatggtattg tatgagatca    2100
ggctggatga gaactgatac ttgtaaatac acttttttaga ct                      2142
```

<210> SEQ ID NO 22
<211> LENGTH: 947
<212> TYPE: DNA
<213> ORGANISM: Homo sapiens
<400> SEQUENCE: 22

```
ccatccctga gatcttttta taaaaaaccc agtctttgct gaccagacaa agcataccag      60
atctcaccag agagtcctag gggactacag aaggaaaaag acaagaggca gtaggatatc     120
tgtgtgtcct cccgctgacc acacttcctt tagtgacccg attgcctcct caagtcgcag     180
acactatgct gcctcccatg gccctgccca gtgtgtcctg gatgctgctt tcctgcctca     240
ttctcctgtg tcaggttcaa ggtgaagaaa cccagaagga actgccctct ccacggatca     300
gctgtcccaa aggctccaag gcctatggct cccctgcta tgccttgttt ttgtcaccaa      360
aatcctggat ggatgcagat ctggcttgcc agaagcggcc ctctggaaaa ctggtgtctg     420
tgctcagtgg ggctgaggga tccttcgtgt cctccctggt gaggagcatt agtaacagct     480
attcatacat ctggattggg ctccatgacc ccacacaggg ctctgagcct gatggagatg     540
gatgggagtg gagtagcact gatgtgatga attactttgc atgggagaaa aatccctcca     600
ccatcttaaa ccctggccac tgtgggagcc tgtcaagaag cacaggattt ctgaagtgga     660 agattataa ctgtgatgca aagttacct atgtctgcaa gttcaaggac tagggcaggt      720
gggaagtcag cagcctgagc ttggcgtgca gctcatcatg acatgagac cagtgtgaag     780 actcaccctg gaagagaata ttctccccaa actgccctac ctgactacct tgtcatgatc     840
ctccttcttt ttccttttttc ttcaccttca tttcaggctt ttctctgtct tccatgtctt     900
gagatctcag agaataataa taaaaatgtt actttatacg taaaaaa                  947
```

<210> SEQ ID NO 23
<211> LENGTH: 942
<212> TYPE: DNA
<213> ORGANISM: Homo sapiens

<400> SEQUENCE: 23

```
atgtccatta tcaacacatc atatgttgaa atcaccacct tcttcttggt tgggatgcca        60
gggctagaat atgcacacat ctggatctct atccccatct gcagcatgta tcttattgct       120
attctaggaa atggcaccat tcttttttatc atcaagacag agccctcctt gcatgggccc      180
atgtactatt ttcttttccat gttggctatg tcagacttgg gtttgtcttt atcatctctg      240
cccactgtgt taagcatctt cctgttcaat gcccctgaaa cttcttctag tgcctgcttt       300
gcccaggaat tcttcattca tggattctca gtactggagt cctcagtcct cctgatcatg       360
tcatttgata gattcctagc catccacaat cctctgagat acacctcaat cctgacaact       420
gtcagagttg cccaaatagg gatagtattc tcctttaaga gcatgctcct ggttcttccc       480
ttcccctttca ctttaagaag cttgagatat tgcaagaaaa accaattatc ccattcctac      540
tgtctccacc aggatgtcat gaagttggcc tgttctgaca acagaattga tgttatctat       600
ggctttttttg gagcactctg ccttatggta gactttattc tcattgctgt gtcttacacc      660
ctgatcctca agactgtacc gggaattgca tccaaaaagg aggagcttaa ggctctcaat       720
acttgtgttt cacacatctg tgcagtgatc atcttctacc tgcccatcat caacctggcc      780
gttgtccacc gctttgccgg gcatgtctct ccctcatta tgttctcat ggcaaatgtt        840
ctcctacttg tacctccgct gatgaaacca attgtttatt gtgtaaaaac taaacagatt      900
agagtgagag ttgtagcaaa attgtgtcaa tggaagattt aa                         942
```

<210> SEQ ID NO 24
<211> LENGTH: 726
<212> TYPE: DNA
<213> ORGANISM: Homo sapiens

<400> SEQUENCE: 24

```
gcttcctgtt tttccctccg accaaccccg agcgcaaaga aattgacctc gcagcggtcc        60
tacaatactt ttatatcatt ggccaagctt taccccgccc ctgcctcatg cagcctatgg       120
gctaggcttt agggtccgcg gttggtcaga ccggagcact tggcctgaag acctggaatt       180
ggcgacttcg atattaacaa ggatggcggc ggccgcagca agtcgaggag tcggggcaaa       240
gctgggcctg cgtgagattc gcatccactt atgtcagcgc tcgcccggca gccagggcgt       300
cagggacttc attgagaaac gctacgtgga gctgaagaag gcgaatcccg acctacccat       360
cctaatccgc gaatgctccg atgtgcagcc caagctctgg gcccgctacg catttggcca       420
agagacgaat gtccctttga caacttcag tgctgatcag gtaaccagag ccctggagaa       480
cgttctaagt ggtaaagcct gaagcctcca ctgaggatta agagcaacag ccccagagcc      540
tgggctctgc tggacttagt ataatgtgaa aaaatgtgt tctcctattc ctcataaagc      600
ttgtgctgta aatactttc tcagggtgtt cttgtcctca tctaccctct acccttact       660
gtgcaaccac tgaggcaaag tagcttaata taaaaataaa actttattct gtctcatcaa      720
aagcta                                                                726
```

<210> SEQ ID NO 25
<211> LENGTH: 2855
<212> TYPE: DNA
<213> ORGANISM: Homo sapiens

<400> SEQUENCE: 25

```
ttccggcact cgcggaactt tggtgcagcc tgatgcgcaa cgtggggact caggcgcgct        60
gggcggcagg agttgcttcc ggccgtgttg gtggtctgaa ttgagaagcc gcgactaagg       120
```

```
gaagatggag acaatactgg agcagcagcg gcgctatcat gaggagaagg aacggctcat      180
ggacgtcatg gctaaagaga tgctcaccaa gaagtccacg ctccgggacc agatcaattc      240
tgatcaccgc actcgggcca tgcaagatag gtatatggag gtcagtggga acctgaggga      300
tttgtatgat gataaggatg gattacgaaa ggaggagctc aatgccattt caggacccaa      360
tgagtttgct gaattctata atagactcaa gcaaataaag gaattccacc ggaagcaccc      420
aaatgagatc tgtgtgccaa tgtcagtgga atttgaggaa ctcctgaagg ctcgagagaa      480
tccaagtgaa gaggcacaaa acttggtgga gttcacagat gaagagggat atggtcgtta      540
tctcgatctc catgactgtt acctcaagta cattaacctg aaggcatctg agaagctgga      600
ttatatcaca tacctgtcca tctttgacca attatttgac attcctaaag aaaggaagaa      660
tgcagagtat aagagatacc tagagatgct gcttgagtac cttcaggatt acacagatag      720
agtgaagcct ctccaagatc agaatgaact ttttgggaag attcaggctg agtttgagaa      780
gaaatgggag aatgggacct ttcctggatg gccgaaagag acaagcagtg ccctgaccca      840
tgctggagcc catcttgacc tctctgcatt ctcctcctgg gaggagttgg cttctctggg      900
tttggacaga ttgaaaatctg ctctcttagc tttaggcttg aaatgtggcg ggaccctaga      960
agagcgagcc cagagactat tcagtaccaa aggaaagtcc ctggagtcac ttgatacctc     1020
tttgtttgcc aaaaatccca agtcaaaggg caccaagcga gacactgaaa ggaacaaaga     1080
cattgctttt ctagaagccc agatctatga atatgtagag attctcgggg aacagcgaca     1140
tctcactcat gaaaatgtac agcgcaagca agccaggaca ggagaagagc gagaagaaga     1200
ggaagaagag cagatcagtg agagtgagag tgaagatgaa gagaacgaga tcatttacaa     1260
ccccaaaaac ctgccacttg gctgggatgg caaacctatt ccctactggc tgtataagct     1320
tcatggccta aatatcaact acaactgtga gatttgtgga aactacacct accgagggcc     1380
caaagccttc cagcgacact tgctgaatgc gcgtcatgct catggcatga ggtgtttggg     1440
catcccaaac actgctcact tgctaatgt gacacagatt gaagatgctg tctccttgtg     1500
ggccaaactg aaattgcaga aggcttcaga acgatggcag cctgacactg aggaagaata     1560
tgaagactca agtgggaatg ttgtgaataa gaagacatac gaggatctga aaagacaagg     1620
actgctctag tgttcaggga tgtagctcag cttttgggct agcccaggct tccctaagat     1680 ctgcttttc tatttctccc aaccaaatcc tcttaaagac cctttgctat gtagtctcat     1740
ggtctagcat gcatcttgta gaaacaaggc atgctggcag attgcagggt tgagatgtgt     1800
tttatctgtt ttatatttta aaagattctg ccagaaaata aaaccagacc ttgttctaaa     1860
gcccagggtt atggaccaac tcagtgcttc aggtcttaac gcctccatac ctcttcctca     1920
ccaactttac tagtagctga gatttaatgg gcacctatta tgctacatat catgttaggt     1980
aaatctgacc tgacctcttt ccccaccctc ctttgttgct gcttccctga atgagtatta     2040
ccccaggatg aggtctgcca tcagcttagt tagccattga tgcaaatact agggaaagac     2100
taggaggatg agccagggtt gctactaagg actaagtgtc gcaccaaggt ttgccttttg     2160
tatttgcata aagaaaggag ttggagctgg gtgcagtggc ttgtgcctgt agtcccagct     2220
acttgggagg ctgaggcagg agggttgctt gagactagcc taggtaacat agtgagaccc     2280
tgtctcatta aaaaaaaaa aaaggcatgg tggcacgcac tgtagtccca gctactcagg     2340
agactgaggc tagaagatcc tttgaaccta ggagtttgag accagcctgg gcgatatagt     2400
gaggccccat ctcaaaaaaa aaaaagggg gggggggggg agttgggctg tgttggaatg     2460
```

| | |
|---|---|
| ggcctgcagc ccaacaaaca agggaactag gaccgacagt gacttcacca gcttgctagg | 2520 |
| tcagaatgag agactggtgg gtctgtctac ctgtttcttc tacaagatcc ctatttgact | 2580 |
| gtaaaagtag ctaatactca catgttctcc aatcccaggt agccatggta gagttgggta | 2640 |
| gagttgagca gctgcccag gatccaaatg tggtgtctga aatggaaaga actaaggcaa | 2700 |
| ccaggaaggc actgatctgc cttataagca cagtcatctg aaagtcaggc ctgctgcagg | 2760 |
| acaggatccc ccagagaccc catttgcctc tcaacactca gaccttcaac tgttttttaa | 2820 |
| taaatctact ttttaaaaaa aaaaaaaaaa aaaaa | 2855 |

<210> SEQ ID NO 26
<211> LENGTH: 592
<212> TYPE: DNA
<213> ORGANISM: Homo sapiens

<400> SEQUENCE: 26

| | |
|---|---|
| ggacgtgtct gtgctcctgt gtgtgaccag ggttgaaaaa gtcgcactga gatgtcctgc | 60 |
| cagcaaaacc agcagcagtg ccagccccct cccaagtgcc ccccaaaatg cccacccaag | 120 |
| tgtcctccaa agtgccgacc tcagtgccca gccccatgcc cacctccagt ctcttcctgc | 180 |
| tgtggtccca gctctggggg ctgctgcggc tccagctctg ggggctgctg cagctctggg | 240 |
| ggtggcggct gctgcctgag ccaccacagg ccccgtctct tccaccggca ccggcaccag | 300 |
| agccccgatt gttgtgagtg tgaaccttct ggggctctg gctgctgcca cagctctggg | 360 |
| gactgctgct gaccagacct cgaacatcac agagcaaccc ttatggagaa acttgcaacc | 420 |
| aggacctgtc ccagagtgat gcttctcctg cccctttttc tcctttcctt gggctgacac | 480 |
| accttgtgag gtgttttgtc tgttgtcatg gcccaagagc ccatcctgga tcctgatctt | 540 |
| accttcccac tttacctcat acaacaataa agctcttttg cctcttcgtg aa | 592 |

<210> SEQ ID NO 27
<211> LENGTH: 1057
<212> TYPE: DNA
<213> ORGANISM: Homo sapiens

<400> SEQUENCE: 27

| | |
|---|---|
| gtctcagcgg ctgccaacag atcatgagcc atcagctcct ctggggccag ctataggaca | 60 |
| acagaactct caccaaagga ccagacacag tgagcaccat ggacagtgt cggtcagcca | 120 |
| acgcagagga tgctcaggaa ttcagtgatg tggagagggc cattgagacc ctcatcaaga | 180 |
| actttcacca gtactccgtg gagggtggga aggagacgct gaccccttct gagctacggg | 240 |
| acctggtcac ccagcagctg cccatctca tgccgagcaa ctgtggcctg aagagaaaa | 300 |
| ttgccaacct gggcagctgc aatgactcta aactggagtt caggagtttc tgggagctga | 360 |
| ttggagaagc ggccaagagt gtgaagctgg agaggcctgt ccgggggcac tgagaactcc | 420 |
| ctctggaatt cttggggggt gttggggaga gactgtgggc ctggagataa aacttgtctc | 480 |
| ctctaccacc accctgtacc ctagcctgca cctgtcctca tctctgcaaa gttcagcttc | 540 |
| cttccccagg tctctgtgca ctctgtcttg gatgctctgg ggagctcatg ggtggaggag | 600 |
| tctccaccag agggaggctc aggggactgg ttgggcagg gatgaatatt tgagggataa | 660 |
| aaattgtgta agagccaaag aattggtagt agggggagaa cagagaggag ctgggctatg | 720 |
| ggaaatgatt tgaataatgg agctgggaat atggctggat atctggtact aaaaaagggt | 780 |
| cttttaagaac ctacttccta atctcttccc caatccaaac catagctgtc tgtccagtgc | 840 |
| tctcttcctg cctccagctc tgccccaggc tcctcctaga ctctgtccct gggctagggc | 900 |

```
aggggaggag ggagagcagg gttggggag aggctgagga gagtgtgaca tgtggggaga    960
ggaccagctg ggtgcttggg cattgacaga atgatggttg ttttgtatca tttgattaat   1020
aaaaaaaaat gaaaaagtg aaaaaaaaaa aaaaaaa                             1057
```

<210> SEQ ID NO 28
<211> LENGTH: 1330
<212> TYPE: DNA
<213> ORGANISM: Homo sapiens

<400> SEQUENCE: 28

```
gcggacgcgg ggcgccagca ggtggcgctg gacgcgcaac ggacaaggag gcggggcctg     60
cagctggctt ggaggctccg cgctctggag gctcaggcgc cgcgtggggc ccgcacctct    120
gggcagcagc ggcagccgag actcacggtc aagctaaggc gaagagtggg tggctgaagc    180
catactattt tatagaatta atggaaagca gaaaagacat cacaaaccaa gaagaacttt    240
ggaaaatgaa gcctaggaga aatttagaag aagacgatta tttgcataag gacacgggag    300
agaccagcat gctaaaaaga cctgtgcttt tgcatttgca ccaaacagcc catgctgatg    360
aatttgactg cccttcagaa cttcagcaca caggaact cttccacag tggcacttgc      420
caattaaaat agctgctatt atagcatctc tgacttttct ttacactctt ctgagggaag    480
taattcaccc tttagcaact tcccatcaac aatatttta taaaattcca atcctggtca     540
tcaacaaagt cttgccaatg gtttccatca ctctcttggc attggtttac ctgccaggtg    600
tgatagcagc aattgtccaa cttcataatg gaaccaagta taagaagttt ccacattggt    660
tggataagtg gatgttaaca agaaagcagt ttgggcttct cagtttcttt tttgctgtac    720
tgcatgcaat ttatagtctg tcttacccaa tgaggcgatc ctacagatac aagttgctaa    780
actgggcata tcaacaggtc aacaaaata aagaagatgc ctggattgag catgatgttt     840
ggagaatgga gatttatgtg tctctgggaa ttgtgggatt ggcaatactg gctctgttgg    900
ctgtgacatc tattccatct gtgagtgact cttgacatg gagagaattt cactatattc     960
agagcaagct aggaattgtt tcccttctac tgggcacaat acacgcattg attttttgcct   1020
ggaataagtg gatagatata aaacaatttg tatggtatac acctccaact tttatgatag    1080
ctgtttttcct tccaattgtt gtcctgatat ttaaaagcat actattcctg ccatgcttga   1140
ggaagaagat actgaagatt agacatggtt gggaagacgt caccaaaatt aacaaaactg    1200
agatatgttc ccagttgtag aattactgtt tacacacatt tttgttcaat attgatatat    1260
tttatcacca acattcaag tttgtatttg ttaataaaat gattattcaa ggaaaaaaaa     1320
aaaaaaaaa                                                            1330
```

<210> SEQ ID NO 29
<211> LENGTH: 1212
<212> TYPE: DNA
<213> ORGANISM: Homo sapiens

<400> SEQUENCE: 29

```
aatctttttt gcctctcaac ctgtctccca ggtagtgtac ctgtcaccat taataactct     60
ttagccgctc cctagtgatt tgacctatca gttgtcgttc acagaaaagt ggtgctctgg    120
cctgctattg aagcttatgc aggttctttc agctcctcag tcaccccagc agccatatac    180
ttgtaggaag ttgtgttggt gggcttcaca agcaggcagc tgaacacttc gtacagtttg    240
ataaaggtgg cattacattt tgaacaatag atgataagac tcccatttag accgcaaaac    300
```

| | |
|---|---|
| agtgccacag gggtagacag gggtctgggg gagataagat gggtggtgag gatgaccaac | 360 |
| agcaaataaa ctttcctgtc tctttgatgc taattatctc tttgcaccta attatcatgg | 420 |
| catcatcatc atcctctgat gtttgcaaac taagagttga tgtgtttgat caggttagtg | 480 |
| aatctgtcag gtatggcatt ctgcctgttt ctgaagctta agaatgagaa gccagtagct | 540 |
| atcatgcgga agatgtgaac tgccccccag tcctcgtcct ttagcagtgt gtcattcctc | 600 |
| tgtttggaca tgtgctctct tgcttcctct cttcccctct ctgttcctga agtgtgctgc | 660 |
| ttccaacact tccccagatt aattcctacc tgcatttagg tctcaaccta gccatcactt | 720 |
| tttcaggaaa ctgctactgc tctctctatt tggcattgac tgtaccaact aaaatgccca | 780 |
| tatggcagtt ttcatttatt tcttattatg ctctacaata actgcttgtt tacttgtctt | 840 |
| tttctcctac tggattgtaa gttttttcat ggatggtaca tagtgttgtt tgctatatcc | 900 |
| acgttctggg agtgtcatag aatctcaata aatttatttg aagagaatga gaatttatt | 960 |
| tttatgaact cactttccat tgacatatca tggtcacatc aatggggagt tcaggcaata | 1020 |
| aattatggca tatattgtct actgtatact gtgctggcac caggggttca gataggaaaa | 1080 |
| catttcgatt gctttttacc cttttagtga gtgactaatg gacatttctt gtctgagga | 1140 |
| tatatcttgg cagtacagga tttcttcaga cgtggctcag gaaatggccg agagtaaggt | 1200 |
| gaatcacaag gc | 1212 |

<210> SEQ ID NO 30
<211> LENGTH: 2691
<212> TYPE: DNA
<213> ORGANISM: Homo sapiens

<400> SEQUENCE: 30

| | |
|---|---|
| ggggagggga aggagcggca catgggggttg agcagaggag aaaatcagaa agatggctta | 60 |
| gagaagtcag cagtctgcga gtctggggag gatggagagt ggtttggggt tttgggtcgg | 120 |
| ggtctaaggt gatcagatgc agaagcatta cacagtggcc tggtttcttt actcagcccc | 180 |
| tggggtagat cccagccccc catgtaggtc ccttggctgg aaaaggaaga gggagtggtc | 240 |
| agatgaatct gaggaggagc cggagaagga gctcgcccct gagcctgagg agacctgggt | 300 |
| agtggagacg ctgtgtgggc tcaagatgaa gctgaagcaa cagcgagtgt cacccatcct | 360 |
| ccttgagcac cacaaggact tcaacagtca gcttgcccct ggggtagatc ccagcccccc | 420 |
| gcataggtcc ttttgctgga aaaggaagat ggagtggtgg gacaaatctg aggagtcgga | 480 |
| ggaggagcca cggaaggtgc tcgcccctga gcctgaggag atctgggtgg cggagatgct | 540 |
| gtgtggcctc aagatgaagc tgaagcgacg gcgagtgtcg ctcgtgctcc ctgagcacca | 600 |
| cgaggccttc aacaggctgc ttgaggatcc tgtcattaaa agattcctgg cctgggacaa | 660 |
| agatctgagg gtgtcggaca gtatctcct tgctatggtc atagcgtatt tcagccgagc | 720 |
| cggcttcccc tcctggcaat accaacgcct tcatttcttc ctggctctct acctggccaa | 780 |
| tgacatggag gaggacgacg aggactccaa acaaaacatc ttccacttcc tgtatgggaa | 840 |
| gaaccgctct cgcatacccct tgctccgtaa gcgtcggttc cagttatacc gttccatgaa | 900 |
| cccgagggcc aggaagaacc gctctcacat acccttggtc cgtaagcgtc ggttccagtt | 960 |
| acgccgttgc atgaacccga gggccaggaa gaaccgctct cagatagtcc tgttccagaa | 1020 |
| acgtcggttc cacttcttct gttccatgag ctgcagggct tgggtttccc cagaggagtt | 1080 |
| ggaggagatc caggcttatg acccagagca ctgggtgtgg gcgcgagatc gcgctcgcct | 1140 |
| ttcctagagc tccagggacc gtggaggcct gaggtcatcg gcctgagaga agaacaccgg | 1200 |

-continued

```
acccagggga gatgtggatt ttcagcagga actttattcc aatgctaatg gcagacacca    1260
ggaaggagga gaggaaccat tgtgcagat catctagaag aacctggacc attcttgatg    1320
gagctgaata cagtgatcac gttgtcctcc taggagcagg ggtgggggga ggggatggg    1380 gtccttctag gagtccttgg agaaaagtaa gaaaccagga gtgtttccag ttccaccctt    1440
tcctggggca ccaccaccct ttttatattg ctgaattcca acctccctgg ggcggaacct    1500
ggaggtcctg tttcttacgg acttggttgc cacagtccag gagcatttga aggcacaatg    1560
caggggctca gattggcaca gaattctttt gtgaaatatc agtgccacag attgtaacag    1620
atagcttcat gcacactctg cattttattg gtttgtttgg aaaatgttgg ccattgaatt    1680
attcatagat ttatttcaaa tagtttggaa attgttgtac ttttgaaaac atgctgttcc    1740
tgtagttttt tgatgagagt tatagttgtt atatatacat aaagataatt ttcttttcat    1800
ttttgagaca attcttttta tcctaaatat tttatcatct ttaaatttgt ttctgtatta    1860
ttatatgtgc tcctgaagcg agcactcttt ttatctatga tacttccata ataatctctt    1920
ctatttatag ctattggtag ttcccctaaa ttctgacgat agaaattttt atttgctgtt    1980
taggtttgtg actgaattgt gagaattcag ttgtgatttt taacatgtgt cagatatata    2040
tactaacacg tctaatatat actattttat tggtttattt tgaaaaacat gggtatagaa    2100
ttatttaaat attattttat ttatttaaat atttattaaa tatatttatt tatttaaatg    2160
ttattattac tttaaatatt attttaaata ttttggaaat actggtattt ttgaatagat    2220
gctgttctca taaagctgtg tgatggtatt ataactgtta tatacacata catataattt    2280
tgttttcctt tttaagagag gattcttttc atcctaaatc ttttaccttt caatctttgt    2340
atctattatt acacgtgctg ctgaagggag catggttttt atctatgata cttagttaac    2400
atatatatta catttatagc tatgtagtag ttcccctaaa ttcttgtaaa aataaatttt    2460
tatttgatat ttcatctatg tttgaaatgt gagaattcag atgtaatttt ttaccttgat    2520
ttggcatgtt tgtatgttac tttaaagagg atgtgtgttc taaaggagga catgagctgt    2580
gtgttttcaa gagaacaata gagtgtgtct cttggggaaa cgtaataaaa atgaactttt    2640
ctcaccttca aaaaaaaaaa aaaaaaaaaa aaaaaaaaaa aaaaaaaaaa a            2691
```

<210> SEQ ID NO 31
<211> LENGTH: 1463
<212> TYPE: DNA
<213> ORGANISM: Homo sapiens

<400> SEQUENCE: 31

```
cttagaggga gctgtgtttt ggtgacctct gaaactcagt actgcagcga atgagctcct      60
gaccttgagg agtacttaac agaattatgt ctcgaagaat cattgtggga acccttcaaa     120
gaacccagcg aaacatgaat tctggaatct cgcaagtctt ccagagggaa ctcacctgcc     180
ccatctgcat gaactacttc atagacccgg tcaccataga ctgtgggcac agcttttgca     240
ggccctgttt ctacctcaac tggcaagaca tcccaattct tactcagtgc tttgaatgca     300
taaagacaat acagcagaga aacctcaaaa ctaacattcg attgaagaag atggcttccc     360
ttgccagaaa agccagtctc tggctattcc tgagctctga ggagcaaatg tgtggcattc     420
acagggagac aaagaagatg ttctgtgaag tggacaggag cctgctctgt ttgctgtgct     480
ccagctctca ggagcaccgg tatcacagac actgtcccgc tgagtgggct gctgaggaac     540
actgggagaa gcttttaaag aaaatgcagt ctttatggga aaaagcttgt gaaaatcaga     600
```

| | |
|---|---|
| gaaacctgaa tgtggaaacc accagaatca gccactggaa ggcttttgga gacatattat | 660 |
| acaggagtga gtccgtgctg ctgcacatgc cccagcctct gaatctagcg ctcagggcag | 720 |
| ggcccatcac tggactgagg gacaggctca accaattctg agtggatatt actctgcatc | 780 |
| acaatgaagc caacagtcat atcttccgat gtggagattt gagaagcatt tgtattggat | 840 |
| gtgaccgtca aaatccgccc catatcactg caacacctac aagttttctt gcatggggtg | 900 |
| ctcagacttt cacctctggc aaatattact gggaggtcca tgtgggggac tcttggaatt | 960 |
| gggcttttgg tgtctgtaat aagtattgga aagggaagaa tcagaatggc aatatatatg | 1020 |
| gagaggaggg actctttagt cttgggtgtg ttaagaacga cattcagtgc agtctcttta | 1080 |
| ccacctcccc aattacactg cagtatgtcc caagacctac caaccatgta gaattattcc | 1140 |
| tggattgtga agctagaact gtgagcttcg ttgatgttag tcaaagctcc cctatataca | 1200 |
| ccatccctaa ttgctccttc tcacttcctc tcagacctat ctttttctgt attctcctct | 1260 |
| gaccagagac aaatcagaaa tgtgttcatc tgctgtggga accccttat cccagaaagc | 1320 |
| cctcttcctt gtgccttatc aaacaggaca aataggttcg gttttatgtc ttgaattgca | 1380 |
| ttctaatgtt attaaaactc atttattgtg ttactattaa atgtagtaaa aacactaaaa | 1440 |
| gtataaaaaa aaaaaaaaaa aaa | 1463 |

<210> SEQ ID NO 32
<211> LENGTH: 828
<212> TYPE: DNA
<213> ORGANISM: Homo sapiens

<400> SEQUENCE: 32

| | |
|---|---|
| gtgcgccttt ttttttttt ccttcttagt cgtgtgtaca tcattgggaa tggagggaaa | 60 |
| taaatgactg gatggtcgct gcttttaag tttcaaattg acattccaga caagcggtgc | 120 |
| ctgagcccgt gcctgtcttc agatcttcac agcacagttc ctgggaaggt ggagccacca | 180 |
| gcctctcctt gtcctggagg ctggaagtgc aaaaggaagg tgtcggcaag atcgtttttt | 240 |
| tctgagagct ctctccttgg cttgcagatg gcagcctgct cctggcacag tcttttctct | 300 |
| actcatgccc aaagttacgg aggacccagc aaccatctcc tgcagcccct ggaaacctct | 360 |
| tgactcttct gtgatgtccc cagtgatcca gcagccctgg ccttctttg atggcttgaa | 420 |
| catttggtct tcattgaaca gtttgtatat tggaaacttg ccagcctcca tccacattcc | 480 |
| aacctccgtc tgcatccctc gaataactgg gagatgaaac aggaagctct atgacacact | 540 |
| tgatcgaata tgcacagacac cgaaaatcac gactcagccc cctccagcac ctctacctgt | 600 |
| tgcccgccga tcacagccgg aatgcagctg aaagattccc tggggcctgg ttccaaccgc | 660 |
| ccactgtgga ctctgaggcc tctgcatttg cgggtggtct gcctgtgata ttttggtcat | 720 |
| gggctggtct ggtcggtttc ccatttgtct ggccagtctc tatgtgtctt aatcccttgt | 780 |
| ccttcattaa aagcaaaact aaagaaaaaa aaaaaaaaa aaaaaaaa | 828 |

<210> SEQ ID NO 33
<211> LENGTH: 2212
<212> TYPE: DNA
<213> ORGANISM: Homo sapiens

<400> SEQUENCE: 33

| | |
|---|---|
| agttggcctt cagcccctgc ctcggccaga ggtttcattt ttaactgaat atttacgaaa | 60 |
| gctgaaagcg tgcgaggggg gtggggtgga aatagcggct gcttctttc caaggattta | 120 |
| tttaatgggg atgtgttcaa ggcaagaccg aattcagaag gatatcgacg tcgtgatcca | 180 |

```
gaagtccaga gctgaggact gcctgtttgc agggctcttc aaaggcctaa aagctaaagg        240
cgaggatgga ttaattcaac aagtcctagt cgtgcgccct ggtgagtgcc agaccctgct        300
ccccgcgagg ggacccatga gccaccctca ccacgatccc tgccctggtg agccccccgt        360
gcgggacaca ggatccgaag atggcagcgg aagttcctca gcggcctcaa aagtgactgg        420
gcagagtggg cacaggctcc ctcactgggt gaaggaggcg caaagaacgg gaagagccat        480
cccgggagcc caccggcctt tcagtttccc ttgggccccc aggcggttca ggtatgtgtc        540
ggggccgggg cgtttccggc agcttttgat gaaggcgagg ggcaaggtcg tcctggttcc        600
agaatctccc aacctgcgga tctccaatga gactaacacg attcaccact ctaatctctt        660
cagttttcca aagccttgca cagttgtact gtctggtggg ctctgaggtt gggacggttg        720
ggggagtgtt tggtgagtgc acccttccta tagtgcccag aagaaggtac aatacctgtc        780
tctgtggcac aatcggttag cgcgttcggc tgttaatcta gaggttggtg gttagagccc        840
actgagggat gcctcctcca gattttttt tttttttttc tgagacagag tcttgctctg        900
tcgccaggct ggagtgcagt ggcgcgatct cggctcactg caacatccgc tccctggtt         960 caagcgattc ccctgcctca gtctcccgag tagctgagaa tacaggcgag cgccaccccg       1020
cccggctaat gttttgtatt ttagtagaga cagaggtttc accttattgg ccaggatggt       1080
ctcgatcagc tgacctcgtg atccaccgc cttggcctcc caaagtgctg ggattacagg         1140
tgtaagcaac cgcgccctgc ccggctgcct gcttcagctt ttaaagcgtt catgcattat       1200
caatcactag ataaacggcg agattatat cttcccagag tcctaagcca ctagggttgt         1260
gtctctgtgg cacaatcagt tgtcgcatcc aaaaggccta gctaactttt gtatttttg        1320 tagagaaagg gtttcattat gttgcccatg ctggtcccca aactcctggg ctcgggcacc       1380
tccgaggtct cccaaagtgc taggattaca ggcatgagcc actgcacagg gccttataca       1440
atgcttctaa tttcagcaca tttagcaaac ttatcttctg cgggagaggt accaaatcac       1500
attccagttt atttctcaac tctaataatg tccctttctt catttacttg ctgacacaac       1560 aaatttctc ccctcccgta ctttttgttt tgagactagg tgtcactcta tcacccaaga         1620
tggagtgcag tggcatgatc tcatgtcact gcaaactcac cgcccctgca accatggcac       1680
tagtgatcct ccagaagagc tggaactaca gagaggacat cttgctgtgt tttccaggct       1740
ggacctgaat gaactcctgg gctcaatcaa tccttccacc tcagcctaac atttacactg       1800
ggagcagaga tgcatttgga catataaact gttaacatga ggtaagcgcc aaggtctaga       1860
gaaggcagtg gaagagatgg caaactccgg caccatgtct gcgtgtccag tgtgctctgc       1920
tggagcagca cattttgta cattgctgta tttgaaaaaa ccctgcaaga atcatgaaac         1980
tggacgacca tctttataac actcccagtg ataaaacaag taagaatggc tggtttgtag       2040
tcatctgagc agcctctcta gtttcgtaga tatggtttct ctctgatatc gaacgacttc       2100
caatgtcaag cggaatgcta catcacaagg ataaccgtat gtgaaaagaa ccagttttct       2160
ttgtaatcct gaactttcta gtttgcgcat taaaagacat tatttgaaga ag                2212
```

<210> SEQ ID NO 34
<211> LENGTH: 2747
<212> TYPE: DNA
<213> ORGANISM: Homo sapiens

<400> SEQUENCE: 34

```
agacactctc caaaaagcag agacagcagg aagaggggag tggaggcagc ccattcacct         60
```

```
ggggaaatga ctgggttgtc gatggacggt ggcggcagcc ccaaggggga cgtggacccg    120
ttctactatg gtaagcctgg gccctgcgc acccttcctg agccctcagg accccttcca    180
ccaagcagcg gcctctccca gccccaggtc catgctctgt gccccttatc tccctggtt    240 accacgggct gctgcgggca ggctgcggag agagacagct gctgggagag accacccatc    300
ccgctcctct tgccctctct ttccggagac tatgagaccg ttcgcaatgg gggcctgatc    360
ttcgctggac tggccttcat cgtgggctc ctcatcctcc tcagtaagtg gggtggcctc    420
cagggaaggg gtgctgacca gggcacctct cttctcaagg ccgctgagca ggctggcttt    480
cgggagttgc caagggaggg gtgagcctcc ccaccacgcc ccccactgca ggatgtggga    540
atgggtgccc ggtggggtgc caggctcgct gggagcacag tgtgaggttc ctgcttgctc    600
aagtgcaccc tccagtgggc ccgggaggag ccgcagaagt gagagcaaac ccacgggta    660 actgggtaac cggagggcca gacaggggga ctaggccccc cgctgctaac catggtccca    720
aactcatttg ttaaataggg atgatcccac ctgcctcaca agattagggc tagcatccaa    780
agacatggca gtcaggacag cgctctgaga acggtccagt gcagactcgg agtgttctgg    840
gggagacaaa gagagttatg tatcctcaag ccccgagggg cacacagcag gagcttaata    900
actgcacatt gacttgtttt ggtccaaccc aaagaaaaat acacagaaaa cacaacccat    960
ggaaagaaga tacagcaagc acacctgtgg gctctggact tctaatgcac gtgtgccact   1020
gccaccccac cccaaggctc gggcacagt cctgcgggtc tccccatttt cccgtgttgc   1080
ccatggcagc tctctctacg tgtgccactg ccagcccacc ccaaggctcg gccacagtc   1140 ctgcaggtct ccccatttc acatgttgcc cgtggcagct cccggaggc agtgccgggt   1200 ggcagctgat cacataggca caggaggcag gtggcctaag caaggggctc cactttggag   1260
ttgctgccat ccttctccag gtgttcatcg ggcagctgtg ctgggggcac catgatggcc   1320
cagtctctgc tgctactctc gatatgccaa cagaccaccg tggatctgct ccagtaaata   1380
tttgctgact gactgactga cttaggttct taaatgccta tggtccagcc ttatataaag   1440
agagagaagg ctgggcgtgg tggctcatgc ctgtaatgcc ggcatattag gaggccaagg   1500
caggaggatc tcttgagacc aggagtttaa gaccagcctg gtcaatacag tgagacccga   1560
tctatacaaa aaaaatttt tttaattagc tgggcatggt gacatgtacc tatagtccca   1620
gctacttggg aggctgaggc aggaggatta cttgagccca ggagtttgag gctgcagtga   1680
gctacgatcc caccactgca ctccagcctg ggtgacagag taagaccccg tctcaaaaaa   1740
taaaataaaa taaatataa aataaatag agacagtcaa acgtggcctc caagcctgac   1800
cctgcgatga tactggcagg agggaggtag gagagactgg aagaattttg agtcttccag   1860
ggtctccttg gaaaattagt ccatggaaac aaatctcctt ttctcttttc aaggcagaag   1920
attccgctgt gggggcaata agaagcgcag gtgagcgctg cctggggtga ccgatgaggg   1980
ggttggggct ggagaaggag gggcgggctg aggattttgt ctctgacaca gtggaggatc   2040
cccagcctca gagatcccta gacccacccc tcctccctgcc ctctcacctg ttgctttcc   2100 ttcccccacc aggcaaatca atgaagatga gccgtaacag caggtatgct aggagggcct   2160
ggggaaggtg cggggagggc agggcaggct gggagcaac agggaagaat tctggctcct   2220
ggactcggta aataagaatt ttagggtcgt ccacacatca gccaggtggt ctgtcaccca   2280
tcgtgtgttt aaaatgatgg ccaagggcct ggcgtggagt gtgtgccgca ggagatcaca   2340
gaggagccct ggagaaaagt gagatggaca agggggaagt aaaaccccaa cctctgctgc   2400
ctcccaccca accccatcct gcctttgtct tctcagcctc ggcggtgcca cccactgcac   2460
```

```
tggggccagc tgggaagcca agcatggccc tgcctctggc gcctcccctt cttccctggg    2520 cttttagacct ttgtccccgt cactgccagc gcttgggctg aaggaagctc cagactcaat    2580
gtgaccccca ggtggcatcg ccaactcctg cctcgtgcca cctcatgctt ataataaagc    2640
cggcgtcaga gaccgctgct tccctcacct gcctgcctgt ctccctcctc tgtcaccacc    2700
agcctctcca agctcaagta caaatacagc cgggaaaaaa aaaaaaa                   2747

<210> SEQ ID NO 35
<211> LENGTH: 1710
<212> TYPE: DNA
<213> ORGANISM: Homo sapiens

<400> SEQUENCE: 35
ggcccgagct gcacaggcca aggaattcca cagagggtgt gacccaaagc ccctaacaac      60
agactcgctg ggaccccta gacttggcat ggaggctggg tgcagaccta aagacagag      120 gtggtgaagc ccggccagtg aggacaagag ctgcggggaa ggacaccgag gtgacttgac    180
ggcagcagca ggcctgaagg ctctggctgc tttggaagat atttcaatga gatgcaaatc    240
gcaatcgact gaccattagt ttccactgca gtgtttgcag atggagtcga atgtaacccc    300
ccgggaatgg agccgggagg gtcagagaac gcggctgcgc tctggatctc cgaaggggg    360 cggggggcctg gaagaggtcc gggcccagaa tggacctcca ggtccctgct gccgcaatct    420
ggccctgccc tccagcctac cccttactcc cagaggaagg gacccaggga gacccaccca    480
gatgccctga aggaggtgg aggatggggg tgggcaata cgcagagttt gtctggtgaa      540
tgcaggaaag gggtggggc tggagaggaa aaggatggag cagccgtcag cttgtcaact    600
ccgcatctgc tggctgcctc ggccgggctc cagcctgcgc cctcgcccct cggaacagcg    660
gtatgtccat tctctccgca ttcgtctcca tcgttcagcc accaccgcac cctttctcta    720
ttcatttctc ctgctcccctt gtcctgcccc gcccctcgtg cccaggtcca tcggtctaca    780
cccatgggcc gagccctcct caccagggtc ctcctggaac cgctccggcc ttgggcttgt    840
ccgcggctcc cacggtcccc gcccggcggg gcacagagcg ggaggggagg ggcactagca    900
caacctaccc tgcgctgcgc agctgcaccc ctgcgcgcat gggcgtggcg tagctcagac    960
ccgcccccag cgtttagcgt cttttgtcac ccacctagag ggtttgatat atcctaagct  1020
tttggcccct gggtcctggt tccgtgcagc gagtcctccc agcaccccac cctgcacatt   1080
ctggaaagtg ccagactctg gctgggccga gcaagaacag aaccacaaga aggttacacg   1140
attatttatt gagagcctcc tctccccgcc cttgcaatct ctaggtcact ttctccgctt   1200
gtagattttg cgcgcaagcc ccagaaagac ggctgggggc agggtgctg cgtactgttc   1260 aatgagagcc ataatgtggc tgtaactgtc ttcctcatat tgcaagaaca ctgctggcag   1320
atccagctcc tcatatagcg ccttcacccg ggccactttc tcagcctcct tctgcccgta   1380
attttcctgg aagaggttga aagacaggaa aacgggcttg ccttcccca gagcctccag   1440 gaccccctcca ctcccctcat tcacatattc cagaacatct ccaaagccac ccactccttt   1500 cctcccctcca attttcaagt gtctctacgt agctaaaatc ccaagcttcc cttccctatc   1560
ccaaatattg cctcatacca ggcatcctct actccagggt ttctccacct tggcactatt   1620
gaaatttggg accagaaaaa aaaaaaaaaa aaaaaaaaaa aaaaaaaaaa aaaaaaaaaa   1680
aaaaaaaaaa aaaaaaaaaa aaaaaaaaaa                                    1710

<210> SEQ ID NO 36
```

<211> LENGTH: 2221
<212> TYPE: DNA
<213> ORGANISM: Homo sapiens

<400> SEQUENCE: 36

```
ggccaggaac gccagccgtt cacgcgttcg gtcctccttg gctgactcac cgccctggcc      60
gccgcaccat ggacgccccc aggcaggtgg tcaactttgg gcctggtccc gccaagctgc     120
cgcactcagt gttgttagag atacaaaagg aattattaga ctacaaagga gttggcatta     180
gtgttcttga aatgagtcac aggtcatcag attttgccaa gattattaac aatacagaga     240
atcttgtgcg ggaattgcta gctgttccag acaactataa ggtgattttt ctgcaaggag     300
gtgggtgcgg ccagttcagt gctgtcccct aaaacctcat tggcttgaaa gcaggaaggt     360
gtgctgacta tgtggtgaca ggagcttggt cagctaaggc cgcagaagaa gccaagaagt     420
ttgggactat aaatatcgtt caccctaaac ttgggagtta tacaaaaatt ccagatccaa     480
gcacctggaa cctcaaccca gatgcctcct acgtgtatta ttgcgcaaat gagacggtgc     540
atggtgtgga gtttgacttt atacccgatg tcaagggagc agtactggtt tgtgacatgt     600
cctcaaactt cctgtccaag ccagtggatg tttccaagtt tggtgtgatt tttgctggtg     660
cccagaagaa tgttggctct gctggggtca ccgtggtgat tgtccgtgat gacctgctgg     720
ggtttgccct ccgagagtgc ccctcggtcc tggaatacaa ggtgcaggct ggaaacagct     780
ccttgtacaa cacgcctcca tgtttcagca tctacgtcat gggcttggtt ctggagtgga     840
ttaaaaacaa tggaggtgcc gcggccatgg agaagcttag ctccatcaaa tctcaaacaa     900
tttatgagat tattgataat tctcaaggat tctacgtttg tccagtggag ccccaaaata     960
gaagcaagat gaatattcca ttccgcattg caatgccaa aggagatgat gctttagaaa    1020
aaagatttct tgataaagct cttgaactca atatgttgtc cttgaagggg cataggtctg    1080
tgggaggcat ccgggcctct ctgtataatg ctgtcacaat tgaagacgtt cagaagctgg    1140
ccgccttcat gaaaaaattt ttggagatgc atcagctatg aacacatcct aaccaggata    1200
tactctgttc ttgaacaaca tacaaagttt aaagtaactt ggggatggct acaaaaagtt    1260
aacacagtat ttttctcaaa tgaacatgtt tattgcagat tcttcttttt tgaaagaaca    1320
acagcaaaac atccacaact ctgtaaagct ggtgggacct aatgtcacct taattctgac    1380
ttgaactgga agcattttaa gaatcttgt tgcttttcta acaaattccc gcgtattttg     1440
cctttgctgc tacttttttct agttagattt caaacttgcc tgtggactta ataatgcaag    1500
ttgcgattaa ttatttctgg agtcatggga acacacagca cagagggtag gggggccctc    1560
taggtgctga atctacacat ctgtggggtc tcctgggttc agcggctgtt gattcaaggt    1620
caacattgac cattggagga gtggtttaag agtgccaggc gaagggcaaa ctgtagatcg    1680
atctttatgc tgttattaca ggagaagtga catactttat atatgtttat attagcaagg    1740
tctgttttta ataccatata ctttatattt ctatacattt atatttctaa taatacagtt    1800
atcactgata tatgtagaca cttttagaat ttattaaatc cttgaccttg tgcattatag    1860
cattccatta gcaagagttg tacccctcc ccagtcttcg ccttcctctt tttaagctgt     1920
tttatgaaaa agacctagaa gttcttgatt cattttacc attctttcca taggtagaag     1980
agaaagttga ttggttggtt gttttcaat tatgccatta aactaaacat ttctgttaaa      2040
ttaccctatc ctttgttctc tactgttttc tttgtaatgt atgactacga gagtgatact     2100
ttgctgaaaa gtctttcccc tattgtttat ctattgtcag tattttatgt tgaatatgta     2160
aagaacatta aagtcctaaa acatctaaaa aaaaaaaaa aaaaaaaaa aaaaaaaaa       2220
```

| | |
|---|---|
| a | 2221 |

<210> SEQ ID NO 37
<211> LENGTH: 4601
<212> TYPE: DNA
<213> ORGANISM: Homo sapiens

<400> SEQUENCE: 37

| | |
|---|---:|
| cgggccgggg cgcgcaggtc ccgtcgccgg tgagcacggg ctccctctcg cgtggcctcg | 60 |
| ccgggtccgc ctggcctgcc cacctccgga gccacctctg ccccgcatg ggctggcgaa | 120 |
| gttgggagga gcgagctgga gccagagcgc gcgccgggcg cgcccgtcg ctgcctgact | 180 |
| cggcgcccgc agttcgggcg cagcacgccg gccgcaggag cacggatgcc ccccggagcc | 240 |
| gcgggctggc aggtctgggg tcctgaggct gctggcagac tatgggtaca acggccagca | 300 |
| cagcccagca gacggtctcg gcaggcaccc catttgaggg cctacagggc agtggcacga | 360 |
| tggacagtcg gcactccgtc agcatccact ccttccagag cactagcttg cataacagca | 420 |
| aggccaagtc catcatcccc aacaaggtgg ccctgttgt gatcacgtac aactgcaagg | 480 |
| aggagttcca gatccatgat gagctgctca aggctcatta cacgttgggc cggctctcgg | 540 |
| acaacacccc tgagcactac ctggtgcaag gccgctactt cctggtgcgg gatgtcactg | 600 |
| agaagatgga tgtgctgggc accgtgggaa gctgtgggggc ccccaacttc cggcaggtgc | 660 |
| agggtgggct cactgtgttc ggcatgggac agcccagcct ctcagggttc aggcgggtcc | 720 |
| tccagaaact ccagaaggac ggacataggg agtgtgtcat cttctgtgtg cgggaggaac | 780 |
| ctgtgctttt cctgcgtgca gatgaggact ttgtgtccta cacacctcga gacaagcaga | 840 |
| accttcatga gaacctccag ggccttggac ccggggtccg ggtggagagc ctggagctgg | 900 |
| ccatccggaa agagatccac gactttgccc agctgagcga gaacacatac catgtgtacc | 960 |
| ataacaccga ggacctgtgg ggggagcccc atgctgtggc catccatggt gaggacgact | 1020 |
| tgcatgtgac ggaggaggtg tacaagcggc ccctcttcct gcagcccacc tacaggtacc | 1080 |
| accgcctgcc cctgcccgag caagggagtc cctggaggc ccagttggac gcctttgtca | 1140 |
| gtgttctccg ggagaccccc agcctgctgc agctccgtga tgcccacggg cctccccag | 1200 |
| ccctcgtctt cagctgccag atgggcgtgg gcaggaccaa cctgggcatg gtcctgggca | 1260 |
| ccctcatcct gcttcaccgc agtgggacca cctcccagcc agaggctgcc cccacgcagg | 1320 |
| ccaagcccct gcctatggag cagttccagg tgatccagag cttctccgc atggtgcccc | 1380 |
| agggaaggag gatggtggaa gaggtggaca gagccatcac tgcctgtgcc gagttgcatg | 1440 |
| acctgaaaga agtggtcttg gaaaaccaga agaagttaga aggtatccga ccggagagcc | 1500 |
| cagcccaggg aagcggcagc cgacacagcg tctggcagag ggcgctgtgg agcctggagc | 1560 |
| gatacttcta cctgatcctg tttaactact accttcatga gcagtacccg ctggcctttg | 1620 |
| ccctcagttt cagccgctgg ctgtgtgccc acctgagct gtaccgcctg cccgtgacgc | 1680 |
| tgagctcagc aggccctgtg gctccgaggg acctcatcgc caggggctcc ctacgggagg | 1740 |
| acgatctggt ctccccggac gcgctcagca ctgtcagaga gatggatgtg gccaacttcc | 1800 |
| ggcgggtgcc ccgcatgccc atctacgca cggcccagcc cagcgccaag gcctggggga | 1860 |
| gcatcctggc ctacctgacg gacgccaaga ggaggctgcg gaaggttgtc tgggtgagcc | 1920 |
| ttcggggagga ggccgtgttg gagtgtgacg ggcacaccta cagcctgcgg tggcctgggc | 1980 |
| cccctgtggc tcctgaccag ctggagaccc tggaggccca gctgaaggcc catctaagcg | 2040 |

```
agcctccccc aggcaaggag ggcccctga cctacaggtt ccagacctgc cttaccatgc    2100
aggaggtctt cagccagcac cgcagggcct gtcctggcct cacctaccac cgcatcccca    2160
tgccggactt ctgtgccccc cgagaggagg actttgacca gctgctggag ccctgcggg     2220
ccgccctctc caaggaccca ggcactggct tcgtgttcag ctgcctcagc ggccagggcc    2280
gtaccacaac tgcgatggtg gtggctgtcc tggccttctg gcacatccaa ggcttccccg    2340
aggtgggtga ggaggagctc gtgagtgtgc ctgatgccaa gttcactaag ggtgaatttc    2400
aggtagtaat gaaggtggtg cagctgctac ccgatgggca ccgtgtgaag aaggaggtgg    2460
acgcagcgct ggacactgtc agcgagacca tgacgcccat gcactaccac ctgcgggaga    2520
tcatcatctg cacctaccgc caggcgaagg cagcgaaaga ggcgcaagaa atgcggaggc    2580
tgcagctgcg gagcctgcag tacttggagc gctatgtctg cctgattctc ttcaacgcgt    2640
acctccacct ggagaaggcc gactcctggc agaggccctt cagcacctgg atgcaggagg    2700
tggcatcgaa ggctggcatc tacgagatcc ttaacgagct gggcttcccc gagctggaga    2760
gcggggagga ccagcccttc tccaggctgc gctaccggtg gcaggagcag agctgcagcc    2820
tcgagccctc tgcccccgag gacttgctgt agggggcctt actccctgtc cccccaccca    2880
cagggcccca cgcaggcctg gggtgtctga ggtgctcttg gctgggagcg gccctgaggg    2940
gtgctggcct tgaaatgatt cccccacttc ctggagagac tgagcggagt tgggagcctt    3000
tttagaaaga acttttata ggacaggag acagcacagc catcccttgc aaaccaccaa     3060
ggtgtgtggc tgacctccag ggaggagcac tcactggagt gctcacaagg tgcacactgc    3120
tgtgtgtacc ttgcagacag gccggcgttc agcctccaag gggctcactc ccccagttgc    3180
caaacactgt ggatctctct gtcctcttct ccctctctc agattggcct ggcagcccct     3240
ggcacagagc agacccggcc actggtagct ccccacttcc ttactcctgc tgctctgcca    3300
ttgccgctcc ccttgttgct gcccaagcac tgccctcggg cgtctggcag cctgaggtgg    3360
gtggagggga cagtgttctg gatagatcta ttatgtgaaa ggcagcttca cccagttttc    3420
tggactctca tgcccccatc tccgacctgg gagacttcag gaatgacaac ctacccagcc    3480
tggtggggct ggcaggatgg tggaggtttc tcaaggagct ggagacttca gggagccct     3540
ctcatgggga ggaaagagct tccaggggc gaacgcagca cagaggaaga ggcctgctcc    3600
acttgtctgg gaacctggc aggaggcaca gaggaagcca aggcctggag ctgcaggtcc     3660
cccggcatct ctctctgtcc cggcagccca ggatggcctg gtgcccccac ctgctgcagc    3720
aggagcccca aggagtgcta gctgagggtg gttgctgggg tggtcctcat ggacagtgag    3780
gtgtgcaagg gtgcactgag ggtggtggga ggggatcacc tgggttccag gccatccttg    3840
ctgagcatct ttgagcctgc cttccggtgg gagcagaaaa ggccagaccc tgctgagtta    3900
gaggctgctg ggatccactg tttccacaca gcgggaaggc tgctgggaac aggtggcaga    3960
gaagtgccat gtttgcgttg agccttgcag ctcttccagc tggggactgg tgcttgctga    4020
aacccaggag ctgaacagtg aggaggctgt ccaccttgct tggctcactg ggaccaggaa    4080
agcctgtctt tggttaggct cgtgtacttc tgcaggaaaa aaaaaaagg atgtgtcatt     4140
ggtcatgata tttgaaaagg ggaggaggcc gaagttgttc ccatttatcc agtattggaa    4200
aatatttgac ccccttggct gaattctttt gcagaactac tgtgtgtctg ttcactacct    4260
tttcaggttt attgttttta tttttgcatg aattaagacg ttttaatttc tttgcagaca    4320
aggtctagat gcggagtcag agatgggact gaatggggag ggatcctttg tgttctcatg    4380
gttggctctg actttcagct gtgttgggac cactggctga tcacatcacc tctctgcctc    4440
```

```
agtttcccca tctgtaaaat gggagaataa tacttgccta cctacctcac agggtgttg      4500 tgaggattca tttgtgattt tttttttttt tgtacagagc ttttaagcat taaaaacagc      4560
taaatgtgaa aaaaaaaaaa aaaaaaaaaa aaaaaaaaaa a                          4601
```

<210> SEQ ID NO 38
<211> LENGTH: 924
<212> TYPE: DNA
<213> ORGANISM: Homo sapiens

<400> SEQUENCE: 38

```
atgctacgtg tagtggaagg catcttcatt tttgttgtag ttagtgagtc agtgtttggg        60
gttttgggga atggatttat tggacttgta aactgcattg actgtgccaa gaataagtta       120
tctacgattg gctttattct caccggctta gctatttcaa gaattttttct gatatggata      180 ataattacag atggattat acagatattc tctccaaata tatatgcctc cggtaaccta        240
attgaatata ttagttactt ttgggtaatt ggtaatcaat caagtatgtg gtttgccacc       300
agcctcagca tcttctattt cctgaagata gcaaattttt ccaactacat atttctctgg      360
ttgaagagca gaacaaatat ggttcttccc ttcatgatag tattcttact tatttcatcg      420
ttacttaatt ttgcatacat tgcgaagatt cttaatgatt ataaaacgaa gaatgacaca      480
gtctgggatc tcaacatgta taaaagtgaa tactttatta aacagatttt gctaaatctg      540
ggagtcattt tcttctttac actatcccta attacatgta ttttttttaat catttccctt    600 tggagacaca acaggcagat gcaatcgaat gtgacaggat tgagagactc caacacagaa      660
gctcatgtga aggcaatgaa agttttgata tctttcatca tcctctttat cttgtatttt     720
ataggcatgg ccatagaaat atcatgtttt actgtgcgag aaaacaaact gctgcttatg      780 tttgaatga caaccacagc catctatccc tggggtcact catttatctt aattctagga      840
aacagcaagc taaagcaagc ctcttttgagg gtactgcagc aattgaagtg ctgtgagaaa      900
aggaaaaatc tcagagtcac atag                                             924
```

<210> SEQ ID NO 39
<211> LENGTH: 857
<212> TYPE: DNA
<213> ORGANISM: Homo sapiens

<400> SEQUENCE: 39

```
atatttcctg ttccggggcg tgtgggaccc ggatgcaagc gtgctatata agcgttgctc        60
aagtcccacc cctttctttt tgaggaagac gcggtcgtaa gggctgagga ttttttggtcc     120 gcacgctcct gctcctgact caccgctgtt cgctctcgcc gaggaacaag tcggtcagga      180
agcccgcgcg caacagccat ggcttttaag gataccggaa aaacaccgt ggagccggag       240 gtggcaattc accgaattcg aatcacccta caagccgca acgtaaaatc cttggaaaag      300
gtgtgtgctg acttgataag aggcgcaaaa gaaaagaatc tcaaagtgaa aggaccagtt     360
cgaatgccta ccaagacttt gagaatcact acaagaaaaa ctccttgtgg tgaaggttct     420
aagacgtggg atcgtttcca gatgagaatt cacaagcgac tcattgactt gcacagtcct    480
tctgagattg ttaagcagat tacttccatc agtattgagc caggagttga ggtggaagtc    540
accattgcag atgcttaagt caactatttt aataaattga tgaccagttg ttaacttctg     600 ttggtttta ttcagaatac tggcagattt taggaatata aaggtgtact atgagcttc      660 cacttttcag gtggaatata tgggtatctt agagtggtct atcctgtttt cgttgtcgtt    720
```

| | |
|---|---:|
| tgagtcattt gaaaactgga ttccgttaac tacataatat gtgagacctg actggtttta | 780 |
| ttggacactg gcagtttata actttggcat actctagata aattctgatt ggtatgggga | 840 |
| aaaaaaaaaa aaaaaaa | 857 |

<210> SEQ ID NO 40
<211> LENGTH: 2840
<212> TYPE: DNA
<213> ORGANISM: Homo sapiens

<400> SEQUENCE: 40

| | |
|---|---:|
| ggctctcggg gctgccttt agccggacgc gcggaggtgg gcaatccgct ccttcccttg | 60 |
| agcagtccac gccttgtggc ggctttgcgg agctgctgct ttggcgggag ttggaagctg | 120 |
| gtgtgaggtg agaggcgcgg tggtcgctcc ccggcgaggc caggtttctg tggggagaag | 180 |
| gagagtgcca gaggtgactg gttcatggtt cttctaggct ctcatggcca ccatgttgga | 240 |
| aggcagatgc caaactcagc caaggagcag ccccagtggc cgagaggcta gcctgtggtc | 300 |
| gtcaggcttt gggatgaagc tggaggctgt cactccattc ctggggaagt atcgcccctt | 360 |
| tgtgggtcgc tgttgccaga cctgcacccc caagagctgg gagtccctct tccacagaag | 420 |
| cataacggac ctaggcttct gcaatgtgat cctggtgaag gaggagaaca caaggtttcg | 480 |
| gggctggctg gttcggaggc tctgctattt cctgtggtcc ctggagcagc acatcccccc | 540 |
| ctgccaggat gtcccacaga agatcatgga aagcaccggg gtgcagaacc tcctctcagg | 600 |
| gagggtccca ggaggcactg gggaaggcca ggtgcctgac cttgtgaaga aggaggtaca | 660 |
| gcgcatcctg ggtcacatcc aggccccacc ccgtcccttc ctggtcaggc tgttcagctg | 720 |
| ggcgctgctg aggttcctga actgcctgtt cctgaatgtg cagctccaca agggtcagat | 780 |
| gaagatggtc cagaaggccg cccaggcagg cttgccgctt gtcctcctct ctactcacaa | 840 |
| aaccctcctg gatgggatcc tgctgccctt tatgctgctc tcccagggcc tgggtgtgct | 900 |
| tcgtgtggcc tgggactccc gcgcctgctc ccctgccctc agagctctgc tgaggaagct | 960 |
| tggggggctt ttcctgcccc cagaggccag cctctccctg gacagctctg aggggctcct | 1020 |
| tgccagggct gtggtccagg cggtcataga gcagctgctg gttagtgggc agcccctgct | 1080 |
| catcttcctg gaggaacctc ctggggctct ggggccacgg ctgtcagccc tgggccaggc | 1140 |
| ttgggtgggg tttgtggtgc aggcagtcca ggtgggcatc gtcccagatg ctctgctggt | 1200 |
| accagtggcc gtcacctatg acctggttcc ggatgcaccg tgtgacatag accatgcctc | 1260 |
| ggcccccctg gggctgtgga caggagctct ggctgtccta cgtagcttgt ggagccgctg | 1320 |
| gggctgcagc caccggatct gctcccgggt gcacctagct cagcccttt ccctgcagga | 1380 |
| atacatcgtc agtgccagaa gctgctgggg cggcagacag accctggagc agctactgca | 1440 |
| gcccatcgtg ctgggccaat gtactgctgt cccagacact gagaaggagc aggagtggac | 1500 |
| ccccataact gggcctctcc tggccctcaa ggaagaggac cagctcctgg tcaggagact | 1560 |
| gagctgtcat gtcctgagtg ccagtgtagg gagctctgcg gtgatgagca cggccattat | 1620 |
| ggcaacgctg ctgctcttca agcatcagaa gctcctgggg gagttctcct ggctgacgga | 1680 |
| ggagatactg ttgcgtggct ttgatgtagg cttctctggg cagctgcgga gcctgctgca | 1740 |
| gcactcactg agcctgctgc gggcgcacgt ggccctgctg cgcatccgtc agggtgactt | 1800 |
| gctggtggtg ccgcagcctg gcccaggcct cacacacctg gcacaactga gtgctgagct | 1860 |
| gctgcccgtc ttcctgagcg aggctgtggg cgcctgtgca gtgcggggc tgctggcagg | 1920 |
| cagagtgccg ccccaggggc cctgggagct gcagggcata ttgctgctga gccagaatga | 1980 |

```
gctgtaccgc cagatcctgc tgctgatgca cctgctgccg caagacctgc tgctgctaaa    2040
gccctgccag tcttcctact gctactgtca ggaggtgctg gaccggctca tccaatgcgg    2100
gctcctggtt gctgaggaga ccccaggctc ccggccagcc tgtgacacag ggcgacagcg    2160
attgagcaga aagctgctgt ggaaaccgag tggggacttt actgatagtg acagtgatga    2220
cttcggagag gctgacggcc ggtacttcag gctcagccag cagtcacact gcccagattt    2280
cttctttttc ctctgccgcc tgctcagccc gctgctcaag gcctttgcac aggctgccgc    2340
cttcctccgc cagggccagc tgcccgatac tgagttgggc tacacagagc agctgttcca    2400
gttcctgcag gccaccgccc aggaagaagg gatcttcgag tgtgcggacc caaagctcgc    2460
catcagtgct gtctggacct tcagagacct aggggttctg cagcagacgc cgagccctgc    2520
aggccccagg ctccacctgt cccctacttt tgccagcctg acaatcagg aaaaactaga    2580 acagttcatc cggcagttca tttgtagcta gaactgtgag gaggagcctg tgctgagact    2640
tctcagcccc agaacacagc tgtgtcctag agccagaaga tggagaggag gctgcaaacc    2700
cttagctgct ctataaatat aatcattgag gcttgattgt cccttgccat ctcttgcttt    2760
ttcccttctt tgatgtgata acaaggggga cgagacgagt tgtcttttcc ccagcccagc    2820
agcaaaaaaa aaaaaaaaaa                                                2840
```

```
<210> SEQ ID NO 41
<211> LENGTH: 1566
<212> TYPE: DNA
<213> ORGANISM: Homo sapiens

<400> SEQUENCE: 41
```

```
cacagcccca gcagaaggcc ctcacctcac aaggaacatg aggcgccttg ccgggcgcgc      60
aggccactcc caggtcactc aggattccaa gttctccccc aagacgcctt cagatgctga     120
gcggcacaag ggcctcccca gggactggtt gcaaagcctc ctgctcagct tgagagggcc     180
accagctccc cactgtttac tgttgttcct gagagaggcc agagggaggg accagccagg     240
gagtggccag agggacagaa ggggtggcct tcctgagggc agggtgggtg ccccagacct     300
gagagcgctg caggactccc ctccacaggc tcaggtggag cctccccagg gtcctcctgg     360
ccaggaaggc agagagccga cttctttctt cagctcccaa cccaggccca gcccacggcg     420
tgggagtcgg ggagagggag aggaggagga aggaggagga gagagggagc ttgtcttgtc     480
cctgagcagc gctctcaggg cagaggtgag gcaccgggac atgaagttgg aggacaagtt     540
cccaagcagg gcttcctcgg gctccccctc gcgacggtaa tttgacactt ggatctccag     600
gacgaccaac aacaaaaaag ccaggcagag acagcagctg gctgtcagca gaggagctgg     660
gctgaggcgc ccaggggagc agcggcgccc acgaaggaag tacgaggaca gcacgtggag     720
gctccgcgct ggggcactgc tgctcagccc ccaacacctg agctcccaga gcccggcagg     780
agccccaaca ggaagccagc gcggcatggc tgccaccgac ttcgtgcagg agatgcgcgc     840
cgtgggcgag aggctgctgc tcaagctgca gagactgccc caggctgagc ccgtggagat     900
cgtggccttc tcagtcatca tccttttcac agctactgtt ctgctgttgc tgctgatagc     960
ctgcagctgc tgctgcactc actgctgctg ccctgagcgg agaggcagga aggtccaggt    1020
gcagccgaca ccaccatgac ggacgggcga tggctgagga aagctggag aggagatggc    1080 caatgccatg acacaggcca tcagcctggc cctgcagccc ttaccctca agaccaggct    1140 cccctggccc cagctctggc ccagcccagg tacctggaca ctgacaactt gagccctacc    1200
```

| | |
|---|---:|
| aaggaaacaa gggctggtat aggtgcaaac ctctcatctg ccagtggaca ctgggtgctg | 1260 |
| gggagtcagc tgtttcaaag actgggtcaa ctgcctgggc ttcttcgcct acctgcactt | 1320 |
| tttaacaaaa caaggaagta ggggtcccca taccttgatg agaacagtc cccacctgtg | 1380 |
| ggcaattggc ccttggggct ctgctgatac atgccaaaga ggagcaaggc aatcagaggg | 1440 |
| gctttgtgca atagcttctg catccgagct cccgccagag cgtgagcatg tcagtattct | 1500 |
| agtccagtat ttgccagttt ccaagtaaaa gcttttgtgt tacgtgttaa aaaaaaaaaa | 1560 |
| aaaaaa | 1566 |

<210> SEQ ID NO 42
<211> LENGTH: 189
<212> TYPE: DNA
<213> ORGANISM: Homo sapiens

<400> SEQUENCE: 42

| | |
|---|---:|
| atgtgcggca gctactacgg aaactactac ggcgaccatg gctatgggtg ctgtggatac | 60 |
| gaaggcctag gctatggcta tggaagcctg cgctgtggct atagctcctg ctgtggctat | 120 |
| ggtcatggct acggctcccg cttcttctgt ggctgtggct atggatgcgg ctctggctac | 180 |
| tactattga | 189 |

<210> SEQ ID NO 43
<211> LENGTH: 445
<212> TYPE: DNA
<213> ORGANISM: Homo sapiens

<400> SEQUENCE: 43

| | |
|---|---:|
| gcatgtgtct gctgctccct agtctgggcc atgagtgagg gtggaggcca agtctcatgc | 60 |
| attttttgcag cccccacaag actgtgcagg tggccggccc tcattgaatg cggggttaat | 120 |
| ttaactcagc ctctgtgtga gtggatgatt caggttgcca gagacagaac cctcagctta | 180 |
| gcatgggaag tagcttccct gttgaccctg agttcatctg aggttggctt ggaaggtgtg | 240 |
| ggcaccattt ggcccagttc ttacagctct gaagagagca gcaggaatgg ggctgagcag | 300 |
| ggaagacaac tttccattga aggccccttt cagggccaga actgtccctc ccaccctgca | 360 |
| gctgccctgc ctctgcccat gagggggtgag agtcaggcga cctcatgcca agtgtagaaa | 420 |
| ggggcagacg ggagccccag gttat | 445 |

<210> SEQ ID NO 44
<211> LENGTH: 957
<212> TYPE: DNA
<213> ORGANISM: Homo sapiens

<400> SEQUENCE: 44

| | |
|---|---:|
| atggaaggca accagacatg gatcacagac atcaccctgc tgggattcca ggttggtcca | 60 |
| gcactggcga ttctcctctg tggactcttc tctgtcttct atacactcac cctgctgggg | 120 |
| aatgggtca tctttgggat tatctgcctg gactctaagc ttcacacacc catgtacttc | 180 |
| ttcctctcac acctggccat cattgacatg tcctatgctt ccaacaatgt tcccaagatg | 240 |
| ttggcaaacc taatgaacca gaaaagaacc atctcctttg ttccatgcat aatgcagact | 300 |
| tttttgtatt tggcttttgc tgttacagag tgcctgattt tggtggtgat gtcctatgat | 360 |
| aggtatgtgg ccatctgcca cccttttcag tacactgtca tcatgagctg gagagtgtgc | 420 |
| acgatcctgg ttctcacgtc ctggtcatgt gggtttgccc tgtccctggt acatgaaatt | 480 |
| ctccttctaa ggttgccctt ctgtgggccc gggatgtga accacctctt ctgtgaaatt | 540 |

```
ctgtctgtcc tcaagctggc ctgtgctgac acctgggtta accaagtggt catatttgct    600
acctgtgtgt ttgtcttagt cgggcctctt tccttgattc tggtctccta catgcacatc    660
ctcggggcca tcctgaagat ccagacaaag gagggccgca taaaggcctt ctccacctgc    720
tcctcccacc tgtgtgtggt tggactattc tttggcatag ccatggtggt ttacatggtc    780
ccagactcta atcaacgaga ggagcaggag aaaatgctgt ccctgtttca cagtgtcttt    840
aatccaatgc tgaaccccct gatctacagc ctgaggaatg ctcagttgaa gggcgccctc    900
cacagagcac tccagaggaa gaggtccatg agaacggtgt atgggctttg cctttaa      957
```

<210> SEQ ID NO 45
<211> LENGTH: 1001
<212> TYPE: DNA
<213> ORGANISM: Homo sapiens

<400> SEQUENCE: 45

```
cgtgggtgca ccctggaccc caccatggct caccggcccc ccagccctgc cctggcgtcc     60
gtgctgctgg ccttgctgct gagcggtgct gcccgagctg cggagatcgt gggcgggcac    120
gaggcgcagc cacactcccg gccctacatg gcctccctgc agatgcgggg gaacccgggc    180
agccacttct gcggaggcac cttgatccac cccagcttcg tgctgacggc cgcgcactgc    240
ctgcgggaca tacccagcg cctggtgaac gtggtgctcg gagcccacaa cgtgcggacg    300
caggagccca cccagcagca cttctcggtg gctcaggtgt ttctgaacaa ctacgacgcg    360
gagaacaaac tgaacgacgt tctcctcatc cagctgagca gcccagccaa cctcagtgcc    420
tccgtcgcca cagtccagct gccacagcag gaccagccag tgcccacgg cacccagtgc    480 ctggccatgg gctggggccg cgtgggtgcc cacgacccc cagcccaggt cctgcaggag    540
ctcaatgtca ccgtggtcac cttcttctgc cggccacata acatttgcac tttcgtccct    600
cgccgcaagg ccggcatctg cttcggagac tcaggtggcc ccctgatctg tgatggcatc    660
atccaaggaa tagactcctt cgtgatctgg ggatgtgcca cccgcttttt ccctgacttc    720
ttcacgcggg tagccctcta cgtggactgg atccgttcca cgctgcgccg tgtggaggcc    780
aagggccgcc cctgaaccgc ccctcccaca gcgctggccg ggaccccgag cctggctcca    840
aaccctcgag gcggatcttt ggacagaagc agctcttccc cgaacactgt ggcgtccggg    900
acggccccac ccgtcccccc acactccctc ccacggggct ccgggagaca ggccggccct    960
gcacctcacc ccaccgtgac ctcaataaac gttgaaactc c                      1001
```

<210> SEQ ID NO 46
<211> LENGTH: 1706
<212> TYPE: DNA
<213> ORGANISM: Homo sapiens

<400> SEQUENCE: 46

```
acagaaggag gaaggacagc acagctgaca gccgtgctca gacagcttct ggatcccagg     60
ctcatctcca cagaggagaa cacacaggca gcagagacca tggggcccct cccagcccct    120
tcctgcacac agcgcatcac ctggaagggg ctcctgctca cagcatcact tttaaacttc    180
tggaacccgc ccaccactgc cgaagtcacg attgaagccc agccaccaa agtttctgag    240 gggaaggatg ttcttctact tgtccacaat ttgccccaga atcttcctgg ctacttctgg    300
tacaaagggg aaatgacgga cctctaccat tacattatat cgtatatagt tgatggtaaa    360
ataattatat atgggcctgc atacagtgga agagaaacag tatattccaa cgcatccctg    420
```

```
ctgatccaga atgtcacccg gaaggatgca ggaacctaca ccttacacat cataaagcga      480
ggtgatgaga ctagagaaga aattcgacat ttcaccttca ccttatactt ggagactccc      540
aagccctaca tctccagcag caacttaaac cccagggagg ccatggaggc tgtgcgctta      600
atctgtgatc ctgagactct ggacgcaagc tacctatggt ggatgaatgg tcagagcctc      660
cctgtgactc acaggttgca gctgtccaaa accaacagga ccctctatct atttggtgtc      720
acaaagtata ttgcaggacc ctatgaatgt gaaatacgga acccagtgag tgccagtcgc      780
agtgacccag tcaccctgaa tctcctcccg aagctgccca tccctacat caccatcaac       840
aacttaaacc ccagggagaa taaggatgtc ttagccttca cctgtgaacc taagagtgag      900
aactacacct acatttggtg gctaaacggt cagagcctcc ccgtcagtcc cggggtaaag      960
cgacccattg aaaacaggat actcattcta cccagtgtca cgagaaatga acaggaccc      1020
tatcaatgtg aaatacggga ccgatatggt ggcctccgca gtaacccagt catcctaaat     1080
gtcctctatg gtccagacct ccccagaatt taccctttcat tcacctatta ccgttcagga    1140
gaaaacctcg acttgtcctg cttcacggaa tctaacccac cggcagagta ttttttggaca    1200
attaatggga agtttcagca atcaggacaa aagctcttta tcccccaaat tactagaaat     1260
catagcgggc tctatgcttg ctctgttcat aactcagcca ctggcaagga aatctccaaa     1320
tccatgacag tcaaagtctc tggtccctgc catggagacc tgacagagtc tcagtcatga    1380
ctgcaacaac tgagacactg agaaaaagaa caggctgata ccttcatgaa attcaagaca     1440
aagaagaaaa aaactcaatg ttattggact aaataatcaa aaggataatg ttttcataat     1500
tttttattgg aaaatgtgct gattctttga atgttttatt ctccagatttt atgaactttt    1560
tttcttcagc aattggtaaa gtataccttt gtaaacaaaa attgaaatat ttgcttttgc    1620
tgtctatctg aatgccccag aattgtgaaa ctattcatga gtattcatag gtttatggta    1680
ataaagttat ttgcacatgt tccgta                                          1706

<210> SEQ ID NO 47
<211> LENGTH: 597
<212> TYPE: DNA
<213> ORGANISM: Homo sapiens

<400> SEQUENCE: 47
gacagcggca gggggaaccc agggagcgcg atgggctgca gggctgcatc agggctcctg       60
ccaggagtgg ccgtggtcct cctgctgctg ctgcagagca cagtcagt ctacatccag       120
taccaaggct tccgggtcca gctggaatcc atgaagaagc tgagtgacct ggaggcacag      180
tgggcaccca gccccgcct gcaggcccag agcctcctgc ccgccgtgtg ccaccaccct      240
gctctgcctc aggaccttca gcctgtctgc gcctcgcagg aggcttccag catcttcaag      300
accctgagga ccatcgctaa cgacgactgt gagctgtgtg tgaacgttgc gtgtaccggc      360
tgcctctgag atagccctgg gtaccctgag cccaccaggg acacctcgcc cttcagccca      420
ccaccctggc aggcttccat ccccgtccat gctcaagatg ggtccctggc caccatggtc      480
atcaccaccc ttccagggcc tgagcagctg atctggtac aaagcaatcg gacatagagt       540
tggaggggga ggcccctgag gcagcccagc tcctgaataa agattctaca acacacg         597

<210> SEQ ID NO 48
<211> LENGTH: 2629
<212> TYPE: DNA
<213> ORGANISM: Homo sapiens

<400> SEQUENCE: 48
```

```
accgccccgc gctccgctgc caggggcggg agggaggaat ggttgcttca cgccccgggg    60
gaagagacgg gaagctcggc tctgggttgc gggccccggc gtctccgcgt ggggcgcacc   120
gtccgacccc cccctcccgg tgtgcagcgc cccgcaccgc cccgcctcgc ctgggagaag   180
ccgccgggac gcgccgggct ggagtgggcg gttataggct ttgagctagg ccgtttccgg   240
gaggcggagc tcagacccca tttccttcct ccacatccag gtcaggtggc gtttgctgtg   300
gcggctaggc ccgcgtgcgc tggagacctc cgcgctggcc cccgcgagcc tcctgccctg   360
gcccggcgct gcggctctgc cgcggcggca gcatgggtgg ccccggggc gcgggctggg    420 tggcggcggg cctgctgctc ggcgcgggcg cctgctactg catttacagg ctgacccggg   480
gtcggcggcg gggcgaccgc gagctcggga tacgctcttc gaagtccgca ggtgccctgg   540
aagaagggac gtcagagggt cagttgtgcg ggcgctcggc ccggcctcag acgggaggta   600
cctgggagtc acagtggtcc aagacctcgc agcctgaaga cttaactgat ggttcatatg   660
atgatgttct aaatgctgaa caacttcaga aactccttta cctgctggag tcaacggagg   720
atcctgtaat tattgaaaga gctttgatta ctttgggtaa caatgcagcc ttttcagtta   780
accaagctat tattcgtgaa ttgggtggta ttccaattgt tgcaaacaaa atcaaccatt   840
ccaaccagag tattaaagag aaagctttaa atgcactaaa taacctgagt gtgaatgttg   900
aaaatcaaat caagataaag atatacatca gtcaagtatg tgaggatgtc ttctctggtc   960
ctctgaactc tgctgtgcag ctggctggac tgacattgtt gacaaacatg actgttacca  1020
atgaccacca gcacatgctt cacagttaca ttacagacct gttccaggtg ttacttactg  1080
gaaatggaaa cacgaaggtg caagttttga aactgctttt gaatttgtct gaaaatccag  1140
ccatgacaga aggacttctc cgtgcccaag tggattcatc attcctttcc ctttatgaca  1200
gccacgtagc aaaggagatt cttcttcgag tacttacgct atttcagaat ataaagaact  1260
gcctcaaaat agaaggccat ttagctgtgc agcctacttt cactgaaggt tcattgtttt  1320
tcctgttaca tggagaagaa tgtgcccaga aaataagagc tttagttgat caccatgatg  1380
cagaggtgaa ggaaaaggtt gtaacaataa tacccaaaat ctgattggtc atattttcc   1440 aaagagtaat gcagtctgga tataaacgta ttttctgtct tccttataag gggattctcc   1500
cagctgctaa atttaaacag taaatatcac attttgtcat taacacagct ataacttgcc   1560
gtggttctca gatttatttt ggactatttt gatgccaagt gaatataaga gcttgtactg   1620
aaaccattta tttctttcta ttttgctatt tgcaaatgct tgttatcttc cctacatgaa   1680
gtggcagtaa ccttttttcac atttaagcta cccttctacc ttttgaagtg atttgcagtt  1740
actcatctga gacagcatca gtatttgact aaatcattgt ttcacaactg aatagtcttg   1800
ttcttttagt agcaacgaaa tcctaagctc ttgaggccat tcacctgcca acctgaccat   1860
actgctttca aaagtctttt ctcatcagta gaatctattt tggtcacttc tagtcaatga   1920
aaaatgtaaa cttttaggag agaatgtttc ttaggactca cccactccat tcaatgttat   1980
atataaaata gtgtgatcaa tcacaatgtc catctttaga cagttggtta aataaattat   2040
ctggtctttg aaaagaccgt gctgggcgcg gtggctcttg cctgtaatcc cagcactttg   2100
ggaggctgag gcgggcagat cacctgagat cgggagtttg agaccaagcc tgaccaatat   2160
ggagaaaccc tgtctctact aagaacacaa aattagctgg gcatggtggt gcatgcctgt   2220
aatcccagct acttgggagg ccgaggcagg agaattgctt gaacccggga ggcagaggtt   2280
gcagtgagct gagatagcgc cattgcactc cagcctgggc aacaagagca aaactctgtc   2340
```

```
tcaaaaaaaa aaaaaaatga tggagctccg aatgtgctta agtggaaaga tatctatgaa      2400
atatggtggt ttttaaaac acaaaaatta tagaatatgg gatcccgtgt gtgtgtgtgt        2460
gtgtttgaat gaaaatgct tatgtattga cagaacactt ctagaatgat acccaaactc        2520
ctggagtggg agtggggaat gccttctacg tacacactgt tctactgttt gaatttttta      2580
atatgagccc aaattgtata atcttttttt aataaggggg agaaaaatc                  2629
```

<210> SEQ ID NO 49
<211> LENGTH: 1198
<212> TYPE: DNA
<213> ORGANISM: Homo sapiens

<400> SEQUENCE: 49

```
gggtattga ctgaggcggc caagcggctc cgggacaggg ggtacggggg gtggggcgg         60 gtggttgcct gcgggaggcc gccgcgggtc atgtgaccgg aagggctcct cacggacgcc      120
gtccctcctc ggcgcggcct gagcgcccgg cccgaccccg gccatggggt gctgctacag      180
cagcgagaac gaggactcgg accaggaccg agaggagcg aagctgctgc tggaccctag      240 cagccccct accaaagctc tcaatggagc cgagcccaac taccacagcc tgccttccgc      300
tcgcactgat gagcaggccc tgctctcttc catccttgcc aagacagcca gcaacatcat      360
tgatgtgtct gctgcagact cacagggcat ggagcagcat gagtacatgg accgtgccag     420
gcagtacagc acccgcttgg ctgtgctgag cagcagcctg acccattgga agaagctgcc     480
accgctgccg tctcttacca gccagcccca ccaagtgctg gccagtgagc ccatcccgtt      540
ctctgatttg cagcaggtct ccaggatagc tgcttatgcc tacagtgcac tttctcagat     600
ccgtgtggac gcaaaagagg agctggttgt acagtttggg atcccatgaa gagaggggtc     660
cttggacagc tcttctcctc tcttcatccc atctctaccc caccccttg gccccagcc      720 tcactgcggc ttatacagta ccctaacctg ctactaatca cagagaaaaa tgtgaagaag     780
gaggagaaga ggaaggctag aagcctgagc aagtgagggt agaaccttt gggactggcc      840 tttgaagctc tggccaggga tggggtgggg gccaaagga cagagcctgg tatgtcttca      900
tagtcattga gaatgtggag ataccagttt gggtggggg tgatcaccag ggacctagg       960 gagatcccct tcccaccctc tctgttggcc tcagagtcac tcctgcccc tctccctgac      1020 ttggtgctca catgcacctc actagggttt gtgaccaggg tctggatgag cttgaatttg     1080
aatgaattga gtttgtattt ctagaaccct gggttttac atgtttggtc ttttttttgtt     1140 ttggtttgtc accctcgata aaggaagtat attcatccaa aaaaaaaaaa aaaaaaa       1198
```

<210> SEQ ID NO 50
<211> LENGTH: 749
<212> TYPE: DNA
<213> ORGANISM: Homo sapiens

<400> SEQUENCE: 50

```
gacaagcgct gcggcatttg tccccgcgac agcaccgctg ccgccgtctc taaggtcgcc       60
cgggtcccac cgccgccacc atgcctcggg aagccgcag cgcggcctcc cggccagcca      120 gccgccagc cgcgccctct gcccaccgc ccgcgcaccc accgccctcg gcagccgccc       180 cagccccgc cccttcgggc cagccggggc tcatggctca gatggcgacc acggccgcag      240 ggtagccgt gggctcggct gtgggacacg tcatgggcag cgccctgacc ggagccttca     300
gcggggggag ctcggagccc tcccagcctg ctgtccagca ggccccacc ccgctgccc     360 cccagcccct gcagatgggg ccctgcgcct acgagatcag gcagttcctg gactgttcca    420
```

```
ccactcagag tgacctgtcc ctgtgtgagg gcttcagcga ggccctgaag cagtgcaagt      480
actaccatgg tctgagctcc ctgccctgaa gaggtcggtg cagactcggg ggccagtcct      540
gcacccacct ctaccctcg ccgacagcca gaccacaaca ccagattgta cccagatagc       600
tgggattgga agtgaggagg tttctcaccc cacagataac ccaagacaca aatgtgcaat      660
taaaagttta ttttagacca caaaaaaaaa aaaaaaaaa aaaaaaaaa aaaaaaaaaa         720 aaaaaaaaaa aaaaaaaaaa aaaaaaaa                                          749

<210> SEQ ID NO 51
<211> LENGTH: 2080
<212> TYPE: DNA
<213> ORGANISM: Homo sapiens

<400> SEQUENCE: 51
gtacagggct ggatgattga agcaccagcg ggaactagtc ggacctccga gctctttaaa      60
ctgtcctcag ctcggctggt tctccacgag ctccgggcag acggcggggg gtgggtcggc     120
gtttaagtca aaggccttgg ggctccgagt cccttcctct ccccgtcctg tgaaggcacg     180
acccagttca gctgtctgta aagtggagcc attagtccct gcctcgtagt gggaaaactg     240
ggaggcggaa cgaggaggcc gccggtccca acccggccca ggagcatctt tctccgcaga     300
ccgtttcctg gcgagatcct gcgcagccga ggctgtgtta gcgccaagga cttccagcag     360
ctgttagcag aggctgctgc cagggctgct gccccgctcc ctcctcctcc ttcccctgga     420
gtcagtggtg ggaagcttcc caggagagtc ctcagcaacc tctggaacac aggacttggc     480
catgactgtc tcctgtccct gtgtgggccc agatggttga gcttgagcag gaggtggagc     540
ggcggcagcg gctggggcag gagtcagcag ctaggaaagc cctcatcgcg agttcctacc     600
acccggcacg gcctgaggtc tacgactcac tgcaggatgc agctctggcc ccgagttcc      660 tggccgtgac tgagtacagc gtgtccccag acgcagacct caagggcctt ctccagcggc     720
tggagacagt atcggaggag aagcgcatct accgggtgcc tgttttcaca gcgcccttct     780
gccaggccct gctggaagag ctggagcact tcgagcaatc ggacatgcct aaggggaggc     840
ccaacaccat gaacaactac ggggtgctgc tgcacgagct cgggctggac gagccgctga     900
tgacaccact gcgggagcgc ttcctgcagc cgctgatggc cctgctgtac cctgactgtg     960 gcggggggccg gctcgacagc caccgggcct ttgtggtcaa atacgcaccg ggccaggacc    1020
tggagctggg ctgccactat gataatgccg agctcaccct caatgtggcc ttgggcaagg    1080
tcttcacagg gggcgccctg tattttgggg gcctcttcca ggcacccaca gccctgacgg    1140
agcccctgga ggtggagcac gtggtgggcc agggtgtcct ccaccgtggc ggccagctgc    1200
atggagcccg gccttgggc actggtgagc gttggaacct tgtcgtctgg ctccgagcct    1260
ctgctgtgcg caacagcctc tgtcccatgt gctgccgtga gcccgacctg gtggacgatg    1320
agggcttcgg tgatggcttc acccgagagg agcccgccac ggtggatgta tgtgcgctca    1380
cctgagcttg cttgggccca gtgtgggggt ggcaggcagg tgagggctcc gttgccttgg    1440
tctgggggca gaaataaaat ccccgcagcc tactgcactt cttggctcaa cggtgtgcca    1500
gcttctgggt cattctatgg gcaaagatgc tgccttagtt caggtttgtc agaagcaggg    1560
tctggaatgg ggcttcagcg agggagtcag ggaagcaggg gaggggaggg agcagctggg    1620
caaggaagtg gcttcagagg acgtccagcc tcagctggcc ccacgagag ctccaggcag    1680 agcccacagt accacagtgt gcccacacca ccggttactg gctcctggat gagggggcca    1740
```

```
gagaggagtg aataacttcc cagacactta cctccagggc agggtgcctt ccagtagcca    1800
agggaagcct ccagagagca cagatgtgaa ccctcagcag caggcatcac cccccagtgg    1860
actcgggtgg gccaccagta gcatcttcta gatggcaggg gggtgaatgg cagggccagg    1920
aaccaggctg cccgggttcc cattctgctt ctgccacttc cagctgtgtg gctttaggtg    1980
agccttcacc ttttggtgcc ttcgtttcct catttagcac ctacctccta gagctgtttt    2040
gggagtcaaa tgcgctgacg tatataaagt gctttgcaag                          2080

<210> SEQ ID NO 52
<211> LENGTH: 590
<212> TYPE: DNA
<213> ORGANISM: Homo sapiens

<400> SEQUENCE: 52
acagcggtca cgtgacatgg ccccggggag ccgaggtgag cgttccagct tccggagccg      60
gagggggccc ggcgtaccca gccccagcc cgacgtgacc atgctgtccc gcctcctaaa     120
agaacaccag gccaagcaga atgaacgcaa ggagctgcag gaaaagagga ggcgagaggc     180
tatcactgca gcgacctgcc tgacagaagc tttggtggat cacctcaatg tgggtgtggc     240
ccaggcctac atgaaccaga gaaagctgga ccatgaggtg aagaccctac aggtccaggc     300
tgcccaattt gccaagcaga caggccagtg gatcggaatg gtggagaact tcaaccaggc     360
actcaaggaa attggggatg tggagaactg ggctcggagc atcgagctgg acatgcgcac     420
cattgccact gcactggaat atgtctacaa agggcagctg cagtctgccc cttcctagcc     480
cctgttccct ccccccaaccc tatccctcct acctcacccg cagggggaag agggaggct     540 gacaagcctt gaataaaaca caagcctccg ttaaaaaaaa aaaaaaaaa                 590

<210> SEQ ID NO 53
<211> LENGTH: 897
<212> TYPE: DNA
<213> ORGANISM: Homo sapiens

<400> SEQUENCE: 53
agagactgcg agaaggaggt cccccacggc ccttcaggat gaaagctgcg gtgctgacct      60
tggccgtgct cttcctgacg gggagccagg ctcggcattt ctggcagcaa gatgaacccc     120
cccagagccc ctgggatcga gtgaaggacc tggccactgt gtacgtggat gtgctcaaag     180
acagcggcag agactatgtg tcccagtttg aaggctccgc cttgggaaaa cagctaaacc     240
taaagctcct tgacaactgg gacagcgtga cctccacctt cagcaagctg cgcgaacagc     300
tcggccctgt gacccaggag ttctgggata acctggaaaa ggagacagag ggcctgaggc     360
aggagatgag caaggatctg gaggaggtga aggccaaggt gcagccctac ctggacgact     420
tccagaagaa gtggcaggag gagatggagc tctaccgcca aaggtggag ccgctgcgcg     480 cagagctcca agagggcgcg cgccagaagc tgcacgagct gcaagagaag ctgagcccac     540
tgggcgagga gatgcgcgac cgcgcgcgcg cccatgtgga cgcgctgcgc acgcatctgg     600 cccctacag cgacgagctg cgccagcgct tggccgcgcg ccttgaggct ctcaaggaga     660
acggcggcgc cagactggcc gagtaccacg ccaaggccac cgagcatctg agcacgctca     720
gcgagaaggc caagcccgcg ctcgaggacc tccgccaagg cctgctgccc gtgctggaga     780
gcttcaaggt cagcttcctg agcgctctcg aggagtacac taagaagctc aacacccagt     840
gaggcgcccg ccgccgcccc ccttcccggt gctcagaata acgtttcca aagtggg         897
```

<210> SEQ ID NO 54
<211> LENGTH: 1534
<212> TYPE: DNA
<213> ORGANISM: Homo sapiens

<400> SEQUENCE: 54

```
tattgtcaga gtcctcttgt ttggccttct aggaaggctg tgggacccag ctttcttcaa      60
ccagtccagg tggaggcctc tgccttgaac gtttccaagt gaggtaaaac ccgcaggccc     120
agaggcctct ctacttcctg tgtggggttc agaaaccctc ctcccctccc agcctcaggt     180
gcctgcttca gaaaatgaag tagtaagtct gctggcctcc gccatcttag taaagtaaca     240
gtcccatgaa acaaagatgc agtcgggcac tcactggaga gttctgggcc tctgcctctt     300
atcagttggc gtttggggc aagatggtaa tgaagaaatg ggtggtatta cacagacacc      360
atataaagtc tccatctctg gaaccacagt aatattgaca tgccctcagt atcctggatc     420
tgaaatacta tggcaacaca atgataaaaa cataggcggt gatgaggatg ataaaaacat     480
aggcagtgat gaggatcacc tgtcactgaa ggaattttca gaattggagc aaagtggtta     540
ttatgtctgc taccccagag aagcaaacc agaagatgcg aacttttatc tctacctgag     600
ggcaagagtg tgtgagaact gcatggagat ggatgtgatg tcggtggcca caattgtcat     660
agtggacatc tgcatcactg ggggcttgct gctgctggtt tactactgga gcaagaatag     720
aaaggccaag gccaagcctg tgacacgagg agcgggtgct ggcggcaggc aaaggggaca     780
aaacaaggag aggccaccac ctgttcccaa cccagactat gagcccatcc ggaaaggcca     840
gcgggacctg tattctggcc tgaatcagag acgcatctga ccctctggag aacactgcct     900
cccgctggcc caggtctcct ctccagtccc cctgcgactc cctgtttcct gggctagtct     960
tggaccccac gagagagaat cgttcctcag cctcatggtg aactcgcgcc ctccagcctg    1020
atccccgct ccctcctccc tgccttctct gctggtaccc agtcctaaaa tattgctgct     1080
tcctcttcct ttgaagcatc atcagtagtc acaccctcac agctggcctg ccctcttgcc    1140
aggatattta tttgtgctat tcactccctt ccctttggat gtaacttctc cgttcagttc    1200
cctcctttc ttgcatgtaa gttgtccccc atcccaaagt attccatcta cttttctatc    1260
gccgtccct tttgcagccc tctctgggga tggactggga aaatgttgac agaggccctg    1320
ccccgttcac agatcctggc cctgagccag ccctgtgctc ctccctcccc caacactccc    1380
taccaaccc ctaatcccct actccctcca cccccctcc actgtaggcc actggatggt     1440
catttgcatc tccgtaaatg tgctctgctc ctcagctgag agagaaaaaa ataaactgta    1500
tttggctgca agaaaaaaaa aaaaaaaaa aaaa                                  1534
```

<210> SEQ ID NO 55
<211> LENGTH: 415
<212> TYPE: DNA
<213> ORGANISM: Homo sapiens

<400> SEQUENCE: 55

```
aaacttgacg ccatgaagat cccggtcctt cctgccgtgg tgctcctctc cctcctggtg      60
ctccactctg cccagggagc caccctgggt ggtcctgagg aagaaagcac cattgagaat     120
tatgcgtcac gacccgaggc ctttaacacc ccgttcctga acatcgacaa attgcgatct     180
gcgtttaagg ctgatgagtt cctgaactgg cacgccctct ttgagtctat caaaaggaaa     240
cttccttttcc tcaactggga tgcctttcct aagctgaaag gactgaggag cgcaactcct     300
gatgcccagt gaccatgacc tccactggaa gagggggcta gcgtgagcgc tgattctcaa     360
```
cctaccataa ctctttcctg cctcaggaac tccaataaaa cattttccat ccaaa         415

<210> SEQ ID NO 56
<211> LENGTH: 2131
<212> TYPE: DNA
<213> ORGANISM: Homo sapiens

<400> SEQUENCE: 56
gagcagctcc tcttccatct ccagggtctc attctgttgc ccaggctgga gtgcagtggt    60
gcgatctcgg ctcacagcaa cctctctgcc tccagaaatg acctccacct tcaaccccccg   120
agaatgtaaa ctgtccaagc aagaagggca aaactatggc ttcttcctgc gaattgagaa   180
ggacaccgag ggccacctgg tccgggtggt tgagaagtgt agcccagcag agaaggctgg   240
ccttcaagat ggagacagag ttcttaggat caatggtgtc tttgtggaca agaagaaca    300
tatgcaggtt gtggatctgg tcagaaagag tgggaattca gtgactttac tagttctgga   360
tggggattcc tatgagaaag cagtgaaaac acggtggac ttgaaagagt tgggtcaaag    420
tcagaaggag caaggtttga gtgataatat actttcccct gtgatgaatg gaggtgtgca   480
aacttggacc cagccccggc tctgctatct cgtgaaggaa ggaggcagct atggcttctc   540
tctgaaaact gtccaaggta aaaggggggt gtacatgact gatattacac ctcaaggtgt   600
ggctatgaga gctggagttc tggctgatga tcacttgatt gaagtgaatg gagagaatgt   660
agaggatgcc agccatgagg aagtggttga aaaggtgaag aagtcaggaa gccgtgtcat   720
gttcctgctg gtggacaaag aaactgacaa gcgtcatgtt gagcagaaga tacaattcaa   780
aagagaaaca gccagtttga aactgttacc ccaccagccc cgaattgtgg agatgaagaa   840
aggaagcaat ggctatggtt tctatctgag ggcaggctca gaacagaaag gtcaaatcat   900
caaggacata gattctggaa gtccagcaga ggaggctggc ttgaagaaca atgatctggt   960
agttgctgtc aacggcgagt ctgtggaaac cctggatcat gacagtgtgg tagaaatgat  1020
tagaaagggt ggagatcaga cttcactgtt ggtggtagac aaagagacgg acaacatgta  1080
cagactggct catttttctc catttctcta ctatcaaagt caagaactgc ccaatggctc  1140
tgtcaaggag gctccagctc ctactcccac ttctctggaa gtctcaagtc caccagatac  1200
tacagaggaa gtagatcata agcctaaact ctgcaggctg gctaaaggtg aaaatggcta  1260
tggctttcac ttaaatgcga ttcggggtct gccaggctca ttcatcaaag aggtacagaa  1320
gggcggtcct gctgacttgg ctgggctaga ggatgaggat gtcatcattg aagtgaatgg  1380
ggtgaatgtg ctagatgaac cctatgagaa ggtggtggag agaatccaga gcagtgggaa  1440
gaatgtcaca cttctagtct gtggaaagaa ggcctatgat tatttccaag ctaagaaaat  1500
ccctattgtt tcctccctgg ctgatccact tgacacccct ccagattcta agaaggaat   1560
agtggtggag tcaaaccatg actcgcacat ggcaaaagaa cgggcccaca gtacagcctc  1620
acattcttct tccaattctg aagatacaga gatgtgatga aaacaagtaa tagctttggc  1680
tgtttatttg atagctgttt ctgggtattt aataggaatc ctttctcaag gaatgagttg  1740
tgacctgttt actgtctctt tagaagaaaa actccactgg aaaccattca ccatgtgtga  1800
ttgtcttctg ttatcatttg tcttacaggc ggctattgca gacggctaat ttatgcttaa  1860
cttaggaaga gataaggcaa gagctagatt tttttcatgt gatctttttcc aagcttcaac  1920
ttaacttaac tacatttctc tgtatgatga tgtctcttac ttctacaggt tccttgagca  1980
ccaaagatga ttcataactc tgtataggtg acagctgctt ataaaagcat cttagcagat  2040
aagcctatta aaattgtgct tttgtaacaa tgttgtggtt gctagaataa ataccattaa  2100
caaatgcaaa aaaaaaaaaa aaaaaaaaaa a                                    2131

<210> SEQ ID NO 57
<211> LENGTH: 1368
<212> TYPE: DNA
<213> ORGANISM: Homo sapiens

<400> SEQUENCE: 57

| | | | | | |
|---|---|---|---|---|---|
| ttccgcccgc | gaccccttc | cagacccgct | cccgaaacct | tgtcgaagga | ccaaaggcga | 60 |
| ccggtgcagg | tgcacgacgc | cagctccctt | ctgggggggcc | ggggcctggg | ggttgccatg | 120 |
| gccccagcc | acctgtcagt | gcgggagatg | agggaagatg | agaagcccct | ggtgctggag | 180 |
| atgctgaagg | ccggcgtgaa | ggacacggaa | aaccgcgtgg | ccctccatgc | cttgacacgg | 240 |
| ccgccggcc | tgctcctcct | ggcggcggcc | agcagcggcc | tgcgctttgt | cctggcttcc | 300 |
| ttcgccctgg | ccctcctcct | gccggtgttc | ctggctgtgg | ccgccgtgaa | gctgggcctg | 360 |
| cgggcccgat | ggggctcgct | gcctccgccg | ggtggcctgg | ggggcccctg | ggtggccgtg | 420 |
| cggggctccg | gtgacgtgtg | tggggtcctg | gctctggccc | ctggcacaaa | tgcaggggac | 480 |
| ggggcccggg | tcacccgcct | gtctgtctct | cgctggcacc | gccgccgggg | cgtgggcagg | 540 |
| aggctgctgg | ccttcgcgga | ggcccgggct | cgggcctggg | ctgggggcat | ggggggagccc | 600 |
| cgggcccggc | tcgtggtccc | cgtggctgtg | ccgcctggg | gggtggggagg | gatgctggag | 660 |
| ggctgtggct | accaggccga | gggggggctgg | ggctgcctgg | gctacacgct | ggtgagggaa | 720 |
| ttcagcaaag | acctgtgaag | ctacagactg | acagccaggg | caggggagga | gggaggggcg | 780 |
| ccagcacctg | atgatcgcct | actgtctgcg | ggttcttta | cctgctctcc | ctcagtgagt | 840 |
| cctcaaccac | cctgggccca | gaaacagagg | cctgccgagg | ggaggagcct | ggcctctgtc | 900 |
| cacccgtcag | cagtgtgaag | tctgttgtgt | ttgagcttct | cagagtggaa | tgactccttt | 960 |
| tccttcctgg | ccctcggggg | cctctcgagg | tcagcctctc | caaccccctac | ctcagctcct | 1020 |
| gtctgcactg | agaaacctcc | ccgggtgatg | tctgcaaagt | ctgtgctgtc | cgtgcccag | 1080 |
| gctgggagag | ctatctgggg | aggggagag | gaggccgagc | agaatacacc | ccagagttag | 1140 |
| ggtttgcgac | tccgcctccc | tgggacctgg | attgggtcag | atgcctgtcc | ttggagggga | 1200 |
| caaggttgac | tgcttaggag | gcgcgacgca | cagggctgcc | aggcctggcc | cctctctggg | 1260 |
| aaggttgaga | gctgagacgg | gcagccctgt | cccttcctcc | agatccgtct | ggttttttac | 1320 |
| accgtttgtt | aataaagcct | gaaaccgctg | aaaaaaaaaa | aaaaaaaa | | 1368 |

<210> SEQ ID NO 58
<211> LENGTH: 1574
<212> TYPE: DNA
<213> ORGANISM: Homo sapiens

<400> SEQUENCE: 58

| | | | | | |
|---|---|---|---|---|---|
| atcgctacgc | ccacttggtg | gcctataaag | gaagcgggcg | aaccccggca | gccctacaca | 60 |
| acttggggcc | cctctcctct | ccagcccttc | tcctgtgtgc | ctgcctcctg | ccgccgccac | 120 |
| catgaccacc | tccatccgcc | agttcacctc | ctccagctcc | atcaagggct | cctccggcct | 180 |
| gggggggcggc | tcgtcccgca | cctcctgccg | gctgtctggc | ggcctgggtg | ccggctcctg | 240 |
| caggctggga | tctgctggcg | gcctgggcag | caccctcggg | ggtagcagct | actccagctg | 300 |
| ctacagctttt | ggctctggtg | gtggctatgg | cagcagcttt | gggggtgttg | atgggctgct | 360 |
| ggctggaggt | gagaaggcca | ccatgcagaa | cctcaatgac | cgcctggcct | cctacctgga | 420 |

```
caaggtgcgt gccctggagg aggccaacac tgagctggag gtgaagatcc gtgactggta      480
ccagaggcag gccccggggc cgcccgtga ctacagccag tactacagga caattgagga      540
gctgcagaac aagatcctca cagccaccgt ggacaatgcc aacatcctgc tacagattga      600
caatgcccgt ctggctgctg atgacttccg caccaagttt gagacagagc aggccctgcg      660
cctgagtgtg gaggccgaca tcaatggcct gcgcagggtg ctggatgagc tgaccctggc      720
cagagccgac ctggagatgc agattgagaa cctcaaggag gagctggcct acctgaagaa      780
gaaccacgag gaggagatga cgccctgcg aggccaggtg ggtggtgaga tcaatgtgga      840
gatggacgct gccccaggcg tggacctgag ccgcatcctc aacgagatgc gtgaccagta      900
tgagaagatg gcagagaaga accgcaagga tgccgaggat tggttcttca gcaagacaga      960
ggaactgaac cgcaggtgg ccaccaacag tgagctggtg cagagtggca agagtgagat     1020
ctcggagctc cggcgcacca tgcaggcctt ggagatagag ctgcagtccc agctcagcat     1080
gaaagcatcc ctggagggca acctggcgga cacagagaac cgctactgcg tgcagctgtc     1140
ccagatccag gggctgattg cagcgtgga ggagcagctg gcccagcttc gctgcgagat     1200
ggagcagcag aaccaggaat acaaaatcct gctggatgtg aagacgcggc tggagcagga     1260
gattgccacc taccgccgcc tgctggaggg agaggatgcc cacctgactc agtacaagaa     1320
agaaccggtg accacccgtc aggtgcgtac cattgtggaa gaggtccagg atggcaaggt     1380
catctcctcc cgcgagcagg tccaccagac cacccgctga ggactcagct accccggccg     1440
gccacccagg aggcagggag gcagccgccc catctgcccc acagtctccg gcctctccag     1500
cctcagcccc ctgcttcagt cccttcccca tgcttccttg cctgatgaca ataaagcttg     1560
ttgactcagc tatg                                                      1574

<210> SEQ ID NO 59
<211> LENGTH: 952
<212> TYPE: DNA
<213> ORGANISM: Homo sapiens

<400> SEQUENCE: 59
ccacgcgtcc ggcacttccg cccatccccc tccggatccc tctgttcggg ctcgggtttc       60
cgccgagacg acagggactg ccaggtcgga agtagtgtga ggctcgtggg cggagccaag      120
cgccgccatg tccgccgccc tgctgcggcg gggcctggag ctgctggcgg cgtccgaggc      180
cccccgggac cctccaggtc aggccaagcc gagagggggct ccggtgaaac ggccccggaa      240
gacgaaggca attcaggccc agaaactgcg gaactcggcc aagggaaagg tgcccaagtc      300
ggcactggac gagtaccgga agcgagagtg tcgagaccac ctcagagtaa acctgaagtt      360
tctgaccagg acgagaagca ccgtggctga gtctgtgagc cagcagattt tgcgccagaa      420
ccggggccgc aaggcctgtg accggcctgt ggccaagacc aagaagaaga aggctgaggg      480
caccgtgttc accgaggaag acttccagaa gttccagcag gaatacttcg gcagctaggc      540
tccctggagg gcacggtgaa gaggccttca agccctgcag cctccgactc ctgctggctc      600
caggaaccgg ccgtgccgcg cggccagcag atggcgatgc aggaccagcc tggctcgagg      660
aagccgcgga gctgagccga gtggaggctg aatggagct ggtgggccgg aagtcctggg      720
gaggatttac acacagaccg gagctggctt ccgcaggcct gggcagagca tctgcacctg      780
ccggaaagga acgtatctgt tttgtttgct tttgcccagg tggggcctct gggctgtttg      840
ctgtggagca aggctaattc ctgagcccctt ggggacgaca gctccaggag taggaagaag      900
ggtgggcttc caagttacaa taaatgtgaa cccaagaaaa aaaaaaaaaa aa              952
```

<210> SEQ ID NO 60
<211> LENGTH: 2129
<212> TYPE: DNA
<213> ORGANISM: Homo sapiens

<400> SEQUENCE: 60

```
ggacagggca gcggcggtga cccgagctgc cgcccgacat gaactcgctg gagcaggcgg      60
aagccccgcg agttgtatcc ctgattcctg cggtggtttc cggtaactgc caagatctca     120
aggcttttga gaggagactt actgaatata ttcattgttt gcaacctgct actggacgct     180
ggagaatgct tcttatagtg gtatctgtct gtacagctac tggtgcctgg aactggttaa     240
tagaccctga gacacaaaag gtgtccttct tcacatcatt atggaatcac ccattttca      300
ccattagctg tatcactcta ataggcttgt tctttgctgg aatacacaag agagtagttg     360
caccatcaat tatagctgct cgatgtcgaa cggtattagc agaatacaat atgtcttgtg     420
atgatacaga aaaactaatt ttgaaaccta ggcctcatgt tcaatgacaa tcttcactca     480
ttgttatggg acttaaaata gcctttcttc gaataagtga tacagcaaaa agccataaag     540
gattcctttt gcggttggat atgtaaaggt catagcagca actgacaaga agtgtgcaat     600
atttacctgg attatcttga tgatggtgac tcattatcag tgctttggta cttttgatta     660
cctgtgtttc agtattagtg tcactttagt acttcagatc ctgcaaatat ttttgcagat     720
gaagtatgta tgtatgttac taagttaaac ttagaaacag aacctcattc agtttttata     780
atgtattttt gcaaactact gtaaatagca aatcaatgcc aatgttaaac aaagaggaaa     840
acgttgtgtg gactttgttc tcttgcaccg gtatttcagg aacatctgct tgccatcccc     900
acagctcttt aaaactggct attatgtgtg cctttcattc ttacatttct aatcatactg     960
caggaaaaac attggattca gcttagactg aggaaaactc tccattatgt tgtaagaaat    1020
tatagatgtt ttgagagaca cttttttgtta aaccagatat tgaactccag caactattgt    1080
ggttatattt ttagttcatt gttctcattt aatgctaaat atcctttata ttgctttaat    1140
aatttctttt tttttttttt ttttttaga cggagtctcg ctctgttgcc aggctggagg    1200
gcagtggcac gatcttggct ttctgcaacc tctgcctccc aggttcaagc gattctcctg    1260
cttcagcctt ccgagtagct gggactacag gcgcatgcca ccatgcccag ctaatttttt    1320
tgtattttta gtagagacgg gtttcacca cgttggccag gatggtttcg atctcctgac    1380
ctcgtgatcc tcctgcctca tcctcccaaa atgctgggat tacaggcata agccaccgtg    1440
cctggcctct ttaataattt ttaaaatacc ctaaaggctt gtgaatatac aagtctactg    1500
ataaattatg tattgtctgg gaatttgata gtcattgttt tagataactg gattttacgc    1560
tgtggtagac aggctgtgac actagtgttg cacaggtgta attggtcatc ctatgccttc    1620
accagaataa cttgggagtg gtgccagaaa ctagagtcta caattctcac tgtttagaga    1680
gtgttaatga catactgtgt atgcataata gccgcatgta ctataatagc ccttaaaatt    1740
aaactattgg gattgctgta aatattttaa agtactggag gtgccttta cctgtttatt    1800
agattttgaa aaggtttaaa ttatttcatg agcaatcttt taaatttcat ttaacataaa    1860
gctgaaaatt caataacagg ataaaaaagc ttttaacaa ggctgccatt taacttaaat    1920
gtgttcatct tagctttcac ttgtataaaa tttgattctt tgaactgcag caataaaacc    1980
ctcagctcct aagaagtctt aagagggtat tctatatatt ctgctttgtt ttattttctg    2040
taaattttgt aggtaaatat gtgcattaaa aataaatact ttatatataa ctcgtgaaaa    2100
```

```
aaaaaaaaaa aaaaaaaaaa aaaaaaaaa                                      2129

<210> SEQ ID NO 61
<211> LENGTH: 901
<212> TYPE: DNA
<213> ORGANISM: Homo sapiens

<400> SEQUENCE: 61
gggatctcgg actccctgga ccctcccctcc agcccagcct cgctagctcc gcctgcggta     60
cgtgctcccg cctccgactc aaaatgcctg tctggggagg tggaaacaag tgtggggcct    120
gtgggaggac cgtgtaccac gcagaagagg tgcagtgtga tggcaggagc ttccaccgct    180
gctgctttct ctgcatggtt tgcaggaaaa atttagatag cacaacagtg caattcacg     240 atgaagagat ctactgcaaa tcctgctacg gaaagaagta tgggccaaaa ggctacggtt    300
atggccaggg cgctggcacg cttaacatgg accgtggcga gaggctgggc atcaaaccag    360
agagtgttca gcctcacagg cctacaacaa atccaaacac ttctaaattt gctcagaaat    420
atggaggtgc tgagaagtgt tccagatgtg ggattctgt atatgctgcc gagaagataa     480
ttggagctgg aaagccctgg cacaaaaact gtttccgatg tgcaaagtgt gggaagagtc    540
ttgaatcaac aactctgact gaaaagaag gtgaaatcta ttgtaaagga tgctatgcaa     600
agaactttgg gcccaaggga tttggctatg ccaaggagc aggggctctt gttcatgccc     660
agtaagatgt aaaccctgaa ctaaacatca cacactgaga atctcttcat aatctaggca    720
cagataatct ttaacactaa actactgtga aattctacca gcattaagta ctgtatatcg    780
ccctgtactt ggataggctg gctaactcgt aggaagagag cactgtatgg tatccttttg    840
ctttattcac cagcattttg gggaacatt tcttttacat tttaaataaa acttcagctt     900
g                                                                    901

<210> SEQ ID NO 62
<211> LENGTH: 933
<212> TYPE: DNA
<213> ORGANISM: Homo sapiens

<400> SEQUENCE: 62
atggaaccac agaacaccac acaggtatca atgtttgtcc tcttagggtt ttcacagacc     60
caagagctcc agaaattcct gttccttctg ttcctgttag tctatgttac caccattgtg    120
ggaaacctcc ttatcatggt cacagtgact tttgactgcc ggctccacac acccatgtat    180
tttctgctcc gaaatctagc tctcatagac ctctgctatt ccacagtcac ctctccaaag    240
atgctggtgg acttcctcca tgagaccaag acgatctcct accagggctg catggcccag    300
atcttcttct tccaccttttt gggaggtggg actgtctttt ttctctcagt catggcctat    360
gaccgctaca tagccatctc ccagcccctc cggtatgtca ccatcatgaa cactcaattg    420
tgtgtgggcc tggtagtagc cgcctgggtg ggggctttg tccactccat tgtccaactg    480
gctctgatac ttccactgcc cttctgtggc cccaatatcc tagataactt ctactgtgat    540
gttccccaag tactgagact tgcctgcact gatacctccc tcctggagtt cctcatgatc    600
tccaacagtg ggctgctagt tatcatctgg ttcctcctcc ttctgatctc ttatactgtc    660
atcctggtga tgctgaggtc ccactcggga aaggcaagga ggaaggcagc ttccacctgc    720 accaccaca tcatcgtggt gtccatgatc ttcattccct gtatctatat ctatacctgg    780
cccttcaccc cattcctcat ggacaaggct gtgtccatca gctacacagt catgacccc     840 atgctcaacc ccatgatcta caccctgaga aaccaggaca tgaaagcagc catgaggaga    900
```

```
ttaggcaagt gcctagtaat ttgcagggag taa                                 933
```

<210> SEQ ID NO 63
<211> LENGTH: 903
<212> TYPE: DNA
<213> ORGANISM: Homo sapiens

<400> SEQUENCE: 63

```
agataaggcc gctcgctgac gccgtgtttc ctctttcggc cgcgctggtg aacaggaccc     60
gtcgccatgg gccgtgtgat ccgtggacag aggaagggcg ccgggtctgt gttccgcgcg    120
cacgtgaagc accgtaaagg cgctgcgcgc ctgcgcgccg tggatttcgc tgagcggcac    180
ggctacatca agggcatcgt caaggacatc atccacgacc cgggccgcgg cgcgcccctc    240
gccaaggtgg tcttccggga tccgtatcgg tttaagaagc ggacggagct gttcattgcc    300
gccgagggca ttcacacggg ccagtttgtg tattgcggca agaaggccca gctcaacatt    360
ggcaatgtgc tccctgtggg caccatgcct gagggtacaa tcgtgtgctg cctggaggag    420
aagcctggag accgtggcaa gctggcccgg gcatcaggga actatgccac cgttatctcc    480
cacaaccctg agaccaagaa gacccgtgtg aagctgccct ccggctccaa gaaggttatc    540
tcctcagcca acagagctgt ggttggtgtg gtggctgagg gtggccgaat tgacaaaccc    600
atcttgaagg ctgccgggc gtaccacaaa tataaggcaa agaggaactg ctggccacga    660
gtacggggtg tggccatgaa tcctgtggag catccttttg gaggtggcaa ccaccagcac    720
atcggcaagc cctccaccat ccgcagagat gcccctgctg ccgcaaagt gggtctcatt    780
gctgcccgcc ggactggacg tctccgggga accaagactg tgcaggagaa agagaactag    840
tgctgagggc tcaataaag tttgtgttta tgccaaaaaa aaaaaaaaa aaaaaaaaa       900
aaa                                                                  903
```

<210> SEQ ID NO 64
<211> LENGTH: 934
<212> TYPE: DNA
<213> ORGANISM: Homo sapiens

<400> SEQUENCE: 64

```
agctcagcct cagtccccgc agcttgtgcg gcggcgtcgg caccatgagg cgagggcccc     60
ggagcctgcg gggcagggac gcgccagccc ccacgcccctg cgtcccggcc gagtgcttcg   120
acctgctggt ccgccactgc gtggcctgcg ggctcctgcg cacgccgcgg ccgaaaccgg   180
ccggggccag cagccctgcg cccaggacgg cgctgcagcc gcaggagtcg gtgggcgcgg   240
ggccgcggcga ggcggcgctg ccctgccccg ggctgctctt tggcgccccc gcgctgctgg   300
gcctggcact ggtcctggcg ctggtcctgg tgggtctggt gagctggagg cggcgacagc   360
ggcggcttcg cggcgcgtcc tccgcagagg ccccgacgg agacaaggac gccccagagc   420
ccctggacaa ggtcatcatt ctgtctccgg gaatctctga tgccacagct cctgcctggc   480
ctcctcctgg ggaagaccca ggaaccaccc cacctggcca cagtgtccct gtgccagcca   540
cagagctggg ctccactgaa ctggtgacca ccaagacggc cggccctgag caacaatagc   600
agggagccgg caggaggtgg ccctgccct ccctctggac ccccagccag gggcttggaa   660
atcaaattca gctcttcact ccagcatgca catgccctct ttctgggacc aggctaactc   720
tgcagaagca cagacactac agaccacagc attcagcccc catggagttt ggtgtgcttg   780
cctttggctt cagacctcac catctttgac agcccttgaa ggtggtagcc cagctcctgt   840
```

| | |
|---|---|
| tcctgtgcct tcaaaaggct ggggcactat gagtaaaaga ccgctttttaa aatggggaag | 900 |
| gcaccattaa gccaaaatga atctgaaaaa agac | 934 |

<210> SEQ ID NO 65
<211> LENGTH: 945
<212> TYPE: DNA
<213> ORGANISM: Homo sapiens

<400> SEQUENCE: 65

| | |
|---|---|
| gcttccggta gtgagaaccc ttccggtggg ctaggtactg agcgcgcgag gtgaggagtt | 60 |
| gtgcagggtt tggggaaagg aaggctggct tggcgagagg gcaggtttgc gggctttcgc | 120 |
| cccctttttcc aaagaccaac aaagagtcct tccccaactc ccaactcaac ccctttttgga | 180 |
| actatgtgtg gtggttggga ccctgtggcg catccttgtc gctcgtgtcc ttctcatgcc | 240 |
| cggcgacgcg tctttgtggt aacgccctgc tgccatctct tttcttctct atgcgaggat | 300 |
| ttggactggc agtgagaata agagacaacg attcacgtct actttctagg atgacttcca | 360 |
| tgtgctccat ctcgcgcgtc cctgagcatg ttgaatttcc aaatcctaaa taagccgcgc | 420 |
| ggtgtagttt gtattatgtt gcgtttctct ttctgctttc ctcgcccttt ctccatcatc | 480 |
| ctttaggctc tacagagtga aggtttaaat ccaaggtcat ggcaaaacat ctgaagttca | 540 |
| tcgccaggac tgtgatggta caggaaggga acgtggaaag cgcatacagg accctaaaca | 600 |
| gaatcctcac tatggatggg ctcattgagg acattaagca tcggcggtat tatgagaagc | 660 |
| catgccgccg gcgacagagg gaaagctatg aaaggtgccg gcggatctac aacatggaaa | 720 |
| tggctcgcaa gatcaacttc ttgatgcgaa agaatcgggc agatccgtgg cagggctgct | 780 |
| gaggcctgtg ggtgggacac ccagtgcgaa accctcatcc agttttctct ccatctcttt | 840 |
| tctttgtaca atcccatttc ctattaccat tctctgcaat aaactcaaat cacatgtctg | 900 |
| caagaaggcc tccaaatata gaaacaatcc cattagtcaa aaaaa | 945 |

<210> SEQ ID NO 66
<211> LENGTH: 1460
<212> TYPE: DNA
<213> ORGANISM: Homo sapiens

<400> SEQUENCE: 66

| | |
|---|---|
| tgcagcgcag gtgagctctc ctgaggacct ctctgtcagc tcccctgatt gtagggagga | 60 |
| tccagtgtgg caagaaactc ctccagccca gcaagcagct caggatgttc ctgaaggccg | 120 |
| tggtcctgac cctggccctg gtggctgtcg ccggagccag ggctgaggtc agtgctgacc | 180 |
| aggtggccac ggtgatgtgg gactacttca gccagctgag caacaatgcc aaggaggccg | 240 |
| tggaacatct ccagaaatct gaactcaccc agcaactcaa tgccctcttc caggacaaac | 300 |
| ttggagaagt gaacacttac gcaggtgacc tgcagaagaa gctggtgccc tttgccaccg | 360 |
| agctgcatga acgcctggcc aaggactcgg agaaactgaa ggaggagatt gggaaggagc | 420 |
| tggaggagct gagggcccgg ctgctgcccc atgccaatga ggtgagccag aagatcgggg | 480 |
| acaacctgcg agagcttcag cagcgcctgg agccctacgc ggaccagctg cgcacccagg | 540 |
| tcagcacgca ggccgagcag ctgcggcgcc agctgacccc ctacgcacag cgcatggaga | 600 |
| gagtgctgcg ggagaacgcc gacagcctgc aggcctcgct gaggccccac gccgacgagc | 660 |
| tcaaggccaa gatcgaccag aacgtggagg agctcaaggg acgccttacg ccctacgctg | 720 |
| acgaattcaa agtcaagatt gaccagaccg tggaggagct cgccgcagc ctggctccct | 780 |
| atgctcagga cacgcaggag aagctcaacc accagcttga gggcctgacc ttccagatga | 840 |

```
agaagaacgc cgaggagctc aaggccagga tctcggccag tgccgaggag ctgcggcaga      900
ggctggcgcc cttggccgag gacgtgcgtg gcaacctgag gggcaacacc gaggggctgc      960
agaagtcact ggcagagctg ggtgggcacc tggaccagca ggtggaggag ttccgacgcc     1020
gggtggagcc ctacgggaaa aacttcaaca aagccctggt gcagcagatg aacagctca      1080 ggcagaaact gggcccccat gcggggacg tggaaggcca cttgagcttc ctggagaagg     1140
acctgaggga caaggtcaac tccttcttca gcaccttcaa ggagaaagag agccaggaca    1200
agactctctc cctccctgag ctggagcaac agcaggaaca gcagcaggag cagcagcagg    1260
agcaggtgca gatgctggcc cctttggaga gctgagctgc ccctggtgca ctggccccac    1320
cctcgtggac acctgccctg ccctgccacc tgtctgtctg tctgtcccaa agaagttctg    1380
gtatgaactt gaggacacat gtccagtggg aggtgagacc acctctcaat attcaataaa    1440
gctgctgaga atctagcctc                                                 1460

<210> SEQ ID NO 67
<211> LENGTH: 1145
<212> TYPE: DNA
<213> ORGANISM: Homo sapiens

<400> SEQUENCE: 67
tcctccgtcc tgtccacaag gctcagcaaa gcggctggcg gcctggcctg ggacctgctg       60
ctgctccagc catgtccatg acaaccagag cctgggagga gctggatggc ggcctgggca     120
gctgccaggc cctggaggac cactctgcgc tggccgagac ccaggaggac agggcttcag     180
cgacacccag gctggccgac tccggcagcg tgccccacga ctctcaggtg gctgaaggcc     240
ccagtgtgga caccaggccc aagaagatgg aaaaagagcc tgccgccagg ggacccccag     300
gaacggggaa ggagaggctg aaagccggag cgagccctcg gagcgtcccc gcgcgcaaga     360
aggcgcagac cgcgccgccc ctgcagccgc cgccgccgcc cccggccctg agcgaggagc     420
tgccctgggg agacctgtcg ctcaacaagt gcctggtgct cgcctcgctg gtggcgctgc     480
tgggctcggc tttccagctg tgccgcgacg ccgtccctgg ggaggcagca ctccaagcac     540
gtgtgcccga gccctgggtc ccgccaagct cagccccgag ggagccatcg tcgcccctgc     600
ctaagttcga ggcccaggcg cctccatcag cgccgcctgc gccccgggcc gaggcagagg     660
tcagacccaa gattcccggg agtcgggagg ctgcagagaa cgacgaagag gagcccggcg     720
aggccaccgg agaggccgtc cggaggacc gtgtgaccct cgcagaccgg ggacccaagg     780
agaggcctcg gagagagggg aagccgcgga aggagaagcc gcggaaggag gagagaccta    840
agaaagagag gccgcggaaa gaggagaggc cacgggccgc cagggagccc cgggaagccc    900
taccccagcg ctgggagtca cgcgaagggg gccaccggcc gtgggcacgg gactccaggg    960
acgccgagcc caggaagaag caggcctggg tgtccccgag gcgtcccgac gaggagcagc   1020
ggcctgggag tcgccagaag ctccgcgcag gcaaggggcg ggactgagcc ggccccgcgc   1080
cggagtccag gggccccttc tggacgcccc gcgactctgg cgaaataaag cgagtgctgc   1140
ggccg                                                                1145

<210> SEQ ID NO 68
<211> LENGTH: 829
<212> TYPE: DNA
<213> ORGANISM: Homo sapiens

<400> SEQUENCE: 68
```

| | |
|---|---|
| tggggagtga aagcgaaagc ccgggcgact agccgggaga ccagagatct agcgactgaa | 60 |
| gcagcatggc caagccgtgt gggtgcgcc tgagcgggga agcccgcaaa caggtggagg | 120 |
| tcttcagaca gaatcttttc caggaggctg aggaattcct ctacagattc ttgccacaga | 180 |
| aaatcatata cctgaatcag ctcttgcaag gactccct caatgtggct gacttgactt | 240 |
| ccctccgggc cccactggac atccccatcc cagaccctcc acccaaggat gatgagatgg | 300 |
| aaacagataa gcaggagaag aaagaagtcc ataagtgtgg atttctccct gggaatgaga | 360 |
| aagtcctgtc cctgcttgcc ctggttaagc cagaagtctg gactctcaaa gagaaatgca | 420 |
| ttctggtgat tacatggatc caacacctga tccccaagat tgaagatgga aatgattttg | 480 |
| gggtagcaat ccaggagaag gtgctggaga gggtgaatgc cgtcaagacc aaagtggaag | 540 |
| cttttccagac aaccatttcc aagtacttct cagaacgtgg ggatgctgtg gccaaggcct | 600 |
| ccaaggagac tcatgtaatg gattaccggg ccttggtgca tgagcgagat gaggcagcct | 660 |
| atggggagct cagggccatg gtgctggacc tgagggcctt ctatgctgag ctttatcata | 720 |
| tcatcagcag caacctggag aaaattgtca acccaagggg tgaagaaaag ccatctatgt | 780 |
| actgaacccg ggactagaag gaaaataaat gatctatatg ttgtgtgga | 829 |

<210> SEQ ID NO 69
<211> LENGTH: 4654
<212> TYPE: DNA
<213> ORGANISM: Homo sapiens

<400> SEQUENCE: 69

| | |
|---|---|
| agagtgctgc ggcgaactgg ctggaggagc taggggacta gaggcggggt gggaggggg | 60 |
| cgggtggaag gggaggaag tcccgtaacg gagacgctgg tcaggacgtt cccacctcct | 120 |
| ctgacactgc cgagtccgat cggagagggg tcaccgcctc cttcagcgag gaggagggg | 180 |
| gcggagcccg actcaggatc atggatttc ctggtcactt tgaacaaatc ttccagcagc | 240 |
| tgaactacca gagacttcat ggccagctct gtgattgtgt cattgtagtg gggaatagac | 300 |
| actttaaagc ccaccgctcc gtgctggcag catgcagcac gcatttccga gccctgttct | 360 |
| cagtggcaga aggagatcag accatgaaca tgatccagct ggatagcgag gtggtgacag | 420 |
| cagaggcctt tgctgcactg attgacatga tgtatacctc caccctcatg ctgggggaga | 480 |
| gcaatgtaat ggatgtctta ttggcagcct ctcacctgca tttgaactct gttgttaagg | 540 |
| catgtaaaca ttacttaacg acaaggacgc tgcccatgtc tccccccagt gagcgcgttc | 600 |
| aggagcagag cgcccgcatg cagcgctcct ttatgctaca gcagctggga ctaagcatcg | 660 |
| tgagctcagc cctcaattcc agccagaatg gcgaggagca gccagccccc atgagctctt | 720 |
| ccatgcgcag taacctggat cagcgcacgc ccttccccat gagacgcctt cataagcgca | 780 |
| agcagtctgc agaggagcgg gccaggcagc gcctccgacc ctccatagat gagtctgcca | 840 |
| tttcagatgt tacaccggag aatgggcctt caggggttca ttctcgggag gagttctttt | 900 |
| caccagattc tctgaaaatt gtggataatc ctaaagctga tggaatgact gataaccagg | 960 |
| aagatagtgc gatcatgttt gatcagtctt ttggcactca agaagatgcc caggtgccca | 1020 |
| gccagtctga taacagtgct ggcaacatgg cacagttgtc catggcctct cgtgcaactc | 1080 |
| aggttgagac tagttttgat caggaagctg cacctgagaa aagtagtttt cagtgtgaaa | 1140 |
| accctgaggt tggccttggt gagaaggagc acatgagagt ggtggttaaa tctgagcccc | 1200 |
| tgagctcacc tgagcctcag gatgaagtga gcgatgtgac ctcacaagca gaaggcagcg | 1260 |
| agtctgtgga agtggaagga gttgtggtca gtgccgagaa gatagacctc agccctgaaa | 1320 |

-continued

```
gcagtgatcg gagtttttca gatccccagt ctagcacaga cagggtaggt gatatccata    1380
ttttggaagt cacaaataac ctagagcata agtccacttt tagtatttcg aattttctta    1440
acaagagcag aggaaataac tttactgcaa atcagaacaa tgatgataat attccaaaca    1500
ccactagtga ctgcaggctg gagagtgagg ccccctattt gttgagtcca gaggctgggc    1560
ctgcaggtgg gccctcctct gcccctggct cccatgtaga gaacccattt agtgaacctg    1620
cagactccca cttcgtcagg cctatgcagg aggtgatggg cctgccgtgt gtgcagactt    1680
caggctacca aggaggagaa cagtttggga tggacttttc caggtctggt ttgggcctcc    1740
actcctcctt ctccagggta atgataggtt ccccaagggg aggagccagt aactttcctt    1800
actaccgccg catagctccc aaaatgccag ttgtaacttc cgtcaggagc tcacagatcc    1860
cagaaaactc taccagttct cagctaatga tgaatggagc tacgtcctca tttgaaaatg    1920
gccatccttc ccagcctggc cctccacagt tgaccagggc atctgcagat gttctgtcaa    1980
agtgcaagaa ggccttatca gagcacaatg ttttggttgt agagggagct cgcaagtatg    2040
cctgcaaaat ctgctgcaaa acttttctga cttttgacaga ttgcaagaag cacatccgtg    2100
```

```
ttttatgttt tatatagctt tcttagacat accaaaccat cattcataaa tcagataaat      3720
tattcagttt ttgtgtttag aaagctaagt atgtgtagct ggaaacaaaa atgagcgtgt      3780
tttctctcct gttaatctag agtgtgcagt tacacatgtg tggataattt catgttccag      3840
gggcgcttgg catctcccat ggactgattc ccaggaagaa aagcccaaag gaaacccac       3900 gattcctttc gagtagatgt gggaaagagc ccattggagg atatgaggtc ctgtgaaatt      3960
cagttgtgtg tgtggctcct tgttagcagt catgttgaca tggtgttagg aggctcccca      4020
tccacccttt acatgatgta gggaccagtg tcttgtgaga ttaaccttgg acacagtgg       4080 gttagcctgg agaaaatgag aggccctgcc tggacccagg gagaggagcc agtgacacag      4140
gcagagcggt gcagccctcc ttcccttcca tttggaggag gtggtgccag gagcctgccc     4200
gcttacctct gctgaagcat aagtggactt tgcttttggg gcttatctct gatacatgct      4260
ggagccctgc ctctccactg ctagatggaa cctggaatct ctcatctacc tcttagtctg      4320
tcagtttcta cgtgtgagaa gcaagcttgt gggccagtgt ccttgtacat gctgtagcac      4380
ttaaaaaata attccagggt tccctggaaa accagtccca gggttcctat gatctgtagt      4440
ttctacctgg attataactg gttttgggta cctgaatttt gattggttag ccttaattat      4500
agtctggcgt gatcatgtag aatcttttct ggtgaacaga tcataaagtt ctatcaagga     4560
gttctatcaa ggcatccatg tcagtggtgc tatgctggtt acaacttgag attttgaaa      4620 taaaaatttt gtcatattca tgcctctaaa aaaa                                 4654

<210> SEQ ID NO 70
<211> LENGTH: 864
<212> TYPE: DNA
<213> ORGANISM: Homo sapiens

<400> SEQUENCE: 70
aggagtggct gaggcagggc atggagcgga gcaacgcagc tacaaagtgc ggagaggagc       60
cccgctctgg atcccgccgg ctccccaagg ctgaaggaga caagtctgga tccgcaggag      120
cccccagtaa gaacagcagc cgcctggggg gccgaccatg tatgtgtaca gctggccgcc      180
gcccaaacag ggcgtctggc cgccgccgcc gcagctgctc acctgcacct acctggccgc      240
ccctctgctg ctaccccag tccaggccca cagcttccgc agccggcccg ggagcctgca       300
tgcgggcgag tgggcggccc cacgggaata ccaccgcttc tacggccccg ccgcgccacc      360
cgaggccgcg ccgccctggt gggcctgccc tccggcctac gccacgaccc tgcgccggcc      420
ctgcgccgcc gccggcatct cgggactgtc gctgcaggcg cccgcggcgg tggccgagag      480
ctgggcgccg tggccggagg gcgggagcct gcaaaccgag ctgcgctggg gccgcgtgga      540
gcgcgcgcgg ggccccccctc tgcagctacc ggacttcgtg cgccgggagc tgcggcgcgc     600
gtacggcacc taccccgcg ccgacgtgcg cgtcacccag cgccgcggcc agttcctgct       660
gcaggcgacg ccgcgcgtgc tcgagcccga ccaccgcgtg gagtggcgcg tgcggcgccg      720
gcccgacagc ggcgacagca gcccagcccg ggaagccgcg gagcgcggcc gccccaggaa      780
gagcaagggc ctgagctgaa gccgccgcaa ggcctagggg cgggcccgcg tgcacgcgct      840
tggctctttc ctgtgtgtgc cgcc                                            864

<210> SEQ ID NO 71
<211> LENGTH: 4593
<212> TYPE: DNA
<213> ORGANISM: Homo sapiens

<400> SEQUENCE: 71
```

-continued

```
gctgccgcgc cccgcccttt ctcggccccc ggagggtgac ggggtgaagg cgggggaacc      60
gaggtgggga gtccgccaga gctcccagac tgcgagcacg cgagccgccg cagccgtcac     120
ccgcgccgcg tcacggctcc cgggcccgcc ctcctctgac ccctcccctc tctccgtttc     180
cccctctccc cctcctccgc cgaccgagca gtgacttaag caacgagcg cggtgaagct      240
cattttctc cttcctcgca gccgcgccag ggagctcgcg gcgcgcggcc cctgtcctcc     300
ggcccgagat gaatcctgcg gcagaagccg agttcaacat cctcctggcc accgactcct     360
acaaggttac tcactataaa caatatccac ccaacacaag caaagtttat tcctactttg     420
aatgccgtga aaagaagaca gaaaactcca aattaaggaa ggtgaaatat gaggaaacag     480
tattttatgg gttgcagtac attcttaata agtacttaaa aggtaaagta gtaaccaaag     540
agaaaatcca ggaagccaaa gatgtctaca agaacattt ccaagatgat gtctttaatg      600
aaaagggatg gaactacatt cttgagaagt atgatgggca tcttccaata gaaataaaag    660
ctgttcctga gggctttgtc attcccagag gaaatgttct cttcacggtg aaaacacag     720
atccagagtg ttactggctt acaaattgga ttgagactat tcttgttcag tcctggtatc    780
caatcacagt ggccacaaat tctagagagc agaagaaaat attggccaaa tatttgttag    840
aaacttctgg taacttagat ggtctggaat acaagttaca tgattttggc tacagaggag    900
tctcttccca agagactgct ggcataggag catctgctca cttggttaac ttcaaaggaa    960
cagatacagt agcaggactt gctctaatta aaaaatatta tggaacgaaa gatcctgttc   1020
caggctattc tgttccagca gcagaacaca gtaccataac agcttggggg aaagaccatg   1080
aaaaagatgc ttttgaacat attgtaacac agttttcatc agtgcctgta tctgtggtca   1140
gcgatagcta tgacatttat aatgcgtgtg agaaaatatg gggtgaagat ctaagacatt   1200
taatagtatc aagaagtaca caggcaccac taataatcag acctgattct ggaaaccctc   1260
ttgacactgt gttaaaggtt ttggagattt taggtaagaa gtttcctgtt actgagaact   1320
caaagggtta caagttgctg ccaccttatc ttagagttat tcaaggggat ggagtagata   1380
ttaataccctt acaagagatt gtagaaggca tgaaacaaaa aatgtggagt attgaaaata   1440
ttgccttcgg ttctggtgga ggtttgctac agaagttgac aagagatctc ttgaattgtt   1500
ccttcaagtg tagctatgtt gtaactaatg gccttgggat taacgtcttc aaggacccag   1560
ttgctgatcc caacaaaagg tccaaaaagg gccgattatc tttacatagg acgccagcag   1620
ggaattttgt tacactggag gaaggaaaag gagaccttga ggaatatggt caggatcttc   1680
tccatactgt cttcaagaat ggcaaggtga caaaaagcta ttcatttgat gaaataagaa   1740
aaaatgcaca gctgaatatt gaactggaag cagcacatca ttaggcttta tgactgggtg   1800
tgtgttgtgt gtatgtaata cataatgttt attgtacaga tgtgtggggt ttgtgtttta   1860
tgatacatta cagccaaatt atttgttggt ttatggacat actgccctt cattttttt    1920
cttttccagt gtttaggtga tctcaaatta ggaaatgcat ttaaccatgt aaaagatgag   1980
tgctaaagta agcttttag ggcccttttgc caataggtag tcattcaatc tggtattgat   2040
cttttcacaa ataacagaac tgagaaactt ttatatataa ctgatgatca cataaaacag   2100
atttgcataa aattaccatg attgctttat gtttatattt aacttgtatt tttgtacaaa   2160
caagattgtg taagatatat ttgaagtttc agtgatttaa cagtcttttcc aacttttcat   2220
gattttatg agcacagact ttcaagaaaa tacttgaaaa taaattacat tgcctttgt    2280
ccattaatca gcaaataaaa catggcctta acaaagttgt ttgtgttatt gtacaatttg   2340
```

```
aaaattatgt cgggacatac cctatagaat tactaacctt actgcccctt gtagaatatg    2400
tattaatcat tctacattaa agaaaataat ggttcttact ggaatgtcta ggcactgtac    2460
agttattata tatcttggtt gttgtattgt accagtgaaa tgccaaattt gaaaggcctg    2520
tactgcaatt ttatatgtca gagattgcct gtggctctaa tatgcacctc aagattttaa    2580
ggagataatg tttttagaga gaatttctgc ttccactata gaatatatac ataaatgtaa    2640
aatacttaca aaagtggaag tagtgtattt taaagtaatt acacttctga atttattttt    2700
catattctat agttggtatg acttaaatga attactggag tgggtagtga gtgtacttaa    2760
atgtttcaat tctgttatat ttttttattaa gttttttaaaa aattaaattg gatattaaat    2820
tgtatggaca tcatttatta attttaaact gaatgccctc aataagtaat actgaagcac    2880
attcttaaat gaagataaat tatctccaat gaaaagcatg acatgtgttt caatagaaga    2940
atcttaagtt ggctaaattc aaagtgcttg acatcaaaat gttctagagt gattagctac    3000
tagattctga atcatacatc acatctgact agagaccagt ttctttcgaa tgattctttt    3060
atgtatgtag atctgttctt ctgaggcagc ggttggccaa ctatagccca aaggccaaat    3120
ttggacttct ttttataaat gcagattgtc tatggctgct ttcccactac tccagcctaa    3180
ggtaaacagc tgcaatagaa gccaaatgag aatcgcaaag cccaaaatgt ttattaacct    3240 gcccttaca caaaattaca caaaaagttt cctgatctct gttctaagaa aaggagtgtg    3300
ccttgcattt aaaaggaaat gttggtttct agggaaggga ggaggctaaa taattgatac    3360
ggaattttcc tcttttgtct tctttttttct cacttaagaa tccgatactg gaagactgat    3420
ttagaaaagt ttttaacatg acattaaatg tgaaattttta aaaattgaaa agccataaat    3480
catctgtttt aaatagttac atgagaaaat gatcactaga ataacctaat tagaagtgtt    3540
atcttcatta aatgttttttt gtaagtggta ttagaaagaa tatgtttttc agatggttct    3600
ttaaacatgt agtgagaaca ataagcatta ttcacttttta gtaagtcttc tgtaatccat    3660
gatataaaat aattttaaaa tgattttttta atgtatttga gtaaagatga gtagtattaa    3720
gaaaaacaca catttcttca caaaatgtgc taaggggcgt gtaaagaatc aaaagaaact    3780
attaccaata atagttttga taatcaccca taattttgtg tttaaacatt gaaattatag    3840
tacagacagt attctctgtg ttctgtgaat ttcagcagct tcagaataga gtttaattta    3900
gaaatttgca gtgaaaaaag ctatctcttt gttcacaacc ataaatcagg agatggagat    3960
taattctatt ggctcttagt cacttggaac tgattaattc tgactttctg tcactaagca    4020
cttggtattt ggccatctcc attctgagca ccaaacggtt aacacgaatg tccactagaa    4080
ctctgctgtg tgtcaccctt aaatcagtct aaatcttcca gacaaaagca aatggcattt    4140
atggatttaa gtcattagat tttcaactga cattaattaa tccctcttga ttgattatat    4200
catcaagtat ttatatctta aataggaggt aggatttctg tgttaagact cttatttgta    4260
ccctataatt aaagtaaaat gttttttatg agtatcccett gttttccctt cttaaattgt    4320
tatcaaacaa ttttttataat gaaatctatc ttggaaaatt agaagaaaaa atggcaaggt    4380
atttattgtt ctgtttgcca taatttagaa ctcacactta agtattttgt agttttacat    4440 tccttttttaa cccattcagt ggagaatgtc agcttttctc ccaagttgta tgttaagtct    4500
attctaatat gtactcaaca tcaagttata aacatgtaat aaacatggaa ataaagttta    4560
gctctattag tgaagtgtta aaaaaaaaaa aaa                                 4593
```

<210> SEQ ID NO 72
<211> LENGTH: 1038

<212> TYPE: DNA
<213> ORGANISM: Homo sapiens

<400> SEQUENCE: 72

```
atgagcagca attcatccct gctggtggct gtgcagctgt gctacgcgaa cgtgaatggg      60
tcctgtgtga aaatcccctt ctcgccggga tcccgggtga ttctgtacat agtgtttggc     120
tttggggctg tgctggctgt gtttggaaac ctcctggtga tgatttcaat cctccatttc     180
aagcagctgc actctccgac caattttctc gttgcctctc tggcctgcgc tgatttcttg     240
gtgggtgtga ctgtgatgcc cttcagcatg tcaggacgg tggagagctg ctggtatttt      300
gggaggagtt tttgtacttt ccacacctgc tgtgatgtgg cattttgtta ctcttctctc     360
tttcacttgt gcttcatctc catcgacagg tacattgcgg ttactgaccc cctggtctat     420
cctaccaagt tcaccgtatc tgtgtcagga atttgcatca gcgtgtcctg gatcctgccc     480
ctcatgtaca gcggtgctgt gttctacaca ggtgtctatg acgatgggct ggaggaatta     540
tctgatgccc taaactgtat aggaggttgt cagaccgttg taaatcaaaa ctgggtgttg     600
acagattttc tatccttctt tatacctacc tttattatga taattctgta tggtaacata     660
tttcttgtgg ctagacgaca ggcgaaaaag atagaaaata ctggtagcaa gacagaatca     720
tcctcagaga gttacaaagc cagagtggcc aggagagaga gaaaagcagc taaaaccctg     780
ggggtcacag tggtagcatt tatgatttca tggttaccat atagcattga ttcattaatt     840
gatgcccttta tgggctttat aacccctgcc tgtatttatg agatttgctg ttggtgtgct     900
tattataact cagccatgaa tcctttgatt tatgctttat tttacccatg gtttaggaaa     960
gcaataaaag ttattgtaac tggtcaggtt ttaaagaaca gttcagcaac catgaatttg    1020
ttttctgaac atatataa                                                  1038
```

<210> SEQ ID NO 73
<211> LENGTH: 758
<212> TYPE: DNA
<213> ORGANISM: Homo sapiens

<400> SEQUENCE: 73

```
gtcatcggga cgtactaaga ctagggttgg gccgagagtc ggagccatta ctgcaggaaa      60
aggtcccgga gagctgagca gtcaagatgt gtgacttcac cgaagaccag accgcagagt     120
tcaaggaggc cttccagctg tttgaccgaa caggtgatgg caagatcctg tacagccagt     180
gtggggatgt gatgagggcc ctgggccaga accctaccaa cgccgaggtg ctcaaggtcc     240
tggggaaccc caagagtgat gagatgaatg tgaaggtgct ggactttgag cactttctgc     300
ccatgctgca gacagtggcc aagaacaagg accagggcac ctatgaggat tatgtcgaag     360
gacttcgggt gtttgacaag gaaggaaatg gcaccgtcat gggtgctgaa atccggcatg     420
ttcttgtcac actgggtgag aagatgacag aggaagaagt agagatgctg gtggcagggc     480
atgaggacag caatggttgt atcaactatg aagcgtttgt gaggcatatc ctgtcggggt     540
gacgggccca tggggcggag ctcgtccgca tggtgctgaa tggctgagga ccttcccagt     600
ctccccagag tccgtgcctt tccctgtgtg aattttgtat ctagcctaaa gtttccctag     660
gctttcttgt ctcagcaact ttcccatctt gtctctcttg gatgatgttt gccgtcagca     720
ttcaccaaat aaacttgctc tctgggccct cggtaaaa                             758
```

<210> SEQ ID NO 74
<211> LENGTH: 898
<212> TYPE: DNA

<213> ORGANISM: Homo sapiens

<400> SEQUENCE: 74

| | | | | | |
|---|---|---|---|---|---|
| ccacgttacg | gatcggctta | ctccgcggag | ttggcctcat | ttctgcagtc | ggcgctccct | 60 |
| gtagtttctc | ctctcgaacg | ccaggtggag | caaccggccg | gataccgcca | cagccctggc | 120 |
| aggcggcgct | gtgatgcctg | agctgatcct | gtatgttgca | atcactctat | ccgtggctga | 180 |
| gcgactcgtt | ggcccgggtc | acgcatgcgc | tgagccttcc | tttcgctctt | cccgctgctc | 240 |
| cgcccctctc | tgtcttctct | gcagtgggag | cagctctcct | gccacagctc | ctcacccct | 300 |
| gaaaatgttc | gcctgctcca | gtttgtctc | cactccctcc | ttggtcaaga | gcacctcaca | 360 |
| gctgctgagc | cgtccgctat | ctgcagtggt | gctgaaacga | ccggagatac | tgacagatga | 420 |
| gagcctcagc | agcttggcag | tctcatgtcc | ccttacctca | cttgtctcta | gccgcagctt | 480 |
| ccaaaccagc | gccatttcaa | gggacatcga | cacagcagcc | aagttcattg | gagctggggc | 540 |
| tgccacagtt | ggggtggctg | gttctggggc | tgggattgga | actgtgtttg | ggagcctcat | 600 |
| cattggttat | gccaggaacc | cttctctgaa | gcaacagctc | ttctcctacg | ccattctggg | 660 |
| ctttgccctc | tcggaggcca | tggggctctt | ttgtctgatg | gtagcctttc | tcatcctctt | 720 |
| tgccatgtga | aggagccgtc | tccacctccc | atagttctcc | cgcgtctggt | tggccccgtg | 780 |
| tgttccttt | cctatacctc | cccaggcagc | ctggggaacg | tggttggctc | agggtttgac | 840 |
| agagaaaaga | caaataaata | ctgtattaat | aagatgtttc | ttgaaaaaaa | aaaaaaaa | 898 |

<210> SEQ ID NO 75
<211> LENGTH: 1632
<212> TYPE: DNA
<213> ORGANISM: Homo sapiens

<400> SEQUENCE: 75

| | | | | | |
|---|---|---|---|---|---|
| gctcgccccg | ccccgctcg | ccccgcccct | ggatttgctc | cctcaaagcg | gaggtgaggc | 60 |
| cggactgagg | ctcttacagt | ggtccctgct | ggcccttggt | gacgggtcgc | gtcagttccg | 120 |
| acccggaccc | gtacgctgct | gcgctgacgt | ggctcctgga | agcagggctg | gcgtagggcc | 180 |
| gccatgttgc | agcaggatag | taatgatgac | actgaagatg | tttcactgtt | tgatgcggaa | 240 |
| gaggagacga | ctaatagacc | aagaaaagcc | aaaatcagac | atccagtagc | atcgttttc | 300 |
| cacttattct | ttcgagtcag | tgcaatcatc | gtctgtcttc | tctgtgagtt | gctcagcagc | 360 |
| agctttatta | cctgtatggt | tacaattatc | ttgttgttgt | cgtgtgactt | tgggcagtg | 420 |
| aagaatgtca | caggtagact | aatggttggc | ctacgttggt | ggaatcacat | tgatgaagat | 480 |
| ggaaagagcc | attgggtgtt | tgaatctaga | aaggagtcct | ctcaagagaa | taaaactgtg | 540 |
| tcagaggctg | aatcaagaat | cttttggttg | ggacttattg | cctgttcagt | actgtgggtg | 600 |
| atatttgcct | ttagtgcact | cttctccttc | acagtaaagt | ggctgagacg | tctcgccac | 660 |
| attgcccaga | ctggtctgaa | agtcttgggc | tcaagagatc | ctcccgcttc | cgccttccaa | 720 |
| agcgctggga | taacaggcgt | gagccgctgc | ccgggccatc | cctcgaggaa | gtttcatcag | 780 |
| gtagacatta | attctttcac | gaggatcacg | gatcgagctc | tttactggaa | acctgcgccc | 840 |
| cgccttagtt | ctccacctct | tcgtgcggct | ccaggcaact | gccaacagat | ggcgcccgcc | 900 |
| cgcctatttc | tctccttgcg | gctttgggcc | tggaggggag | gtggggagag | tcccaatagc | 960 |
| agaggaactg | gtgagcccgg | gccaaaattt | catctggcat | ccggaatgca | ttaaaaacaa | 1020 |
| cccacaaatc | tgaagctcct | cgcaggagag | agagagagag | agagagagga | gagagaggag | 1080 |
| agaggagaga | gggagggaag | agagtgacgg | agaaggagag | aaagagacgg | gagagaggag | 1140 |

```
agagaaagag agagagagga gagagagaaa gaacgaacga acaggggaact tgtaaaacta    1200 aggggaaaag ggcagaagag aggcagcagc gtggtccctg caagcgtccg ctttcctggc    1260
caagcagccc ccagcacgcc tgctttgtgg ggcagggcca tgcggccccg aggaaggatg    1320
cggtgagcca gagggttcca gacaaaggag gggatcccca aggctctggg ccagccagtc    1380
cctgttttac tggcaccacg gtccctccta ggcgaggacg aagagggaag gggtggagac    1440
ctccaccttc tctgcgtgtg gctgcgtccc tttacagaat gacaggccct tacttccgag    1500
ggcggggact aatgtgtaag gcttaacaga tccaattcca gaaattatct gtgtttttt     1560 caatcaccct cttgtgcccc cccaccccc attaaatttc atcttttatc ttttaaaaaa    1620
aaaaaaaaaa aa                                                        1632

<210> SEQ ID NO 76
<211> LENGTH: 3794
<212> TYPE: DNA
<213> ORGANISM: Homo sapiens

<400> SEQUENCE: 76
gactcagatc tcacctccta ccactcccct aggagagctg ggggccactg tttcctggat      60
tatcctaaaa gcttctgagg ccgtgaggac ttggcagcat ccctgctccc tccttcacct     120 cccccttttgg cactgcctgt cacctccttt ataaagcctg gctctttat caccgccact     180 tggccctcac tgccgccgcc agctctgggc tccatggact ggtcccgtct gaggtgcccc     240
tgaccgtccc tgccctcacc ccaccccgga tcccggcaat gctaaccgct gtctgcggct     300
ctctgggcag ccagcacacg gaagcgccgc acgcctcccc gccgcgcctc gacctgcagc     360
ctctccaaac ttaccagggc cacacgagcc ctgaggccgg ggactacccc tccccgctgc     420
agcctggaga gctgcagagc ctcccgctgg gcccggaggt ggacttctcg cagggctatg     480
agctgccagg ggcctcctcg cgggtaacct gcgaggacct ggaaagcgac agtcccttgg     540
ccccgggccc cttttccaag ctcctgcagc cggacatgtc acaccattat gaatcgtggt     600
tcaggccgac tcacccaggc gcggaggatg gctcgtggtg ggaccttcat ccgggcacca     660
gctggatgga cctcccccac actcagggcg cgctgacctc acctggccac ccgggggcgc     720
ttcaggcggg cttggggggc tacgtcggag accaccagct ttgtgcccg ccaccccacc     780 cgcatgcgca ccacctcctt ccagctgccg gagggcagca tctcctaggg ccgcccgacg     840
gggctaaggc cttggaagta gccgccccgg agtctcaagg gctggattcc agcctggacg     900
gggcggcgcg tcccaaaggc tcccggcggt cggtgccccg cagctcaggc cagaccgtct     960
gtcgctgccc caactgtctg gaggcggagc gactgggggc tccatgtggg cccgatgggg    1020
gcaagaagaa gcatttgcac aactgccaca tcccggctg cggaaagcc tacgccaaga    1080 cgtcgcacct gaaggcgcac ctgcgctggc acagcggcga ccgtccctc gtgtgcaact    1140 ggctcttctg cggcaagcgc ttcacgcgct cggacgagct gcagcgccac ctccagaccc    1200
acaccggcac caagaagttc ccctgtgcag tctgcagccg cgtcttcatg cgcagcgacc    1260
acctggccaa gcacatgaaa acccacgagg gcgccaagga ggaggcggct ggggcggcct    1320
cgggagaggg caaggccggc ggcgcagtgg agccccccgg gggcaaaggc aaacgcgagg    1380
ccgagggcag cgtggctccc tccaactgag ctcctcagtg ccgcctccct gcgggtatcc    1440
cggggggcac tggatgcgag ccccccaggtc tgacgtcctt gggggtggct tgaggaagag    1500
gggaaggtgc gtatttattc agggaggagg aaaagtggtg cagggacagg gagatggggc    1560
```

```
gctagggggtt cttagtctct ggggctacta ggcaggatga atttgactgg gtcggtagga    1620
gctgcgcaat gccccctctgt tctccctgc ctcacagttt ccctcgcccc tgggctgggg     1680
ggttggggtg ggacacccgt accgcggctg gctggcgggg acaggctaga ggagacagca    1740
agtcccagtc cccggagcag agagaagtgg ggccggcccg gggcgctggt ggtggctgtc    1800
tggacacgtc cttagcgcct gggaaccagg acataaaagc gcctccggag ccgccctgcg    1860
gcggggtccc tttcatccca cttaaagtgc ttctgcccct agggtttccg gagggagagc    1920
cgagatggga tggggagcc tgggggtccc ccttggcagg ggtgtctctt tctggtttgg     1980
agggttgttg ctgtaaaaat aactcctttg atgagcttcc ttattaaccc tttcagaccc    2040
agtctgttgg agccatgaag gaagagggaa agagggctgc cattcctgac agcctcccag    2100
ccagggctgg cgataaagga ccagatagaa tggaggggggc gagtagggaa gtcctcttct    2160
aaaatgagag atagggatt ggtggggtat ggaaggaact aaccccttcc ctctccacct     2220
ctgattcagc ccttaattct tggtctatga taaataaagt tcagtagtct cacattcccc    2280
atctattacc ctaggtgtgt tttcaaggca gccagcggta gaatccatgt agttcccacc    2340
agttgccttc ccctcaggga tggaaggaag agggtttctt gggctggttg agggcagatt    2400
gggggtgtct catcagaggg acctccactg gttcccactc agagtggagg cctgcagcct    2460
acctgaccat ctctttagct gtcaccaaga aaataaaccc cactgtctct ctagcttggc    2520
ccttgtcttt cccttgcccc tgccatagca tgttcattag gggattcctt cctccccctc    2580
atctcacagg ggaagggaga ggaaagagtt gttctcccac tggaaggggt tctgccttct    2640
gaggtgacat ccaggaagct gtccccattc ccttctcctt tagatgctag aaacacattt    2700
tgattctgat catggggtgg gggagagagg aaaggaggga ggggagaagc ccagcagaag    2760
ctgagccagg cagaggggaa agaagctgat atgaggaagg gtctgacagg ccacagccct    2820
tgcagccgga gggctttccc acactcaaga gaggggcctt acagtccctc tgacacccct    2880 ccccccttccc ctcgctccct ttcttcaccc ggagccctct gcagagatta gctgtgtatt    2940
gatttttaag ttataagcaa agggtatttt atttaatatt aggttatgtg tgtgcatgtt    3000
gtgtgtacct gtgtgcatgt atgtgtgttt ctctactgag cctgggtct ctagccaggg     3060 agaccccatc ttattcacca tgtccaagat cctgggatct gggcccagca tctcttcctc    3120
ctttgtagat gctggagccc agccaaggtc tgggagctat atgggaagtg ggggctggga    3180
tctgggtggg aatatgtgtt tgtatacaaa ggggccctcc ttaaagggga caggatgacc    3240
ttcccgagga actcattggc ctggggtagt ttaagaagta atgttctttc tttctttctc    3300
ttttccctac ctcctgctaa cccaaccaga gatcccttc cttgctgaga gggttggggg     3360
caggaggaga tttggcagtg cctgcaggtt gcctggccag gtggagaggg ggaaagagga    3420
agggcaccgt gggtgtaaga tgcctttctc ctccacccat cgaaaccagc cacccttcc    3480 ctgtgccacc aagacagcct ttccagtgg ccatcctaag gggaactccc aaatgggtgt     3540
tgctggtgga cacagatgct cccccaatg gaagccccaa gctctgaggt atgcgggtag     3600
aggctttgga taggttttct tctgctcccc tcttttatag atctaggctg cttggctgcc    3660 tgtcttctcta ggcagtcccc ctagaggaaa aatgtaggaa tttatttttt ctttaactgc    3720
tgtgaactca ctttgagggg gtaggaggag ggagaaacag cctgtgtttt ttatgcaata    3780
aagtcatcaa ctac                                                      3794
```

<210> SEQ ID NO 77
<211> LENGTH: 4725

<212> TYPE: DNA
<213> ORGANISM: Homo sapiens

<400> SEQUENCE: 77

```
cgccccgcgc cgccaggag ccaccgtccg agccttgcgg agcgcggcag tgggcgccgg      60
ctgcccgcag cccctgaccc ggccccggac ggagcgccgg ccgcaccacc gccctctggc     120
cgttgcctca ccggctcggc aagatgtcgg tgaaggaggg cgcacagcgc aagtgggcag     180
cgctgaagga gaagctgggg ccacaggatt cggaccccac ggaggccaac ctggagagcg     240
cggaccccga gctgtgcatc cggctgctcc agatgccctc tgtggtcaac tactccggcc     300
tgcgcaagcg cctggagggc agcgacggcg gctggatggt gcagttcctg gagcagagcg     360
gcctggacct gctgctggag gcgctggcgc ggctgtcggg ccgcggcgtt gcacgtatct     420
ccgacgccct gctgcagctc acctgcgtca gtgcgtgcg cgccgtcatg aactcgcggc     480
agggcatcga gtacatcctc agcaaccagg gctacgtgcg ccagctctcc caggccctgg     540
acacatccaa cgtgatggtg aagaagcagg tgtttgagct actggctgcc ctgtgcatct     600
actctcccga gggccacgtg ctgaccctgg acgccctgga ccactacaag acggtgtgca     660
gccagcagta ccgcttcagc attgtcatga cgagctctc cggcagcgac aacgtgccct     720
acgtggtcac cctgcttagc gtgatcaacg ccgtcatctt gggccccgag gacctgcgcg     780
cgcgcaccca gctgcggaac gagtttatcg ggctgcagct gctggacgtc ctggctcgcc     840
tgcgagacct ggaggatgcc gacctgctga tccagctgga ggctttcgag gaggctaagg     900
ccgaggacga ggaggagctg ctgcgagtct ctggcgggt cgacatgagc agccaccagg     960
aggtctttgc ctccctgttc cacaaggtga gctgctcccc ggtgtctgcc cagctcctgt    1020
cggtgctgca gggcctcctg cacctggagc ccaccctccg ctccagccag ctgctctggg    1080
aggccctgga gagcctcgtg aaccgggccg tgctcctggc cagcgatgcc caggaatgca    1140
ccctggagga agtggttgag cggctcctgt ctgtcaaggg gcgacccaga ccgagccccc    1200
tggtcaaggc ccataaaagc gtccaggcca acctagacca gagccagagg ggcagctccc    1260
cgcaaaacac tacaaccccc aagcccagct ggagggcca gcagcagca gcagctgctg    1320
cctgcgagcc cgtggaccac gcccagagtg agagcatcct gaaagtttcg cagcccagag    1380
ccctggagca gcaggcgtcc accccacccc caccccacc cccacccctg ctccctggtt    1440
ccagtgccga gcccctccc cctccccac cacccccct gcccagtgtg ggggctaagg    1500
ccctcccaac agcaccccg ccccacccc tgccaggcct gggggccatg gcccccccag    1560
cacctcctct accaccaccc ctgccaggct cctgtgagtt cctgcccca ccacctccac    1620
cactcccggg cttgggatgc ccgccccac cccaccccct gctgcctggt atgggctggg    1680
gccctcctcc accccacct ccactactgc cctgcacctg cagccccccc gtggcggag    1740
gcatggagga ggtcatcgtg gcccaggtgg accatggctt gggctcagca tgggtcccca    1800
gccatcggcg ggtgaaccca cccacactgc gcatgaagaa gctgaactgg cagaagctgc    1860
catccaacgt ggcacgtgag cacaactcta tgtgggcgtc cctgagcagc cccgacgccg    1920
aggctgtgga gcccgacttc tccagcatcg agcgactatt ctccttccct gcagccaagc    1980
ccaaggagcc caccatggtg gccccgggg ccaggaagga gcccaaggag atcactttcc    2040
tcgatgccaa gaagagcctg aacctcaaca tcttcctgaa gcaatttaag tgctccaacg    2100
aggaggtcgc tgctatgatc cgggctggag ataccaccaa gtttgatgtg gaggttctca    2160
aacaactcct taagctcctt cccgagaagc acgagattga aaacctgcgg gcattcacag    2220
```

```
aggagcgagc caagctggcc agcgccgacc acttctacct cctcctgctg gccattccct    2280
gctaccagct gcgaatcgag tgcatgctgc tgtgtgaggg cgcggccgcc gtgctggaca    2340
tggtgcggcc caaggcccag ctggtgctgg ctgcctgcga aagcctgctc accagccgcc    2400
agctgcccat cttctgccag ctgatcctga gaattgggaa cttcctcaac tacggcagcc    2460
acaccggtga cgccgacggc ttcaagatca gcacattgct gaagctcacg gagaccaagt    2520
cccagcagaa ccgcgtgacg ctgctgcacc acgtgctgga ggaagcggaa aagagccacc    2580
ccgacctcct gcagctgccc cgggacctgg aacagccctc gcaagcagca gggatcaacc    2640
tggagatcat ccgctcagag gccagctcca acctgaagaa gcttctggag accgagcgga    2700
aggtgtctgc ctccgtggcc gaggtccagg agcagtacac cgagcgcctc caggccagca    2760
tctcggcctt ccgggcactg gatgagctgt tgaggccat cgagcagaag caacgggagc    2820
tggccgacta cctgtgtgag gacgcccagc agctgtccct ggaggacacg ttcagcacca    2880
tgaaggcttt ccgggacctt ttcctccgcg ccctgaagga gaacaaggac cggaaggagc    2940
aggcggcgaa ggcagagagg aggaagcagc agctggcgga ggaggaggcg cggcggcctc    3000
ggggagagga cgggaagcct gtcaggaagg ggcccgggaa gcaggaggag gtgtgtgtca    3060
tcgatgccct gctggctgac atcaggaagg gcttccagct gcggaagaca gcccggggcc    3120
gcggggacac cgacggggc agcaaggcag cctccatgga tcccccaaga gccacagagc    3180
ctgtggccac cagtaaccct gcaggagatc ccgtgggcag cacgcgctgt cccgcctctg    3240
agcccggcct tgatgctaca acagccagcg agtcccgggg ctgggacctt gtagacgccg    3300 tgaccccgg ccctcagccc accctggagc agttggagga gggtggtcca cggcccctgg    3360
agaggcgttc ttcctggtat gtggatgcca gcgatgtcct aaccactgag gatccccagt    3420
gcccccagcc cttggagggg gcctggccgg tgactctggg agatgctcag gccctgaagc    3480
ccctcaagtt ctccagcaac cagcccctg cagccggaag ttcaaggcaa gatgccaagg    3540
atcccacgtc cttgctgggc gtcctccagg ccgaggccga cagcacaagt gaggggctgg    3600
aggacgctgt ccacagccgt ggtgccagac cccctgcagc aggcccaggt ggggatgagg    3660
acgaggacga ggaggacacg gccccagagt ccgcactgga cacatccctg gacaagtcct    3720
tctccgagga tgcggtgacc gactcctcgg ggtcgggcac actccccagg gcccggggcc    3780
gggcctcaaa ggggaccggg aagcgaagga agaagcgtcc ctccaggagc caggaagagg    3840
ttccccctga ttctgatgat aataaaacaa agaaactgtg tgtgatccag taaggcctca    3900
ggcccaggcc caaggccaag tgagagagcc caggccacag gacatgctgc cattctgcca    3960
agagaggctc ttctggggc caggctggga ctgggccccg gaaaccaaaa ctccgtgcct    4020
tacccagccg gggccctcct ggagccttct tggggtgttg tggctgggaa cccgacaggc    4080
accagtgccc tgccaggcct ggtgccctcc tggaccgcct gcacgtgcca gcctcccacc    4140
tgcttcctaa aggcaaccct ggcccacacc cgcatgcgcc cggtgcagcc tgccaagggc    4200
cagtcggggg gtgctgcgtc ctgccagtgt ccaccacagc tctgcctgcc cttcagccca    4260
gcaaggttta atcaaaatgc aatgctttgc aagtctttac tgcttggagg tggctgagtt    4320
gggggccctg gcaggggta agctggcagg cagtgccatg gcaggccagg tcccctccc    4380 atgggtctg gccccgttc cagcatgtcc agccctgaa gttggagtgg ggcgtct     4440 gcctttgctg ccactgccag gcctctgccc tgcagctgaa acttggccat cacatcaaca    4500
gaaaccccct cccagtgcca gctgcccagc gtgggcaggc cctggggaca atacaggtcc    4560
acctgagggg ctgcagggtg acacccagca gccgctgccc cctcactgcc cacccagcga    4620
```

```
gggcagccta cccgagcctg cccctgcca ggtgtgtgcc ctgaggctgg cggctggatg    4680
cgtggccaat aaaaagcaga cctagcccgg aaaaaaaaaa aaaaa                  4725
```

<210> SEQ ID NO 78
<211> LENGTH: 1956
<212> TYPE: DNA
<213> ORGANISM: Homo sapiens

<400> SEQUENCE: 78

```
gagcggaagt ctcgtgaccc cggaagtgac aggcagggcg ggcggggcgg ccgacgacgt     60
tcgtcattta gtgcgggagg gatcctgaac cgcgcggccg aaccctccgg tgtcccgacc    120
caggctaagc ttgagcatgg ctgagcagga gcccacagcc gagcagctgg cccagattgc    180
agcggagaac gaggaggatg agcactcggt caactacaag cccccggccc agaagagcat    240
ccaggagatc caggagctgg acaaggacga cgagagcctg cgaaagtaca aggaggccct    300
gctgggccgc gtggccgttt ccgcagaccc caacgtcccc aacgtcgtgg tgactggcct    360
gaccctggtg tgcagctcgg ccccgggccc cctggagctg gacctgacgg gcgacctgga    420
gagcttcaag aagcagtcgt tgtgctgaa ggagggtgtg gagtaccgga taaaaatctc    480
tttccgggtt aaccgagaga tagtgtccgg catgaagtac atccagcata cgtacaggaa    540
aggcgtcaag attgacaaga ctgactacat ggtaggcagc tatgggcccc gggccgagga    600
gtacgagttc ctgaccccccg tggaggaggc acccaagggt atgctggccc ggggcagcta    660
cagcatcaag tcccgcttca cagacgacga caagaccgac cacctgtcct gggagtggaa    720
tctcaccatc aagaaggact ggaaggactg agcccagcca gaggcgggca gggcagactg    780
acggacggac gacggacagg cggatgtgtc cccccagcc cctcccctcc ccataccaaa    840
gtgctgacag gccctccgtg cccctcccac cctggtccgc ctccctggcc tggctcaacc    900
gagtgcctcc gacccccctc ctcagccctc ccccacccac aggcccagcc tcctcggtct    960
cctgtctcgt tgctgcttct gcctgtgctg tgggggagag aggccgcagc caggcctctg   1020
ctgccctttc tgtgccccccc aggttctatc tccccgtcac acccgaggcc tggcttcagg   1080
agggagcgga gcagccattc tccaggcccc gtggttgccc ctggacgtgt gcgtctgctg   1140
ctccggggtg gagctggggt gtgggatgca cggcctcgtg ggggccgggc cgtcctccag   1200
ccccgctgct ccctggccag cccccttgtc gctgtcggtc ccgtctaacc atgatgcctt   1260
aacatgtgga gtgtaccgtg gggcctcact agcctctaac tccctgtgtc tgcatgagca   1320
tgtggcctcc ccgtcccttc ccggtgcgcg aacccagtga cccagggaca cgtgggtgt   1380 gctgctgctg ctccccagcc caccagtgcc tggccagcct gcccccttcc ctggacaggg   1440
ctgtggagat ggctccggcg gcttgggaa agccaaattg ccaaaactca agtcacctca   1500
gtaccatcca ggaggctggg tattgtcctg cctctgcctt ttctgtctca gcgggcagtg   1560
cccagagccc acaccccccc aagagccctc gatggacagc ctcacccacc ccacctgggc   1620
ccagccagga gcccgcctg gccatcagta tttattgcct ccgtccgtgc cgtccctggg   1680
ccactggcct ggcgcctgtt ccccaggct ctcagtgcca ccaccccgg caggccttcc   1740 ctgacccagc caggaacaaa caagggacca agtgcacaca ttgctgagag ccgtctcctg   1800
tgcctccccc gccccatccc cggtcttcgt gttgtgtctg ccaggctcag gcagaggcgc   1860
ctgtccctgc ttcttttctg accgggaaat aaatgcccct gaaggaaaaa aaaaaaaaa   1920 aaaaaaaaa aaaaaaaaa aaaaaaaaa aaaaa                                1956
```

<210> SEQ ID NO 79
<211> LENGTH: 1689
<212> TYPE: DNA
<213> ORGANISM: Homo sapiens

<400> SEQUENCE: 79

| | | | | | |
|---|---|---|---|---|---|
| agcaaatttc | aactcccgct | tgccattcaa | catcatggat | gatccgaaga | gtgaacagca | 60 |
| gcgcatactg | cgccgccacc | aacgcgagag | gcaggagctg | caggcccaga | tccggagctt | 120 |
| aaaaaactcg | gtccccaaga | ccgacaagac | gaaaagaaag | cagttgctcc | aagacgtggc | 180 |
| ccgcatggag | gccgagatgg | ctcagaagca | ccggcaggag | ctggagaagt | tccaagacga | 240 |
| cagtagcatt | gaatctgtcg | tcgaagacct | ggccaagatg | aatctggaaa | accggcctcc | 300 |
| ccgctcctcc | aaagcccaca | gaaagagaga | aagaatggag | tccgaggaga | gggagcgcca | 360 |
| ggagagcatc | ttccaggctg | agatgtcgga | gcacctggcc | ggcttcaagc | gcgaggagga | 420 |
| ggagaagctc | gccgccatcc | tgggagccag | gggtctggag | atgaaagcga | tcccggccga | 480 |
| cggccactgc | atgtaccgcg | ccatccaaga | ccagctggtg | ttcagcgtgt | ctgtggagat | 540 |
| gctgcgctgc | cgcaccgcca | gctacatgaa | gaagcacgtc | gacgagttcc | tgcccttctt | 600 |
| cagcaacccc | gagaccagcg | actccttcgg | ctacgacgac | ttcatgatct | actgcgacaa | 660 |
| catcgtgcgc | accacggcat | ggggaggcca | gctggagctg | agggccctgt | cgcacgtcct | 720 |
| gaagaccccc | atcgaggtga | tccaggccga | ctcgcccacc | ttgatcatcg | gggaggagta | 780 |
| cgtcaagaag | ccgatcatcc | tggtctacct | gcgctatgcc | tacagcctcg | gcgagcacta | 840 |
| caactccgtg | acaccgctcg | aggccggcgc | cgccgggggc | gtgctcccgc | gtctcctgta | 900 |
| ggccccaagg | cgctgagcag | ccccgggaaa | ctgtcgccgt | cgccgcatct | cctcagtagg | 960 |
| ctcagtttat | tttcccctt | tgcttttctc | tgttttcctt | ttccttcctt | ttaatcaaaa | 1020 |
| ctacccgccc | ccgccccgcc | cccgctttcc | taaccttgct | gctttcacag | ggtgggaaac | 1080 |
| gaaattcgag | ggaaattccc | cggaaatatg | agggaaatct | ctgcattgca | ccaccagagg | 1140 |
| ggcataaatt | tgaaagttct | aacctcttct | tgcccttaag | ggtcttttac | ctccctcacc | 1200 |
| aactaagatt | tggtcatgtt | gcgtataact | tcaccacaaa | aatggaaata | ttggccgggc | 1260 |
| gcggtggctc | acgcctgtaa | tcccagcact | ttgggaggcc | gaggcgggcg | gatcacgagg | 1320 |
| tcaggagttc | gagaccagcc | tggccaacat | ggtgaaaccc | cacctctaca | aaaatacaa | 1380 |
| aaattagccg | ggcgtggtgg | caggcacctg | tagtcccaga | tactcgggag | gctaaggcag | 1440 |
| gagaatcgct | tgacgggaag | cggaggttgc | agtgagccga | gatcgtgcct | ttgcactcca | 1500 |
| gcgtggaaga | cagtgagact | ccgtctcaaa | aaatgaaaa | attagccagg | caggttggcg | 1560 |
| ggggcctgta | atcctagcta | cttggggtgc | tgaggcagga | gaatcaactg | aacccgggag | 1620 |
| gcggaggctg | cagtgggccg | ggatcatact | actgcactcc | agcatggaag | acagcgagac | 1680 |
| tccgtctcc | | | | | | 1689 |

<210> SEQ ID NO 80
<211> LENGTH: 1865
<212> TYPE: DNA
<213> ORGANISM: Homo sapiens

<400> SEQUENCE: 80

| | | | | | |
|---|---|---|---|---|---|
| cgcccacgcg | gagccggccc | cgcgcgcgcg | cgcgtcccgt | gcatcccgc | gcctgcgcgc | 60 |
| tgcccaggcc | ctgcccgtgt | gtgggggtcg | ctgccggccc | cggggggggg | tggggaaaat | 120 |
| aagggattaa | aaaaacagcg | cgcggaaccg | ggccagggtt | gcccacccc | gccacaatgg | 180 |

```
cctctggggt ggaagtcctg cgcttccagc tgcccggcca cgaggccgca acgctacgga    240
acatgaacca gctccgggca gaggagcggt tctgcgacgt gaccattgtg gccgacagcc    300
tcaagtttcg aggccacaag gtcatcttgg ccgcctgctc acccttcctg cgggaccagt    360
tcctgctgaa ccccagctcg gagctgcagg tctccctgat gcacagtgca cgcatcgtgg    420
ccgacttgct cctctcctgc tacacgggcg ccttggaatt cgctgttagg gacatcgtca    480
actaccttac agccgcctcc tacctgcaga tggagcacgt ggtggagaaa tgccggaatg    540
ccctcagcca gttcattgag cccaaaatag gcctcaaaga ggatggggtc agtgaggcta    600
gccttgtgag cagcatcagc gccaccaagt ccctcctccc tccagccagg accccaaagc    660
cagccccgaa gccccaccc ccacctcctc taccccctcc actcctgcgg ccagtgaagc    720
tggagttccc actggatgaa gacttggagc tgaaagccga ggaagaggat gaggatgagg    780
atgaggacgt gtctgacatc tgcatcgtca aggtggagtc ggccctggag gtggcacacc    840
ggctcaaacc ccctggaggc ctgggagggg gtctgggcat tggaggctcc gtgggtggcc    900
accttgggga gctggcccag agcagcgttc ccccagcac tgtagcccca ccgcagggtg    960
tggtgaaggc ctgctatagc ctgtcggaag atgcagaagg ggagggcctg ctgttgattc    1020
ccggaggccg ggccagcgtg ggggccacct cgggcctggt ggaagcagca gcggtggcca    1080
tggctgcccg gggggcgggg ggcagcctgg gggcggggg cagccgggga cccctgcctg    1140
ggggcttctc agtggaaac cccttaaaga acatcaagtg caccaagtgc ccggaagtgt    1200
tccagggcgt ggagaagctg gtcttccaca tgcgggcgca gcacttcatc ttcatgtgcc    1260
ctcgctgtgg caagcagttc aaccacagca gcaacctcaa ccgccacatg aacgtgcatc    1320
gtggtgtcaa gtcacactcg tgcggcatct gcggcaagtg cttcacacag aagtccaccc    1380
ttcacgacca cctcaacctg cactcgggag cgcggcccta ccgctgctcc tactgcgacg    1440
tgcgcttcgc ccacaagcct gccattaggc ggcacctcaa ggagcaacac ggcaagacca    1500
cggccgagaa cgtgctggag gccagtgtgg ccgagattaa cgtcctcatc cgctagccgc    1560
gcaggcgtgg aggccaggag gctggggccc ctggctgcg tggaaaaagg gctctttggc    1620
ccaggagaat tggggggtgg ggggtctggg gcagaaaggt aagagtggga ggctgagcag    1680
atgcacacat cctgagagag ggaagatgat tccttggaga gacttgctct tgagagtgca    1740
agaatctgga gctgggaaaa gggttcttgg aggccagggg aatacggggt cccagagaaa    1800
gatttccttc tcttagaagt gcatgtatat gtggagggag ggaaaagggt cctatagaat    1860
gaggg                                                                 1865

<210> SEQ ID NO 81
<211> LENGTH: 967
<212> TYPE: DNA
<213> ORGANISM: Homo sapiens

<400> SEQUENCE: 81
tttcttgaaa gaggcatttta ccgagcgccc aatgtatgcc tggcactggg ctgggtgctg    60
ccacctaagc gagcacgacc aatgcagtct atcagggagg cccagatcgc caagcagcgg    120 accccctgcgg tccgccatgc cactcccggc tcctagagcg ccgctcagca caccgtgagc    180
gcccaataac tgttgggctt caatgacgcc gcggaggcgg ccccgtcccc gcgctcccgc    240
ccctcccgcc agggcagccc gggaggccag acgttgacgc tgcagggaga gggtggtggg    300
cgcagccgct aggggggcgcg gcggggcgga gcgcaccttt ccgcgggccg cggggatggc    360
```

```
ggcgcagggc gtagggcctg ggccggggtc ggcggcgccc ccggggctgg aggcggcccg    420
gcagaagctg gcgctgcggc ggaagaaggt gctgagcacc gaggagatgg agctgtacga    480
gctggcgcag gcggcgggcg gcgctatcga ccccgacgtg ttcaagatcc tggtggacct    540
gctgaagctg aacgtggccc ccctcgccgt cttccagatg ctcaagtcca tgtgtgccgg    600
gcagaggcta gcgagcgagc cccaggaccc tgcggccgtg tctctgccca cgtcgagcgt    660
gcccgagacc cgagggagaa acaaaggcag cgctgccctc gggggagcat ggccctggc     720 ggaacgcagc agccgcgaag gatccagcca gaggatgcca cgccagccca gcgctaccag    780
gctgcccaag gggggcgggc ctgggaagag ccctacacgg ggcagcacct aggatggggc    840
agagacttgt tgcatctttg tccccagcaa aggctacatg ttacctcctt caattgataa    900
taaacctttc tgagatgcag agggtccagg tcaaaaaaaa aaaaaaaaaa aaaaaaaaa    960 aaaaaaa                                                              967

<210> SEQ ID NO 82
<211> LENGTH: 978
<212> TYPE: DNA
<213> ORGANISM: Homo sapiens

<400> SEQUENCE: 82
atgttccttc ccaatgacac ccagtttcac ccctcctcct tcctgttgct ggggatccca     60
ggactagaaa cacttcacat ctggatcggc tttcccttct gtgctgtgta catgatcgca    120
ctcataggga acttcactat tctacttgtg atcaagactg acagcagcct acaccagccc    180
atgttctact tcctggccat gttggccacc actgatgtgg gtctctcaac agctaccatc    240
cctaagatgc ttggaatctt ctggatcaac tcagaggga tcatctttga agcctgcctc    300
acccagatgt ttttttatcca caacttcaca cttatggagt cagcagtcct tgtggcaatg    360
gcttatgaca gctatgtggc catctgcaat ccactccaat atagcgccat cctcaccaac    420
aaggttgttt ctgtgattgg tcttggtgtg tttgtgaggg cttttaatttt cgtcattccc    480 tctatacttc ttatattgcg gttgccctc tgtgggaatc atgtaattcc ccacacctac    540
tgtgagcaca tgggtcttgc tcatctatct tgtgccagca tcaaaatcaa tattatttat    600
ggtttatgtg ccatttgtaa tctagtgttt gacatcacag tcattgccct ttcttatgtg    660
catattcttt gtgctgtttt ccgtcttcct actcatgaag cccgactcaa gtccctcagc    720
acatgtggtt cacatgtgtg tgtaatcctt gccttctata caccagccct cttttccttt    780
atgactcatc gctttggccg aaatgtgccc cgctatatcc atatactcct agccaatctc    840
tatgttgtgg tgccaccaat gctcaatcct gtcatatatg gagtcagaac caagcagatc    900
tataaatgtg tgaagaaaat attattgcag gaacaaggaa tggaaaagga agagtaccta    960
atacatacga ggttctga                                                  978

<210> SEQ ID NO 83
<211> LENGTH: 11868
<212> TYPE: DNA
<213> ORGANISM: Homo sapiens

<400> SEQUENCE: 83
agtctggctg gagctggacc ggctggtggc gccaggcagt gccaagcacc cctggcagcc     60
ctgcagaggg ttctcaaatc cagatttcat tctgcagtcc cggcagtgtt ttgacgactg    120
cctcactaaa ggaagctaaa agctgtgctg atgcctccca gacgagcctc gttgaagcca    180
cagaaccttc acggctcgga gccgctgaca ccgtgacaaa gggagccctg ctcaggagaa    240
```

```
agagcaaatg agaggcagtt gcactttttc aggtgtcagg ctggaggaag ccacttgaag    300
atgaatctac ctctgcctta ggattgcctg atggcctgtg ccattccatg ttatatctac    360
tgatttgctc cctgtattca aagattttt tttttactt aattctctct tactgaccct     420
gagagtgacc atattttaa ccatttggt cttcagcctc aaaacttagc tctttccttt     480
tgtggtcccc gaatcctatc acgtgtcatg gtggctgtga agatgtttgc caagcctgct    540
gagaaggctc atctgtggca tccaaaagca gagatttcaa ctctggaccc ctgtgacctg    600
cctttgtaat tatggatacc cagcactgtt ttgaaatatc agtggacatc cagttttaa    660 aagccctcag agctttggga gacacccctt tatctctctg gcatgtcaga gaaccgattc    720
aacccttctc atctcctcct ccttccctct cttgggccat caggatgcgg cagcaactca    780
ctgtgcatgt tttacagct cttctccagt aatgctgcca tttccactgc agaccacagg     840
ataaaaggac cgcttcaccg tgcccagga tacccttta agtaggaggt aactattcag      900
tttcgtagtg gcccatacat aaacttgatt atgttcttcg ttgctccaat atactatttg    960
tgtgttttgt ttttccaga gggagaagaa agtactgctt tgatctaaaa ttaagcaaac    1020
gttcttcaat aaacccacca tgagacttga ccactaatgg tgaccagcag tggctttgtc    1080
atggccctgc ccactggggg caggcacatg ccggggccag ggcaggctgc cagctggtga   1140
gcacgaatag gtggctggtg gagcgcatgc agtgggaagg gcagatggct ccattttgat   1200
ttgttagcag gccacttcct cggaaggggc tttcccttca gtggggtctg caccgccagc   1260
ctcagctgtc ttggagcaga tgtgtatagt tagagatggg gaccttttca ctgtaaatac   1320
tgctcacatg ttcctaggct gactttacta tgtgcagagc ctcttctcaa atatccaaat   1380
cccctctgtt gggtactaca gaacagatgt tacctgcct cctattacat taatttacga    1440
actttacata tgctgagtta cggaccctaa gctgttgcat gtgcttggct cttatgttcc   1500
aaaaagtaca tttgtatggt tttgtggaaa ctgtgctgtt ctgcttttgc agtctgtgag   1560
attctgattt ttttttctc atcagcaatt atccttgtct tggaacatca gagcttgaag    1620
aaagggattc tagcagccca cctctctcct tcctaatcca gatggttaga ggcttagaga   1680
gaggtggtgg ttgctctgag tttaccagat tcagtgacaa acccccttcta atttctaatc   1740 aatctggcag ccttcattta ccaaaagttg acttttgata gtataacttt tatacaccgt   1800
gagacaactt atttaaaaa acagtttaga aatatttaat tttttttga aagacttttt     1860 aaggtcaggc accatgggtc atgcctatca tctcaacgct ttgaggactg aagtgggagg   1920
atcatttgag gccaagattt caagatcagc ttgggcaaca tagtgagact ctgtctctaa    1980
aaaattaaaa aaaaaatag ccaggtgtgg tggcgcatgc ctgtagtccc agctacttcg     2040
gaggctgaag tgggaggatc cattgagcct aagagatggc gattgagtaa gccatgattg    2100
caccactgca ctccagcctg gacgacagag atgtcagaaa aaattagtt ttattattat      2160 tagtttataa taatattatt ttaatattaa tattatttaa taatttcata ttatttatta    2220
ttattagttt tattattagc aaaactgagt ggaaggcaca gagattttcc atattcttcc    2280
tgcctctcca acaaacatgt ctccctcatt atcaacattt cttcccagag tggtacactt    2340
tttataattg atgatcctac actgacacat catcatcaca atgagttcat agttgacgcc    2400
agggttcact cttggtgttg tacattccag gcatttggac aaatgtataa tgacatgact    2460
ccaccatttt agtatcatac agacgagttt cactgcccta aaatcctctg tgctccactg    2520
atacttactc cttcatcccc ttgctccctc agcccctgac aaccactgat cttttttattg    2580
```

```
tctccatagt ttggtcttat ttaatatttt ttgaggttgc actgttgccc caggacatcg    2640
tatgagtaga gggttaacca ccttagccaa gagtaatttg gtctggtgag ttctccacct    2700
tcaggacaaa agcatttcag aaccatccta acaatagtgt tcccataagt aaccagacac    2760
tgtttgtatc catagcaaca tggctccatg agccctgctt ccgaggagca gctgcccttc    2820
ctgggcactg tcaagagttg ttcttctctg acatccacac ccttctttac ctggcacata    2880
ccccagccca ggcaccaggc atccagggcc ttctatggct gtccggatgc attccttcac    2940
agctggaatg tggttggctt gttgacttct gttcccagca tagtgaacag tgggcactat    3000
aagccagtag gcactcaatt gatgattctt caatgaaata attgatgcca cttttaggtc    3060
agtctttctt gtacgttaca ccttctgttg ttcaacagag ccccacaata tcccagaact    3120
tggaggtctt atctcggggt ttctcagatg ttggagtacc caggtatcac ctgctgagcc    3180
agtttccctg gcctcacctg caggggctct gagtcagtaa atctgggca ggcccagtac    3240 tttgcatgtg agcacagacc caggtgtttc tgaacctggt ggtccaggga ctgctgcagg    3300
aaggagccaa taggactgca tgccttagag gcagtgggtc tcatccatcc ctatctatgg    3360
cactgactac aggccatgtc caggccacat gggcacatgc tattataatt attttgtgtg    3420
atggatgagt tacagaactg gagccctaag acctgagttc tagtttcagc tctgccagtt    3480
gctggctgat tgaaactgaa caagccacct gccttccctg agactgtctc ttctcctgtg    3540
aaattagggc attagaatac atgaagaccc ctttatgtcc ttaataacct gtaagtttaa    3600
gaacctaggg aatctccatg ctggtggctg cggttatatc cccttatcct caactcgtga    3660
agaaagagtc aaaaatggca gcagggttgt gtcaactgct ctcctcagca gctatcataa    3720
gggaattgcc tttgtcattt tccccagcca tcaccacact cccacacggc caccatcacc    3780
taaaccatct ggcagtgggg gttacctcct aaatctaaga cgcagagacc caccgcaggc    3840 cttttctttct ggctgccctc cactcccacc cagaggctca gttttgctgg gctgcacacc    3900
tccgaggact cagttctttg tgtttcatgt tgtttcatat ccactagtgt tacagaaact    3960
gctgcaaacc agggaccaaa agtccatagg ttctaattct agctgtgaca ctagtgagat    4020
gagtgactgc tggcaagtta ctttatctat ctgacctcac ctcccatgta caaaattggg    4080
tctgtatgca catttgtggt tctaaatcct ggagtccaaa tcagagttct ttgtgcaaaa    4140
tatacgtagc taggtcctaa cctcggagat cctgactcag tctggggaaa ggcgcagatc    4200
ttggggagaa aacaactctc tagaagagtc tcgccttcag tgagtgacaa gatctctcct    4260
gtctctcggt tcacaatgtt accctaacta atccatcctc tgatgtcacc tgctaacaac    4320 ttccccctgtg gcatcaaacc agtagcccat ttgcagctag tacaaacact tctttacatt    4380
taagttttgt ttacgagatt tagcctacaa tcatagaggc tgccagctgg gtttcaaatg    4440
tgtatgttcc attgctaata ggaaaaactg catctattag aaaaattctc tctgggagct    4500
gagcacagag gcaggccttg tattgcaaac atttgaaaag ccataagcag gtattctgga    4560
ctgtgtttta gatcacctga gaacatttct tgaacactag tatttgctta gagtgacaaa    4620
cctattaagt ggttctttca ggtaagtttg catccaagca atgtcgtctg aatcgcagga    4680
ggaagtcagg agttgtgtct ggctttctgg ccatacaaat ggcatatggg aaagtcattg    4740
tatattatta atatcctttg atgtatatta ttatgacttt ctcacggtag taatgttgtt    4800
ggtttttatt aatgttattt ttatagcaat gctaatatta tgagctaaaa gtttctgagc    4860
atctgctggg tgccaaaaat tcttataaat gctttacatg cattagctcc taacaacact    4920
ttgaagtaat tcttattgtc cttacttgac atatacagga ataaaaacct gaccattaga    4980
```

```
ccgagcgtgg tggctcacgc ctgtaatccc aacactttgg gaggccgagg caggcggatc    5040
acctgaggtc aggagtttga gaccagcctg gccaccatgg tgagacccg tctctactaa     5100 aaacacacaa aaaattagcc gggcgtggtg gtgggtactt gtaatctcag ctacccggga    5160
ggctaatgca ggagaatcgc ttgaacccag gaggcggagg ttgcagtgag ccaagattgc    5220
gccattgcac tccagcctgg gcaacaagag caaaactctt tcaaataaac aaacaaaacc    5280
taagcatttg aggggtttgg cctgggcagt ggagcttgtg agctatatga gctgaatct     5340 gagtcaaggc tgggctggtg aaaggagttc actcaagttc ccaaggtatt ctgtcctcca    5400
ggactctgaa tcacctggga ggagaaggaa ttgtggcggg cctaacacct tttctttccc    5460
aaacaccaag agcaggttct ttctgttaca tccattgagg tcacattctt gaagtgcatt    5520
ttgaggaagt cattattttc gctacagcag ggactgatgt atcagtctat tagaattcag    5580
aaaaaagtaa gcaaacaaaa aacgtgttgg aattattctc ttctagcatt ttgaaatgta    5640
caatggttaa tgttaactat agccaccatg atgtattgaa gaccaggtct tattcttttt    5700
atctaactgt acatttgtac ccattaacct aatgctcata gcatcaagaa aagatcaata    5760
tttaaggtga caaatatccc aattatgctg atttgattat atgaatgtgt tgaattatca    5820
tatgtactcc caaaatatgc acatctaaga tgtatcaata aaaataaaga caaaaattaa    5880
agcttttaca gtagaaaaaa ggttttagag aaattatgat tacttgattc acctaaactg    5940
acagtcttgc ttgaatgaa ttactgcttt ttgtaacata gttttagaag agagattcac     6000
atttaatgtt actttgtgct aagcactgta atccatgcct gggtgctcac agcgctcctc    6060
tgggaccagg catcaccatc tcctctgtaa aaggaaggtc agcctgttgc caagaccaca    6120
ggataaacgg cttggctgat ttaggaaacc cagttggtct tatgacaaaa catgcgcatt    6180
tgcccttcac caggtgattt ttctgtaggg ttatcttcaa cagtccgaca aagctgtgtt    6240
ccaccagctc aggcaggctg tgaccaggat caccagccat gtggcatcag gaagaagggg    6300
ctgtgtggcc aggctcaatc tctggtcctg cagccttctg cctttggctt tctgaagcga    6360
gctgaactag agattgggcc cagctcggca gcgcagtttc aggagagcca ggatacaaac    6420
catcccagtc tctgttccca caaggagaa gctaaaccat ttttatttg cccattctaa      6480 gtgctaagtg atatgcaact gcttcacata agccttccag ccttccagcc gactctgctt    6540
tcaggagata tccttatgtc ccttttgcat ggcttaggag agtgaagcac gtgagaattg    6600
aacgaggggt caagggtcac ataacacatg agcacgaaac cgggactctc ctggggtatc    6660
agaccccaaa gccagtggtc tgcgcttgat ctttgctaac gtccgagaag caataagtcc    6720
agggctcttg acacattatt gtgcatttta ctttgggagg gactgtgggt ccactctgct    6780
tttaacagga ggaaattaaa tatttacatt tgattccagt ttggccccat gactgtccgg    6840
cttctttcct gtcaaaggcc caaattccct gttttaaagt agagggtgaa tttgtgtaat    6900
gaggatggat cgggcacgtg tagaacacac tctttcacct gcagattcac actccaaaca    6960
caaagaaata ctggatcata tatggtatat tttaaaagat gccataggca tacttaaaaa    7020
gcacaacaga attctatttt ctcacgtcag agggcagagt cttatgagct attgagagga    7080
aaactgtatc ttagggggttg agagcctaac gtctgcttgg gggtgtttgt ggccctggca    7140
gctgttgtgt gcagtgcaca ttagaactga gcagctttat aaagccagga acaagggtag    7200
agtccctgtg tctctgaata gaaattagcg atgcttagcc ttctgtacca aggaatgcat    7260
cacaaaagct aatgctggga ctgggcctgg tgtgggatag gagtcacaca gaggagtcag    7320
```

```
aacgccaact gtggctggtg taaggggcct ccattcacac tgtctttgct gtttggaaaa    7380
tctgagcaag aatttaaggt aaaagctgat gtggaacagc ttgcaaccca aaagtctcaa    7440
gcccagcata aaaatcattg ctccagtgaa gatgcctgca gagctcaagg catttctgag    7500
actccatggg agaatgattc ctaaggaagg tgtgccccca gcacctgtgg agactcatca    7560
ccttgagggc aaacagactc tgtaaaagga gaattcacct ctaaggagct gcagacaata    7620
gagggattaa aatgggcctt tgatcattca aaaagcattt taaggaaaa aataaagtaa     7680 cataatccaa attccaacag gagacttgaa aaagaaggta ataacaaaat ggaaaataaa    7740
gtcactgaaa taaagcaagt gagttggact atgaatgtct cctgtccatt agctgtgtcc    7800
ccggctgcaa ggtccatggg gactgtgcct cccttgacct tgaatctcaa tgccttagca    7860
aagtgcctgg ttctgggtag gttcacagta cacatgtacc tcccaaatgg atggattgcc    7920
aacttaaatg ttcataggaa ggtgctattt tcaggcactt caggtgtgga catcggtgtt    7980
gtcagatctt ttctgttcta gccaggcatt gtggacatca ccttactatg tgagggaaca    8040
agctgcattg gtggagagga aaccagcagg agcacaatag tgacccattt ctcttgtctt    8100
atgcactgca gtggaaatag cccagtgtgc atggtggatt ttattatggt gccagtagaa    8160
agataggggg tttcctctat gagctggctg acttacatga gctcattctc tgcagcattt    8220
ctctagccat ctcctgtcac atcgtttatt gtgttcacta gtcctgtgct aacgaggatc    8280
tttgaaaaat gactggtatg gtaatgatct acggaactta ctgtagatag caattaaata    8340
tcgttaacgg cgggttacgc tgacacatta aaaggcctac aggctgcgat ttatgaagac    8400
agctctgctg cctcctttgt atgtgatgca tttctctggt ttcggcttag gctgtctggt    8460
ctcagaaggg aatgatttcc aggctttccc catcatcact ccagttgcca ggccacccac    8520
aatcacatta gcaagcttta ttgtccctat tgcacctcct aatgccctca gggtgcttga    8580
ggtagctttt atcaaggtaa ggcctaggtc aacattttgt tgtgcagaaa aggcatctgc    8640
tttcagagga gaaaatttag atacaatatt gaggtgaatc ttataagtga tgtaagataa    8700
tttgatgaca agaattgaga ttatatgctg agatcttact gtcttaaact ttgttgattt    8760
ctgaaaataa tagaaatgca atcctagcta aaggaagaga agtagtctag ctcaccagtg    8820
gccagcaaac tctgtaaaga agtattgcct tcatgcagca atctcaccta atatgagact    8880
ccagatagaa gatagctcct gagaagtcaa aacacaaacc aatatcatgt aaattactct    8940
cacgtgaaaa atagacaaga gataaccaac ccagtcccaa ccgtctcaca cccccactgg    9000
cctcctgcac tcatggatgc cacattcttc aacatttgta cttctgttaa cagagttaaa    9060
gtagagcaaa cataggctct tttaccaaga gcgtatggac taaatacaga tgcaatgcta    9120
ataaccacat gggaaaaaca agatcctgag acactgttat gttttctcc ctcttttgtg     9180 gccaagagtg tgtgctctct tgcctttgta gattttgctc acgttttttgg gtgataggac   9240 caaaagcagt agtgtctagg ccactaggag acaaggcaaa ccattatctg tgaaagcctg    9300
ggttttctga gaggaagcat gctggacact gccagtagag ggagaagtca tggtgtgaag    9360
ttttccatga tgagagataa ggacagctag ggcatgggga tgcagaggat gttcttgttg    9420
ttgatggtgt tgtggaggtt gtaccccaag tctctgggat aagacagccc catgcacata    9480
gaggtcatga aaaatgtgag gaccctggac actgagtgtc acggctttgg ggacagtgat    9540
gacatgtccc tgtgtccaaa cagctcagtc agcttatcta aagggatgg agagtacttc     9600 tgtgggaaca gttggagctg aagaacagag aacatttcct ttgatgtttg gactctacgg    9660
aatctttggg aattgtgttc aagtccagga ggaatggctg aaaacatgat tgagataaat    9720
```

```
ttgcagccag gaggttgaag acaaattagg atctgatttt attcaactgg gagtaaccat   9780
ggccaagcat aattcttctg gtggattctg aagttatttg gaatttgccc ataagatgaa   9840
ttttcctgaa gaaggaagga tgtggaggct gatactgagg ccccatttcc acatgtgaac   9900
ttctaagaaa ccacagcttt catccagagt ggagatgaat ggcactgggg tccacgttgc   9960
cagaatgcct ggggacaagg aatgaggact tgtcacccaa ggcacgagat ccatagtggc  10020
tacgggaatg aagccactgc ctttgtggaa atgactaatt cacccaaatc caaggtgttt  10080
tccacaactg agaggcctgg gctgaggata gagatttgag ccttaactga gacatcctac  10140
tgggaagttg catcagtggt cagtatctga ggccacagaa aatgtcacat gatggtgtgt  10200
cacagggctc cacatttagg acatttgtgt actcaaagag aatctttgac gaccatgact  10260
cagagaaatt tttaatgact taaaacaggt tttggatcat gttgatgatg acagatggtg  10320
caagccacct acctaaatcc ctctggggag gggtggtatt tctgcattgt tctcagagca  10380
gaaatgtgac atggatgtgg aggctctgga cagtgagatg tgaagctgga ggcatggctt  10440
ggcctcccta gaatgggtgt ggccagggca aagctgggac atcctcaacc caaaggtttg  10500
cataactgga tttgaactcc ttatagatat tcctaaacag tggtgatacg aaggggagg  10560 gaggaggaaa aaaggatggc tcttcatcaa gagcaaaagc aagagattca gataggagat  10620
ttcacttggc ttttctagtc ttgggtgggg acccattatg gaagtgaaga gctctggaat  10680
cttccagaga aacaagcatg ggtatccttt aacaggtccc agatagccag ttaccgcaga  10740
acaatgtcct gttaccagaa gcttattgca gaccttgtaa cctgaatcat tgtgttggcc  10800
cagggcacac ccaggagggt ggcttgggaa ggagattcca ggctgaggta aataccgaca  10860 tctgattcc tgacattgag taggaaagca tttcagagac aagctccaag agctttggaa  10920 agggaacat tcacccactt cccacaattt ataaggggc tggcagtggt tgttttgggg  10980
aggataataa tgggaaaaga gaacggggta tgttatggca cacagaacca aaaatgaaga  11040
ttcctaagta gtaatctatt agtgagggaa ttcttgggca atttcaaaaa actcaaaacg  11100
tgttacagag aggagcccct tggactttgt aggagactcg tttgtctatc tggccccaag  11160
gcccagaagt agctgacaaa gagacccagt tgtcccctgg atgccaaact tggggagaga  11220
atggtcctgg gtggcagccc ctcccccatcc agcctcagtc agagctctcc agcaagtcag  11280
cctgcaggta gctatggagt tgcagtgtag tcctgttatt aatggctttc tgcttttggct  11340 ggatttcaga cataaagaag agaagaagga aaggtctggg tgatctgcct cttctgataa  11400
cactaaagtt gcacacatca cctcagctca tatttgatgg gctgggactt agtcactaag  11460
ccacacccat ctgcaaaagt gctggaaagc gttgcactct ctgatgacca catgcccagc  11520
taaatattga ggtcatatat tcctatataa taagacataa gcaaagtgca gtcactgaga  11580
atcactagca gtttacacca cgagtatctt cacagcccag aaaagacact gggttgagtt  11640
aaaatgaaaa ctggaataaa tacaatgaga agatagaaag cctgctgaga acactggggt  11700
acttgagtgg aactttaaac agtgtctttg ctaatgtgta tggtaactgt tcagattgtc  11760
tgtttcttta agctaattgt tttctgattg ttgaagcaat aataactcat atcttgcttg  11820
agaaaaaatt aaaagtatg aaaaatcaaa tataattatc acactacc                11868
```

<210> SEQ ID NO 84
<211> LENGTH: 3275
<212> TYPE: DNA
<213> ORGANISM: Homo sapiens

<400> SEQUENCE: 84

```
gggccgcacg ccgccaccca gcagccaggg ccgcctctta aagggaggtg gccggcctta      60
aaggaccccc gcgcgcccag ccggcgggag cgcggcggcc cggctcccgc agggccgcgc     120
cgaggcaggc gagcccccgc ggcgcccagg cgcgggcccg ggccccccgcc gccgccgccg    180
ccgccgggcg cggcattttt attcaggcga cgcttaaggg agcccggccg cgcccggtgc     240
attgtgggag cggcccgcgg cccgttttcg ggaggaggcg gagggcgcaa agcgagccgg     300
tggatccata agaacccag ccaacccgca gagggagggg aggggctgag ctgtgaggag      360
agcggggccc aagaaccatg tctacgcggg agtcctttaa cccggaaagt tacgaattgg     420
acaaaagctt ccggctaacc agattcactg aactgaaggg cacaggctgc aaagtgcccc    480
aagatgtcct gcaaaaattg ctggaatctt tacaggagaa ccacttccaa gaagatgagc    540
agtttctggg agccgttatg ccaaggcttg gcattggaat ggatacttgt gtcattcctt    600
tgaggcacgg tgggctttcc ttggttcaaa ccacagatta catttacccg atcgtagacg    660
acccttacat gatgggcagg atagcgtgtg ccaatgtcct cagtgacctc tatgcaatgg    720
gggtcacgga atgtgacaat atgctgatgc tccttggagt cagtaataaa atgaccgaca    780
gggaaaggga taaagtgatg cctctgatta tccaaggttt taaagacgca gctgaggaag    840
caggaacatc tgtaacaggc ggccaaacag tactaaaccc ctggattgtc ctgggaggag    900
tggctaccac tgtctgccaa cccaatgaat ttatcatgcc agacaatgca gtgccagggg    960
acgtgctggt gctgacaaaa cccctgggga cacaggtggc agtggctgtg caccagtggc   1020
tggatatccc tgagaaatgg aataagatta aactagtggt cacccaagaa gatgtagagc   1080
tggcctacca ggaggcgatg atgaacatgg cgaggctcaa caggacagct gcaggactca   1140
tgcacacgtt caatgcccac gccgccactg acatcacggg cttcgggatt ttgggccatg   1200
cgcagaacct ggccaagcag cagaggaacg aggtgtcgtt tgtaattcac aacctcccgg   1260
tgctggccaa gatggctgcg gtgagcaagg cctgcggaaa catgttcggc ctcatgcacg   1320
ggacctgccc ggagacttca ggcggccttc tgatctgttt accacgtgag caagcagctc   1380
ggttctgtgc agagataaag tcccccaaat atggtgaagg ccaccaagca tggattattg   1440
ggattgtaga gaagggcaac cgcacagcca gaatcataga caaaccccgg atcatcgagg   1500
tcgcaccaca agtggccact caaaatgtga atcccacacc cggggccacc tcttaatcta   1560
gacagaaata gctgtttggt tttgtttttta aatagatcta tttcccttat cacttcaatt   1620
aaaagactata acaacaaaa atctcattgt gtctacacat cggggtgacc ttaggtcggt    1680
ttgtaagtgg atacaattaa taaaataaaa tccattgcct ttttttcctg ttacattaac    1740
tgaagatgca cctaatcttg aggcagcttc tgagttgaga attatattgt tatccaatac    1800
tgttgattca ttttgaatct ttagacactt atctcttgcc gcataggctt tttaaaggtg   1860
ctttcacata gcacaggcat tacccgtagt cgtgtcaaat agcagttggt gtcttcattt   1920
tatgtatatt tatcatataa gtctgatttt ttttttttaag cgtcttgaat ggttttctgg   1980
agagacagca ttggtaagtg gcacatgacg gtatcccagt cataagaggg ttgcatgatt   2040
cctttgagtg tttgatttga aaagcctagt cttgtctctc aagagcatct cggacccaga   2100
acattctcca gtagtgcatt cagttcaaca cagcaagtgc ttcattgcat ggaaaacact   2160
ttgaagacaa aaagaaatc ttatttcttt ttttgtagcc ttcctgatat ttacagtaat    2220
accattaact gttttatcga tagcaaaaaa ggatactttt tgcaatgtta ttagatgttc    2280
tatagtgcta caaggaattg ccttccgaat ggaggttcat gtataatact catttacaat    2340
```

```
tcaatatata attacacaaa taattttaa ataatcaa tagtaaagac tgttctgtgg    2400
atggtagtgt ttaatacatt ttctatttg tacagtgatt tcaggccttt tgttttctta    2460
aaatcagcag ctgtttggcc taattcttag cattattttg tcctttgcgc cagtactttt    2520
ttgtgcacgc ttttttgtgat ctgtgttaaa aacctgcatt gccaacattg cagctcgaac    2580
ttaaacttgt tattcaaata aatatttaat tttttaaatt gctcttgtat aatcagatgc    2640
cccttttagt attatttag aagcgttggg agggttttgc ctaaagtaca atttatcggg    2700
aaaaactaga ttttagtttt ataaaacttt taagtctttc atgggaccta tattttcttg    2760
aattaaattt tgtagttcta gaataaatag gcaatctaaa aagtgttct ctgtgttatg    2820 taaagtggag gcttccttat atttaacct actaagcaat gaggagggat tcctgtcatt    2880
aagcacaagg gcgctggatc ctcaagtgcc catcttcgtg agagaaaaag cagcacatcc    2940
tgcccatttc tggtgctttc tgctcacagg caccaaagct gcacatgtaa actgacttct    3000
tgccaaagga aatgacccct gggaagttca agctcctgga agaggcttta actcggacgc    3060
gccctcctcc aggaaccagt gggcagggca gccttcatgc atgtgtaact ggacctccag    3120
ccataagcat ggtgtgcagt atggaagagc ctgctacgga actgaaagtg attggacatt    3180
ttataggaat tgatagagat gttggtcctc aaaagctaca aaccagtggt ctgcaaaata    3240
aagtgtgttg gaaacctcta aaaaaaaaaa aaaaa    3275
```

<210> SEQ ID NO 85
<211> LENGTH: 1179
<212> TYPE: DNA
<213> ORGANISM: Homo sapiens

<400> SEQUENCE: 85

```
ccagtgttcc cagttcccac cagtccaact gcgaggagtg cgacgtgagt ctgagtctga     60
tccctccgaa aaccgtactt ccggcgctgt ctcggaggcc tccgtcccc tcccttgtcc    120 gtcttctaac tcttccccac gccaggtccg tcaagcctaa gtccttgagt tccgggtccg    180
ggcagcagag aaaggaagtc ctctcccctgg aggcctatct ccctcagaac tgcgcgagaa    240
gcgagacctt agaaggcagg gcttcccgcg aaggaccgga aaggagcgcc tactaaggac    300
gccgtcgagg tccggggcgc ctcaactcta tagctctaac tggctagaag tgcccaacgt    360
ggaatgtttc ttttttaaag gcggctcttg aagcgacccg gaagcggaag tggaagaaag    420
ttctagtggc ttgaggtatc cgcaggagcg gccgggtggc gggaggaacc gttacgggaa    480
ctgaagttgc ggattaagcc tgatcaagat gacaacctcc caaaagcacc gagacttcgt    540
ggcagagccc atgggggaga agccagtggg gagcctggct gggattggtg aagtcctggg    600
caagaagctg gaggaaaggg gttttgacaa ggcctatgtt gtccttggcc agtttctggt    660
gctaaagaaa gatgaagacc tcttccggga atggctgaaa gacacttgtg gcgccaacgc    720
caagcagtcc cggactgctt cggatgcctc tcgagagtgg tgcgacgcct tcttgtgatg    780
ctctctggga agctctcaat ccccagccct catccagagt ttgcagccga gtagggactc    840
ctcccctgtc ctctacgaag gaaaagattg ctattgtcgt actcacctcc gacgtactcc    900
ggggtctttt gggagttttc tcccctaacc atttcaactt ttttttggat tctcgctctt    960
gcatgcctcc ccgtcctttt tcccttgcc agttccctgg tgacagttac cagctttcct   1020
gaatggattc ccgccccat ccctcacccc caccctcact ttcaatccgt ttgataccat   1080
ttggctcctt ttttggcaga acagtcactg tccttgtaaa gttttttaga tcaataaagt   1140
```

```
cagtggcttt caaaaaaaaa aaaaaaaaa aaaaaaaa                        1179

<210> SEQ ID NO 86
<211> LENGTH: 1651
<212> TYPE: DNA
<213> ORGANISM: Homo sapiens

<400> SEQUENCE: 86
acgactgcgt gggtgagtcg tctataaaaa ctcatctctg cgcgtctctt cgccacattc    60
gcttcctgct ttcggtgtgt ctgttgtgtc ttgttgcggg caccgcagtc gccgtgaaga   120
tggcgtctac cagccgtttg gatgctcttc aagagtcac atgtccaaac catccagatg   180
cgattttagt ggaggactac agagccggtg atatgatctg tcctgaatgt ggcttggttg   240
taggtgaccg ggttattgat gtgggatctg aatggcgaac tttcagcaat gacaaagcaa   300
caaaagatcc atctcgagtt ggagattctc agaatcctct tctgagtgat ggagatttgt   360
ctaccatgat tggcaagggc acaggagctg caagttttga cgaatttggc aattctaagt   420
accagaatcg gagaacaatg agcagttctg atcgggcaat gatgaatgca ttcaaagaaa   480
tcactaccat ggcagacaga atcaatctac ctcgaaatat agttgatcga acaaataatt   540
tattcaagca agtatatgaa cagaagagcc tgaaggaag agctaatgat gctatagctt   600
ctgcttgtct ctatattgcc tgtagacaag aaggggttcc taggacattt aaagaaatat   660
gtgccgtatc acgaatttct aagaaagaaa ttggtcggtg ttttaaactt attttgaaag   720
cgctagaaac cagtgtggat ttgattacaa ctggggactt catgtccagg ttctgttcca   780
acctttgtct tcctaaacaa gtacagatgg cagctacaca tatagcccgt aaagctgtgg   840
aattggactt ggttcctggg aggagcccca tctctgtggc agcggcagct atttacatgg   900
cctcacaggc atcagctgaa aagaggaccc aaaaagaaat tggagatatt gctggtgttg   960
ctgatgttac aatcagacag tcctatagac tgatctatcc tcgagcccca gatctgtttc   1020
ctacagactt caaatttgac accccagtgg acaaactacc acagctataa attgaggcag   1080
ctaacgtcaa attcttgaat acaaaacttt gcctgttgta catagcctat acaaaatgct   1140
gggttgagcc tttcatgagg aaaaacaaaa gacatggtac gcattccagg gctgaatact   1200
attgcttggc attctgtatg tatatactag tgaaacatat ttaatgattt aaatttctta   1260
tcaaatttct tttgtagcaa tctaggaaac tgtattttgg aagatatttg aaattatgta   1320
attcttgaat aaaacatttt tcaaaactca gttttttgtt atatgttaca tgtaacttat   1380
gatacataat tacaaataat gcaaatcatt gcagctaata aagctgatag actttatttc   1440
cattacttat atatacatag tttttattt taataaattt atggaaagag caaaagcttt   1500
tgagaaccat tgttaacatc aacatcatag tttccagttt gaaaggatgt gtatgtgaga   1560
tttattatgt atattattaa acaagaagtg atgagcttgg gccttgaaag gcaccagctt   1620
gagagacatt aaaatgttct aagtaaaaaa a                                   1651

<210> SEQ ID NO 87
<211> LENGTH: 3227
<212> TYPE: DNA
<213> ORGANISM: Homo sapiens

<400> SEQUENCE: 87
cccactctgc agttgtctcc cgagcgctgg ctgcgccgcc cgagccgctg ggccggggaa    60
gcactggccg ttcgctcccg ggccggctcc gccaggcgct cgcaggcatg cagcccggga   120
gcaggaggcg ctccccgggc cgctgctgag ccggccgggg cggcggggac cagcgccagc   180
```

```
ggagccctc ccaccttgcc ccggggcaga cgagcggcgc cccgacaccc cctcttctcc      240 cgcagcccg ccagcgccac cccccgcggg ccgcagggc tcatgcagcc gccaagggag      300
aggctagtgg taacaggccg agctggatgg atgggtatgg ggagaggggc aggacgttca      360
gccctgggat tctggccgac cctcgccttc cttctctgca gcttcccgc agccacctcc      420 ccgtgcaaga tcctcaagtg caactctgag ttctggagcg ccacgtcggg cagccacgcc      480
ccagcctcag acgacacccc cgagttctgt gcagccttgc gcagctacgc cctgtgcacg      540
cggcggacgg cccgcacctg ccgggtgac ctggcctacc actcggccgt ccatggcata      600
gaggacctca tgagccagca caactgctcc aaggatggcc ccacctcgca gccacgcctg      660
cgcacgctcc caccggccgg agacagccag gagcgctcgg acagccccga gatctgccat      720
tacgagaaga gctttcacaa gcactcggcc acccccaact acacgcactg tggcctcttc      780
ggggacccac acctcaggac tttcaccgac cgcttccaga cctgcaaggt gcagggcgcc      840
tggccgctca tcgacaataa ttacctgaac gtgcaggtca ccaacacgcc tgtgctgccc      900
ggctcagcgg ccactgccac cagcaagctc accatcatct tcaagaactt ccaggagtgt      960
gtggaccaga aggtgtacca ggctgagatg gacgagctcc cggccgcctt cgtggatggc     1020
tctaagaacg gtggggacaa gcacggggcc aacagcctga agatcactga aaggtgtca     1080 ggccagcacg tggagatcca ggccaagtac atcggcacca ccatcgtggt gcgccaggtg     1140
ggccgctacc tgacctttgc cgtccgcatg ccagaggaag tggtcaatgc tgtggaggac     1200
tgggacagcc agggtctcta cctctgcctg cggggctgcc ccctcaacca gcagatcgac     1260
ttccaggcct tccacaccaa tgctgagggc accggtgccc gcaggctggc agccgccagc     1320
cctgcaccca gcccccga gaccttccca tacgagacag ccgtggccaa gtgcaaggag     1380
aagctgccgg tggaggacct gtactaccag gcctgcgtct tcgacctcct caccacgggc     1440
gacgtgaact tcacactggc cgcctactac gcgttggagg atgtcaagat gctccactcc     1500
aacaaagaca aactgcacct gtatgagagg actcgggacc tgccaggcag gcggctgcg     1560 gggctgcccc tggccccccg gcccctcctg ggcgccctcg tcccgctcct ggccctgctc     1620
cctgtgttct gctagacgcg tagatgtgga gggaggcgcg ggctccgtcc tctcggcttc     1680
cccatgtgtg ggctgggacc gcccacgggg tgcagatctc ctggcgtgtc caccatggcc     1740
ccgcagaacg ccaggaccg cctgctgcca agggctcagg cacggacccc tccccttcta     1800
gtgcacgtga caaggttgtg gtgactggtg ccatgatgtt tgacagtaga gctgtgtgag     1860
agggagagca gctcccctcg ccccgcccct gcagtgtgaa tgtgtgaaac atcccctcag     1920
gctgaagccc cccacccca ccagagacac actgggaacc gtcagagtca gctccttccc     1980
cctcgcaatg cactgaaagg cccggccgac tgctgctcgc cgatccgtgg ggcccctgt     2040 gcccgccaca cgcacgcaca cactcttaca cgagagcaca ctcgatcccc ctaggccagc     2100
ggggacaccc cagccacaca gggaggcatc cttgggctt ggcccaggc agggcaaccc      2160 cggggcgctg cttggcacct tagcagactg ctggaacctt ttggccagta ggtcgtgccc     2220
gcctggtgcc ttctggcctg tggcctccct gcccatgttc acctggctgc tgtgggtacc     2280
agtgcaggtc ccggttttca ggcacctgct cagctgcccg tctctggcct gggccctgc      2340 cccttccacc ctgtgcttag aaagtcgaag tgcttggttc taaatgtcta aacagagaag     2400
agatccttga cttctgttcc tctctctcct gcagatgcaa gagctcctgg gcaggggtgc     2460
ctgggcccca gggtgtggca ggagacccag tggatggggc cagctggcct gccctgatcc     2520
```

| | |
|---|---|
| tctgcttcct cctcacaacc ccaagagccc ccagcccggt ccatccacgt ctggagtctg | 2580 |
| gggagaggag cagggtctta ggactctcag ctctgagcat ccctggcagg gtcttcaacc | 2640 |
| tctaatctct tcccttaagc cctgtggcca cacagccagg agagacttgc cgctggctcc | 2700 |
| cgcctcattt cagcccaggg tgctcatcca ggggcccaga acagtcccac ctgtgctgct | 2760 |
| gtgcccacag cacaaagcca ggcttcactc ccaaaagtgc agccaggccc tggagggtga | 2820 |
| tcctgccagc agcccacag ctccacaccc tacccaccca tcggcagccc ctctgctgtt | 2880 |
| ccccagggac ctctcataca ctggccagga ggctgcagaa cgtgtgtctc ccctcccctc | 2940 |
| caagaggtcc tgctccctct gccagaaccg tgtgtgggcg ggtgggaggg cgctcggggc | 3000 |
| ccggcccctc cctctccctg ctggttttag ttggtcccta tgttggaagt aaaaagtgaa | 3060 |
| gcactttatt ttggttgtgt ttgctcacgt tctgcttgga agtggggacc cctcactgcg | 3120 |
| tccacgtgtc tgcgacctgt gtggagtgtc accgcgtgta catactgtaa attatttatt | 3180 |
| aatggctaaa tgcaagtaaa gtttggtttt tttgttattt tcttta | 3227 |

<210> SEQ ID NO 88
<211> LENGTH: 1980
<212> TYPE: DNA
<213> ORGANISM: Homo sapiens

<400> SEQUENCE: 88

| | |
|---|---|
| atttggatcc gttcagctcc cgcggagaag cgagaccgga tcaccgacgt gggcagagga | 60 |
| ctaccgaggg ccagcagaaa ttctgccct tcttcccgcg agtgctttcc cgctctccaa | 120 |
| accccactcc caggtggcca tggcctcatc gaccactcgg ggccccaggg tttctgactt | 180 |
| attttctggg ctgccgccgg cggtcacaac tcccgccaac cagagcgcag aggcctcggc | 240 |
| gggcaacggg tcgtggctg gcgcggacgc tccagccgtc acgcccttcc agagcctgca | 300 |
| gctggtgcat cagctgaagg ggctgatcgt gctgctctac agcgtcgtgg tggtcgtggg | 360 |
| gctggtgggc aactgcctgc tggtgctggt gatcgcgcgg gtgcgccggc tgcacaacgt | 420 |
| gacgaacttc ctcatcggca acctggcctt gtccgacgtg ctcatgtgca ccgcctgcgt | 480 |
| gccgctcacg ctggcctatg ccttcgagcc acgcggctgg gtgttcggcg gcggcctgtg | 540 |
| ccacctggtc ttcttcctgc agccggtcac cgtctatgtg tcggtgttca cgctcaccac | 600 |
| catcgcagtg gaccgctacg tcgtgctggt gcaccgctg aggcggcgca tctcgctgcg | 660 |
| cctcagcgcc tacgctgtgc tggccatctg ggcgctgtcc gcggtgctgg cgctgccgc | 720 |
| cgccgtgcac acctatcacg tggagctcaa gccgcacgac gtgcgcctct gcgaggagtt | 780 |
| ctggggctcc caggagcgcc agcgccagct ctacgcctgg gggctgctgc tggtcaccta | 840 |
| cctgctccct ctgctggtca tcctcctgtc ttacgtccgg gtgtcagtga agctccgcaa | 900 |
| ccgcgtggtg ccgggctgcg tgacccagag ccaggccgac tgggaccgcg ctcggcgccg | 960 |
| gcgcaccttc tgcttgctgg tggtggtcgt ggtggtgttc gccgtctgct ggctgccgct | 1020 |
| gcacgtcttc aacctgctgc gggacctcga ccccacgcc atcgaccctt acgcctttgg | 1080 |
| gctggtgcag ctgctctgcc actggctcgc catgagttcg gcctgctaca acccccttca t | 1140 |
| ctacgcctgg ctgcacgaca gcttccgcga ggagctgcgc aaactgttgg tcgcttggcc | 1200 |
| ccgcaagata gccccccatg ccagaatat gaccgtcagc gtggtcatct gatgccactt | 1260 |
| agccaggcct tggtcaagga gctccacttc aactggcctc ctagggcacc actcgaggtc | 1320 |
| aatctggtgc ttattctcag caccagagct agctaagcca catagggca acatttccag | 1380 |
| cccagccctc ttgtccggct gtctgtcttg tccttgtgtg tttgtaaaat gttaagcggg | 1440 |

| | |
|---|---:|
| ctttggtgag agtcttgctc tttgcttggg ggaggccaaa gagagggaag aggatttctt | 1500 |
| atttcttctt tatgcccttg aaggacaaac aaaactttt ctccacgttc agaaaagtat | 1560 |
| ttcagaacca cgattgcctt cctggcgtcc cctcctcctg ctcgttggtg aaatgaacaa | 1620 |
| tatgaatggg atttaaaagg aatgcattgg gcttggtaaa gattttcagt ttgcctttag | 1680 |
| aaaaaggacc cagctgagag taccatgata ttgcttagtc catttgaacc cttgcattcc | 1740 |
| tagaatttca ggtaaatatg tattaaaact ctacatctag gatttcagca tttcctgagt | 1800 |
| aagacccttta tatgccaaaa gggtttcgtt ttaaaaccac ttgagtttat agtacaaaaa | 1860 |
| cacctacaag ctccctttag aaaggtcttg ctattgtttc tcccctttcc tccccaacta | 1920 |
| ctatttaaaa atgatgagac gaattagtca atgaagagat agataaataa agaggaaaag | 1980 |

<210> SEQ ID NO 89
<211> LENGTH: 3700
<212> TYPE: DNA
<213> ORGANISM: Homo sapiens

<400> SEQUENCE: 89

| | |
|---|---:|
| atttcacagt cgccatgacg accaggaggt ccgctagtca acggctcgtc aacggctgcg | 60 |
| gggacaagtc cgttgaggct gccaggcgag tcaggccttt ctggacctcg cctgactcgg | 120 |
| ctgggctgtg cctgaaattg acccagctcc actaggaatt atgaagaaac aaggactccg | 180 |
| ggaagaggtg cacgaactgc aggcgcggtg gttccccagc agaaccactc tgcatcgggg | 240 |
| aattgaaaac aaggaattcc ccaaccaaac aggggcacag gctgtgtttg cagctcctgt | 300 |
| aaaagctcca tacccagagc cgtgtctccc agctcccagc cgtctttgtg gcaattctac | 360 |
| attggttaca tttagtaaca ctttttgaaa atgatcatca tttctctcac ctctcatctt | 420 |
| tggaacggga gatgactttt tgcattgaaa cggttaggtt tcttcttcta acgaattaat | 480 |
| ttgtggttta agaatagcca gaccgagagg tgacagcatg ctggcagtcc tcagagccct | 540 |
| tgcttgctct cggcacctcc cctgcctggg ctcccgcttt ggtggcattt gaggagccct | 600 |
| tcagtcccc actgcactgt gggagcccct ttctgggctg gccaaggccg gagcccactc | 660 |
| cctcagcttg cagggaggtg tggagggaga gacacgagcg ggaaccgggg ctgtgtgctg | 720 |
| cacttgcggg ccatctggag ttccgggtgg gcgtgggctt ggtgggcccc gcactcagag | 780 |
| cagccagcca gccctgctgg ccccgggcaa tgggggactt agcacctggg ccagtggctg | 840 |
| cggagggtgt actgagtccc ccagcagtgc tggcccaccg gcgctgcgct cgatttctcg | 900 |
| ctgggccttg gctgccttcc cacggggcag ggctcgggac ctgcagcccg ccatgcctga | 960 |
| gcctcctacc caatccatgg gctcctgtgc ggcctgagcc tccccgacga gcaccacccc | 1020 |
| ctgctccacg gcgcccagtc ccatcgacca cgcaagggct gaggaatgcg agcgcccggc | 1080 |
| acaggactgg caggcagctc cacctgcagc cccagtgcag gatccactag gtgaagccag | 1140 |
| ctgggctcct gagtctggtg gggacgtgga gagtctttat atctagctca gggattgtaa | 1200 |
| atacaccaat cagcaccctg tgtttagctc aaggtttgtg agtgcaccag tcaacactct | 1260 |
| gtatctagct gctctggtga gggcgtggag agtctttatg tctagctcaa ggattgtaaa | 1320 |
| tacaccaatc agcactctgt gtctagctca aggattgtaa atacaccaat cggcactctg | 1380 |
| tatctagctc aaggtttgta aacacaccaa tcagcaccct gtgtttagct caaggtttgt | 1440 |
| gagtgcacca gtcgacactc tgtatctagc tgccctgatg gggacgtgga gaacctttgt | 1500 |
| atctagctca gggattgtaa acgcaccaat cagcgccctg acgaaacagg ccactcggct | 1560 |

```
ctaccaatca gcaggatgta ggtggggcca gataagagaa taaaagcggg ctgcccgagc      1620
cagcattggc aacccgctcg ggtccccttc cacactgtgg aagctttgtt ctttcgctct      1680
ttgcaataaa tcttgctact gctcactctt tgggtccacg ctgcttttgt gagctgtaac      1740
actcaccatg aagatctgca gcttcactcc tgagcccagc gagaccacga gcccaccggg      1800
aggaacgaac aactccagac acgccacctt aagagctgta acactcaccg cgagggtcca      1860
ccgcttcatt cttgaagtca gtgagaccaa gaacccacca attccggaca caagactatg      1920
agggacttta ttattcttac ttcaagacca ttattgaagc accttcattt ttgggaggac      1980
tgtggatgat tatgaatgac aggcttactg aatatcctct tgtaattaat gcagtaaaac      2040
gcttccatat ttatccagag aattctggag tccaaggaag accaagatca aggcgccagc      2100
agatttggtg tctggtgaag gctgctctcc gcttccaaga tggtgccttg atgttgcatc      2160
ttcctgaagg agaggaacac tgtgtcctca catggcagac agtaggagag taatcatagc      2220
ctcctggtat cgcacattca tgggaatagt gaatttattt ggactagaaa ctaagacctg      2280
ctggaatgtc accagaatag aacctcttaa tgaagttcaa agctgtgaag gattgcgaga      2340
tcctgcttgc ttttatgttg gtgtaatctt tattttaaat ggactaatga tgggattgtt      2400
cttcatatat ggaacatacc taagtggtac tgaactggga ggtcttatta cagtactgtg      2460 cttcttttc aaccatggag aggccacctg tgtgatgtgg acaccacctc tccgtgaaag      2520
tttttcctat cctttccttg tacttcagat gtatgtttta actttgattc tcaggacctc      2580
aagcaatgat agaaggccct tcattgcact ctgtctttcc aatgttgctt ttatgcttcc      2640
ctggcaattt gctcagttta tacttttac acagatagca tcattatttc ccatgtatgt      2700
tgtgggatac attgaaccaa gcaaatttca gaagatcatt tatatgaaca tgatttcagt      2760
tacccttagt ttcattttga tgtttggaaa ttcaatgtac ttatcttctt attattcttc      2820
atctttgtta atgacatggg caataattct aaagagaaat gaaattcaaa aactgggagt      2880
atctaaactc aactgctggc taattcaagg tagtgcctgg tggtgtggaa caatcatttt      2940
gaaatttctg acatctaaaa tcttaggcgt ttcagaccat atttgcctga gtgatcttat      3000
agcagccgga atcttaaggt atacagattt tgatacttta aaatacacct gttctcccga      3060
atttgacttc atggaaaaag cgactctgct gatatacaca aagacattat tgcttccagt      3120
tgttatggtg attacatgtt ttatctttaa aaagactgtt ggtgatattt cgcgtgtttt      3180
agctacaaac gtttatctaa gatgctgtct ttgcaggtgc catgcctaca atggcaagtg      3240
tcaagctgtc tacacttcat cccattgtga atcatccaca ttacgaagat gcagacttga      3300
ggcctggttg cagcatgctt gaaatctggg atgtggaaga cccttccaat gcagctaacc      3360
ctcccttatg tagcgtcctc cttgagccga gattgtgcca ctgcactcca gcctgggcga      3420
caaatcaaga ccccgtctcc aaaaaaaaaa aaaacaaaac ttgattggga tccaaaatca      3480
tacaactata cactaaaatc agtgaatatt accttatgta aattaaaaat taggaaatca      3540
aaagaaaagc atacatataa aaaacagttt tttctaagca tttctcattt gtagggtgtt      3600
tgaattacgt tgtatgttgt ctcatttcac ccccataaca aatctatgaa agaggtactt      3660
ttatccccat gttaacgtga ataaacccag gtttggaaaa                          3700
```

<210> SEQ ID NO 90
<211> LENGTH: 1109
<212> TYPE: DNA
<213> ORGANISM: Homo sapiens

<400> SEQUENCE: 90

```
gcttcgccgg ggccgggcgg ccggcgcccc cggctgctcc cgccgccgcc cggacccgcg      60
ccccgccggg gcagcggtgg tgagagcccc gactccccgg acgccgcccg ccgtgccatg     120
gggttcccgg ccgcggcgct gctctgcgcg ctgtgctgcg gcctcctggc cccggctgcc     180
cgcgccggct actccgagga gcgctgcagc tggaggggca gcggcctcac ccaggagccc     240
ggcagcgtgg ggcagctggc cctggcctgt gcggagggcg cggttgagtg gctgtacccg     300
gctggggcgc tgcgcctgac cctgggcggc cccgatccca gagcgcgcc  cggcatcgcc     360 tgtctgcggc cggtgcggcc cttcgcgggc gcccaggtct tcgcggagcg cgcagggggc     420
gccctggagc tgctgctggc cgagggcccg ggccggcag ggggccgctg cgtgcgctgg       480
ggtccccgcg agcgccgggc cctcttcctg caggccacgc cgcaccagga catcagccgc     540
cgcgtggccg ccttccgctt tgagctgcgc gaggacgggc gccccgagct gccccccgcag    600 gcccacggtc tcggcgtaga cggtgcctgc aggccctgca gcgacgctga gctgctcctg    660
gccgcatgca ccagcgactt cgtaattcac gggatcatcc atggggtcac ccatgacgtg    720
gagctgcagg agtctgtcat cactgtggtg gccgcccgtg tcctccgcca gacaccgccg    780
ctgttccagg cggggcgatc cggggaccag gggctgacct ccattcgtac cccactgcgc    840
tgtggcgtcc acccgggccc aggcaccttc ctcttcatgg gctggagccg ctttggggag    900
gcccggctgg gctgtgcccc acgattccag gagttccgcc gtgcctacga ggctgcccgt    960
gctgcccacc tccaccctg  cgaggtggcg ctgcactgag gggctgggtg ctggggaggg   1020
gctggtagga gggagggtgg gcccactgct ttggaggtga tgggactatc aataagaact   1080
ctgttcacgc aaaaaaaaaa aaaaaaaa                                      1109

<210> SEQ ID NO 91
<211> LENGTH: 923
<212> TYPE: DNA
<213> ORGANISM: Homo sapiens

<400> SEQUENCE: 91
cggcggcccc atggacctgc ccccgcagct ctccttcggc ctctatgtgg ccgcctttgc      60
gctgggcttc ccgctcaacg tcctggccat ccgaggcgcg acggcccacg cccggctccg     120 tctcaccccct agcctggtct acgccctgaa cctgggctgc tccgacctgc tgctgacagt    180
ctctctgccc ctgaaggcgg tggaggcgct agcctccggg gcctggcctc tgccggcctc    240
gctgtgcccc gtcttcgcgg tggcccactt cttcccactc tatgccggcg ggggcttcct    300
ggccgccctg agtgcaggcc gctacctggg agcagccttc cccttgggct accaagcctt    360
ccggaggccg tgctattcct gggggtgtg cgcggccatc tgggccctcg tcctgtgtca    420
cctgggtctg gtctttgggt tggaggctcc aggaggctgg ctggaccaca gcaacacctc    480
cctgggcatc aacacaccgg tcaacggctc tccggtctgc ctggaggcct gggacccggc    540
ctctgccggc ccgccccgct tcagcctctc tctcctgctc ttttttctgc ccttggccat    600
cacagccttc tgctacgtgg gctgcctccg ggcactggcc cgctccggcc tgacgcacag    660
gcggaagctg cgggccgcct gggtggccgg cggggccctc ctcacgctgc tgctctgcgt    720
aggaccctac aacgcctcca acgtggccag cttcctgtac cccaatctag gaggctcctg    780
gcggaagctg gggctcatca cgggtgcctg gagtgtggtg cttaatccgc tggtgaccgg    840
ttacttggga aggggtcctg gcctgaagac agtgtgtgcg gcaagaacgc aagggggcaa    900
gtcccagaag taacgccact gct                                            923
```

<210> SEQ ID NO 92
<211> LENGTH: 708
<212> TYPE: DNA
<213> ORGANISM: Homo sapiens

<400> SEQUENCE: 92

```
ccccgcaggc tgagggcagg tgggaagcaa acccggacgc atcgcagcag cagcagcagc      60
agcagaagca gcagcagcag cctccgcagt ccctccagag acatggatcc ccagacagca     120
ccttcccggg cgctcctgct cctgctcttc ttgcatctgg cttttcctggg aggtcgttcc    180
cacccgctgg gcagcccggg ttcagcctcg gacttggaaa cgtccgggtt acaggagcag     240
cgcaaccatt tgcagggcaa actgtcggag ctgcaggtgg agcagacatc cctggagccc     300
ctccaggaga gcccccgtcc cacaggtgtc tggaagtccc gggaggtagc caccgagggc     360
atccgtgggc accgcaaaat ggtcctctac accctgcggg caccacgaag ccccaagatg     420
gtgcaagggt ctggctgctt tgggaggaag atggaccgga tcagctcctc cagtggcctg     480
ggctgcaaag tgctgaggcg gcattaagag gaagtcctgg ctgcagacac ctgcttctga     540
ttccacaagg ggcttttttcc tcaaccctgt ggccgccttt gaagtgactc atttttttaa    600
tgtatttatg tatttatttg attgttttat ataagatggt tcttaccttt gagcacaaa     660
atttccacgg tgaaataaag tcaacattat aagctttaaa aaaaaaaa                   708
```

<210> SEQ ID NO 93
<211> LENGTH: 1535
<212> TYPE: DNA
<213> ORGANISM: Homo sapiens

<400> SEQUENCE: 93

```
cctccgctca gtccgggagc gcacgtgggc cgcggcgctc cgacctccgc tttcccaccg      60
cccgcagctg aagcacatcc cgcagcccgg cgcggactcc gatcgccgca gttgccctct     120
ggcgccatgt cgcagaacgg agcgcccggg atgcaggagg agagcctgca gggtcctgg    180
gtagaactgc acttcagcaa taatgggaac gggggcagcg ttccagcctc ggtttctatt     240
tataatggag acatggaaaa aatactgctg gacgcacagc atgagtctgg acggagtagc    300
tccaagagct ctcactgtga cagcccacct cgctcgcaga caccacaaga taccaacagg    360
gcttctgaaa cagatacccca tagcattgga gagaaaaaca gctcacagtc tgaggaagat   420
gatattgaaa gaaggaaaga agttgaaagc atcttgaaga aaaactcaga ttggatatgg   480
gattggtcaa gtcggccgga aaatattccc cccaaggagt tcctctttaa cacccgaag    540
cgcacggcca ccctcagcat gaggaacacg agcgtcatga agaaaggggg catattctct    600
gcagaatttc tgaaagtttt ccttccatct ctgctgctct ctcatttgct ggccatcgga    660
ttggggatct atattggaag gcgtctgaca acctccacca gcacctttg atgaagaact   720
ggagtctgac ttggttcgtt agtggattac ttctgagctt gcaacatagc tcactgaaga   780
gctgttagat cctgggtgg ccacgtcact tgtgtttatt tgttctgtaa atgctgcgtt    840
cctaatttag taaataaaa gaatagacac taaaatcatg ttgatctata attcacccta    900
tgggatcaat aagcatgtca gactgattaa tgtctactgt gaaaatttgg tagtaaattt   960
tcatttgata ttagatataa atatctgaat ataataatt ttaatatact agtcatgatg    1020
tgtgttgtat tttaaaaatt atctgcaacc ttaattcagc tgaagtactt tatatttcaa    1080
aagaatgaat aacattgata ataaaatcgc tactttaagg ggtttgtcca aaataaatat   1140
tgtggcctta tatcacacac tattgtagaa agtattattt aatttaaatg gatgcaggtt    1200
```

```
gtctactaaa gaaagattat atataactat gctaattgtt cataatcaac agaaaccaag    1260
atagagctac aaactcagct gtacagttcg tacactaaac tcttcttgct tttgcattat    1320
aaggaattaa gtctccgatt attaggtgat caccctggat gatcagtttt ctgctgaagg    1380
cacctactca gtatcttttc ctctttatca ctctgcattg gtgaatttaa tcctctcctt    1440
tgtgttcaac ttttgtgtgc ttttaaaatc agctttattc taagcaaatc tgtgtctact    1500
ttaaaaaact ggaaatggaa aaaaaaataa atctt                               1535
```

<210> SEQ ID NO 94
<211> LENGTH: 706
<212> TYPE: DNA
<213> ORGANISM: Homo sapiens

<400> SEQUENCE: 94

```
agctccaagg gcctcacctt cctgccgcca cctcctagga cagccagtcc agggccatga     60
agaccaagaa ccggccccca cggcgccggg ccccggtgca ggacacagag ccacccccg    120 gggaggggac gcccgacggg tccctgccga acccggggcc agagccggcc aagggtctgc   180
ggagccggcc ggcccgggcc gcagcaaggg ctccgggcga gggcaggcgc aggcggccag   240
gaccctccgg gcccggtggc cgtcgtgaca gcagcatcca gcggcggctg gagagcaacg   300
agagggagcg gcagcggatg cacaagctaa ataacgcctt ccaggccctg cgtgaagtca   360
tcccccacgt gcgcgcggac aagaagctct ccaagatcga gacgctcacg ctggccaaga   420
actacatcaa atcgctgacg gccaccatcc tgaccatgtc cagcagccgc ctcccaggcc   480
tggaggggcc gggccccaag ctctaccagc actaccagca gcagcagcag gtggctgggg   540
gtgcgttggg ggccacggag gcccagcccc agggccacct gcagaggtac tccacgcaga   600
tccacagctt ccgagagggc acctagcgcc cagtcctggg tggggtggc ggtggccgca   660 gctgcctggc ctgctcctcc cagccccagt ccctccaagc cacgag                  706
```

<210> SEQ ID NO 95
<211> LENGTH: 579
<212> TYPE: DNA
<213> ORGANISM: Homo sapiens

<400> SEQUENCE: 95

```
gcgcggtcgc tcagcagtga cgtgacacgc agcccacggt ctgtactgac gcgccctcgc    60
ttcttcctct ttctcgactc catcttcgcg gtagctggga ccgccgttca gtcgccaata   120
tgcagctctt tgtccgcgcc caggagctac acaccttcga ggtgaccggc caggaaacgg   180
tcgcccagat caaggctcat gtagcctcac tggagggcat tgccccggaa gatcaagtcg   240
tgctcctggc aggcgcgccc tggaggatg aggccactct gggccagtgc ggggtggagg    300
ccctgactac cctggaagta gcaggccgca tgcttggagg taaagtccat ggttccctgg   360
cccgtgctgg aaaagtgaga ggtcagactc taaggtggc caaacaggag aagaagaaga    420
agaagacagg tcgggctaag cggcggatgc agtacaaccg gcgctttgtc aacgttgtgc   480 ccaccttgg caagaagaag ggccccaatg ccaactctta gtcttttgt aattctggct     540 ttctctaata aaaagccac ttagttcagt catcgaaaa                           579
```

<210> SEQ ID NO 96
<211> LENGTH: 730
<212> TYPE: DNA
<213> ORGANISM: Homo sapiens

<400> SEQUENCE: 96

```
ctaaaaaagg gtagttgtgg ttggctctgc ctttgctgtc tttacctgaa tagaggtcag      60
gcccgggtcc aggggagcgt cccacggtcc cttcagcagc agcatctcta ggggaagtgg     120
ccggctgcag ggactgcacg gtgaggcaat ctgtgagcag gtctggatgg agctctgtgc     180
tggaccgcaa ctaagaggac aaaacggaag agacatcgat aaggagagcc ggtccttgga     240
atattttcct gggaaggcat catgctctat cagtgcaact cagcccacaa aaatttatca     300
agcagcaact acgggtcctc tgaacgggcc acaccacggt tgagccattg tgaccctgc      360
gacacacagg tccaggcctc ctggagtcac aaagctttga gcaacaggag aaccactaaa     420
gaagaagaaa cagctagctc ctgccttaac tgattaaccg aacttgcaac attccaccat     480
tgtgatatgt tcctgcccta ccctaaataa tcaatcggcc ttgtgatatc ctgccatgtg     540
aactccctcc acctcgtgac tacgcacctt gtgacattct tccctgccc gaaaagactg      600
ccccaactgt aaccttccac tacctatccc aaacctataa aaccagttcc actcccaccg     660
cccttcgctg actccctttt cagactcagc ccgctcgcac cggagtgaat aaacagcctt     720
gttgctcaca                                                            730
```

<210> SEQ ID NO 97
<211> LENGTH: 524
<212> TYPE: DNA
<213> ORGANISM: Homo sapiens

<400> SEQUENCE: 97

```
cctttctcgt tccccggcca tcttagcggc tgctgttggt tgggggccgt cccgctccta      60
aggcaggaag atggtggccg caagaagac gaaaaagtcg ctggagtcga tcaactctag     120
gctccaactc gttatgaaaa gtgggaagta cgtcctgggg tacaagcaga ctctgaagat     180
gatcagacaa ggcaaagcga aattggtcat tctcgctaac aactgcccag ctttgaggaa     240
atctgaaata gagtactatg ctatgttggc taaaactggt gtccatcact acagtggcaa     300
taatattgaa ctgggcacag catgcggaaa atactacaga gtgtgcacac tggctatcat     360
tgatccaggt gactctgaca tcattagaag catgccagaa cagactggtg aaaagtaaac     420
cttttcacct acaaaatttc acctgcaaac cttaaacctg caaaattttc ctttaataaa     480
atttgcttgt tttaaaaaca ttgtaaaaaa aaaaaaaaa aaaa                       524
```

<210> SEQ ID NO 98
<211> LENGTH: 1348
<212> TYPE: DNA
<213> ORGANISM: Homo sapiens

<400> SEQUENCE: 98

```
gcgggggggcg cgcgacgtga ccacccggac tcgaagcccg ccccgccccc gcccggctcg      60
ccggctccgg ggtctgctcc gggggtcgcg gacgcgggc cggcggcgg agccggcgcc       120
agagcatgcg gggcgcggcg cggcgcgcct ggggcgcgc ggggcagccg tggccgcgac       180
ccccgccc gggcccgccc ccgccgccgc tccgctgct gctcctgctc ctggccgggc        240
tgctgggcgg cgcgggcgcg cagtactcca gcgaccggtg cagctggaag gggagcgggc     300
tgacgcacga ggcacacagg aaggaggtgg agcaggtgta tctgcgctgt gcggcgggtg     360
ccgtggagtg gatgtaccca acaggtgctc tcatcgttaa cctgcggccc aacaccttct     420
cgcctgcccg gcacctgacc gtgtgcatca ggtccttcac ggactcctcg ggggccaata     480
tttatttgga aaaaactgga gaactgagac tgctggtacc ggacggggac ggcaggcccg     540
```

```
gccgggtgca gtgttttggc ctggagcagg gcggcctgtt cgtggaggcc acgccgcagc      600
aggatatcgg ccggaggacc acaggcttcc agtacgagct ggttaggagg cacagggcgt      660
cggacctgca cgagctgtct gcgccgtgcc gtccctgcag tgacaccgag gtgctcctag      720
ccgtctgcac cagcgacttc gccgttcgag gctccatcca gcaagttacc cacgagcctg      780
agcggcagga ctcagccatc cacctgcgcg tgagcagact ctatcggcag aaaagcaggg      840
tcttcgagcc ggtgcccgag ggtgacggcc actggcaggg gcgcgtcagg acgctgctgg      900
agtgtggcgt gcggccgggg catggcgact cctcttcac tggccacatg cacttcgggg       960
aggcgcggct cggctgtgcc ccacgcttca aggacttcca gaggatgtac agggatgccc     1020
aggagagggg gctgaaccct tgtgaggttg gcacggactg actccgtggg ccgctgccct     1080
tcctctcctg atgagtcaca ggctgcggtg ggcgctgcgg tcctggtggg gccgtgcggt     1140
gagggccgcg cgctgggagc cgcatgccct gggcccaggc ctgaccctgg taccgaagct     1200
gtggacgttc tcgccacact caaccccatg agcttccagc caaggatgcc ctggccgatt     1260
ggaaatgctg taaatgcaa actaagttat tatattttt tttggtaaaa agaaatgtc       1320 cataggaaac aaaaaaaaaa aaaaaaaa                                       1348

<210> SEQ ID NO 99
<211> LENGTH: 537
<212> TYPE: DNA
<213> ORGANISM: Homo sapiens

<400> SEQUENCE: 99
aacttccgct tccggttcct agcgttaact gcgaccgggg ttcagcgctc gggtgaggag       60
ctggtggcgt cggcaggttc gaggcgattc gaggtgaggg ggtcaagcgg agaggctcgg      120
agtcggagaa agctgtcgcg acccagccac ccagggtctg gggtcggtgg gagctccagc      180
taggatgatc gaggttgttt gcaacgaccg tctggggaag aaggtccgcg ttaaatgcaa      240
cacggatgat accatcgggg accttaagaa gctgattgca gcccaaactg gtaccgttg       300 gaacaagatt gtcctgaaga agtggtacac gatttttaag gaccacgtgt ctctggggga      360
ctatgaaatc cacgatggga tgaacctgga gctttattat caatagatga gaatcctcat      420
cttcctgccc cgctttcctc tcccatcctc atccccaca ctgggataga tgcttgtttg       480
taaaaactca ccttaataaa gacttagatg ttgctttgta aaaaaaaaa aaaaaaa        537

<210> SEQ ID NO 100
<211> LENGTH: 2063
<212> TYPE: DNA
<213> ORGANISM: Homo sapiens

<400> SEQUENCE: 100
gagcggcgcg ggacggccgg gacgcgcgga gaccccaaga cccacgcgca gaccgagcgg       60
cagccgggga ggggagcgcg ggccggccgg ccgagttcgc gggcaggggg cgccgggact      120
cccctctccg cgcccgggac gccgcccgcc ggatcgcgcc ttgggatgta gcgcccgctc      180
gccgcctccc ggactctcgt cggaccctcc gcccagcggc cctgcgtctt cccaggtgac      240
cacgccggct tcaggacatg cacggacaca gccgcaacgg ccaggcccac gtgccccggc      300
ggaagcgccg caaccgcttc gtcaagaaga acggccaatg caacgtgtac ttcgccaacc      360
tgagcaacaa gtcgcagcgc tacatggcgg acatcttcac cacctgcgtg gacacgcgct      420
ggcgctacat gctcatgatc ttctccgcgg ccttccttgt ctcctggctc tttttcggcc      480
```

-continued

```
tcctcttctg gtgtatcgcc ttcttccacg gtgacctgga ggccagccca ggggtgcctg      540
cggcggggg cccggcggcg ggtggtggcg gagcagcccc ggtggccccc aagccctgca      600
tcatgcacgt gaacggcttc ctgggtgcct tcctgttctc ggtggagacg cagacgacca      660
tcggctatgg gttccggtgc gtgacagagg agtgcccgct ggcagtcatc gctgtggtgg      720
tccagtccat cgtgggctgc gtcatcgact ccttcatgat tggcaccatc atggccaaga      780
tggcgcggcc caagaagcgg gcgcagacgt tgctgttcag ccaccacgcg gtcatttcgg      840
tgcgcgacgg caagctctgc ctcatgtggc gcgtgggcaa cctgcgcaag agccacattg      900
tggaggccca cgtgcgggcc cagctcatca agccctacat gacccaggag ggcgagtacc      960
tgcccctgga ccagcgggac ctcaacgtgg gctatgacat cggcctggac cgcatcttcc     1020
tggtgtcgcc catcatcatt gtccacgaga tcgacgagga cagcccgctt tatggcatgg     1080
gcaaggagga gctggagtcg gaggactttg agatcgtggt catcctggag ggcatggtgg     1140
aggccacggc catgaccacc caggcccgca gctcctacct ggccagcgag atcctgtggg     1200
gccaccgctt tgagcctgtg gtcttcgagg agaagagcca ctacaaggtg gactactcac     1260
gttttcacaa gacctacgag gtggccggca cgccctgctg ctcggcccgg gagctgcagg     1320
agagtaagat caccgtgctg cccgccccac cgccccctcc cagtgccttc tgctacgaga     1380
acgagctggc ccttatgagc caggaggaag aggagatgga ggaggaggca gctgcggcgg     1440
ccgcggtggc cgcaggcctg gcctggagg cgggttccaa ggaggaggcg ggcatcatcc     1500
ggatgctgga gttcggcagc cacctggacc tggagcgcat gcaggcttcc ctcccgctgg     1560
acaacatctc ctaccgcagg gagtctgcca tctgacctcc aggcccggcc ctcaccactg     1620
cccacaagag cctctgccgg gggtgggatg ccaggacacc ccctcccaca ctcaggacag     1680
agccaaccct ggctccgtgg accttctgga ggaaggtggg ggtttcaaag actgggggac     1740
cccttcctcc tgactccagc acccaggcct gggaagagct cggccccgat cagcctgagt     1800
tccgccagcg cctacttctg gtggctctag gtccccggat ccaccaccct tcccccactg     1860
actcttcaag gacgtgccct cttgctctc agaaccttgg ggaaggtggc tggactgctg     1920
ggcggggac atctcggggt ttcagggtgg gcagggggtt agtttgggga ggggggggtg     1980
cgtttctttt gcatgactgt ggcctgttgc tcatgacttt cttttgtaaa tatctataaa     2040
tggagacaga tggagacacc aaa                                             2063
```

<210> SEQ ID NO 101
<211> LENGTH: 6650
<212> TYPE: DNA
<213> ORGANISM: Homo sapiens

<400> SEQUENCE: 101

```
ggagtctgct tagttctgag gactgcgtgg gtccgcgcag agagctcctg ctaggcctgc       60
gcgtcccgtt ctaaattctt acccctttagt ccttgtcacc accccgccg tgggaacggc      120
ctgacagtca ctcgtcaaag gaagtggctg ccggcagctc ttgaccccgga atcggatcct     180
agtcccaccc cctccgctcc aggcttcctt ctgcaacagg cgtgggtcac gctctcgctc     240
ggtctttctg ccgccatctt ggttccgcgt tccctgcaca aaatgcccgg cgaagccaca     300
gaaaccgtcc ctgctacaga gcaggagttg ccgcagcccc aggctgagac agctgtgcta     360
cctatgtctt cagccttgag tgtcactgct gccttagggc agcctggacc tacccctccc     420
cctccttgct ctcctgcccc acaacagtgc cctctctcag ctgctaacca ggcttcccca     480
ttcccttccc cctctactat tgcctcgacc cctttagaag ttccttttcc ccagtcatcc     540
```

```
tctggaacag ccctacccttt gggaactgcc cctgaagccc caaccttcct accaaaccta    600
ataggggcctc ccatctcccc agctgcctta gctctagcct ctcccatgat agctccaact    660
ctgaaaggga cccccttcctc ttcagctccc ttagctctgg ttgccctggc tccccactca    720
gttcagaaga gttctgcttt tccacctaac cttcttactt cacctccttc agtggctgta    780
gctgagtcag ggtcagtgat aactctgtca gctcccattg ctccctcaga accaaagact    840
aatcttaata aagttccctc tgaggtagtc cctaatccaa aaggcacccc cagccctcca    900
tgtatagtca gtactgttcc ttaccactgt gtgactccca tggcctctat tcaatctgga    960
gtggcctccc ttcctcagac aacacccaca actaccctag ccatcgcttc ccctcaagtc   1020
aaagatacca ccatttcctc agttctgatt tctccacaaa acccaggaag cctcagcctg   1080
aaggggcctg ttagtccacc tgctgcctta tctctttcaa ctcagtctct tcctgtggtg   1140
acctcttctc aaaagactgc gggtcccaac acccccccag attttcccat ttctctgggc   1200
tctcatcttg cacctttaca tcagagttct tttggttctg tccaactttt aggtcaaaca   1260
ggtcctagtg ctttgtcaga ccctacagtg aagaccattt ctgtagatca ttcttccaca   1320
ggggcctctt atccttctca gagatctgta attcctcccc ttccttccag aaatgaggta   1380
gttcctgcta ctgtggctgc ctttccagtg gtggctccat ctgttgacaa aggtccctct   1440
accatctcta gcataacctg cagcccttct ggctccttaa atgtagctac ctcttttttca   1500
ttatctccta caacctctct cattctcaaa agctctccta atgccactta tcattatcct   1560
ttagtggccc aaatgcccgt ttcttctgtt ggaaccaccc cacttgtggt gactaaccc    1620
tgtacaattg ctgcagcacc tactactacc tttgaggtag ctacttgtgt ttctcctcca   1680
atgtcatcag gtcccataag taacatagaa ccaacttccc ctgctgcctt ggttatggca   1740
cctgtggctc ccaaagagcc ttctactcaa gtagcaacca ctctgaggat accagtctct   1800
cctcctctgc cagaccctga agacctcaaa aatctcccca gttcagtatt ggttaaattt   1860
ccaacacaaa aagacctcca aactgtacct gcctctcttg aaggagcccc tttctctcca   1920
gcccaagcag gactcaccac caagaaagac cctactgtat taccgttagt ccaggcagcc   1980
cctaaaaatt cccccttcttt ccaaagtaca tcctcttctc cagagatacc tctttctcct   2040
gaagccaccc tagcaaagaa aagccttggg gagcctctcc ctataggtaa gccagccagc   2100
agtatgacct cccctctggg tgttaactcc tcggcctctg taatcaagac agattcttat   2160
gcaggcccag actctgctgg tccgcttctc aaaagttctc tcattacccc aacagtggct   2220
gcatttcctt tggaaagtgc tgaccctgcc ggggtggctc ccacaactgc caaaggtacc   2280
tcaacttata caactacagc cagccctttt ctagaaggaa ctgtctcttt agctcctaaa   2340
aaccacccag ttaaggaagg tactcttact actttacccct tggttcctac agcttcagaa   2400
aattgccctg tggctccatc ccccagaat acctgtgctc ctctggctac cttagtgctg   2460
gcccctgaaa tccaaagtc tgtgccctca ccctctcttc cccagctgg gactcctcca   2520
ggtacaaaaa aggttgatgg tatttctcat acttcagcat tggcacctgt tgcttcctct   2580
cccaaagagt gcccaactga ggactctggt gcttctgcta ctgcatcttc caaaggaact   2640
ctgacttacc tagctgattc cccatctcct ttagggggtta gtgtgtctcc tcagactaaa   2700
agacctccaa ccaagaaggg ttctgctggc cctgatactc ctattggaaa tctctcatcc   2760
cctgttctc cagttgaagc ttcatttctt ccagagaata gtctttcttt ccaaggctct   2820
aaagactcac cagccacgac gcattctccc actcctccat cccccaaagg ggcccctact   2880
```

```
ccctcagctg tgactcctct gtctcccaaa ggagtaacac tacccccaa agagaccccc    2940
actccttcag tggtgaatct gcccttcccc aaagagggtc cagctactcc agcacccaaa    3000
caggctcctg ctctatccat gacttcttcc tcccccaaaa aggcccgagc aactccagcc    3060
cctaaaggaa tccagcttc cccatccccc aaaggggccc ccacaccccc agctgcaact    3120
cctcctccc ctaaaggagg cccagctacc ccatcccga aatgggcccc cacacccca    3180
gctgcaactc ctccctcccc aaaaggaggt ccagctactc catccccaa aggggcccc    3240
acaccccag ctgcaactcc tccctccccc aaggaggtc cagctactcc atccccaaa    3300
ggggccccca caccccagc tgtgactcct ccctccccca aggaagtcc agcagctacc    3360
ccattcccca aggggcatc cacaccccca gctgcaactc ctccctcccc caaaggaagt    3420
ccagcagcta ccccactccc caagggggcc cccacaaccc cagctgcaac tcttccctcc    3480
ccaaaaggag gtccagctac cccatccctc aaggggccc ccactccccc agctgcgact    3540
cctcctccc caaaggagg cccagctacc ccatccccca aggggcccc catgccccca    3600
gctgcaactc ctccctcccc aaaaggaggt ctagctaccc caccccacaa aggggcaccc    3660
acaaccccag ctgcaactcc tccctcccca aaaggaggtc tagctacccc acccccaaaa    3720
gggcccccca caacccagc tgcaactcct ccttccccaa aaggaggtct agctacccca    3780
ccccaaaag gggccccac aaccccagct gcaactcctc cttccccaaa aggaggtcta    3840
gctaccccat ccccaaagg ggccccaca acccagctg caactcctcc ctccccaaaa    3900
ggaggtctag ctaccccatc cccaaaggg gccccacaa cccagctgc aactcctccc    3960
tccccaaaag gaggtctggc tacccatcc cccaaagggg ccccacaac cccagctgca    4020
actcctccct ccccaaaagg aggcccagct accccacccc caaagggggc cccactccc    4080
ccagctgcaa ctcctccctc cctaaaagga ggtctagcta ccccacccca caaagggcc    4140
cccaatcccg cagttgtaac tcctccctct ccaaaaggag gcccagctac ctcacccccc    4200
aaggggcccc ccactcctcc agctgcaact cctccctccc caaaggaag cccaggtacc    4260
ccaccccca aggggcccc cactccccca gctgtaactc ctccctcccc taagggggacc    4320
cctactctcc cagctacaac tccctcctct aaaggaggcc caactactcc atcctccaaa    4380
gagggcccca ctcccccagc tgcaaccccc tcccacaaag gaggtcccgc tatgactcct    4440
ccctccccca aaagaggacc agctatccca tctcccaaag gggaccccac ttccccagca    4500
gtgattcctc tctccccaa aaaggctcca gcaactccag tcaccagaga aggcgcagcc    4560
acccatcca aaggagatct cactcccca gcagtgactc ctgtctccct caaaaaggcc    4620
ccagcaactt cagccccaa aggaggccca gctacccat cctccaaagg ggatcccacc    4680
ctcccagcag tgactcctcc ttccccaag gagcccccag cccccaaaca gttgccact    4740
tcttcctctc ccaaaaggc cccagcaact ccagccccca tggggccccc cactctgcca    4800
gctgtgattc cttcttcccc caaagaggtc cagctaccc catcctccag aaggggacccc    4860
attgccccaa cagcgactct tctctaaa agacccag caactctagc ccccaaagag    4920
gccctcattc cccagctat gactgttccc tccctaaaa agacccagc aattccaacc    4980
cccaaagaag cccagctac ccatcctcc aagaggcct ccagtcccc agcagtgact    5040
ccttccactt acaaggggc cccatcccc aaagagctcc tcattccacc agctgtgact    5100
tctccttccc ccaaagaggc acctactcct ccagctgtga ctcctccatc ccccgaaaag    5160
ggcccagcaa ctcagccccc caaagggact cccactccc cacctgtgac tccttcctcc    5220
ctcaaagact cccctacttc cccagcttct gtcacatgta aaatggggg cactgttcct    5280
```

```
caagcatcta aagggcttcc agcaaagaaa ggccccacag ctctgaaaga agtacttgtt    5340
gccccagctc cagaaagcac gccaatcatc acagctccca ctcggaaagg tccacagacc    5400
aaaaagagtt ctgctacttc acctcctata tgcccagatc cctcagctaa gaatggttct    5460
aaaggacccc tttccacagt ggctccagcc cctctactcc ctgttcagaa agactcttca    5520
aagacagcaa aaggcaaaga tgcttctcat tccccaaagg gccccttggc tcctcctgag    5580
tctaaggcgt ccacccctct aacagcagct gcctttgaga aggtccttcc taaacctgaa    5640
tcagcatctg tctctgcagc accctcccca ccagtctctc tgcctcttgc ccctcccca    5700 gttcccactc tgcctcctaa acagcaattt ctgccgtcct ctcctgggct ggtgttggaa    5760
tcaccctcta accccttgc ccctgctgat gaggatgagc tgctgcctct gattccccg     5820 gaaccaatct ctgggggagt gccttttccag tcggtcctcg tcaacatgcc caccccctaaa   5880 tctgctggaa tccctgtccc aaccccctct gccaagcaac ctgttacgaa gaacaacaag    5940
gggtctggaa cagaatctga cagtgatgaa tcagtaccag agcttgaaga acaggattcc    6000
acccaggcaa ccacacaaca agcccagctg gcggcagcag ctgaaattga tgaagaacca    6060
gtcagtaaag caaaacagag tcggagtgaa aagaaggcac ggaaggctat gtccaaactg    6120
ggtcttcggc aggttacagg agttactaga gtcactatcc ggaaatctaa gaatatcctc    6180
tttgtcatca caaaccaga tgtctacaag agccctgctt cagatactta catagttttt    6240
ggggaagcca agatcgaaga tttatcccag caagcacaac tagcagctgc tgagaaattc    6300
aaagttcaag gtgaagctgt ctcaaacatt caagaaaaca cacagactcc aactgtacaa    6360
gaggagagtg aagaggaaga ggtcgatgaa acaggtgtag aagttaagga cattgaattg    6420
gtcatgtcac aagcaaatgt gtcgagagca aaggcagtcc gagccctgaa gaacaacagt    6480
aatgatattg taaatgcgat tatggaatta acaatgtaac catatggaag caactttttt    6540
tggtgtctca aaggagtaac tgcagcttgg tttgaaattt gtactgtttc tatcataaat    6600
aaagttatgg cttcttgttg gatgaattca aaaaaaaaaa aaaaaaaaa              6650
```

<210> SEQ ID NO 102
<211> LENGTH: 2611
<212> TYPE: DNA
<213> ORGANISM: Homo sapiens

<400> SEQUENCE: 102

```
aggaacgact gtgctacgtt gccagaaggg gcgggacctg caacgtccga cagaacgagg      60
ggacgtaacg gaggcaggtt ggagccgctg ccgtcgccat gacccgcggt aaccagcgtg     120
agctcgcccg ccagaagaat atgaaaaagc agagcgactc ggttaaggga aagcgccgag     180
atgacgggct ttctgctgcc gcccgcaagc agagggactc ggagatcatg cagcagaagc     240
agaaaaaggc aaacgagaag aaggaggaac ccaagtagct ttgtggcttc gtgtccaacc     300
ctcttgccct tcgcctgtgt gcctggagcc agtcccacca cgctcgcgtt tcctcctgta     360
gtgctcacag gtcccagcac cgatggcatt ccctttgccc tgagtctgca gcgggtccct     420
tttgtgcttc cttcccctca ggtagcctct ctccccctgg gccactcccg ggggtgaggg     480 ggttaccct tcccagtgtt ttttattcct gtggggctca ccccaaagta ttaaaagtag      540
ctttgtaatt ccttgagcgc ctggtttgac tggggacttg ggggatggg gttggaagaa      600 tgactgccct ttcccaccaa aaaagggaga actctttaga ttcagattgt gggtatgtag     660
acttaataag tgaaacatca cagaagaagc ctttattata caatgacaac caaacaagta     720
```

```
ctccggatat gcagtagagg aatcctctaa gaaccataga gacttctttt ctgtgatttt     780
tgttccccac ccttgaacac catctctagg atggagttgg cctaagagtg aatgctgcaa     840
gatctgtgtt tatgcctctt ttcctcattc ttcctcagtt tgttcgtctg cttgaaagtt     900
ggccaaaaaa tcctgctgct caccgacttc ccgtggtcag ctgctgtcaa gcgttcactt     960
tctcttctgt cattcctcat ggaatgaggg tggttttgtc ttcccgcttc ccttgacctc    1020
aaaatcagga ttaaaacctg gggtagcctc tgtgctcctt tcttctatgc cctggtttgt    1080
tctgtggttc tgggcttctt atatccgtgt gcccagggct gaactcctta ttttcctttc    1140
tccaagggca gagccgagtc ttcagtccct gttggtcttt ccccaccccc acttccagcc    1200
caagagccag gaaagggctg gtgccacact gtctgctggg atcagcggtg gttctttgag    1260
ctgctgattt gggtgttagg ctcttgagct gggatgcaga tgtaacagta gctccagtga    1320
gtcagacact ctgcccagca cattagactg tgtttgacca cttcttccag ttcatagtat    1380
tgacttcagc ccaaacggag ataactccct gtgtgtcctt gaggtattga gctgggctgg    1440
acagctcccc ttgagccaac tctaggagta caatgtcagg gaaccccag tttgtgaaaa     1500
ggacttagac tggaggatat ttgttatctg gggatatgat gcggtggcgg cggcgcctca    1560
agataagggg ctggggtttc tgggtggggg gccaacagag tggtgccagt aacagcccca    1620
gatagaggag tacgcaggcc cagcatgagg caaccttgac ccagaaggtg gcccagctac    1680
ccttgatgaa ggtcttttcc agttctgctc cctcatagct gtgtaaccaa aggctctggt    1740
tagagaatat gaagggcctt agcttttaga cctgttctac ctcctcacca aatataatgg    1800
cagacccatg tgtgtctgga atggccttga attgctcttt ccttaaaata gctagctctt    1860
caggagagta tctaaggccc actccatctt acctgaacca gttggtaagg gtaaccatga    1920
catagagtga ggcaaggaag aagacgaagt ggaaggcaga atagttgtag gaaagatgct    1980
ggacttggac tggaggagct ggaggggttt cttggtcagc tggcctcgca gccccacccc    2040
tttgccctgg agagaggaaa tggctgctgg gagcagagct gctgaaacac ctcttcccct    2100
ctcccccaac tacctttgtt aaggctcttg agggttctta tggcactcca cagagatcta    2160
ccacttctta tggttcctca cttggcactc acctttgtct gcctccactg tttcagggca    2220
gcagaaacac agtgagggct ctgcaaaac agaacgcagg ttttggaatg gtcttaaaag     2280
atgtgagggt gttaatctag gaaacttccc ccgtgaaaag attggtctag tattaaaaag    2340
tggaggcaca cctgggttca aattctagct ccagcatata agtggctgtg cagactttgg    2400
taagatgttt aatcttttgt gcctcgattt ctccatttgt aaaatggagc aaataccac     2460
ctcacagggt tgttgtgagg gttaaattaa atgagattat gtaaaagtat ctagcacagt    2520
tgcctagcac attgtgggta ctcaataaaa ggtaacagca gctataatct gagcattctg    2580
ggtagaggtt ggtaaaaaaa aaaaaaaaaa a                                   2611
```

<210> SEQ ID NO 103
<211> LENGTH: 1348
<212> TYPE: DNA
<213> ORGANISM: Homo sapiens

<400> SEQUENCE: 103

```
gtttgtcctg gagcccagat ggactgtggc cgggcaagtg gatcacaggc ctggccagcc      60
taggagttgc cacatgtgag gggccgaggg gctcaaggag gggaacatcg gggagaggag     120
cctactgggt ggaggctggg ggtcccagca ggaaatggtg agacaaaggg cgctggctgg     180
caggaagaca gcacaggaag gtcctagagg ttcctcagtg cagctggact ctcctggaga    240
```

```
ccttcacaca ccctgacatc tgggccccgc gccacgaggg tgctttcact ggtctgcacc      300
atggcccagg ccctgggatt ttgaacagct ccgcaggtga atgaaaggaa catggagctg      360
atccaggaca tctctcgccc gccactggag tacgtgaagg gggtcccgct catcaagtac      420
tttgcagagg cactggggcc cctgcagagc ttccaggccc ggcctgatga cctgctcatc      480
agcacctacc ccaagtccgg caccacctgg gtgagccaga ttctggacat gatctaccag      540
ggcggtgacc tggaaaagtg tcaccgagct cccatcttca tgcgggtgcc cttccttgag      600
ttcaaagtcc cagggattcc ctcagggatg gagactctga aaacacacc agccccacga       660 ctcctgaaga cacacctgcc cctggctctg ctcccccaga ctctgttgga tcagaaggtc      720
aaggtggtct atgttgcccg caacgcaaag gatgtggcgg tttcctacta ccacttctac      780
cacatggcca aagtgtaccc tcaccctggg acctgggaaa gcttcctgga aagttcatg       840 gctggagaag tgtcctatgg gtcctggtac cagcacgtgc aagagtggtg ggagctgagc      900
cgcacccacc ctgttctcta cctcttctat gaagacatga aggagaaccc caaagggag       960 attcaaaaga tcctggagtt tgtggggcgc tccctgccag aggagactgt ggacctcatg     1020
gttgagcaca cgtcgttcaa ggagatgaag aagaacccta tgaccaacta caccaccgtc     1080
cgccgggagt tcatggacca cagcatctcc cccttcatga ggaaaggcat ggctggggac     1140
tggaagacca ccttcaccgt ggcgcagaat gagcgcttcg atgcggacta tgcggagaag     1200
atggcaggct gcagcctcag cttccgctct gagctgtgag aggggttcct ggagtcactg     1260
cagagggagt gtgcgaatca agcctgacca agaggctcca gaataaagta tgatttgtgt     1320
tcaaaaaaaa aaaaaaaaa aaaaaaaa                                         1348

<210> SEQ ID NO 104
<211> LENGTH: 945
<212> TYPE: DNA
<213> ORGANISM: Homo sapiens

<400> SEQUENCE: 104
atgaccctgg gatccctggg aaacagcagc agcagcgttt ctgctacctt cctgctgagt       60
ggcatccctg ggctggagcg catgcacatc tggatctcca tcccactgtg cttcatgtat      120 ctggttttcca tcccgggcaa ctgcacaatt cttttttatca ttaaaacaga gcgctcactt     180
catgaaccta tgtatctctt cctgtccatg ctggctctga ttgacctggg tctctccctt      240
tgcactctcc ctacagtcct gggcatcttt tgggttggag cacgagaaat tagccatgat      300
gcctgctttg ctcagctctt tttcattcac tgcttctcct tcctcgagtc ctctgtgcta      360
ctgtctatgg cctttgaccg ctttgtggct atctgccacc ccttgcacta tgtttccatt      420
ctcaccaaca cagtcattgg caggattggc ctggtctctc tgggtcgtag tgtagcactc      480 attttttccat taccttttat gctcaaaaga ttcccctatt gtggctcccc agttctctca      540
cattcttatt gtctccacca agaagtgatg aaattggcct gtgccgacat gaaggccaac      600
agcatctacg gcatgtttgt catcgtctct acagtgggta tagactcact gctcatcctc      660
ttctcttatg ctctgatcct gcgcaccgtg ctgtccatcg cctccagggc tgagagattc      720
aaggccctta acacctgtgt ttcccacatc tgtgctgtgc tgctcttcta cactcccatg      780
attggcctct ctgtcatcca tcgctttgga aagcaggcac cccacctggt ccaggtggtc      840
atgggtttca tgtatctctt cttcctcct gtgatgaatc ccattgtcta cagtgtgaag      900
accaaacaga tccgggatcg agtgacgcat gccttttgtt actaa                     945
```

<210> SEQ ID NO 105
<211> LENGTH: 1262
<212> TYPE: DNA
<213> ORGANISM: Homo sapiens

<400> SEQUENCE: 105

| | | | | | | |
|---|---|---|---|---|---|---|
| tgtgtcactt | ccggcctccc | tttagctgcc | atcttgcgtc | ccgcgtgtg | tgcgcctaat | 60 |
| ctcaggtggt | ccacccgaga | cccttgagc | accaaccta | gtccccgcg | cggcccctta | 120 |
| ttcgctccga | caaggtacaa | aaaggctctg | gacggcggcg | tggtaggagg | acgggagcgg | 180 |
| gggcgggaag | ttccctgaag | gagcgagaca | gggagggaca | gggcagagga | ggagaggaag | 240 |
| gcgatgcgac | ggacaggcgc | acccgctcag | gctgactctc | ggggcgagg | tcgagccagg | 300 |
| ggcggctgcc | ctggggcga | ggcgacgctg | tctcaacctc | cacctcgcgg | cggaacccga | 360 |
| ggacaggagc | ctcagatgaa | agaaacaatc | atgaaccagg | aaaaactcgc | caaactgcag | 420 |
| gcacaagtgc | gcattggtgg | gaaaggaact | gctcgcagaa | agaagaaggt | ggttcataga | 480 |
| acagccacag | cagatgacaa | aaaacttcag | ttctccttaa | agaagttagg | ggtaaacaat | 540 |
| atctctggta | ttgaagaggt | gaatatgttt | acaaaccaag | gaacagtgat | ccactttaac | 600 |
| aaccctaaag | ttcaggcatc | tctggcagcg | aacactttca | ccattacagg | ccatgctgag | 660 |
| acaaagcagc | tgacagaaat | gctacccagc | atcttaaacc | agcttggtgc | ggatagtctg | 720 |
| actagtttaa | ggagactggc | cgaagctctg | cccaaacaat | ctgtggatgg | aaaagcacca | 780 |
| cttgctactg | gagaggatga | tgatgatgaa | gttccagatc | ttgtggagaa | ttttgatgag | 840 |
| gcttccaaga | atgaggcaaa | ctgaattgag | tcaacttctg | aagataaaac | ctgaagaagt | 900 |
| tactgggagc | tgctatttta | tattatgact | gcttttaag | aaattttgt | ttatggatct | 960 |
| gataaaatct | agatctctaa | tatttttaag | cccaagcccc | ttggacactg | cagctctttt | 1020 |
| cagttttgc | ttatacacaa | ttcattcttt | gcagctaatt | aagccgaaga | agcctgggaa | 1080 |
| tcaagtttga | aacaaagatt | aataaagttc | tttgcctagt | atacagtttt | atttttttat | 1140 |
| ttcattgaca | ccgatctgta | cacagtaaaa | aaaattgctt | atagaaagct | aatcatggca | 1200 |
| tgtaatatgg | ctgataacct | ttggaattttg | attaaagatt | taaaatcaca | aaaaaaaaaa | 1260 |
| aa | | | | | | 1262 |

<210> SEQ ID NO 106
<211> LENGTH: 869
<212> TYPE: DNA
<213> ORGANISM: Homo sapiens

<400> SEQUENCE: 106

| | | | | | | |
|---|---|---|---|---|---|---|
| ggacagagcg | gcccggtcgc | cggcatggtt | tctccgtcct | gctgcagccg | gcgggaggca | 60 |
| gccagtccag | gcgcccgcta | gcttcggcgg | cgacccagac | ggggaaagcg | gaaggaatgt | 120 |
| cgcgtgcaag | caggcagctg | gtgtggaaga | atggcggtga | gccattcagt | gaaggagcgg | 180 |
| accatctctg | agaacagcct | gatcatccta | ctgcagggcc | tccagggccg | ggtaaccact | 240 |
| gtggacctgc | gggatgagag | cgtggcccac | ggacgcatag | acaatgtcga | tgctttcatg | 300 |
| aacatccgcc | tggccaaagt | cacctacacg | gaccgttggg | ggcatcaggt | caagctggat | 360 |
| gacctctttg | tgacaggccg | caatgtccgc | tacgtccaca | tcccagatga | cgtgaacatc | 420 |
| acctcgacca | ttgagcagca | gctgcagatt | atccatcggg | tgcgaaactt | tggtggcaag | 480 |
| ggccaaggcc | ggtgggaatt | tccccaaaa | aactgtaagt | gaggccctca | gcaagccctg | 540 |
| gccccaactc | ggagtcctcc | agtgatctcc | agagctagtt | ccctgccctc | acaccctgtc | 600 |

```
tggtacccga gaagaaagca gggccaggcc agaagctggt gtccaacaga caccacctgt    660
caaagctgcc tttcacaggg ttccacctcc cagactcact ctgggaccca gaatcctata    720
tgtggccttg gggtaggtga caatccccct ttttgatgat ctgaatctct gacttattga    780
ttatggaacc tgtcaagtag ttttcaactc tcccagtgag gataattaaa catgctcagc    840
ctgagccacc aaaaaaaaaa aaaaaaaaa                                       869
```

<210> SEQ ID NO 107
<211> LENGTH: 43
<212> TYPE: DNA
<213> ORGANISM: Homo sapiens

<400> SEQUENCE: 107

```
ttggggtccg aactgctggc tggaccatct gcctggcagg gac                       43
```

<210> SEQ ID NO 108
<211> LENGTH: 24
<212> TYPE: DNA
<213> ORGANISM: Homo sapiens

<400> SEQUENCE: 108

```
tccaatgacc acagtgcaaa ataa                                            24
```

<210> SEQ ID NO 109
<211> LENGTH: 24
<212> TYPE: DNA
<213> ORGANISM: Homo sapiens

<400> SEQUENCE: 109

```
cctttctttt ccatccaaca atta                                            24
```

<210> SEQ ID NO 110
<211> LENGTH: 24
<212> TYPE: DNA
<213> ORGANISM: Homo sapiens

<400> SEQUENCE: 110

```
tagcaacaag acggatgggg aagc                                            24
```

<210> SEQ ID NO 111
<211> LENGTH: 24
<212> TYPE: DNA
<213> ORGANISM: Homo sapiens

<400> SEQUENCE: 111

```
ccctcccaa gagtgtaggt gaat                                             24
```

<210> SEQ ID NO 112
<211> LENGTH: 24
<212> TYPE: DNA
<213> ORGANISM: Homo sapiens

<400> SEQUENCE: 112

```
gaagagcctg cgctccgagg accc                                            24
```

<210> SEQ ID NO 113
<211> LENGTH: 25
<212> TYPE: DNA
<213> ORGANISM: Homo sapiens

<400> SEQUENCE: 113
tatgatgcag tcagggggga tggtc                                    25

<210> SEQ ID NO 114
<211> LENGTH: 59
<212> TYPE: DNA
<213> ORGANISM: Homo sapiens

<400> SEQUENCE: 114
gacctcagct gaccccttct accagaacac acctcacagc agccgctgcg tggcacaca   59

<210> SEQ ID NO 115
<211> LENGTH: 39
<212> TYPE: DNA
<213> ORGANISM: Homo sapiens

<400> SEQUENCE: 115
gctcctcccg cagcatggcg agctcctgtt gcagggcct                     39

<210> SEQ ID NO 116
<211> LENGTH: 34
<212> TYPE: DNA
<213> ORGANISM: Homo sapiens

<400> SEQUENCE: 116
gtactctgcc tcctgctaca atggctctga agga                          34

<210> SEQ ID NO 117
<211> LENGTH: 25
<212> TYPE: DNA
<213> ORGANISM: Homo sapiens

<400> SEQUENCE: 117 tgctcccca acaaagccgc ctacc                                     25

<210> SEQ ID NO 118
<211> LENGTH: 30
<212> TYPE: DNA
<213> ORGANISM: Homo sapiens

<400> SEQUENCE: 118
ctggctggac agtcaatgtg gagggcagcg                               30

<210> SEQ ID NO 119
<211> LENGTH: 25
<212> TYPE: DNA
<213> ORGANISM: Homo sapiens

<400> SEQUENCE: 119
gatgccctcc atgaaggctg ggtag                                    25

<210> SEQ ID NO 120
<211> LENGTH: 83
<212> TYPE: DNA
<213> ORGANISM: Homo sapiens

<400> SEQUENCE: 120 gcagggctc cagataatcg ggcagggatg gcggccgagg cttcagagct ggcggcagcc   60
cgggtcccca agcgcgatga ggt                                         83

<210> SEQ ID NO 121
<211> LENGTH: 24
<212> TYPE: DNA
<213> ORGANISM: Homo sapiens

<400> SEQUENCE: 121
cccagctctg cacggagcct gttc						24

<210> SEQ ID NO 122
<211> LENGTH: 24
<212> TYPE: DNA
<213> ORGANISM: Homo sapiens

<400> SEQUENCE: 122
gggaaagtga ctcctgtttt ctgt						24

<210> SEQ ID NO 123
<211> LENGTH: 82
<212> TYPE: DNA
<213> ORGANISM: Homo sapiens

<400> SEQUENCE: 123
cctggcccgc atggcgagac acagtgccaa caccagcatg catgcccgca acctggccat		60 tgtctgggca cccaacctgc ta						82

<210> SEQ ID NO 124
<211> LENGTH: 24
<212> TYPE: DNA
<213> ORGANISM: Homo sapiens

<400> SEQUENCE: 124
tcaagagctg gttcgagccc ctgg						24

<210> SEQ ID NO 125
<211> LENGTH: 24
<212> TYPE: DNA
<213> ORGANISM: Homo sapiens

<400> SEQUENCE: 125
gaacaccagg tccagttcac agac						24

<210> SEQ ID NO 126
<211> LENGTH: 63
<212> TYPE: DNA
<213> ORGANISM: Homo sapiens

<400> SEQUENCE: 126
gttttggtgg cgaggacgca caaagaggca tttatctccc tggacaggta ggcggtcatc		60 aat									63

<210> SEQ ID NO 127
<211> LENGTH: 50
<212> TYPE: DNA
<213> ORGANISM: Homo sapiens

<400> SEQUENCE: 127
tgcaggcagg caaacagccc cagcagcagt agcagcaggc ccttcagcag			50

<210> SEQ ID NO 128
<211> LENGTH: 24
<212> TYPE: DNA
<213> ORGANISM: Homo sapiens

<400> SEQUENCE: 128
ctgggtggca tcaatgtcca gcct						24

```
<210> SEQ ID NO 129
<211> LENGTH: 30
<212> TYPE: DNA
<213> ORGANISM: Homo sapiens

<400> SEQUENCE: 129
cgggagaagc gacgtctggg tgggcaggaa                                          30

<210> SEQ ID NO 130
<211> LENGTH: 24
<212> TYPE: DNA
<213> ORGANISM: Homo sapiens

<400> SEQUENCE: 130
tcccggcggg gataccctgcc caca                                               24

<210> SEQ ID NO 131
<211> LENGTH: 76
<212> TYPE: DNA
<213> ORGANISM: Homo sapiens

<400> SEQUENCE: 131
ggcccctaga ctcatctctt ggagcattct gtggtgcgat tgtctttgca ggacttcttc         60
gtgaagggat gtgatg                                                         76

<210> SEQ ID NO 132
<211> LENGTH: 24
<212> TYPE: DNA
<213> ORGANISM: Homo sapiens

<400> SEQUENCE: 132
tgccccgagg cctagcttgg ccag                                                24

<210> SEQ ID NO 133
<211> LENGTH: 49
<212> TYPE: DNA
<213> ORGANISM: Homo sapiens

<400> SEQUENCE: 133
caagccatcc tcccttcttg ttctcccaaa acgttgggat tacaggcat                     49

<210> SEQ ID NO 134
<211> LENGTH: 24
<212> TYPE: DNA
<213> ORGANISM: Homo sapiens

<400> SEQUENCE: 134
tggcactgtg gctctgggga gctg                                                24

<210> SEQ ID NO 135
<211> LENGTH: 115
<212> TYPE: DNA
<213> ORGANISM: Homo sapiens

<400> SEQUENCE: 135
agggctgtgt atccatgttc atgctgatga caatttacat cggctccatg tcgcagtagt         60
aatttgcaca tatcgagttt tcctttatat gctgcatgca ttagaggagt cattc              115

<210> SEQ ID NO 136
<211> LENGTH: 24
<212> TYPE: DNA
<213> ORGANISM: Homo sapiens
```

```
<400> SEQUENCE: 136
acatatctta cccaagcctg cact                                          24

<210> SEQ ID NO 137
<211> LENGTH: 24
<212> TYPE: DNA
<213> ORGANISM: Homo sapiens

<400> SEQUENCE: 137
ccatggccca aagaccctcc tccc                                          24

<210> SEQ ID NO 138
<211> LENGTH: 24
<212> TYPE: DNA
<213> ORGANISM: Homo sapiens

<400> SEQUENCE: 138
tgatggcata acaccccccc caac                                          24

<210> SEQ ID NO 139
<211> LENGTH: 24
<212> TYPE: DNA
<213> ORGANISM: Homo sapiens

<400> SEQUENCE: 139
caaagcagtc aaggagccac cacc                                          24

<210> SEQ ID NO 140
<211> LENGTH: 176
<212> TYPE: DNA
<213> ORGANISM: Homo sapiens

<400> SEQUENCE: 140
accttgtgcg acatactgct gtaatgaact tgaggagaca attctgggat atgataaact   60
ctcactgagg tctgcttcct gcagttcatg acatgctgct gactcaagag atgttacagc  120
agggctggcc caggcatggg tttcctgcct ttccgctggt ggtgatatgc tagact      176

<210> SEQ ID NO 141
<211> LENGTH: 30
<212> TYPE: DNA
<213> ORGANISM: Homo sapiens

<400> SEQUENCE: 141
gctttccctc ctctgccctc atccctctag                                    30

<210> SEQ ID NO 142
<211> LENGTH: 24
<212> TYPE: DNA
<213> ORGANISM: Homo sapiens

<400> SEQUENCE: 142
cgagccagca ccactgaacc cacc                                          24

<210> SEQ ID NO 143
<211> LENGTH: 34
<212> TYPE: DNA
<213> ORGANISM: Homo sapiens

<400> SEQUENCE: 143
gcttttctcc ctaactcagg ccccgtctc caac                                34
```

<210> SEQ ID NO 144
<211> LENGTH: 24
<212> TYPE: DNA
<213> ORGANISM: Homo sapiens

<400> SEQUENCE: 144
ggacaaaaag cgagacccgc ttct                                          24

<210> SEQ ID NO 145
<211> LENGTH: 94
<212> TYPE: DNA
<213> ORGANISM: Homo sapiens

<400> SEQUENCE: 145
tggcggcctt cagcaagtac ttgacggcgc gaaactcctc gctggctggt gccgcgttcc   60
tgctgctctg cctgctccac aagcggcgcc gcgc                               94

<210> SEQ ID NO 146
<211> LENGTH: 380
<212> TYPE: DNA
<213> ORGANISM: Homo sapiens

<400> SEQUENCE: 146
gctggtttat cctccgcact tacttggtac tcgatctcca gcgaggcctt caggggcatg   60
ggctggtaga agcactcctt ctggccggcg ggaagggtaa aggtgaagtc gctatcgagg  120
gaaggtgtga agccggccgc cccaggcagc agcaccggag gcagagcggc cagaaggagc  180
acggggaagg gcagccagat cttgtcgccc atccctgctg gggcgatccc gggctgaaag  240
aggcgtcagg tactgttgtc tccgctccgc gtttcctctc tggactcctc gtggttgaca  300
gggaaatctg gagtctgaag aaactccagg tggcggccgc ggcggcggcg aacactccct  360
ccgaaagaga agcgcagttc                                              380

<210> SEQ ID NO 147
<211> LENGTH: 34
<212> TYPE: DNA
<213> ORGANISM: Homo sapiens

<400> SEQUENCE: 147
ccactatgcc gcaggccgcc ctacccacct tcag                               34

<210> SEQ ID NO 148
<211> LENGTH: 24
<212> TYPE: DNA
<213> ORGANISM: Homo sapiens

<400> SEQUENCE: 148
tgagctgggg gcctaattcc tgac                                          24

<210> SEQ ID NO 149
<211> LENGTH: 29
<212> TYPE: DNA
<213> ORGANISM: Homo sapiens

<400> SEQUENCE: 149
atgatggaca cccgcgtgca agatgctgt                                     29

<210> SEQ ID NO 150
<211> LENGTH: 93
<212> TYPE: DNA
<213> ORGANISM: Homo sapiens

```
<400> SEQUENCE: 150
gccaggactc caggtctagg gcaggggtcc aggagcagag gccatcaggg cctacagtcc      60
ctcgtacctt gctaccctga ccggtgtccc agg                                  93

<210> SEQ ID NO 151
<211> LENGTH: 24
<212> TYPE: DNA
<213> ORGANISM: Homo sapiens

<400> SEQUENCE: 151
tggcccggca cgtgttccta acgg                                            24

<210> SEQ ID NO 152
<211> LENGTH: 24
<212> TYPE: DNA
<213> ORGANISM: Homo sapiens

<400> SEQUENCE: 152
acccggagtc tgcagagcgc gccg                                            24

<210> SEQ ID NO 153
<211> LENGTH: 24
<212> TYPE: DNA
<213> ORGANISM: Homo sapiens

<400> SEQUENCE: 153
tgcgggggcg gggtctcgcg tcat                                            24

<210> SEQ ID NO 154
<211> LENGTH: 49
<212> TYPE: DNA
<213> ORGANISM: Homo sapiens

<400> SEQUENCE: 154
catctgtgcg tggcgactcc aagagagcac ccgactccag atggcgaca                 49

<210> SEQ ID NO 155
<211> LENGTH: 94
<212> TYPE: DNA
<213> ORGANISM: Homo sapiens

<400> SEQUENCE: 155
cggcggtacg aggcgcgcgc tcggggtccc ggtcgcgagg aggaggagga tgtggcgcgc      60
ggaggggaaa tggctgccga aaacaagccg gaag                                 94

<210> SEQ ID NO 156
<211> LENGTH: 46
<212> TYPE: DNA
<213> ORGANISM: Homo sapiens

<400> SEQUENCE: 156
caaggacagc caaaaggccc ggcagccttt ctgacgcagc caggaa                    46

<210> SEQ ID NO 157
<211> LENGTH: 24
<212> TYPE: DNA
<213> ORGANISM: Homo sapiens

<400> SEQUENCE: 157
gctggacggt ggagcccgag aggg                                            24
```

<210> SEQ ID NO 158
<211> LENGTH: 26
<212> TYPE: DNA
<213> ORGANISM: Homo sapiens

<400> SEQUENCE: 158
actagtaaat ctctccgggc tctggg                                                26

<210> SEQ ID NO 159
<211> LENGTH: 145
<212> TYPE: DNA
<213> ORGANISM: Homo sapiens

<400> SEQUENCE: 159
cggatcaaca tgccccaaaa ggaggaggcc cgggagcgaa gcgggtcagt tcccctttgc           60
cctgccctat ccaggccaca cagatcgaag cggcccggct ccttcctcct ccccgggc           120 gtgactaagg tcacgaatcc ggccc                                               145

<210> SEQ ID NO 160
<211> LENGTH: 29
<212> TYPE: DNA
<213> ORGANISM: Homo sapiens

<400> SEQUENCE: 160
gtggagaggc ctggcagaac gaagaggat                                             29

<210> SEQ ID NO 161
<211> LENGTH: 32
<212> TYPE: DNA
<213> ORGANISM: Homo sapiens

<400> SEQUENCE: 161
gttatggctg actcacggcc ttcgactcca gc                                         32

<210> SEQ ID NO 162
<211> LENGTH: 79
<212> TYPE: DNA
<213> ORGANISM: Homo sapiens

<400> SEQUENCE: 162
aggagccaga cgtgtggagt cccagcagag gccaacctgt gtctcttcat ctccgtgaga           60
aaggtgcccc cgaagtgaa                                                        79

<210> SEQ ID NO 163
<211> LENGTH: 24
<212> TYPE: DNA
<213> ORGANISM: Homo sapiens

<400> SEQUENCE: 163
ggggaaagtg ctaaagccgc tgag                                                  24

<210> SEQ ID NO 164
<211> LENGTH: 29
<212> TYPE: DNA
<213> ORGANISM: Homo sapiens

<400> SEQUENCE: 164
cgagtcctcg ttctcgctgc tgtagcagc                                             29

<210> SEQ ID NO 165
<211> LENGTH: 319

```
<212> TYPE: DNA
<213> ORGANISM: Homo sapiens

<400> SEQUENCE: 165
gacctccgct atgacccgaa ctggaagagt aagaaggagg aagggcagct gctgtctgtg      60
gaagcgttgc cggagtccac ggacagctct ttagaaaatc tgcctttggc tcccctctac    120
ccttcccagg agacgtcaat ggaactctcc gggggaaaag gcgagcagaa agagagtcca    180
cagagtgcag cttctttact tggtagtgaa tttttaagcc caaactatga gcatggtgcc    240
cgtcgcagca agccgttttc agagctgagc gacagtgacc tggaggagaa gtcgagcagc    300
ctttctccgt acgtgaaga                                                  319

<210> SEQ ID NO 166
<211> LENGTH: 168
<212> TYPE: DNA
<213> ORGANISM: Homo sapiens

<400> SEQUENCE: 166
acgcgggcct cagtgaggtc tgtcctcatg gccagctgtt cccgcgcata cacgtctggg     60
tagtgggtct tctggaagac cttctccagc tcctccagct ggtagctggt gaaggtggtc   120
cggttccgcc gcttcttgcc cttgttgctc tctgagtcgg ccttctcc                168

<210> SEQ ID NO 167
<211> LENGTH: 25
<212> TYPE: DNA
<213> ORGANISM: Homo sapiens

<400> SEQUENCE: 167
atggggatgg ccgtgttcat gaaaa                                           25

<210> SEQ ID NO 168
<211> LENGTH: 25
<212> TYPE: DNA
<213> ORGANISM: Homo sapiens

<400> SEQUENCE: 168
ccttccgcag ggcgaggttg tcttt                                           25

<210> SEQ ID NO 169
<211> LENGTH: 24
<212> TYPE: DNA
<213> ORGANISM: Homo sapiens

<400> SEQUENCE: 169
tgcagtcggg cactcactgg agag                                            24

<210> SEQ ID NO 170
<211> LENGTH: 30
<212> TYPE: DNA
<213> ORGANISM: Homo sapiens

<400> SEQUENCE: 170
tgggcgaccc ggatctcctg gaagtgttgg                                      30

<210> SEQ ID NO 171
<211> LENGTH: 26
<212> TYPE: DNA
<213> ORGANISM: Homo sapiens

<400> SEQUENCE: 171
```
tggccggcaa cgtgaagaag agctct                                          26

<210> SEQ ID NO 172
<211> LENGTH: 24
<212> TYPE: DNA
<213> ORGANISM: Homo sapiens

<400> SEQUENCE: 172
accccagccc ccttcggagg agca                                            24

<210> SEQ ID NO 173
<211> LENGTH: 28
<212> TYPE: DNA
<213> ORGANISM: Homo sapiens

<400> SEQUENCE: 173
ttctgcccTt gcgagggttc ctcctcac                                        28

<210> SEQ ID NO 174
<211> LENGTH: 189
<212> TYPE: DNA
<213> ORGANISM: Homo sapiens

<400> SEQUENCE: 174
agggactcgg tcccccttgc cgtgctcccc tccctcctcg tctgccaagc ctcgcctcct     60
accacaccac accaggccac cccagctgca agtgccttcc ttggagcaga gaggcagcct    120
cgtcctcctg tcccctctcc tcccagccac catcgttcat ctgctccggg cagaactgtg    180
tggcccctg                                                            189

<210> SEQ ID NO 175
<211> LENGTH: 24
<212> TYPE: DNA
<213> ORGANISM: Homo sapiens

<400> SEQUENCE: 175
tgtaccggct cacgctgcgc acaa                                            24

<210> SEQ ID NO 176
<211> LENGTH: 106
<212> TYPE: DNA
<213> ORGANISM: Homo sapiens

<400> SEQUENCE: 176
gcttcagcac catgccgctc aggtcggccg tgctctcctg cgacgggttg aagatgcgga     60
cgaacttctc ccggcagctc acagccacga tcttcaggcc tgtcgg                   106

<210> SEQ ID NO 177
<211> LENGTH: 30
<212> TYPE: DNA
<213> ORGANISM: Homo sapiens

<400> SEQUENCE: 177
tagggGcctg gagggtgcag ggtcattaat                                      30

<210> SEQ ID NO 178
<211> LENGTH: 32
<212> TYPE: DNA
<213> ORGANISM: Homo sapiens

<400> SEQUENCE: 178
tcggcccctc tgtcgtacca ggagcccag ac                                    32

<210> SEQ ID NO 179
<211> LENGTH: 25
<212> TYPE: DNA
<213> ORGANISM: Homo sapiens

<400> SEQUENCE: 179 aaaaggggggg aaatgcatct cagtt                                          25

<210> SEQ ID NO 180
<211> LENGTH: 73
<212> TYPE: DNA
<213> ORGANISM: Homo sapiens

<400> SEQUENCE: 180
agactgggac ggaagtccct cagtccccca ggagcctcct tcatggaccc ggggatccca    60 agagggctg cct                                                         73

<210> SEQ ID NO 181
<211> LENGTH: 25
<212> TYPE: DNA
<213> ORGANISM: Homo sapiens

<400> SEQUENCE: 181
gaaggcccgg aggagaacaa gatcc                                           25

<210> SEQ ID NO 182
<211> LENGTH: 43
<212> TYPE: DNA
<213> ORGANISM: Homo sapiens

<400> SEQUENCE: 182
tgtatgacga ctcctacgtg cccgggtttg aggactcgga ggc                       43

<210> SEQ ID NO 183
<211> LENGTH: 35
<212> TYPE: DNA
<213> ORGANISM: Homo sapiens

<400> SEQUENCE: 183
aaacatcatt tgtcgaccgt cctttcactg ccatg                                35

<210> SEQ ID NO 184
<211> LENGTH: 28
<212> TYPE: DNA
<213> ORGANISM: Homo sapiens

<400> SEQUENCE: 184
cagctgtcag ggtttatcct ggcccgtt                                        28

<210> SEQ ID NO 185
<211> LENGTH: 25
<212> TYPE: DNA
<213> ORGANISM: Homo sapiens

<400> SEQUENCE: 185
cagcgaggac tccagcgtat ccgcc                                           25

<210> SEQ ID NO 186
<211> LENGTH: 33
<212> TYPE: DNA
<213> ORGANISM: Homo sapiens

```
<400> SEQUENCE: 186
ggcgagagcc atacggccac ctggggcccg cag                          33

<210> SEQ ID NO 187
<211> LENGTH: 24
<212> TYPE: DNA
<213> ORGANISM: Homo sapiens

<400> SEQUENCE: 187
cttctcgtct cttccgaagc tctt                                   24

<210> SEQ ID NO 188
<211> LENGTH: 26
<212> TYPE: DNA
<213> ORGANISM: Homo sapiens

<400> SEQUENCE: 188
ttgcgtgagg tactcgggtc cgtccc                                 26

<210> SEQ ID NO 189
<211> LENGTH: 101
<212> TYPE: DNA
<213> ORGANISM: Homo sapiens

<400> SEQUENCE: 189
tgccggcccg cgaatgagta ctttgccaag aagctgcggg acgccgtggt tgatggcacc    60
ccctgctacc aggtccgagc cagccgggac ctctgcatca a                      101

<210> SEQ ID NO 190
<211> LENGTH: 57
<212> TYPE: DNA
<213> ORGANISM: Homo sapiens

<400> SEQUENCE: 190
tggggctacc aacctgcctg cctgcaagga tggctccgag ccgtggccct atgtggt       57

<210> SEQ ID NO 191
<211> LENGTH: 216
<212> TYPE: DNA
<213> ORGANISM: Homo sapiens

<400> SEQUENCE: 191
gctgacacct ctcaagggcc cggaggcggc ccaccccaa gccaaagcca aaggctctaa    60
gagtccatct gctggcagga aaggctccca gctgagtcct cagccccaga agaaaggcct   120
ccctagtcct cagggcaccc ggaagagtgc tccaagttcc aaggccaccc ctcaggcctc   180
agagccagtc accactcagt tgttgggaca gcctcc                           216

<210> SEQ ID NO 192
<211> LENGTH: 42
<212> TYPE: DNA
<213> ORGANISM: Homo sapiens

<400> SEQUENCE: 192
tcctgacctt ccagctcctc cttgtcttcc ttcatatccc ac                     42

<210> SEQ ID NO 193
<211> LENGTH: 32
<212> TYPE: DNA
<213> ORGANISM: Homo sapiens

<400> SEQUENCE: 193
```

```
ctacaactga gacccggagg agactagacc cc                                        32
```

<210> SEQ ID NO 194
<211> LENGTH: 24
<212> TYPE: DNA
<213> ORGANISM: Homo sapiens

<400> SEQUENCE: 194

```
tgcggcaggc ccgagtgagg ccat                                                 24
```

<210> SEQ ID NO 195
<211> LENGTH: 120
<212> TYPE: DNA
<213> ORGANISM: Homo sapiens

<400> SEQUENCE: 195

```
agtgctgtcc gctgacggtg tgctcagagc cgtgcgggtc attcgggttc ccccagtgca         60
ggtgcagctg cgtggcactg tagcgagact ggaggccctg gatgtgcatg tccgagggca        120
```

<210> SEQ ID NO 196
<211> LENGTH: 24
<212> TYPE: DNA
<213> ORGANISM: Homo sapiens

<400> SEQUENCE: 196

```
tgggagcact gtggttctgc ctca                                                 24
```

<210> SEQ ID NO 197
<211> LENGTH: 30
<212> TYPE: DNA
<213> ORGANISM: Homo sapiens

<400> SEQUENCE: 197

```
ctcaaaaacg acatacccag gcaggagaag                                           30
```

<210> SEQ ID NO 198
<211> LENGTH: 92
<212> TYPE: DNA
<213> ORGANISM: Homo sapiens

<400> SEQUENCE: 198

```
aggcagctcg aaggcggcct tgcagagctg gtgagaagca cagcagccgc tcattctcag         60
ccagcagctt caaggtccct ttgtccaggt tg                                        92
```

<210> SEQ ID NO 199
<211> LENGTH: 196
<212> TYPE: DNA
<213> ORGANISM: Homo sapiens

<400> SEQUENCE: 199

```
gtcctgcgcc tcacacctgc tgtgcctctc gacctttggc tgcctcctct cgtgggccgg         60
cttctcgggg ccaggccctg ctgggcccca gacttgccag acctgtcttc tccgggctct        120
gggagccctg ctcctctctg tggctcaggg caagtctgta cttccagctc agcctggtga        180
ttgctccacc ccaggg                                                        196
```

<210> SEQ ID NO 200
<211> LENGTH: 24
<212> TYPE: DNA
<213> ORGANISM: Homo sapiens

<400> SEQUENCE: 200
gtggtgacaa aggagtagcc acgc                                           24

<210> SEQ ID NO 201
<211> LENGTH: 27
<212> TYPE: DNA
<213> ORGANISM: Homo sapiens

<400> SEQUENCE: 201
tccttgctac gagccctgtc tcccagg                                        27

<210> SEQ ID NO 202
<211> LENGTH: 186
<212> TYPE: DNA
<213> ORGANISM: Homo sapiens

<400> SEQUENCE: 202
gtcatcgacc gctgtaacta tgtgcgagtt ggcaccaccc gggtgccact gacggggccg    60
gtgaaggaaa agatcatggc ggtgatcaag gagtggggca ctggccggga caccctgcgc   120
tgcttggccc tggccacccg ggacaccccc ccgaagcgag aggaaatggt cctggatgac   180
tctgcc                                                              186

<210> SEQ ID NO 203
<211> LENGTH: 34
<212> TYPE: DNA
<213> ORGANISM: Homo sapiens

<400> SEQUENCE: 203 gggacccag gagactcaag cctctgaagc ctcc                                34

<210> SEQ ID NO 204
<211> LENGTH: 25
<212> TYPE: DNA
<213> ORGANISM: Homo sapiens

<400> SEQUENCE: 204
cagaggtatt gggagggcac agggg                                          25

<210> SEQ ID NO 205
<211> LENGTH: 171
<212> TYPE: DNA
<213> ORGANISM: Homo sapiens

<400> SEQUENCE: 205
aataggtgct tgtcgtccac cggaggaacc ctgtcctgct cgtcgtcctc atcaaactca    60
tactcgtcct tgacggggc cgtggccttc tgtggctctg ggttcttggc cttgtgcttg   120 aggcctttttt cgaactcgga gtccgtgttg ttgccgtcga ctgaactgga a           171

<210> SEQ ID NO 206
<211> LENGTH: 32
<212> TYPE: DNA
<213> ORGANISM: Homo sapiens

<400> SEQUENCE: 206
ccatcaagaa ggaggaaaag gtgctgccta ag                                  32

<210> SEQ ID NO 207
<211> LENGTH: 27
<212> TYPE: DNA
<213> ORGANISM: Homo sapiens

<400> SEQUENCE: 207
ggagcaacgg ttgagggtcg tgtcctc                                              27

<210> SEQ ID NO 208
<211> LENGTH: 24
<212> TYPE: DNA
<213> ORGANISM: Homo sapiens

<400> SEQUENCE: 208
gagaaaggct cctagaggct actg                                                 24

<210> SEQ ID NO 209
<211> LENGTH: 58
<212> TYPE: DNA
<213> ORGANISM: Homo sapiens

<400> SEQUENCE: 209
cctcccaggt gaggtcggcc accagcccca tggagtcgta gccgctgctc accagctg            58

<210> SEQ ID NO 210
<211> LENGTH: 135
<212> TYPE: DNA
<213> ORGANISM: Homo sapiens

<400> SEQUENCE: 210
gccagacatc ctgcgacctg tctccttcct cccggggaag ctgcagggcc ccagctccgc          60
cgggggcccc tccttccctg gcgggcaggg ccaggcccgg ctccgtgcct ttcccattgc         120
gtttgggcaa ggtac                                                         135

<210> SEQ ID NO 211
<211> LENGTH: 77
<212> TYPE: DNA
<213> ORGANISM: Homo sapiens

<400> SEQUENCE: 211
caggtgcaca gaggcgtgtt ggccggtgca ggtgaagata cacatggtga caaagtggca          60
aacctggtcc cgagcct                                                        77

<210> SEQ ID NO 212
<211> LENGTH: 152
<212> TYPE: DNA
<213> ORGANISM: Homo sapiens

<400> SEQUENCE: 212
cagggtctcg atgaggcggg catagccctg ggcagcagcc aggtgcagaa ggctcatgcc          60
ccggaagggg cttccatggg ccagacgttc aggacccttc caggtggagc gtgggatcat        120
gctttctacc aagaccacta cccgtgcttc ga                                      152

<210> SEQ ID NO 213
<211> LENGTH: 30
<212> TYPE: DNA
<213> ORGANISM: Homo sapiens

<400> SEQUENCE: 213
cctctggtgg tcaattagcg gctgcacgct                                           30

<210> SEQ ID NO 214
<211> LENGTH: 24
<212> TYPE: DNA

```
<213> ORGANISM: Homo sapiens

<400> SEQUENCE: 214
tcctcactca ccgggataga taga                                         24

<210> SEQ ID NO 215
<211> LENGTH: 24
<212> TYPE: DNA
<213> ORGANISM: Homo sapiens

<400> SEQUENCE: 215
ttccggtacc ggtcctccga tctg                                         24

<210> SEQ ID NO 216
<211> LENGTH: 24
<212> TYPE: DNA
<213> ORGANISM: Homo sapiens

<400> SEQUENCE: 216
agtgagggtg gtccgcactc cgat                                         24

<210> SEQ ID NO 217
<211> LENGTH: 104
<212> TYPE: DNA
<213> ORGANISM: Homo sapiens

<400> SEQUENCE: 217
ctcgatgcca tggtcggggt tgcagctgaa ggcgatggtg atggcgtaac gggtgcccca   60
gtggaccttc tccacgcggt gtaggttctc ggaccccgag gtga                  104

<210> SEQ ID NO 218
<211> LENGTH: 28
<212> TYPE: DNA
<213> ORGANISM: Homo sapiens

<400> SEQUENCE: 218
ctccagattg ggcctgtccc caaagctc                                     28

<210> SEQ ID NO 219
<211> LENGTH: 38
<212> TYPE: DNA
<213> ORGANISM: Homo sapiens

<400> SEQUENCE: 219
gcctgcatct tgacgggcct cctgtcggct gctggagg                          38

<210> SEQ ID NO 220
<211> LENGTH: 29
<212> TYPE: DNA
<213> ORGANISM: Homo sapiens

<400> SEQUENCE: 220
tctggggatg agtcggaggt gggcaggca                                    29

<210> SEQ ID NO 221
<211> LENGTH: 28
<212> TYPE: DNA
<213> ORGANISM: Homo sapiens

<400> SEQUENCE: 221
cccagcagcc ttggaccttc acctggtg                                     28
```

```
<210> SEQ ID NO 222
<211> LENGTH: 24
<212> TYPE: DNA
<213> ORGANISM: Homo sapiens

<400> SEQUENCE: 222
gacaaggtgc cttggccttt tcct                                              24

<210> SEQ ID NO 223
<211> LENGTH: 29
<212> TYPE: DNA
<213> ORGANISM: Homo sapiens

<400> SEQUENCE: 223
ggcttggagt tgccggtggt tctccttca                                         29

<210> SEQ ID NO 224
<211> LENGTH: 31
<212> TYPE: DNA
<213> ORGANISM: Homo sapiens

<400> SEQUENCE: 224
tggatcccag agacggtgaa gtaggggatc t                                      31

<210> SEQ ID NO 225
<211> LENGTH: 56
<212> TYPE: DNA
<213> ORGANISM: Homo sapiens

<400> SEQUENCE: 225
ggccagggtg aacactcccg gctccagccc cttctccacc atagtggggc tccctt           56

<210> SEQ ID NO 226
<211> LENGTH: 29
<212> TYPE: DNA
<213> ORGANISM: Homo sapiens

<400> SEQUENCE: 226
gaaagggaga agtacagaa gacagatga                                          29

<210> SEQ ID NO 227
<211> LENGTH: 94
<212> TYPE: DNA
<213> ORGANISM: Homo sapiens

<400> SEQUENCE: 227
gagaagccct ggtggttgat ctgatgttcc gagccggctc cgtcgcgagc tccaaacagc       60
agccgcagtt cactgagtcg gtggctgtaa agga                                   94

<210> SEQ ID NO 228
<211> LENGTH: 175
<212> TYPE: DNA
<213> ORGANISM: Homo sapiens

<400> SEQUENCE: 228
ccttgcggaa caccttgccg atcttcttaa atgtccccac gggctttagg gcttccacga       60
ggacgtccaa atccacatct ttgcagacat cggggacgct ccaaagaatg aggcagtcgg      120
gggacggcag gaagccccag gggaaccagc ccccacgtg gcttttctcg agagt            175

<210> SEQ ID NO 229
<211> LENGTH: 24
<212> TYPE: DNA
```

<213> ORGANISM: Homo sapiens

<400> SEQUENCE: 229
gaccaggtgc caggccttgc gcgg         24

<210> SEQ ID NO 230
<211> LENGTH: 43
<212> TYPE: DNA
<213> ORGANISM: Homo sapiens

<400> SEQUENCE: 230
cagcagagat ggatccccgg cctggagggg agctggcagc agg         43

<210> SEQ ID NO 231
<211> LENGTH: 26
<212> TYPE: DNA
<213> ORGANISM: Homo sapiens

<400> SEQUENCE: 231
cagttctgta actttctccc agagag         26

<210> SEQ ID NO 232
<211> LENGTH: 51
<212> TYPE: DNA
<213> ORGANISM: Homo sapiens

<400> SEQUENCE: 232
cttctgcggg ggtgccctga tccatgcccg cttcgtgatg accgcggcca g         51

<210> SEQ ID NO 233
<211> LENGTH: 30
<212> TYPE: DNA
<213> ORGANISM: Homo sapiens

<400> SEQUENCE: 233
agaggaaaga ctgaaggcca ggagggagag         30

<210> SEQ ID NO 234
<211> LENGTH: 29
<212> TYPE: DNA
<213> ORGANISM: Homo sapiens

<400> SEQUENCE: 234
cggtccatgg cctcccgggc ctgggccat         29

<210> SEQ ID NO 235
<211> LENGTH: 26
<212> TYPE: DNA
<213> ORGANISM: Homo sapiens

<400> SEQUENCE: 235
accctgaaac cctctacgcc tgggag         26

<210> SEQ ID NO 236
<211> LENGTH: 30
<212> TYPE: DNA
<213> ORGANISM: Homo sapiens

<400> SEQUENCE: 236
gggggacagc ctcctggaga ccagctgcgg         30

<210> SEQ ID NO 237
<211> LENGTH: 137

```
<212> TYPE: DNA
<213> ORGANISM: Homo sapiens

<400> SEQUENCE: 237
cgagcgcccg gtggcgcccg aggacgcgtg tcgtacgggg ggtggcgcgt cgtaggcccc      60
ggccatggcc tcctcgccgc ccccgctgcc cgggccatcg gcctcgtcgt agtcggagcc     120
ccggtagtag ccatggt                                                   137

<210> SEQ ID NO 238
<211> LENGTH: 27
<212> TYPE: DNA
<213> ORGANISM: Homo sapiens

<400> SEQUENCE: 238
cgcaggaccc cgacatgagc cttgaag                                         27

<210> SEQ ID NO 239
<211> LENGTH: 44
<212> TYPE: DNA
<213> ORGANISM: Homo sapiens

<400> SEQUENCE: 239
agcagccccg taacctccac ctggtctccc gccaacccac ggag                      44

<210> SEQ ID NO 240
<211> LENGTH: 115
<212> TYPE: DNA
<213> ORGANISM: Homo sapiens

<400> SEQUENCE: 240
tgtacctgcc ggcgtcgtag tcgtccaggc tctgctggat caggtcctcc tccatgagca     60
ccgcctcgcc ctcgccctcg ccctcaccgt ccccgtcgcc gtcgccctct gtcgg         115

<210> SEQ ID NO 241
<211> LENGTH: 34
<212> TYPE: DNA
<213> ORGANISM: Homo sapiens

<400> SEQUENCE: 241
ccagggaccg agcctgagaa agacccgggg ccgc                                 34

<210> SEQ ID NO 242
<211> LENGTH: 33
<212> TYPE: DNA
<213> ORGANISM: Homo sapiens

<400> SEQUENCE: 242
acgcggaccc ggtgcacgac cccacctggc gct                                  33

<210> SEQ ID NO 243
<211> LENGTH: 24
<212> TYPE: DNA
<213> ORGANISM: Homo sapiens

<400> SEQUENCE: 243 acagccccg taaggctcct gttc                                             24

<210> SEQ ID NO 244
<211> LENGTH: 24
<212> TYPE: DNA
<213> ORGANISM: Homo sapiens
```

```
<400> SEQUENCE: 244
cctggatcct cttgttccgc tcct                                          24

<210> SEQ ID NO 245
<211> LENGTH: 28
<212> TYPE: DNA
<213> ORGANISM: Homo sapiens

<400> SEQUENCE: 245
ccggagccag aggacccgta gctgctag                                      28

<210> SEQ ID NO 246
<211> LENGTH: 61
<212> TYPE: DNA
<213> ORGANISM: Homo sapiens

<400> SEQUENCE: 246
gggaaaacta cagttcccga catgccctgc cacgggtgcg cctgcgtacc ggagctactg   60
c                                                                   61

<210> SEQ ID NO 247
<211> LENGTH: 97
<212> TYPE: DNA
<213> ORGANISM: Homo sapiens

<400> SEQUENCE: 247
tggcgcctca cgacccgggt agtcttacga ccctggtgcc ctgggctgcc gccctgctcc   60
tcgctctggg cgtggaaagg gctctggcgc tacccga                            97

<210> SEQ ID NO 248
<211> LENGTH: 53
<212> TYPE: DNA
<213> ORGANISM: Homo sapiens

<400> SEQUENCE: 248
ttgagctgca gctcgtctgt gtcagtggcc gtgtagtcgt gctgggcctg tac          53

<210> SEQ ID NO 249
<211> LENGTH: 27
<212> TYPE: DNA
<213> ORGANISM: Homo sapiens

<400> SEQUENCE: 249
cgatctcggc ggctcactac aacctct                                       27

<210> SEQ ID NO 250
<211> LENGTH: 82
<212> TYPE: DNA
<213> ORGANISM: Homo sapiens

<400> SEQUENCE: 250
ctcactctgt cacccaggct ggagtgcact ggtgcgatct tggctcactg caacctccaa   60
ctcccaagtt caagcggttc tc                                            82

<210> SEQ ID NO 251
<211> LENGTH: 31
<212> TYPE: DNA
<213> ORGANISM: Homo sapiens

<400> SEQUENCE: 251
ccctcaagac accgctggct gctggacacc c                                  31
```

<210> SEQ ID NO 252
<211> LENGTH: 31
<212> TYPE: DNA
<213> ORGANISM: Homo sapiens

<400> SEQUENCE: 252
gccggcgcct acgcccacac ggtgaaccgc a                                      31

<210> SEQ ID NO 253
<211> LENGTH: 25
<212> TYPE: DNA
<213> ORGANISM: Homo sapiens

<400> SEQUENCE: 253 gaagggccc ggaacacctg ctctc                                              25

<210> SEQ ID NO 254
<211> LENGTH: 25
<212> TYPE: DNA
<213> ORGANISM: Homo sapiens

<400> SEQUENCE: 254
gctcatcctc ggagtcgtag cccac                                             25

<210> SEQ ID NO 255
<211> LENGTH: 24
<212> TYPE: DNA
<213> ORGANISM: Homo sapiens

<400> SEQUENCE: 255
tggacgaaga gacccacgca ggcg                                              24

<210> SEQ ID NO 256
<211> LENGTH: 24
<212> TYPE: DNA
<213> ORGANISM: Homo sapiens

<400> SEQUENCE: 256
acaggtgcga tcccccagtg gagg                                              24

<210> SEQ ID NO 257
<211> LENGTH: 132
<212> TYPE: DNA
<213> ORGANISM: Homo sapiens

<400> SEQUENCE: 257
ctgctcagcg cagccagtcg cggaggcggg gaggctgcgc ggtcagaggc gcctggagcg       60
agcgaatcct ggcccaccgc ctgcccaacc gcgtgacctt gattgagtta atgaacttca      120
cgcctcagcg tc                                                          132

<210> SEQ ID NO 258
<211> LENGTH: 33
<212> TYPE: DNA
<213> ORGANISM: Homo sapiens

<400> SEQUENCE: 258
gttatgccaa aggctcgtcg cagctgctgc tcc                                    33

<210> SEQ ID NO 259
<211> LENGTH: 26
<212> TYPE: DNA

<213> ORGANISM: Homo sapiens

<400> SEQUENCE: 259
gccgaggcgt tagccctttc ttgcac 26

<210> SEQ ID NO 260
<211> LENGTH: 73
<212> TYPE: DNA
<213> ORGANISM: Homo sapiens

<400> SEQUENCE: 260
cctctctttg ctcctggtgg ctgctgtggt ttggaagatc aaacaaagtt gttgggcctc 60
cagacgtaga gag 73

<210> SEQ ID NO 261
<211> LENGTH: 27
<212> TYPE: DNA
<213> ORGANISM: Homo sapiens

<400> SEQUENCE: 261
gagtgggccg ctggtccggg cacagtg 27

<210> SEQ ID NO 262
<211> LENGTH: 25
<212> TYPE: DNA
<213> ORGANISM: Homo sapiens

<400> SEQUENCE: 262
tgtgaagaca gcgggtgtga ggcgg 25

<210> SEQ ID NO 263
<211> LENGTH: 25
<212> TYPE: DNA
<213> ORGANISM: Homo sapiens

<400> SEQUENCE: 263
tggtcctgag aaagggtgc cagcg 25

<210> SEQ ID NO 264
<211> LENGTH: 25
<212> TYPE: DNA
<213> ORGANISM: Homo sapiens

<400> SEQUENCE: 264
tgtcgaaggc gggcgtctgg gccat 25

<210> SEQ ID NO 265
<211> LENGTH: 89
<212> TYPE: DNA
<213> ORGANISM: Homo sapiens

<400> SEQUENCE: 265
gtccggggca actacaccga aggccgagcg gcggcttcac ggtaccggcc gggcaccgcc 60 ggagggccc aagccggagc tgggagagc 89

<210> SEQ ID NO 266
<211> LENGTH: 27
<212> TYPE: DNA
<213> ORGANISM: Homo sapiens

<400> SEQUENCE: 266
gacttctctg tgccggagtc gtctcat 27

<210> SEQ ID NO 267
<211> LENGTH: 24
<212> TYPE: DNA
<213> ORGANISM: Homo sapiens

<400> SEQUENCE: 267
gcaccccgcg cagcggctga gccg                                             24

<210> SEQ ID NO 268
<211> LENGTH: 24
<212> TYPE: DNA
<213> ORGANISM: Homo sapiens

<400> SEQUENCE: 268
cctgaagtac cctgcacccc aata                                             24

<210> SEQ ID NO 269
<211> LENGTH: 25
<212> TYPE: DNA
<213> ORGANISM: Homo sapiens

<400> SEQUENCE: 269
ttgcaggcca ggcagtgcca ggagt                                            25

<210> SEQ ID NO 270
<211> LENGTH: 358
<212> TYPE: DNA
<213> ORGANISM: Homo sapiens

<400> SEQUENCE: 270
ggctgcgggc gcatcagcgc agccacagca gcgggggctc caccagcccg ggctgcaccc      60
accacgactc catggacccc tcggacgagg agggccgcgg tggcgcgggc ggcggggggcg    120 cgggcagcga gcactcggag accctcagca gcctctcgct cacctccctc ttctgcccgc    180 cgccccgcc gccagccccc ggcctcacgc ccgccaggaa gttcagcagc accagcagcc    240
tggccgcccc cggccgcccc cacgccgccg ccctggccca cggcctggcc cggagcccct    300
cgtgggccgc ggaccgcagc aaggacccc ccggccgggc accgctgccc atgggcct       358

<210> SEQ ID NO 271
<211> LENGTH: 242
<212> TYPE: DNA
<213> ORGANISM: Homo sapiens

<400> SEQUENCE: 271
ggtgccggga tcaacaaatg aaattgtgac gggaagtcct ggcccttggc ccaacctcct      60
gctgtccccg gtctgagggc ccaagccccg cgtctccgcc ttgccgtcca gcctgtcctt    120
ggtgtggggt gcttggaagt gtgagcaccc tctctggctc tttgccggcc ccaagggtcg    180
ttgcggcggc ccccgggccc agtcatcagc cctcttttcc ggtgccggaa ctatcgtact    240
gg                                                                    242

<210> SEQ ID NO 272
<211> LENGTH: 30
<212> TYPE: DNA
<213> ORGANISM: Homo sapiens

<400> SEQUENCE: 272
attgtgaagc aaggcccgag gccttgactg                                       30

<210> SEQ ID NO 273
<211> LENGTH: 25
<212> TYPE: DNA
<213> ORGANISM: Homo sapiens

<400> SEQUENCE: 273
aggagaagaa gacgccggca gccga                                    25

<210> SEQ ID NO 274
<211> LENGTH: 24
<212> TYPE: DNA
<213> ORGANISM: Homo sapiens

<400> SEQUENCE: 274
tgaccacaaa aggacctgga gaca                                     24

<210> SEQ ID NO 275
<211> LENGTH: 24
<212> TYPE: DNA
<213> ORGANISM: Homo sapiens

<400> SEQUENCE: 275
tggtgaatcg aaagacgggg aagt                                     24

<210> SEQ ID NO 276
<211> LENGTH: 51
<212> TYPE: DNA
<213> ORGANISM: Homo sapiens

<400> SEQUENCE: 276
ggagacggcg gctgttccag aggagggagt cgtcataacc ggctactgcc g        51

<210> SEQ ID NO 277
<211> LENGTH: 24
<212> TYPE: DNA
<213> ORGANISM: Homo sapiens

<400> SEQUENCE: 277
attaaggggt tcctctacag cttt                                     24

<210> SEQ ID NO 278
<211> LENGTH: 26
<212> TYPE: DNA
<213> ORGANISM: Homo sapiens

<400> SEQUENCE: 278
tgagggagaa attgcaagca gcgagg                                   26

<210> SEQ ID NO 279
<211> LENGTH: 33
<212> TYPE: DNA
<213> ORGANISM: Homo sapiens

<400> SEQUENCE: 279
aggtcacctt tgtcgccctt ctcacctttg gct                           33

<210> SEQ ID NO 280
<211> LENGTH: 24
<212> TYPE: DNA
<213> ORGANISM: Homo sapiens

<400> SEQUENCE: 280
cccgtgcctg gtccaggttt tctc                                     24

<210> SEQ ID NO 281
<211> LENGTH: 101
<212> TYPE: DNA
<213> ORGANISM: Homo sapiens

<400> SEQUENCE: 281
cactccagcc tggggaacag agcaagactc cgtctcaaaa aaaaaaaaaa aaaaaaaga      60 aaagaaatcc ctcctaattt ccttcttttt aatctctaca g                       101

<210> SEQ ID NO 282
<211> LENGTH: 38
<212> TYPE: DNA
<213> ORGANISM: Homo sapiens

<400> SEQUENCE: 282
gtctttgagc cccagagtag cctttcggat tccctcgt                            38

<210> SEQ ID NO 283
<211> LENGTH: 26
<212> TYPE: DNA
<213> ORGANISM: Homo sapiens

<400> SEQUENCE: 283
ctggagaaga aagcacggac aggcag                                         26

<210> SEQ ID NO 284
<211> LENGTH: 66
<212> TYPE: DNA
<213> ORGANISM: Homo sapiens

<400> SEQUENCE: 284
tgaagagctg gcagtagaag ataaacaggc tggggaagaa gagaaagtgc tcaaggagaa      60
ggagca                                                                66

<210> SEQ ID NO 285
<211> LENGTH: 24
<212> TYPE: DNA
<213> ORGANISM: Homo sapiens

<400> SEQUENCE: 285
aattgagttt agtgccggcc ccca                                           24

<210> SEQ ID NO 286
<211> LENGTH: 36
<212> TYPE: DNA
<213> ORGANISM: Homo sapiens

<400> SEQUENCE: 286
gcctttcccc gaagaactca ctcggcaagc cgtcag                              36

<210> SEQ ID NO 287
<211> LENGTH: 49
<212> TYPE: DNA
<213> ORGANISM: Homo sapiens

<400> SEQUENCE: 287
cgaaagggcg aggagttgga ggaggagtgg acgcctacgg agaaagtca                49

<210> SEQ ID NO 288
<211> LENGTH: 24
<212> TYPE: DNA

```
<213> ORGANISM: Homo sapiens

<400> SEQUENCE: 288
tgttggcgaa gaatgctgtc tgcc                                          24

<210> SEQ ID NO 289
<211> LENGTH: 24
<212> TYPE: DNA
<213> ORGANISM: Homo sapiens

<400> SEQUENCE: 289
ccctggaaga agggacgtca gagg                                          24

<210> SEQ ID NO 290
<211> LENGTH: 24
<212> TYPE: DNA
<213> ORGANISM: Homo sapiens

<400> SEQUENCE: 290
tccagcttgg gaacaggcta cttc                                          24

<210> SEQ ID NO 291
<211> LENGTH: 88
<212> TYPE: DNA
<213> ORGANISM: Homo sapiens

<400> SEQUENCE: 291
cagtggcgaa ccacgtgccg gtaggaggtg gccaggtagt cgaagtagtt gatgttgagt   60
ttccgggcga tgtaacggcc caagtatt                                      88

<210> SEQ ID NO 292
<211> LENGTH: 30
<212> TYPE: DNA
<213> ORGANISM: Homo sapiens

<400> SEQUENCE: 292
tttccagcgc ccggaatcct tccactgtct                                    30

<210> SEQ ID NO 293
<211> LENGTH: 25
<212> TYPE: DNA
<213> ORGANISM: Homo sapiens

<400> SEQUENCE: 293
gtcaccacct ccccttgtcg cctag                                         25

<210> SEQ ID NO 294
<211> LENGTH: 105
<212> TYPE: DNA
<213> ORGANISM: Homo sapiens

<400> SEQUENCE: 294
tccagggtga ggctccgttc tccccatgag actgggggtt cctggtttgc atccctcgct   60
tctcatcatc ctgggggttc cagtaactgg gggttcagga acagg                  105

<210> SEQ ID NO 295
<211> LENGTH: 24
<212> TYPE: DNA
<213> ORGANISM: Homo sapiens

<400> SEQUENCE: 295
ttctcctcgt ggtggccttc tctg                                          24
```

<210> SEQ ID NO 296
<211> LENGTH: 24
<212> TYPE: DNA
<213> ORGANISM: Homo sapiens

<400> SEQUENCE: 296
gctcctgtcc ccaggttttc ccca                                          24

<210> SEQ ID NO 297
<211> LENGTH: 30
<212> TYPE: DNA
<213> ORGANISM: Homo sapiens

<400> SEQUENCE: 297
ggcaaagccg ggagaaactg ctgagacgag                                    30

<210> SEQ ID NO 298
<211> LENGTH: 32
<212> TYPE: DNA
<213> ORGANISM: Homo sapiens

<400> SEQUENCE: 298
aacttgagca ggtcccttc gcccatgggc gt                                  32

<210> SEQ ID NO 299
<211> LENGTH: 30
<212> TYPE: DNA
<213> ORGANISM: Homo sapiens

<400> SEQUENCE: 299
tgccggccgt ggtcgtgctg ttggccttct                                    30

<210> SEQ ID NO 300
<211> LENGTH: 27
<212> TYPE: DNA
<213> ORGANISM: Homo sapiens

<400> SEQUENCE: 300
tgagtggaac cgtgtgaaag agccggg                                       27

<210> SEQ ID NO 301
<211> LENGTH: 19
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 301
gctttgggtc caggaatgg                                                19

<210> SEQ ID NO 302
<211> LENGTH: 22
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 302
gttgtccaca gtcagcaatg gt                                            22

<210> SEQ ID NO 303

```
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 303
agaccagcaa gaagat                                                        16

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 304
ccatggatct ccaggtgggt                                                    20

<210> SEQ ID NO 305
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 305
ccagtggggc tgctgttatc tg                                                 22

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 306
actcaaactg tgggggcact                                                    20

<210> SEQ ID NO 307
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 307
ctctagaggg aagcgctttc tg                                                 22
```

COMBINATIONS OF CELL FREE NUCLEIC ACIDS

CROSS-REFERENCE TO RELATED APPLICATIONS

This patent application a continuation-in-part of U.S. patent application Ser. No. 15/991,725 filed May 29, 2018, which is a continuation-in-part of U.S. patent application Ser. No. 14/851,809 filed Sep. 11, 2015, which is a divisional of U.S. patent application Ser. No. 13/990,495 filed Jul. 9, 2013, which is a section 371 nationalization of PCT/US2011/062661 filed Nov. 30, 2011, which claims the benefit of U.S. Provisional Patent Applications 61/418,368 and 61/418,375, which were both filed on Nov. 30, 2010, and which applications are incorporated herein by specific reference in their entirety.

SEQUENCE LISTING

The instant application contains a Sequence Listing which has been submitted in ASCII format via EFS-Web and is hereby incorporated by reference in its entirety. Said ASCII copy, created on May 22, 2018, is named W2460-10001US05_CIP_Sequence_Listing.txt and is 248 kilobytes in size.

BACKGROUND

Preterm birth remains a major societal problem due to the short and long term health complications of the preterm infants. Many preterm infants live the initial parts of their lives in intensive and critical care units, and often have excess health problems through adulthood compared to infants delivered at term. Approximately 12% of infants delivered are a product of a preterm birth (PTB), which can be characterized as a spontaneous birth before 37 weeks of pregnancy. PTB is also associated with >70% of neonatal deaths and nearly half of long-term neurologic disabilities. Despite great effort among all health sectors, the PTB rate has continued to increases. Accordingly, there remains a great need to identify women at risk of having a PTB and to better understand the mechanisms culminating in PTB.

SUMMARY

In some embodiments, a method of detecting a combination of nucleic acid biomarkers in a human subject can include: obtaining a nucleic acid sample from the human subject; selecting the combination of nucleic acid biomarkers; analyzing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from a transcription standard, wherein the combination of nucleic acid biomarkers includes at least two of: miRNA-let-7 g having a nucleotide sequence of or complementary to SEQ ID NO: 13 with a variation less than the transcription standard; PSME2 having a nucleotide sequence of or complementary to SEQ ID NO: 68 with a variation less than the transcription standard; APOA1 having a nucleotide sequence of or complementary to SEQ ID NO: 53 with a variation less than the transcription standard; and NAMPT having a nucleotide sequence of or complementary to SEQ ID NO: 71 with a variation less than the transcription standard. In some aspects: the variation for miRNA-let-7 g is about −1.8 fold change; the variation for PSME2 is about −5.6 fold change; the variation for APOA1 is about −1.9 fold change; and/or the variation for NAMPT is −2.3 fold change. In some aspects, the analyzing includes hybridizing each nucleic acid biomarker in the nucleic acid sample with a complementary nucleic acid configured as a primer or a probe, the method comprising detecting the hybridizing.

In some embodiments, the combination of nucleic acid biomarkers includes one of: PSME2 and APOA1; PSME2 and miRNA-let-7 g; NAMPT and APOA1; or miRNA-let-7 g, PSME2, APOA1, and NAMPT. In some aspects, the combination of nucleic acid biomarkers includes all of miRNA-let-7 g, PSME2, APOA1, and NAMPT, and further includes: APOA4 having a nucleotide sequence of or complementary to SEQ ID NO: 71, wherein the variation for APOA4 is less than the transcription standard. In some aspects, the variation for APOA4 is about −1.5 fold change.

In some embodiments, the combination of nucleic acid biomarkers includes at least one of: miRNA-99b having a nucleotide sequence of or complementary to SEQ ID NO: 7 with a variation greater than the transcription standard; miRNA-99a having a nucleotide sequence of or complementary to SEQ ID NO: 6 with a variation greater than the transcription standard; and miRNA-548 L having a nucleotide sequence of or complementary to SEQ ID NO: 5 with a variation greater than the transcription standard.

In some embodiments, the combination of nucleic acid biomarkers includes at least one of: miRNA-99b having a nucleotide sequence of or complementary to SEQ ID NO: 7 with about a 1.7 fold change variation greater than the transcription standard; miRNA-99a having a nucleotide sequence of or complementary to SEQ ID NO: 6 with about a 1.6 fold change variation greater than the transcription standard; and miRNA-548 L having a nucleotide sequence of or complementary to SEQ ID NO: 5 with about a 1.5 variation greater than the transcription standard.

In some embodiments, the combination of nucleic acid biomarkers includes at least one of: miRNA-490 having a nucleotide sequence of or complementary to SEQ ID NO: 304 with a variation less than the transcription standard; miRNA-491 having a nucleotide sequence of or complementary to SEQ ID NO: 9 with a variation less than the transcription standard; miRNA-31 having a nucleotide sequence of or complementary to SEQ ID NO: 11 with a variation less than the transcription standard; miRNA-382 having a nucleotide sequence of or complementary to SEQ ID NO: 8 with a variation less than the transcription standard; miRNA-342 having a nucleotide sequence of or complementary to SEQ ID NO: 12 with a variation less than the transcription standard; miRNA-194 having a nucleotide sequence of or complementary to SEQ ID NO: 305 with a variation less than the transcription standard; miRNA-214 having a nucleotide sequence of or complementary to SEQ ID NO: 10 with a variation less than the transcription standard; miRNA-371 having a nucleotide sequence of or complementary to SEQ ID NO: 306 with a variation less than the transcription standard; and/or miRNA-519c having a nucleotide sequence of or complementary to SEQ ID NO: 307 with a variation less than the transcription standard.

In some embodiments, the combination of nucleic acid biomarkers includes at least one of: miRNA-490 having a nucleotide sequence of or complementary to SEQ ID NO: 304 with about a −4.7 fold change variation less than the transcription standard; miRNA-491 having a nucleotide sequence of or complementary to SEQ ID NO: 9 with about a −2.2 fold change variation less than the transcription standard; miRNA-31 having a nucleotide sequence of or complementary to SEQ ID NO: 11 with about a −1.9 fold change variation less than the transcription standard; miRNA-382 having a nucleotide sequence of or complementary to SEQ ID NO: 8 with about a −1.8 fold change variation less than the transcription standard; miRNA-342 having a nucleotide sequence of or complementary to SEQ ID NO: 12 with about a −1.5 fold change variation less than the transcription standard; miRNA-194 having a nucleotide sequence of or complementary to SEQ ID NO: 305 with about a −1.5 fold change variation less than the transcription standard; miRNA-214 having a nucleotide sequence of or complementary to SEQ ID NO: 10 with about a −1.5 fold change variation less than the transcription standard; miRNA-371 having a nucleotide sequence of or complementary to SEQ ID NO: 306 with about a −1.4 fold change variation less than the transcription standard; and/or miRNA-519c having a nucleotide sequence of or complementary to SEQ ID NO: 307 with about a −1.3 fold change variation less than the transcription standard.

In some embodiments, the combination of nucleic acid biomarkers includes at least one of: SF3A3 having a nucleotide sequence of or complementary to SEQ ID NO: 25 with a variation greater than the transcription standard; F1116171 having a nucleotide sequence of or complementary to SEQ ID NO: 21 with a variation greater than the transcription standard; REG3G having a nucleotide sequence of or complementary to SEQ ID NO: 22 with a variation greater than the transcription standard; NDUFA2 having a nucleotide sequence of or complementary to SEQ ID NO: 24 with a variation greater than the transcription standard; LCE2A having a nucleotide sequence of or complementary to SEQ ID NO: 26 with a variation greater than the transcription standard KRTAP6-2 having a nucleotide sequence of or complementary to SEQ ID NO: 42 with a variation less than the transcription standard; CHCHD10 having a nucleotide sequence of or complementary to SEQ ID NO: 50 with a variation less than the transcription standard; OR4D1 having a nucleotide sequence of or complementary to SEQ ID NO: 62 with a variation less than the transcription standard; BLOC1S1 having a nucleotide sequence of or complementary to SEQ ID NO: 52 with a variation less than the transcription standard; PDZK1 having a nucleotide sequence of or complementary to SEQ ID NO: 56 with a variation less than the transcription standard; KRT17 having a nucleotide sequence of or complementary to SEQ ID NO: 58 with a variation less than the transcription standard; CSRP2 having a nucleotide sequence of or complementary to SEQ ID NO: 61 with a variation less than the transcription standard; PSG9 having a nucleotide sequence of or complementary to SEQ ID NO: 46 with a variation less than the transcription standard; ARMC10 having a nucleotide sequence of or complementary to SEQ ID NO: 48 with a variation less than the transcription standard; CD3E having a nucleotide sequence of or complementary to SEQ ID NO: 54 with a variation less than the transcription standard; GUCA2B having a nucleotide sequence of or complementary to SEQ ID NO: 47 with a variation less than the transcription standard; TNFRSF13C having a nucleotide sequence of or complementary to SEQ ID NO: 64 with a variation less than the transcription standard; LOC643008 having a nucleotide sequence of or complementary to SEQ ID NO: 41 with a variation less than the transcription standard; MRPS21 having a nucleotide sequence of or complementary to SEQ ID NO: 65 with a variation less than the transcription standard; NAT14 having a nucleotide sequence of or complementary to SEQ ID NO: 57 with a variation less than the transcription standard; PRTN3 having a nucleotide sequence of or complementary to SEQ ID NO: 45 with a variation less than the transcription standard; OR2A2 having a nucleotide sequence of or complementary to SEQ ID NO: 44 with a variation less than the transcription standard; RPL8 having a nucleotide sequence of or complementary to SEQ ID NO: 63 with a variation less than the transcription standard; TMEM188 having a nucleotide sequence of or complementary to SEQ ID NO: 60 with a variation less than the transcription standard; RPS19BP1 having a nucleotide sequence of or complementary to SEQ ID NO: 59 with a variation less than the transcription standard; and/or JSRP1 having a nucleotide sequence of or complementary to SEQ ID NO: 67 with a variation less than the transcription standard.

In some embodiments, the combination of nucleic acid biomarkers includes at least one of: SF3A3 having a nucleotide sequence of or complementary to SEQ ID NO: 25 with about a 2.7 fold change variation greater than the transcription standard; FLJ16171 having a nucleotide sequence of or complementary to SEQ ID NO: 21 with about a 2.6 fold change variation greater than the transcription standard; REG3G having a nucleotide sequence of or complementary to SEQ ID NO: 22 with about a 1.9 fold change variation greater than the transcription standard; NDUFA2 having a nucleotide sequence of or complementary to SEQ ID NO: 24 with about a 1.6 fold change variation greater than the transcription standard; LCE2A having a nucleotide sequence of or complementary to SEQ ID NO: 26 with about a 2.3 fold change variation greater than the transcription standard KRTAP6-2 having a nucleotide sequence of or complementary to SEQ ID NO: 42 with about a −2.1 fold change variation less than the transcription standard; CHCHD10 having a nucleotide sequence of or complementary to SEQ ID NO: 50 with about a −2.6 fold change variation less than the transcription standard; OR4D1 having a nucleotide sequence of or complementary to SEQ ID NO: 62 with about a −2.3 fold change variation less than the transcription standard; BLOC1S1 having a nucleotide sequence of or complementary to SEQ ID NO: 52 with about a −2.2 fold change variation less than the transcription standard; PDZK1 having a nucleotide sequence of or complementary to SEQ ID NO: 56 with about a −2.0 fold change variation less than the transcription standard; KRT17 having a nucleotide sequence of or complementary to SEQ ID NO: 58 with about a −2.0 fold change variation less than the transcription standard; CSRP2 having a nucleotide sequence of or complementary to SEQ ID NO: 61 with about a −1.8 fold change variation less than the transcription standard; PSG9 having a nucleotide sequence of or complementary to SEQ ID NO: 46 with about a −1.8 fold change variation less than the transcription standard; ARMC10 having a nucleotide sequence of or complementary to SEQ ID NO: 48 with about a −1.7 fold change variation less than the transcription standard; CD3E having a nucleotide sequence of or complementary to SEQ ID NO: 54 with about a −1.7 fold change variation less than the transcription standard; GUCA2B having a nucleotide sequence of or complementary to SEQ ID NO: 47 with about a −1.7 fold change variation less than the transcription standard; TNFRSF13C having a nucleotide sequence of or complementary to SEQ ID NO: 64 with about a −1.6 fold change variation less than the transcription standard; LOC643008 having a nucleotide sequence of or complementary to SEQ ID NO: 41 with about a −1.6 fold change variation less than the transcription standard; MRPS21 having a nucleotide sequence of or complementary to SEQ ID NO: 65 with about a −1.6 fold change variation less than the transcription standard; NAT14 having a nucleotide sequence of or complementary to SEQ ID NO: 57 with about a −1.6 fold change variation less than the transcription standard; PRTN3 having a nucleotide sequence of or complementary to SEQ ID NO: 45 with about a −1.6 fold change variation less than the transcription standard; OR2A2 having a nucleotide sequence of or complementary to SEQ ID NO: 44 with about a −1.6 fold change variation less than the transcription standard; RPL8 having a nucleotide sequence of or complementary to SEQ ID NO: 63 with about a −1.5 fold change variation less than the transcription standard; TMEM188 having a nucleotide sequence of or complementary to SEQ ID NO: 60 with about a −1.5 fold change variation less than the transcription standard; RPS19BP1 having a nucleotide sequence of or complementary to SEQ ID NO: 59 with about a −1.5 fold change variation less than the transcription standard; and/or JSRP1 having a nucleotide sequence of or complementary to SEQ ID NO: 67 with about a −1.5 fold change variation less than the transcription standard.

In some embodiments, the method includes providing the transcription standard for each nucleic acid biomarker for the combination of nucleic acid biomarkers.

In some embodiments, the method includes providing the combination of nucleic acid biomarkers as a set of primers and/or probes.

In some embodiments, the method includes obtaining cell free plasma RNA as the nucleic acid sample. In some embodiments, the nucleic acid biomarkers are RNA.

In some embodiments, the method can include: selecting a normalization nucleic acid; analyzing the transcriptome of the human subject for the normalization nucleic acid in the nucleic acid sample from the human subject; and detecting in the nucleic acid sample the presence of the normalization nucleic acid, wherein normalization nucleic acid has a variation from a transcription standard, wherein the normalization nucleic acid has a nucleotide sequence of or complementary to one of SEQ ID NOs: 1-4 and 301-303.

In some embodiments, the method can include generating a report, the report reciting the presence of the combination of nucleic acid biomarkers being present in the nucleic acid sample of the human subject being present in a biomarker amount that is varied from the transcription standard.

In some embodiments, a method of detecting a combination of nucleic acid biomarkers in a human subject can include: obtaining a nucleic acid sample from the human subject; selecting the combination of nucleic acid biomarkers; providing a transcription standard for each nucleic acid biomarker for the combination of nucleic acid biomarkers; analyzing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from the transcription standard, wherein the combination of nucleic acid biomarkers includes: miRNA-let-7 g having a nucleotide sequence of or complementary to SEQ ID NO: 13 with a variation less than the transcription standard; miRNA-99b having a nucleotide sequence of or complementary to SEQ ID NO: 7 with a variation greater than the transcription standard; miRNA-99a having a nucleotide sequence of or complementary to SEQ ID NO: 6 with a variation greater than the transcription standard; and miRNA-548 L having a nucleotide sequence of or complementary to SEQ ID NO: 5 with a variation greater than the transcription standard.

In some embodiments, a method of detecting a combination of nucleic acid biomarkers in a human subject can include: obtaining a nucleic acid sample from the human subject; selecting the combination of nucleic acid biomarkers; providing a transcription standard for each nucleic acid biomarker for the combination of nucleic acid biomarkers; analyzing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from the transcription standard, wherein the combination of nucleic acid biomarkers includes: miRNA-let-7 g having a nucleotide sequence of or complementary to SEQ ID NO: 13 with a variation less than the transcription standard; miRNA-490 having a nucleotide sequence of or complementary to SEQ ID NO: 304 with a variation less than the transcription standard; miRNA-491 having a nucleotide sequence of or complementary to SEQ ID NO: 9 with a variation less than the transcription standard; miRNA-31 having a nucleotide sequence of or complementary to SEQ ID NO: 11 with a variation less than the transcription standard; miRNA-382 having a nucleotide sequence of or complementary to SEQ ID NO: 8 with a variation less than the transcription standard; miRNA-342 having a nucleotide sequence of or complementary to SEQ ID NO: 12 with a variation less than the transcription standard; miRNA-194 having a nucleotide sequence of or complementary to SEQ ID NO: 305 with a variation less than the transcription standard; miRNA-214 having a nucleotide sequence of or complementary to SEQ ID NO: 10 with a variation less than the transcription standard; miRNA-371 having a nucleotide sequence of or complementary to SEQ ID NO: 306 with a variation less than the transcription standard; and/or miRNA-519c having a nucleotide sequence of or complementary to SEQ ID NO: 307 with a variation less than the transcription standard.

In one embodiment, a kit includes purified or isolated nucleic acids, wherein the nucleic acids have the sequences of each of the nucleic acid biomarkers in the combination of biomarkers. As such, each recited combination can be uniquely included in a kit.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1A:
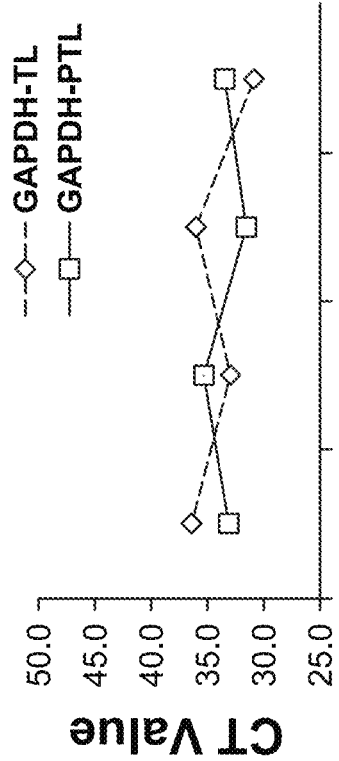
FIGS. 1A-1D illustrate that our new discovered messenger RNA (mRNA) normalization sequences of PPIA are more stabilized (FIG. 1D) compared to published normalization sequences (FIGS. 1A, 1B, and 1C)
Figure 1B:
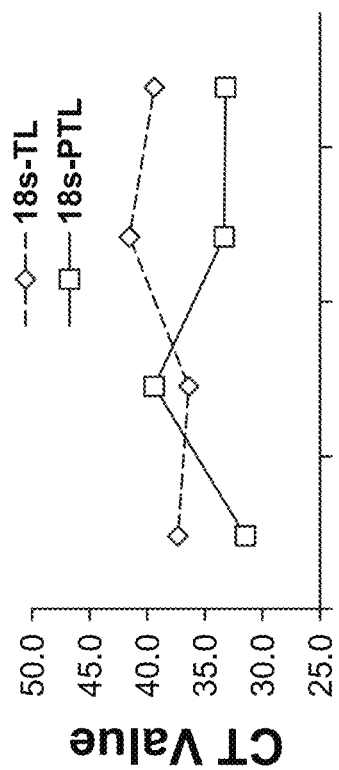
Figure 1C:
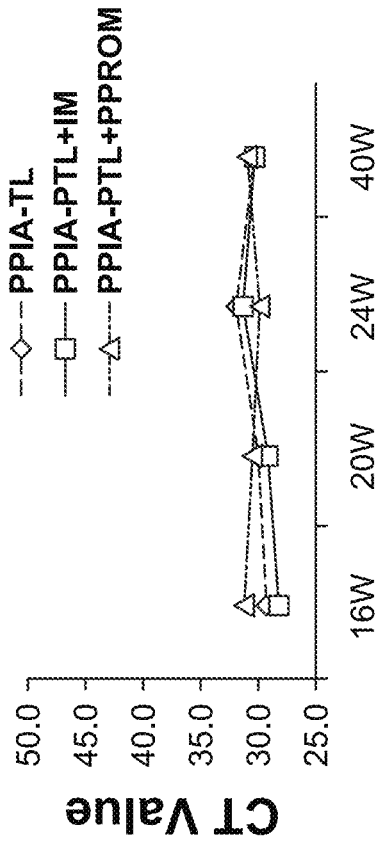

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to the use of nucleic acids to predict preterm birth (PTB) or determine the probability or susceptibility of PTB in a woman. The nucleic acids useful for PTB diagnostics can include nucleic acid primers and/or probes that bind with specific nucleic acid sequences as well as the nucleic acids that are increased or decreased in a woman that may be susceptible to PTB. The nucleic acids can include specific nucleic acid sequences relevant to PTB, which sequences function as biomarkers for PTB. Diagnostic kits can be provided with specific nucleic acid primers and/or probes, labeled or unlabeled, that can selectively bind with nucleic acids associated with PTB. The diagnostic kits can also include nucleic acid primers that can be used for amplifying nucleic acids associated with PTB. The diagnostic kits can include probes that can identify the presence of certain nucleic acid sequences. In one aspect, all PTB specific nucleic acids can be included on customized PCR cards. By utilizing high throughput PCR technique, the PCR cards can be used for diagnostics and determination of nucleic acid presence and/or amount. The methods of the present invention can include diagnosing whether or not a pregnant woman is susceptible to PTB.

The present invention can also include normalization nucleic acids (e.g., mRNA and miRNA) that have normalization sequences that can be used to normalize the relative levels of nucleic acid data from one sample to the next. We illustrate that our new discovered mRNA and miRNA normalization sequence are stabilized and not impacted by gestational age compared to previously published reports. These normalization nucleic acids can be also be included in diagnostic kits. The methods of the present invention can use the normalization nucleic acids in sample normalization protocols. These protocols can be useful for normalizing nucleic acid amounts between samples. While these normalization nucleic acids are useful for PTB diagnostic protocols, they can also be used to normalize nucleic acid amounts for any purpose.

While RNA is a preferred nucleic acid for the compositions and methods described herein, it is possible that DNA or RNA/DNA hybrids could also be used as nucleic acid probes and/or primers for diagnostics or normalization protocols. However, the nucleic acids that are identified to be present, up-regulated, or down-regulated in diagnostic protocols will generally be RNA as it is transcribed from DNA (e.g., complementary RNA) or as processed into mRNA. The RNA may also be regulatory RNA, such as non-coding small RNA (miRNA, siRNA, snRNA, or snoRNA) that are involved in gene silencing or transcription or translation regulation. Also, normalization protocols will generally be performed with RNA.

The nucleic acids can be cell free plasma (CFP) RNA, which refers to RNA derived from a variety of cells within differing organs, and circulates systemically. CFP RNA may include several types including coding RNA (e.g., mRNA) and non-coding RNAs (e.g., siRNA, miRNA, snoRNA, snRNA). Using microarray techniques, we screen all gene mRNA and non-coding RNAs including siRNA, miRNA, snoRNA, and snRNA. We found only some mRNA and miRNA can be altered by preterm labor. In one aspect, the CFP RNAs can include maternal CFP mRNA and CFP miRNA. The CFP RNAs can be detectable in plasma from the mother's peripheral circulation long before any symptoms or signs of preterm labor. The nucleic acids can be characterized as CFP RNA PTB biomarkers as they can individually or in combination provide a biomarker for PTB and prediction of PTB or PTB susceptibility. The CFP RNA PTB biomarkers can be used to provide a pattern of PTB biomarkers that may reflect the underlying mechanisms that result in PTB or susceptibility thereto.

In one embodiment, the CFP RNA can be specific RNA nucleic acid sequences. That is, the sequences can be a whole or portion of an mRNA or miRNA. The sequences themselves can be used for preparing primers and/or probes for the methods described herein, and may be used at targets for detection as well as for further studies in developing targeted therapies. The CFP RNA nucleic acid sequences are provided in the Sequence Listing and have SEQ ID NOs: 1-307. These sequences in the Sequence Listing are provided in DNA format; however, these sequences can be employed with the RNA format with uracil (U) replacing thymine (T). Accordingly, references to the SEQ ID NOs 1-307 of the Sequence Listing can be in RNA format, DNA format, or DNA/RNA hybrid. In a preferred embodiment, the SEQ ID NOs 1-307 of the Sequence Listing are specifically RNA, such as for the miRNA and mRNA described herein, and thereby any "T" is replaced with a "U" as understood by one of ordinary skill in the art. Thus, a recitation of SEQ ID NOs 1-307 of the Sequence Listing can specifically refer to the corresponding RNA nucleic acids, and thereby reference to a SEQ ID NO references the RNA nucleic acid with all of the "T" is replaced with a "U" as understood by one of ordinary skill in the art.

Accordingly, CFP RNA PTB biomarkers can be used for the development of targeted pharmacotherapy that could be initiated before myometrial activation occurs, as opposed to after the onset of symptoms such as cervical shortening or contractions. The CFP RNA PTB biomarkers can be used in order to design a therapy that can modulate the production of certain biological substances, such as proteins associated with myometrial activation or the inhibition of myometrial activation. The PTB biomarkers may also be used in diagnostic protocols for other pregnancy disorders, such as abnormal placentation (e.g., preeclampsia, IUGR, etc.), dysfunctional cervical ripening, short cervix, or others where the pathologic mechanisms overlap or intersect. The PTB biomarkers can be used to identify maternal CFP transcriptome patterns indicative of certain fetal malformations, such as for diagnosis of common triploidies.

In one embodiment, the present invention can use a combination of CFP RNA PTB biomarkers for diagnosing a pregnancy disorder or susceptibility thereof, and providing a therapy in order to treat and/or prevent the pregnancy disorder. For example, a diagnostic protocol can be used to diagnose or predict the ultimate development of a sonographically short cervix, and then a medical professional can treat the condition with progesterone supplementation from information obtained from the PTB biomarkers, which diagnosis and treatment could be as early as 12, 16, 18, or 22 weeks gestation before the cervix has actually shortened.

In one embodiment, a diagnostic kit can be provided with one or more CFP RNA PTB biomarkers and instructions of use that can be used to identify susceptibility of PTB in women as early as possible (e.g., 12, 16, 18, 20, 22, 24, 26, 28, 30, or up to 32 weeks) to allow for intervention before a PTB indicator such as either myometrial activation or cervical ripening or both is irrevocably activated. The diagnostic kit can include one or multiple PTB biomarkers in a single composition or PCR card or PCR card spot, where each PTB biomarker can be used for targeting different causes of PTB. Alternatively, two or more of such PTB biomarkers may be used together to maximize the predictive values of the test. The diagnostic kit can include nucleic acids that are the complement of CFP RNA PTB biomarker sequences that are used to perform the diagnostic. These nucleic acids can be the primers and/or probes for such a diagnostic protocol. The nucleic acids can also be included in plasmids for expression of the PTB biomarker sequences. The diagnostic kit can also identify the CFP RNA PTB biomarker sequences that are to be identified as up-regulated or down-regulated, and may specify the mRNA, miRNA, general sequence thereof, or the exact sequences in such CFP RNA PTB biomarkers that are specific to which the primers and/or probes hybridize. The CFP RNA PTB biomarkers have sequences that are included in the Sequence Listing having SEQ ID NOs: 5-300 and 304-307. In some instances, such as shorter sequences, the entire recited sequence can be used, and in other instances unique portions of the sequences that are unique and specific for that mRNA or miRNA can be used in the invention described herein.

Normalization Sequences

Quantification of nucleic acids (e.g., RNA) extracted from a biological sample can be important data. The actual quantification of RNA in a sample and its comparison to other RNA sequences in a single sample or in multiple samples usually requires a nucleic acid normalization sequence. The normalization sequence can be RNA that has an amount or expression level is generally stable under the conditions studied. That is, the normalization sequence can have an amount or level that is substantially unaffected by any physiological circumstances present in a subject, and thereby the normalization sequence can be used to normalize the amount of nucleic acid in separate samples for comparison. The separate samples can be from different subjects or the same subject at different time points, such as different time points in pregnancy. For example, the normalization sequence can be used to normalize the amount of RNA in Q-rtPCR studies, such as by normalizing the amount of the RNA sequence of interest. The normalization sequences described herein can be used alone or in combination, and may be used to normalize samples to be assayed for PTB biomarkers. However, the normalization sequences can be used to normalize the amount of RNA in different samples for other purposes than for PTB biomarkers. Thereby, the normalization sequences can be used as general normalization sequences to normalize the amount of RNA in different samples for any purpose. Thus, the normalization sequences provided herein can be for quantification of free RNA isolated from biological samples.

Figure 1D:
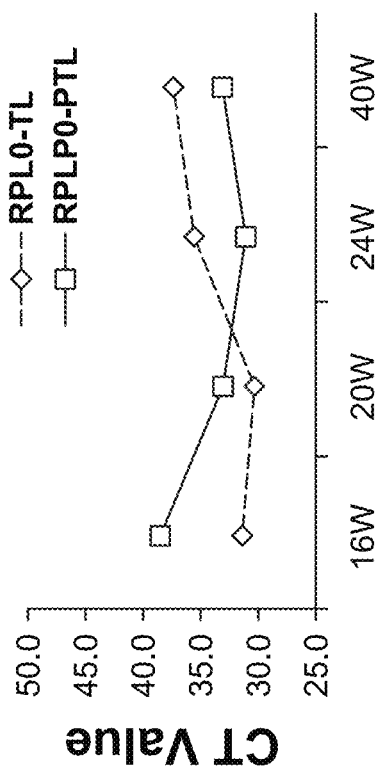
Figure 2B:
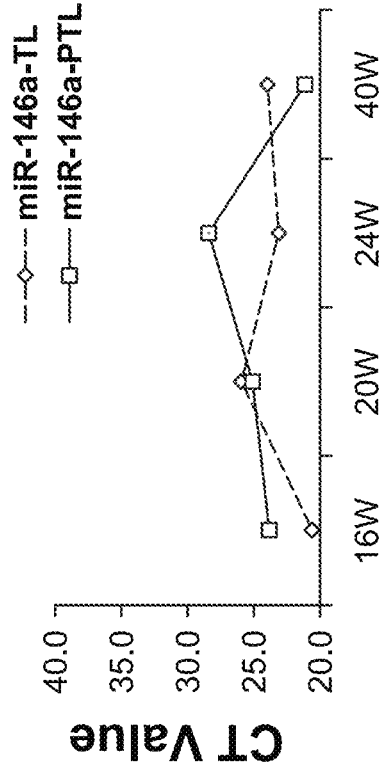
FIGS. 2A-2D illustrate that our new discovered snRNA: U6 is not impacted by different gestational age; snRNA:U6 plays a better role as micro RNA (miRNA) normalization sequences compared to reported sequences.
Figure 2D:
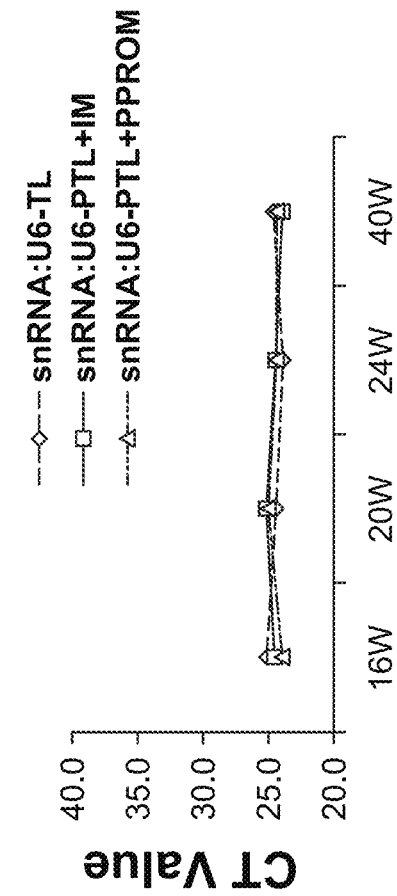
Figure 2A:
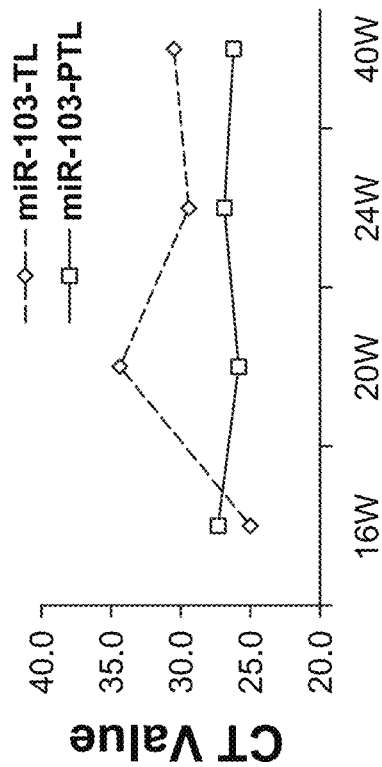
Figure 2C:
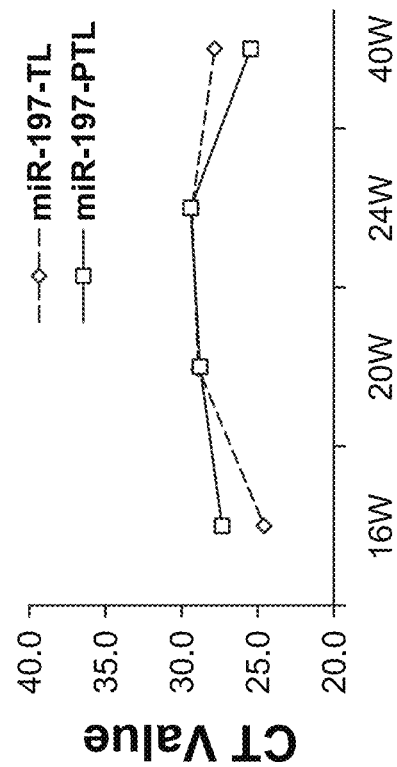

It has been determined that previously reported normalization sequences utilized in other tissues for quantification of isolated RNA (e.g., mRNA: 18s RNA, RPLP0, GAPDH; miRNA: miR-103, miR-146a, and miR-197) were either expressed inconsistently in control plasma samples or were altered by either pregnancy, gestational age or disease (see FIGS. 1A-1C and 2A-2C). Thus, new normalization sequences were sought and identified (see FIGS. 1D, and 2D). These new normalization sequences can include CFP mRNA and CFP miRNA sequences that are substantially unchanged by any condition, such as by pregnancy. However, the CFP RNA normalization sequences and related process can be equally applicable to almost any disease state ranging from pregnancy and PTB to malignancy to cardiovascular disease to bone disease or joint disease or the like.

In one embodiment, the normalization sequence includes a circulating RNA. Such a normalization sequence can be described as human (i.e., *Homo sapiens*) peptidylprolyl isomerase A (i.e., cyclophilin A, rotmase A), which is encoded by the PPIA gene. The normalization sequence can be the mRNA for peptidylprolyl isomerase. The peptidylprolyl isomerase normalization sequence can be found at accession number: NM_021130 and/or NM_001008741, which is incorporated herein by specific reference. The peptidylprolyl isomerase normalization sequence is defined herein as SEQ ID NO: 1), and can be useful for normalization of mRNA.

In one embodiment, the normalization sequence can include miRNA. Such a normalization sequence can be a *Drosophila melanogaster* small nuclear RNA, such as snRNA:U6. The snRNA:U6 normalization sequence can be snRNA:U6 at 96Aa, 96:Ab, and/or 96Ac. These normalization sequences can be described as snRNA:U6:96Aa (SEQ ID NO: 2 for miRNA), snRNA:U6:96Ab (SEQ ID NO: 3 for miRNA), and/or snRNA:U6:96Ac (SEQ ID NO: 4 for miRNA), and can be found at the following accession numbers, respectively: NR_002081 (snRNA:U6:96Aa); NR_002082 (snRNA:U6:96Ab); and NR_002083 (snRNA:U6:96Ac), which accession numbers and information associated therewith are incorporated herein by specific reference. FIGS. 1A-1D and 2A-2D illustrate the impact of gestational age, preterm premature rupture of membranes (PPROM) and ultimate spontaneous preterm birth on some of the sequences rejected and the one mRNA and miRNA selected for normalization (see FIGS. 1D and 2D). Accordingly, SEQ ID NOs: 2-4 for miRNA, and SEQ ID No 1 for mRNA can be used for normalization sequences generally, and particularly for normalization of PTB biomarkers. Primers and probes for these sequences can be readily obtained by one of ordinary skill in the art with this application. For example, sequences for the forward primer, reverse primer, and probe for SEQ ID NO: 1 (e.g., for mRNA normalization sequence of PPIA) will be: Forward primer: GCTTTGGGTCCAGGAATGG—SEQ ID NO: 301; Reverse primer: GTTGTCCACAGTCAGCAATGGT—SEQ ID NO: 302; and Probe: AGACCAGCAAGAAGAT—

SEQ ID NO: 303, which can also be considered normalization sequences for the invention recited herein.

In one embodiment, a normalization kit can be provided that includes one or more of these normalization sequences in nucleic acid format, such as RNA, DNA, or RNA/DNA hybrid. Preferably, the sequences of the normalization kit will include the complement of the sequences recited in the SEQ ID NO: 1-4. Also preferably, the sequences of the normalization kit will include the sequences recited in SEQ ID NO: 301-303 as these sequences are complementary to SEQ ID NO 1. Also, the normalization kit may also be included in a PTB diagnostic kit as described herein. The normalization kit can include individual compositions that have a single normalization sequence, or a single composition can include one, two, three, or all four of the normalization sequences and/or primers and/or probes thereof. Each sequence may be on a separate nucleic acid, or multiple sequences can be on a single nucleic acid. The normalization sequences can be provided with or without a label, such as a visual label or radiolabel. The normalization sequences can be provided on a customized PCR card or similar device configured for use in nucleic acid detection and/or quantification and/or qualification, which card or similar device can be configured as a high-throughput Real-time Q-PCR system. One or more sample spots on a customized PCR card can have one, two, three, or all four of the normalization sequences and/or the primers and/or probes thereof. For example, the PCR card can have one spot with one normalization sequence or a spot with up to all four normalization sequences and/or primers and/or probes thereof. Such a PCR card can have one or more normalization sequences spots, which spots can be reaction wells or the like. The PCR card may also have assay spots having nucleic acids to be assayed. For example, the customized PCR card can be configured as an ABI high-through put Real-time PCR system. The incorporation of these normalization sequences in the various PCR card products allows them to be more readily used for plasma-derived samples, and in repeated measures of CFP mRNA and CFP miRNA or other nucleic acid normalization.

In one embodiment, a normalization sequence can be a nucleic acid that contains or consists of the sequence. The normalization sequence can be identical to one of SEQ ID NOs: 2-4 for miRNA, and SEQ ID NO 1 for mRNA as well as SEQ ID NOs: 301-303, or can be a complement thereof, sense or antisense, as well as a sequence that hybridizes therewith under suitable conditions. The normalization sequence can have perfect complementarity or greater than or about 95% complementarity, greater than or about 90% complementarity, greater than or about 85% complementarity, or greater than or about 80% complementarity. Complementarity can be considered with respect to a nucleic acid in a biological sample or natural nucleic acid obtained therefrom. The normalization sequence can be a continuous or it can have one or more bulges or mismatches upon hybridization. The normalization sequence can also include one or more chemical modifications, such as a 2' carbon modification. The normalization sequence may or may not form an overhang upon hybridization. The normalization sequence can include a sequence from about 15 nucleotides to the full sequence, from about 16 nucleotides to about 100 nucleotides, from about 17 nucleotides to about 50 nucleotides, from about 18 nucleotides to about 30 nucleotides, from about 19 nucleotides to about 25 nucleotides, or from about 20 to about 22 nucleotides in sequence of one of SEQ ID NOs: 2-3 for miRNA, and SEQ ID 1 for mRNA. The normalization sequence can include a unique sequence segment or complement thereof of the full sequence having a length as described.

In one embodiment, the present invention can include a method of identifying a normalization sequence, such as a pregnancy normalization sequence. The method can include obtaining a plurality of plasma free (e.g., CFP) RNA, CFP mRNA, and/or CFP miRNA sequences from a plurality of subjects (e.g., men or women) prior to a particular disease state (e.g. spontaneous preterm birth in women or prostate cancer in men, without limitation thereto). When pregnant women, the sequences can be obtained prior to or at 32 weeks, 30 weeks, 28 weeks, 26 weeks, 24 weeks, 22 weeks, 20 weeks, 18 weeks, 16, or 12 weeks of pregnancy, and possibly even earlier in pregnancy. Once obtained, one or more CFP mRNA and/or CFP miRNA sequences that are unchanged between disease states (e.g. between two or more women destined for a spontaneous preterm birth of less than 32 weeks) can be identified, and these unchanged sequences can be determined to be normalization sequences. Different disease states can be prior to onset of a disease and then after onset of disease. The identified sequences can be assayed and confirmed to be CFP mRNA and/or CFP miRNA or other CFP RNA that are substantially unchanged between two or more of the samples. The unchanged sequences can be further confirmed to be unchanged between additional sequences. The unchanged sequences can be normalization sequences as described herein.

Another embodiment of a method of identifying a CFP normalization nucleic acid can include obtaining a plurality of plasma free (e.g., CFP) mRNA or miRNA sequences from a plurality of nonpregnant women or pregnant women prior to 32 weeks, such as between about 12-32 weeks of pregnancy. The sequences can be from one woman that is or becomes pregnant or from a plurality of women that are or become pregnant, where one or more sequences can be from a woman that becomes pregnant and that is susceptible to PTB. One or more sequences can even be after birth or after a PTB. After obtained, the sequences can be assayed in order to identify one or more plasma cell free mRNA or miRNA sequences unchanged between different pregnancy states. The different pregnancy states can be between two or more women, or between nonpregnant and pregnant, or between early pregnancy (e.g., before about 16 weeks), or late pregnancy (e.g., after about 16 weeks), or between prior to onset of a PTB-indicating symptom or after a PTB-indicating symptom, or between pregnancy and having or had preterm birth of less than 32 weeks, or combination thereof. The sequences can then be analyzed in order to confirm (e.g., by Qrt-PCR) that the CFP mRNA or miRNA are unchanged between two or more samples having the sequences. The analysis can be between different women or different pregnancy states. Unchanged sequence presence or amount of sequence is indicative that the sequence can be a normalization sequence as described herein.

In another embodiment, a method of identifying CFP normalization nucleic acids or sequences thereof can include: obtaining a plurality of CFP mRNA or CFP miRNA sequences from a plurality of women between 16-28 weeks of pregnancy or prior to birth or PTB; identifying one or more CFP mRNA or miRNA sequences unchanged between two or more women having, had, or that will have PTB of less than 32 weeks; and confirming, by Qrt-PCR, that the CFP mRNA or miRNA is unchanged between two or more samples of CFP RNA and/or CFP miRNA from one or more other women that are un-pregnant, pregnant or two or more women having, had, or that will have PTB of less than 32 weeks. Also, a plurality of CFP RNA can be obtained from women after having a term birth or a PTB.

In one embodiment, the unchanged sequences or possible normalization sequences can be assayed by confirming the sequences to be unchanged or normalization sequences between randomly selected samples.

In one embodiment, the present invention includes a method of quantification of CFP RNA. Such a method can include providing a CFP normalization nucleic acid, and comparing a sample of purified plasma RNA (CFP RNA) from a subject with the CFP normalization sequence, such as a nucleic acid having the normalization sequence. Such a comparison can then be used to determine the amount of CFP RNA in the sample and across two or more samples. Accordingly, different samples from different sources can be normalized using the CFP normalization sequence. One, two, three, or four of the different normalization sequences and/or primers and/or probes thereof can be used for quantification of CFP RNA. The method of quantification of CFP RNA can be performed substantially as known or later developed by using the normalizations sequences described herein.

In another embodiment, a method of normalizing CFP normalization nucleic acids or sequences thereof can include: obtaining a plurality of CFP mRNA or CFP miRNA sequences from a plurality of women between 12 and 32 weeks or 16-28 weeks of pregnancy or prior to birth or PTB; providing one or more CFP mRNA or miRNA sequences unchanged between two or more women having, had, or that will have PTB of less than 32 weeks; and normalizing the CFP mRNA or miRNA sequences with the known unchanged CFP mRNA or miRNA sequences.

In one embodiment, a method of normalizing CFP mRNA or miRNA sequences can include normalizing with one or more of SEQ ID NOs: 1-4 or primer and/or probe thereof or SEQ ID NOs: 301-303 via standard normalization protocols.

The methods described can also include obtaining samples that have RNA from a subject and processing the sample in order to obtain CFP RNA.

PTB Biomarker Sequences

Quantification of PTB biomarker nucleic acids (e.g., RNA) extracted from a biological sample can be used in order to determine whether or not a pregnant woman is susceptible to PTB. Accordingly, identification of PTB biomarkers can be important in order to diagnose PTB susceptibility or predict PTB. The present invention generally includes new RNA biomarkers and processes to identify plasma RNA biomarkers, and use of the RNA biomarkers to identify pre-disease states related to PTB. The present invention can use RNA biomarkers associated with pregnancy disease states in order to predict whether a pregnant women may develop or become susceptible to developing a particular disease state that may cause PTB. Generally, the PTB biomarkers include nucleic acids that are CFP RNA as described herein.

CFP RNA biomarkers can include maternal and fetal derived RNA sequences. Since myometrial activation can result in spontaneous birth, and since myometrial quiescence is a genomically rich period, changes in the CFP transcriptome (e.g., RNA transcriptome) can be used to predict spontaneous PTB. Such a change in the CFP transcriptome can be indicative of PTB regardless of whether the stimulus originated in either the maternal or fetal compartments. The CFP RNA PTB biomarkers have now been identified and are provided in the Sequence Listing as SEQ ID NOs: 5-300. These CFP RNA PTB biomarker sequences are involved in the biological and regulatory process of pregnancy, and modulation of these CFP RNA PTB biomarkers can be an indication of disease. Also, modulation of these CFP RNA PTB biomarker may be used to inhibit, prevent, or treat a disease associated with the particular mRNA or miRNA of the CFP RNA PTB biomarker.

Briefly, CFP mRNA was obtained at 26-28 weeks from 5 randomly selected women destined for PTB (e.g., birth <32 weeks) absent PPROM (i.e., preterm, premature rupture of membranes), and from 5 control women destined for delivery at term. In a 'Discovery Phase' of CFP mRNA identification, the extracted RNA were run on the Affymetrix Human Whole-Transcript Expression Array, and the mRNA sequences altered in women destined for PTB were identified based on fold change (e.g., ≥1.5×, a standard cutoff used across science) and p value from control (p<0.01). The CFP mRNA were ordered by narrowness of distribution (e.g., Ingenuity Systems Pathway Analysis) since a narrow distribution is a highly desirable test characteristic for any selected marker, where the narrower the distribution of disease and normal, the smaller the overlap in population distributions. Of the 25,934 RNA sequences identified to comprise the CFP transcriptome at 26 weeks, 88 CFP mRNA PTB biomarkers were altered in women destined for PTB; 22 CFP mRNA PTB biomarkers (SEQ ID NOs: 19-41) were up-regulated and 66 CFP mRNA (SEQ ID NOs: 42-106) were down-regulated. Genomic mapping revealed the CFP mRNA PTB marker sequences were associated with expression, cell growth and proliferation, cell cycle, cell death, and cellular assembly and organization.

CFP RNA PTB biomarkers can include but are not limited to non-coding RNA, such as miRNA and snRNA and snoRNA, and others are mRNA. In one embodiment, the CFP RNA PTB biomarkers can include a biomarker that indicates susceptibility to PTB. These CFP RNA PTB biomarkers can include: (SEQ ID NO: 19) *Homo sapiens* taspase, threonine aspartase, 1 (TASP1), mRNA, accession number NM_017714; (SEQ ID NO: 20) *Homo sapiens* zinc finger protein 99 (ZNF99), mRNA, accession numbers NM_001080409 and XM_001132267; (SEQ ID NO: 21) *Homo sapiens* cDNA FLJ16171 fis, clone BRHIP2003272, accession number AK131247; (SEQ ID NO: 22) *Homo sapiens* regenerating islet-derived 3 gamma (REG3G), transcript variant 1, mRNA, accession number NM_001008387; (SEQ ID NO: 23) *Homo sapiens* olfactory receptor, family 51, subfamily A, member 2 (OR51A2), mRNA, accession numbers NM_001004748 and XM_377159; (SEQ ID NO: 24) *Homo sapiens* NADH dehydrogenase (ubiquinone) 1 alpha subcomplex, 2, 8 kDa (NDUFA2), nuclear gene encoding mitochondrial protein, transcript variant 1, mRNA, accession number NM_002488; (SEQ ID NO: 25) *Homo sapiens* splicing factor 3a, subunit 3, 60 kDa (SF3A3), mRNA, accession number NM_006802; (SEQ ID NO: 26) *Homo sapiens* late cornified envelope 2A (LCE2A), mRNA, accession number NM_178428; (SEQ ID NO: 27) *Homo sapiens* 5100 calcium binding protein A14 (S100A14), mRNA, accession number NM_020672; (SEQ ID NO: 28) *Homo sapiens* six transmembrane epithelial antigen of the prostate 1 (STEAP1), mRNA, accession numbers NM_012449 and XM_940149; (SEQ ID NO: 29) *Homo sapiens* cDNA FLJ11733 fis, clone HEMBA1005426, accession number AK021795; (SEQ ID NO: 30) *Homo sapiens* speedy homolog E1 (*Xenopus laevis*) (SPDYE1), mRNA, accession numbers NM_175064, XM_938448, XM_943679, XM_943682, XM_943684, XM_943688, and XM_943692; (SEQ ID NO: 31) *Homo sapiens* tripartite motif-containing 48 (TRIM48), mRNA, accession number NM_024114; (SEQ ID NO: 32) *Homo sapiens* non-protein coding RNA 152 (NCRNA00152), transcript variant 1, non-coding RNA, accession numbers NR_024204, XR_042051, and XR_042052; (SEQ ID NO: 33) *Homo sapiens* cDNA FLJ39739 fis, clone SMINT2016440, accession number AK097058; (SEQ ID NO: 34) *Homo sapiens* FXYD domain containing ion transport regulator 2 (FXYD2), transcript variant c, mRNA, accession number NM_001127489; (SEQ ID NO: 35) *Homo sapiens* chromosome 1 open reading frame 104, mRNA (cDNA clone MGC:70363 IMAGE:5183308), complete cds, accession number BC062571; (SEQ ID NO: 36) *Homo sapiens* phosphoserine aminotransferase 1 (PSAT1), transcript variant 1, mRNA, accession number NM_058179; (SEQ ID NO: 37) *Homo sapiens* KIAA1274 (KIAA1274), mRNA, accession numbers NM_014431 and XM_166125; (SEQ ID NO: 38) *Homo sapiens* taste receptor, type 2, member 10 (TAS2R10), mRNA, accession number NM_023921; (SEQ ID NO: 39) *Homo sapiens* ribosomal protein S20 (RPS20), transcript variant 2, mRNA, accession number NM_001023; (SEQ ID NO: 40) *Homo sapiens* glycerol-3-phosphate acyltransferase 2, mitochondrial (GPAT2), nuclear gene encoding mitochondrial protein, mRNA, accession number NM_207328; (SEQ ID NO: 41) *Homo sapiens* hypothetical protein LOC643008 (LOC643008), transcript variant 1, mRNA, accession numbers NM_001162995 and NR_024379; (SEQ ID NO: 42) *Homo sapiens* keratin associated protein 6-2 (KRTAP6-2), mRNA, accession number NM_181604; (SEQ ID NO: 43) *Homo sapiens* saitohin (STH), mRNA, accession number NM_001007532; (SEQ ID NO: 44) *Homo sapiens* olfactory receptor, family 2, subfamily A, member 2 (OR2A2), mRNA, accession number NM_001005480 and XM_498253; (SEQ ID NO: 45) *Homo sapiens* proteinase 3 (PRTN3), mRNA, accession number NM_002777; (SEQ ID NO: 46) *Homo sapiens* pregnancy specific beta-1-glycoprotein 9 (PSG9), mRNA, accession number NM_002784; (SEQ ID NO: 47) *Homo sapiens* guanylate cyclase activator 2B (uroguanylin) (GUCA2B), mRNA, accession number NM_007102; (SEQ ID NO: 48) *Homo sapiens* armadillo repeat containing 10 (ARMC10), transcript variant A, mRNA, accession number NM_031905; (SEQ ID NO: 49) *Homo sapiens* chromosome 11 open reading frame 59 (C11orf59), mRNA, accession number NM_017907; (SEQ ID NO: 50) *Homo sapiens* coiled-coil-helix-coiled-coil-helix domain containing 10, (CHCHD10), mRNA, accession number NM_213720; (SEQ ID NO: 51) *Homo sapiens* 2-oxoglutarate and iron-dependent oxygenase domain containing 2 (OGFOD2), mRNA, accession number NM_024623; (SEQ ID NO: 52) *Homo sapiens* biogenesis of lysosomal organelles complex-1, subunit 1 (BLOC1S1), mRNA, accession number NM_001487; (SEQ ID NO: 53) *Homo sapiens* apolipoprotein A-I (APOA1), mRNA, accession number NM_000039; (SEQ ID NO: 54) *Homo sapiens* CD3e molecule, epsilon (CD3-TCR complex) (CD3E), mRNA, accession number NM_000733; (SEQ ID NO: 55) *Homo sapiens* keratinocyte differentiation-associated protein (KRTDAP), mRNA, accession number NM_207392; (SEQ ID NO: 56) *Homo sapiens PDZ domain containing 1* (PDZK1), mRNA, accession numbers NM_002614, XM_936907, XM_943050, XM_943061, and XM_943068; (SEQ ID NO: 57) *Homo sapiens* N-acetyltransferase 14 (GCN5-related, putative) (NAT14), mRNA, accession number NM_020378; (SEQ ID NO: 58) *Homo sapiens* keratin 17 (KRT17), mRNA, accession number NM_000422; (SEQ ID NO: 59) *Homo sapiens* ribosomal protein S19 binding protein 1 (RPS19BP1), mRNA, accession numbers NM_194326 and XM_039373; (SEQ ID NO: 60) *Homo sapiens* transmembrane protein 188 (TMEM188), mRNA, accession number NM_153261; (SEQ ID NO: 61) *Homo sapiens* cysteine and glycine-rich protein 2 (CSRP2), mRNA, accession number NM_001321; (SEQ ID NO: 62) *Homo sapiens* olfactory receptor, family 4, subfamily D, member 1 (OR4D1), mRNA, accession numbers NM_012374 and XM_292627; (SEQ ID NO: 63) *Homo sapiens* ribosomal protein L8 (RPL8), transcript variant 1, mRNA, accession number NM_000973; (SEQ ID NO: 64) *Homo sapiens* tumor necrosis factor receptor superfamily, member 13C (TNFRSF13C), mRNA, accession number NM_052945; (SEQ ID NO: 65) *Homo sapiens* mitochondrial ribosomal protein S21 (MRPS21), nuclear gene encoding mitochondrial protein, transcript variant 2, mRNA, accession number NM_018997; (SEQ ID NO: 66) *Homo sapiens* apolipoprotein A-IV (APOA4), mRNA, accession number NM_000482; (SEQ ID NO: 67) *Homo sapiens* junctional sarcoplasmic reticulum protein 1 (JSRP1), mRNA, accession number NM_144616; (SEQ ID NO: 68) *Homo sapiens* proteasome (prosome, macropain) activator subunit 2 (PA28 beta) (PSME2), mRNA, accession number NM_002818; (SEQ ID NO: 69) *Homo sapiens* zinc finger and BTB domain containing 5 (ZBTB5), mRNA, accession number NM_014872 and XM_376832; (SEQ ID NO: 70) *Homo sapiens* chromosome 10 open reading frame 95, mRNA (cDNA clone MGC:161737 IMAGE:8992175), complete cds, accession number, BC126459; (SEQ ID NO: 71) *Homo sapiens* nicotinamide phosphoribosyltransferase (NAMPT), mRNA, accession number NM_005746; (SEQ ID NO: 72) *Homo sapiens* trace amine associated receptor 6 (TAAR6), mRNA, accession number, NM_175067; (SEQ ID NO: 73) *Homo sapiens* myosin, light chain 6, alkali, smooth muscle and non-muscle (MYL6), transcript variant 1, mRNA, accession numbers NM_021019 and NM_079424; (SEQ ID NO: 74) *Homo sapiens* ATP synthase, H+ transporting, mitochondrial Fo complex, subunit C2 (subunit 9) (ATP5G2), nuclear gene encoding mitochondrial protein, transcript variant 2, mRNA, accession number NM_005176; (SEQ ID NO: 75) *Homo sapiens* family with sequence similarity 18, member B2 (FAM18B2), transcript variant 1, mRNA, accession numbers NM_145301 and XM_936923; (SEQ ID NO: 76) *Homo sapiens* Sp6 transcription factor (SP6), mRNA, accession numbers NM_199262 and XM_292621; (SEQ ID NO: 77) *Homo sapiens* inverted formin, FH2 and WH2 domain containing (INF2), transcript variant 1, mRNA, accession number NM_022489; (SEQ ID NO: 78) *Homo sapiens* Rho GDP dissociation inhibitor (GDI) alpha (ARHGDIA), transcript variant 2, mRNA, accession number NM_004309; (SEQ ID NO: 79) *Homo sapiens* OTU domain containing 6A (OTUD6A), mRNA, accession number NM_207320; (SEQ ID NO: 80) *Homo sapiens* zinc finger and BTB domain containing 12 (ZBTB12), mRNA, accession number NM_181842; (SEQ ID NO: 81) *Homo sapiens* mitotic spindle organizing protein 2B (MZT2B), mRNA, accession number NM_025029; (SEQ ID NO: 82) *Homo sapiens* olfactory receptor, family 52, subfamily E, member 2 (OR52E2), mRNA, accession number NM_001005164 and XM_061610; (SEQ ID NO: 83) *Homo sapiens* hypothetical LOC150622 (LOC150622), non-coding RNA, accession number NR_026832, XR_041760, XR_041761, and XR_041762; (SEQ ID NO: 84) *Homo sapiens* selenophosphate synthetase 1 (SEPHS1), transcript variant 1, mRNA, accession number NM_012247; (SEQ ID NO: 85) *Homo sapiens* barrier to autointegration factor 1 (BANF1), transcript variant 1, mRNA, accession number NM_003860; (SEQ ID NO: 86) *Homo sapiens* general transcription factor IIB (GTF2B), mRNA, accession number NM_001514;

(SEQ ID NO: 87) *Homo sapiens* RGM domain family, member A (RGMA), transcript variant 4, mRNA, accession number NM_020211; (SEQ ID NO: 88) *Homo sapiens* prolactin releasing hormone receptor (PRLHR), mRNA, accession number NM_004248 and NM_005287; (SEQ ID NO: 89) *Homo sapiens* dpy-19-like 2 pseudogene 2 (*C. elegans*) (DPY19 L2P2), transcript variant 2, non-coding RNA, accession number NR_003561; (SEQ ID NO: 90) *Homo sapiens* meteorin, glial cell differentiation regulator (METRN), mRNA, accession number NM_024042; (SEQ ID NO: 91) *Homo sapiens* free fatty acid receptor 1 (FFAR1), mRNA, accession number NM_005303; (SEQ ID NO: 92) *Homo sapiens* natriuretic peptide B (NPPB), mRNA, accession number NM_002521; (SEQ ID NO: 93) *Homo sapiens* BCL2/adenovirus E1B 19 kDa interacting protein 3 (BNIP3), nuclear gene encoding mitochondrial protein, mRNA, accession number NM_004052; (SEQ ID NO: 94) *Homo sapiens* basic helix-loop-helix family, member a15 (BHLHA15), mRNA, accession number NM_177455; (SEQ ID NO: 95) *Homo sapiens* Finkel-Biskis-Reilly murine sarcoma virus (FBR-MuSV) ubiquitously expressed (FAU), mRNA, accession number NM_001997; (SEQ ID NO: 96) *Homo sapiens* chromosome 9 open reading frame 70 (C9orf70), non-coding RNA, accession number NR_026663 and XM_001721481 XM_001723928 XM_001724353; (SEQ ID NO: 97) *Homo sapiens* ribosomal protein L30 (RPL30), mRNA, accession number NM_000989; (SEQ ID NO: 98) *Homo sapiens* meteorin, glial cell differentiation regulator-like (METRNL), mRNA, accession number NM_001004431 and XM_209073; (SEQ ID NO: 99) *Homo sapiens* ubiquitin-like 5 (UBL5), transcript variant 1, mRNA, accession number NM_024292; (SEQ ID NO: 100) *Homo sapiens* potassium inwardly-rectifying channel, subfamily J, member 4, (KCNJ4), transcript variant 1, mRNA, accession number NM_152868; (SEQ ID NO: 101) *Homo sapiens* nascent polypeptide-associated complex alpha subunit (NACA), transcript variant 1, mRNA, accession number NM_001113203; (SEQ ID NO: 102) *Homo sapiens* small EDRK-rich factor 2 (SERF2), mRNA, accession number NM_001018108; (SEQ ID NO: 103) *Homo sapiens* sulfotransferase family, cytosolic, 1A, phenol-preferring, member 2 (SULT1A2), transcript variant 2, mRNA, accession number NM_177528; (SEQ ID NO: 104) *Homo sapiens* olfactory receptor, family 51, subfamily G, member 2 (OR51G2), mRNA, accession number NM_001005238; (SEQ ID NO: 105) *Homo sapiens* basic transcription factor 3 (BTF3), transcript variant 1, mRNA, accession number NM_001037637; and (SEQ ID NO: 106) *Homo sapiens* LSM10, U7 small nuclear RNA associated (LSM10), mRNA, accession number NM_032881, which accession numbers and information associated therewith are incorporated herein by specific reference.

In one embodiment, the CFP RNA PTB biomarkers can include a biomarker that is up-regulated in order to indicate susceptibility to PTB having SEQ ID NOs: 107-142, wherein the Probset ID, accession numbers, Gene Symbols, and start and stop of the sequences thereof are incorporated herein by specific reference:

| SEQ ID NO: | # | Probeset ID | Gene Symbol | RefSeq (Accession) | Seqname | Start | Stop |
|---|---|---|---|---|---|---|---|
| SEQ ID NO: | 107 | 2391026 | C1orf159 | BC008788 | chr1 | 1020631 | 1020674 |
| SEQ ID NO: | 108 | 2465373 | AHCTF1 | NM_015446 | chr1 | 247063497 | 247063521 |
| SEQ ID NO: | 109 | 2321026 | C1orf158 | NM_152290 | chr1 | 12821062 | 12821086 |
| SEQ ID NO: | 110 | 2370564 | CACNA1E | NM_000721 | chr1 | 181705411 | 181705435 |
| SEQ ID NO: | 111 | 2445415 | ASTN1 | NM_004319 | chr1 | 176927594 | 176927618 |
| SEQ ID NO: | 112 | 2383404 | ADCK3 | NM_020247 | chr1 | 227165195 | 227165219 |
| SEQ ID NO: | 113 | 3314648 | C10orf92 | BC034223 | chr10 | 134628211 | 134628236 |
| SEQ ID NO: | 114 | 3332991 | C11orf66 | NM_145017 | chr11 | 61257978 | 61258037 |
| SEQ ID NO: | 115 | 3377201 | CDC42BPG | NM_017525 | chr11 | 64601758 | 64601797 |
| SEQ ID NO: | 116 | 3381279 | ARAP1 | BC056401 | chr11 | 72411090 | 72411124 |
| SEQ ID NO: | 117 | 3403055 | ATN1 | NM_001007026 | chr12 | 7045236 | 7045261 |
| SEQ ID NO: | 118 | 3655114 | CD19 | NM_001178098 | chr16 | 28943903 | 28943933 |
| SEQ ID NO: | 119 | 3739970 | ABR | NM_021962 | chr17 | 913969 | 913994 |
| SEQ ID NO: | 120 | 3774020 | C17orf70 | NR_033338 | chr17 | 79518798 | 79518881 |
| SEQ ID NO: | 121 | 3774725 | CCDC57 | ENST00000324808 | chr17 | 80109446 | 80109470 |
| SEQ ID NO: | 122 | 3741735 | CAMKK1 | AF370377 | chr17 | 3773035 | 3773059 |
| SEQ ID NO: | 123 | 3830886 | ARHGAP33 | NM_052948 | chr19 | 36273687 | 36273769 |
| SEQ ID NO: | 124 | 3835887 | APOE | NM_000041 | chr19 | 45412388 | 45412412 |
| SEQ ID NO: | 125 | 3866306 | AP2S1 | NM_004069 | chr19 | 47342008 | 47342032 |
| SEQ ID NO: | 126 | 2546857 | CAPN13 | NM_144575 | chr2 | 30993219 | 30993282 |
| SEQ ID NO: | 127 | 2576644 | C2orf27B | BC043584 | chr2 | 132552867 | 132552917 |
| SEQ ID NO: | 128 | 2546826 | CAPN13 | NM_144575 | chr2 | 30961299 | 30961323 |
| SEQ ID NO: | 129 | 2708707 | C3orf70 | NM_001025266 | chr3 | 184870647 | 184870677 |
| SEQ ID NO: | 130 | 2622179 | BSN | NM_003458 | chr3 | 49699843 | 49699867 |
| SEQ ID NO: | 131 | 2870730 | BCLAF1 | NM_014739 | chr5 | 110285528 | 110285604 |
| SEQ ID NO: | 132 | 2902959 | C4A | ENST00000428956 | chr6 | 31949811 | 31949835 |
| SEQ ID NO: | 133 | 2953468 | C6orf130 | ENST00000488238 | chr6 | 41043021 | 41043070 |
| SEQ ID NO: | 134 | 3031798 | ABCB8 | NM_007188 | chr7 | 150744493 | 150744517 |
| SEQ ID NO: | 135 | 3039763 | ANKMY2 | NM_020319 | chr7 | 16666684 | 16666799 |
| SEQ ID NO: | 136 | 3023426 | AHCYL2 | NM_001130723 | chr7 | 129008311 | 129008335 |
| SEQ ID NO: | 137 | 3031951 | AGAP3 | NM_031946 | chr7 | 150841064 | 150841088 |
| SEQ ID NO: | 138 | 3031944 | AGAP3 | AL442089 | chr7 | 150838958 | 150838982 |
| SEQ ID NO: | 139 | 3206269 | ATP5A1 | NM_001001937 | chr9 | 41799773 | 41799797 |
| SEQ ID NO: | 140 | 4001353 | BEND2 | NM_153346 | chrX | 18221855 | 18222031 |
| SEQ ID NO: | 141 | 3969900 | CA5B | ENST00000479740 | chrX | 15768063 | 15768093 |
| SEQ ID NO: | 142 | 3966810 | CD99P1 | NR_033380 | chrX | 2541426 | 12541450 |

In one embodiment, the CFP RNA PTB biomarkers can include a biomarker that is down-regulated in order to indicate susceptibility to PTB, wherein the Probset ID, accession numbers, Gene Symbols, and start and stop of the sequences thereof are incorporated herein by specific reference:

| SEQ ID NO: | # | Probeset ID | Gene Symbol | RefSeq (Accession) | Seqname | start | stop |
|---|---|---|---|---|---|---|---|
| SEQ ID NO: | 143 | 2434348 | APH1A | AK125685 | chr1 | 150239436 | 150239470 |
| SEQ ID NO: | 144 | 2347527 | ABCD3 | NM_001122674 | chr1 | 94944215 | 94944239 |
| SEQ ID NO: | 145 | 2347504 | ABCD3 | NM_002858 | chr1 | 94884035 | 94884129 |
| SEQ ID NO: | 146 | 2347024 | CCDC18 | NM_206886 | chr1 | 93645587 | 93645967 |
| SEQ ID NO: | 147 | 2383766 | ARF1 | NM_001024227 | chr1 | 228286406 | 228286440 |
| SEQ ID NO: | 148 | 2411671 | AGBL4 | ENST00000411952 | chr1 | 49052585 | 49052609 |
| SEQ ID NO: | 149 | 2316059 | ATAD3A | NM_018188 | chr1 | 1469347 | 1469376 |
| SEQ ID NO: | 150 | 2391349 | ACAP3 | AB051503 | chr1 | 1240376 | 1240469 |
| SEQ ID NO: | 151 | 2385702 | C1orf57 | NM_032324 | chr1 | 233086457 | 233086481 |
| SEQ ID NO: | 152 | 2393833 | C1orf174 | NM_207356 | chr1 | 3816811 | 3816835 |
| SEQ ID NO: | 153 | 2440696 | B4GALT3 | NM_003779 | chr1 | 161147290 | 161147314 |
| SEQ ID NO: | 154 | 2383363 | ADCK3 | ENST00000366779 | chr1 | 227096295 | 227096344 |
| SEQ ID NO: | 155 | 2318458 | CAMTA1 | NM_015215 | chr1 | 6845541 | 6845635 |
| SEQ ID NO: | 156 | 2392132 | C1orf86 | ENST00000378545 | chr1 | 2130199 | 2130245 |
| SEQ ID NO: | 157 | 2399312 | ALDH4A1 | NM_003748 | chr1 | 19199312 | 19199336 |
| SEQ ID NO: | 158 | 3286039 | CCNYL2 | ENST00000345581 | chr10 | 42965620 | 42965646 |
| SEQ ID NO: | 159 | 3282296 | ACBD5 | ENST00000375888 | chr10 | 27529434 | 27529579 |
| SEQ ID NO: | 160 | 3261217 | BTRC | NM_033637 | chr10 | 103285926 | 103285955 |
| SEQ ID NO: | 161 | 3284165 | C1D | NM_173177 | chr10 | 32800666 | 32800698 |
| SEQ ID NO: | 162 | 3245187 | ANXA8L2 | NM_001630 | chr10 | 47747028 | 47747107 |
| SEQ ID NO: | 163 | 3251356 | ANAPC16 | NM_173473 | chr10 | 73975872 | 73975896 |
| SEQ ID NO: | 164 | 3380994 | C11orf59 | NM_017907 | chr11 | 71814234 | 71814263 |
| SEQ ID NO: | 165 | 3353451 | C11orf63 | NM_024806 | chr11 | 122774660 | 122774979 |
| SEQ ID NO: | 166 | 3370889 | ALX4 | NM_021926 | chr11 | 44296901 | 44297069 |
| SEQ ID NO: | 167 | 3364964 | ABCC8 | NM_000352 | chr11 | 17453766 | 17453791 |
| SEQ ID NO: | 168 | 3377365 | BATF2 | NM_138456 | chr11 | 64757241 | 64757266 |
| SEQ ID NO: | 169 | 3351287 | CD3E | NM_000733 | chr11 | 118175668 | 118175692 |
| SEQ ID NO: | 170 | 3323765 | ANO5 | NM_213599 | chr11 | 22215039 | 22215069 |
| SEQ ID NO: | 171 | 3352074 | CBL | NM_005188 | chr11 | 119077128 | 119077154 |
| SEQ ID NO: | 172 | 3332702 | CD6 | NM_006725 | chr11 | 60785827 | 60785851 |
| SEQ ID NO: | 173 | 3378518 | C1QBP | NM_001212 | chr11 | 66529422 | 66529450 |
| SEQ ID NO: | 174 | 3334998 | CAPN1 | NM_005186 | chr11 | 64978760 | 64978949 |
| SEQ ID NO: | 175 | 3316546 | AP2A2 | NM_012305 | chr11 | 1010548 | 1010572 |
| SEQ ID NO: | 176 | 3358122 | C11orf35 | NM_173573 | chr11 | 556268 | 556374 |
| SEQ ID NO: | 177 | 3457551 | ANKRD52 | NM_173595 | chr12 | 56631722 | 56631752 |
| SEQ ID NO: | 178 | 3440081 | CACNA2D4 | NM_172364 | chr12 | 1909167 | 1909199 |
| SEQ ID NO: | 179 | 3431564 | C12orf24 | AK297684 | chr12 | 110924538 | 110924563 |
| SEQ ID NO: | 180 | 3434501 | CABP1 | NM_031205 | chr12 | 121088358 | 121088431 |
| SEQ ID NO: | 181 | 3435685 | ARL6IP4 | NM_018694 | chr12 | 123466154 | 123466179 |
| SEQ ID NO: | 182 | 3413611 | CACNB3 | NM_000725 | chr12 | 49212713 | 49212756 |
| SEQ ID NO: | 183 | 3523859 | C13orf27 | NM_138779 | chr13 | 103418821 | 103418856 |
| SEQ ID NO: | 184 | 3573232 | ALKBH1 | NM_006020 | chr14 | 78140155 | 78140183 |
| SEQ ID NO: | 185 | 3563711 | C14orf138 | NM_024558 | chr14 | 50583243 | 50583268 |
| SEQ ID NO: | 186 | 3543628 | C14orf169 | NM_024644 | chr14 | 73957998 | 73958031 |
| SEQ ID NO: | 187 | 3576909 | ATXN3 | NR_028453 | chr14 | 92547321 | 92547345 |
| SEQ ID NO: | 188 | 3557166 | ACIN1 | NM_014977 | chr14 | 23564322 | 23564348 |
| SEQ ID NO: | 189 | 3604597 | ADAMTS7 | NM_014272 | chr15 | 82611989 | 82612090 |
| SEQ ID NO: | 190 | 3601544 | CCDC33 | NM_025055 | chr15 | 74536429 | 74536486 |
| SEQ ID NO: | 191 | 3605931 | ALPK3 | NM_020778 | chr15 | 85411431 | 85411647 |
| SEQ ID NO: | 192 | 3619410 | C15orf52 | NM_207380 | chr15 | 40627985 | 40628027 |
| SEQ ID NO: | 193 | 3605398 | ADAMTSL3 | NM_207517 | chr15 | 84324481 | 84324513 |
| SEQ ID NO: | 194 | 3636496 | BTBD1 | NM_025238 | chr15 | 83735879 | 83735903 |
| SEQ ID NO: | 195 | 3628544 | CA12 | NM_001218 | chr15 | 63637686 | 63637806 |
| SEQ ID NO: | 196 | 3601237 | CD276 | NM_001024736 | chr15 | 73992032 | 73992056 |
| SEQ ID NO: | 197 | 3607736 | C15orf42 | NM_152259 | chr15 | 90167064 | 90167094 |
| SEQ ID NO: | 198 | 3620776 | CDAN1 | NM_138477 | chr15 | 43026443 | 43026535 |
| SEQ ID NO: | 199 | 3619407 | C15orf52 | NM_207380 | chr15 | 40627389 | 40627585 |
| SEQ ID NO: | 200 | 3617732 | ACTC1 | NM_005159 | chr15 | 35084610 | 35084634 |
| SEQ ID NO: | 201 | 3619427 | C15orf52 | AK126485 | chr15 | 40631674 | 40631701 |
| SEQ ID NO: | 202 | 3655082 | ATP2A1 | NM_173201 | chr16 | 28909568 | 28909754 |
| SEQ ID NO: | 203 | 3656848 | BCKDK | NM_001122957 | chr16 | 31123381 | 31123415 |
| SEQ ID NO: | 204 | 3695322 | CDH16 | NM_004062 | chr16 | 66944302 | 66944327 |
| SEQ ID NO: | 205 | 3704743 | ANKRD11 | NM_013275 | chr16 | 89351849 | 89352020 |
| SEQ ID NO: | 206 | 3662891 | CCDC135 | NM_032269 | chr16 | 57738788 | 57738820 |
| SEQ ID NO: | 207 | 3687096 | BOLA2 | NM_001031827 | chr16 | 30204743 | 30204770 |
| SEQ ID NO: | 208 | 3686627 | APOB48R | NM_018690 | chr16 | 28507548 | 28507572 |
| SEQ ID NO: | 209 | 3770812 | CASKIN2 | NM_020753 | chr17 | 73499499 | 73499557 |
| SEQ ID NO: | 210 | 3767486 | AXIN2 | NM_004655 | chr17 | 63533032 | 63533167 |
| SEQ ID NO: | 211 | 3742217 | ALOX15 | NM_001140 | chr17 | 4535481 | 4535558 |
| SEQ ID NO: | 212 | 3742483 | CAMTA2 | NM_015099 | chr17 | 4876890 | 4877042 |
| SEQ ID NO: | 213 | 3764300 | BZRAP1 | BX648763 | chr17 | 56382268 | 56382298 |
| SEQ ID NO: | 214 | 3722682 | C17orf88 | NR_026770 | chr17 | 41994608 | 41994632 |
| SEQ ID NO: | 215 | 3766544 | CD79B | NM_000626 | chr17 | 62008702 | 62008726 |
| SEQ ID NO: | 216 | 3748962 | ALDH3A1 | NM_001135168 | chr17 | 19641470 | 19641494 |

-continued

| SEQ ID NO: | # | Probeset ID | Gene Symbol | RefSeq (Accession) | Seqname | start | stop |
|---|---|---|---|---|---|---|---|
| SEQ ID NO: | 217 | 3774985 | C17orf101 | NR_033265 | chr17 | 80350291 | 80350395 |
| SEQ ID NO: | 218 | 3764359 | BZRAP1 | NM_004758 | chr17 | 56404109 | 56404137 |
| SEQ ID NO: | 219 | 3774706 | CCDC57 | NM_198082 | chr17 | 80059693 | 80059731 |
| SEQ ID NO: | 220 | 3773685 | AZI1 | NM_014984 | chr17 | 79172707 | 79172736 |
| SEQ ID NO: | 221 | 3773633 | AATK | ENST00000417379 | chr17 | 79105718 | 79105746 |
| SEQ ID NO: | 222 | 3848059 | C3 | NM_000064 | chr19 | 6684786 | 6684810 |
| SEQ ID NO: | 223 | 3866980 | CARD8 | NM_001184900 | chr19 | 48715191 | 48715220 |
| SEQ ID NO: | 224 | 3850462 | AP1M2 | NM_005498 | chr19 | 10685580 | 10685611 |
| SEQ ID NO: | 225 | 3854387 | ANO8 | NM_020959 | chr19 | 17439225 | 17439281 |
| SEQ ID NO: | 226 | 3837683 | C19orf68 | BC043386 | chr19 | 48700487 | 48700516 |
| SEQ ID NO: | 227 | 3867278 | CA11 | NM_001217 | chr19 | 49143358 | 49143452 |
| SEQ ID NO: | 228 | 3865986 | CCDC8 | NM_032040 | chr19 | 46916087 | 46916262 |
| SEQ ID NO: | 229 | 3846260 | C19orf28 | NM_021731 | chr19 | 3557104 | 3557128 |
| SEQ ID NO: | 230 | 3868520 | ASPDH | NM_001114598 | chr19 | 51014987 | 51015030 |
| SEQ ID NO: | 231 | 3860221 | ALKBH6 | NM_198867 | chr19 | 36502307 | 36502333 |
| SEQ ID NO: | 232 | 3815214 | AZU1 | NM_001700 | chr19 | 828320 | 828371 |
| SEQ ID NO: | 233 | 3817205 | ATCAY | NM_033064 | chr19 | 3917745 | 3917775 |
| SEQ ID NO: | 234 | 3846377 | APBA3 | NM_004886 | chr19 | 3754199 | 3754228 |
| SEQ ID NO: | 235 | 3830369 | CD22 | NM_001771 | chr19 | 35823497 | 35823523 |
| SEQ ID NO: | 236 | 3842076 | BRSK1 | NM_032430 | chr19 | 55805471 | 55805501 |
| SEQ ID NO: | 237 | 3852137 | CACNA1A | NM_000068 | chr19 | 13318294 | 13318431 |
| SEQ ID NO: | 238 | 3824734 | ARRDC2 | NM_015683 | chr19 | 18121452 | 18121479 |
| SEQ ID NO: | 239 | 3834055 | AXL | NM_021913 | chr19 | 41737096 | 41737140 |
| SEQ ID NO: | 240 | 3846299 | C19orf29 | NM_001080543 | chr19 | 3613163 | 3613278 |
| SEQ ID NO: | 241 | 3836141 | BLOC1S3 | NM_212550 | chr19 | 45683121 | 45683155 |
| SEQ ID NO: | 242 | 3832352 | CATSPERG | NM_021185 | chr19 | 38852853 | 38852886 |
| SEQ ID NO: | 243 | 3843980 | A1BG-AS | BC040926 | chr19 | 58864701 | 58864725 |
| SEQ ID NO: | 244 | 3846310 | C19orf29 | NM_001080543 | chr19 | 3620730 | 3620754 |
| SEQ ID NO: | 245 | 3839117 | ATF5 | NM_012068 | chr19 | 50436321 | 50436349 |
| SEQ ID NO: | 246 | 2521240 | CCDC150 | NM_001080539 | chr2 | 197504344 | 197504405 |
| SEQ ID NO: | 247 | 2474325 | C2orf28 | NM_016085 | chr2 | 27435237 | 27435334 |
| SEQ ID NO: | 248 | 2574650 | BIN1 | NM_139343 | chr2 | 127808040 | 127808098 |
| SEQ ID NO: | 249 | 2473975 | C2orf18 | NM_017877 | chr2 | 27001867 | 27001894 |
| SEQ ID NO: | 250 | 2500292 | BCL2L11 | AB071199 | chr2 | 111887709 | 111887791 |
| SEQ ID NO: | 251 | 2505925 | ARHGEF4 | NM_015320 | chr2 | 131804327 | 131804358 |
| SEQ ID NO: | 252 | 2532302 | ALPPL2 | NM_031313 | chr2 | 233272604 | 233272635 |
| SEQ ID NO: | 253 | 2536644 | BOK | NM_032515 | chr2 | 242512472 | 242512497 |
| SEQ ID NO: | 254 | 2566556 | C2orf55 | NM_207362 | chr2 | 99454585 | 99454610 |
| SEQ ID NO: | 255 | 2532289 | ALPP | NM_001632 | chr2 | 233246242 | 233246266 |
| SEQ ID NO: | 256 | 2604401 | ARL4C | NM_005737 | chr2 | 235404210 | 235404234 |
| SEQ ID NO: | 257 | 3874441 | CDC25B | NM_021873 | chr20 | 3776523 | 3776551 |
| SEQ ID NO: | 258 | 3882227 | BPIL3 | NM_174897 | chr20 | 31625440 | 31625473 |
| SEQ ID NO: | 259 | 3894422 | ANGPT4 | NM_015985 | chr20 | 865725 | 865751 |
| SEQ ID NO: | 260 | 3874383 | ATRN | NM_139321 | chr20 | 3614963 | 3615036 |
| SEQ ID NO: | 261 | 3892803 | C20orf200 | NR_033263 | chr20 | 61142540 | 61142567 |
| SEQ ID NO: | 262 | 3914081 | ARFRP1 | NM_001134758 | chr20 | 62331883 | 62331908 |
| SEQ ID NO: | 263 | 3882563 | CBFA2T2 | NM_005093 | chr20 | 32194762 | 32194787 |
| SEQ ID NO: | 264 | 3907034 | ADA | NM_000022 | chr20 | 43280223 | 43280248 |
| SEQ ID NO: | 265 | 3926166 | C21orf91 | ENST00000405964 | chr21 | 19191195 | 19191284 |
| SEQ ID NO: | 266 | 3932407 | C21orf88 | NR_026542 | chr21 | 40984265 | 40984292 |
| SEQ ID NO: | 267 | 3922457 | ABCG1 | NM_016818 | chr21 | 43639267 | 43639291 |
| SEQ ID NO: | 268 | 3918143 | C21orf63 | AK126660 | chr21 | 33829548 | 33829572 |
| SEQ ID NO: | 269 | 3951118 | ACR | ENST00000216139 | chr22 | 51176658 | 51176663 |
| SEQ ID NO: | 270 | 3946042 | CACNA1I | NM_021096 | chr22 | 40081973 | 40082331 |
| SEQ ID NO: | 271 | 3955347 | C22orf13 | ENST00000407973 | chr22 | 24951587 | 24951829 |
| SEQ ID NO: | 272 | 2644874 | BPESC1 | NR_026783 | chr3 | 138824138 | 138824168 |
| SEQ ID NO: | 273 | 2641457 | CCDC48 | NM_024768 | chr3 | 128751743 | 128751767 |
| SEQ ID NO: | 274 | 2627379 | C3orf49 | NR_026866 | chr3 | 63830699 | 63830723 |
| SEQ ID NO: | 275 | 2624738 | CACNA2D3 | NM_018398 | chr3 | 54913057 | 54913081 |
| SEQ ID NO: | 276 | 2681152 | C3orf64 | AK304102 | chr3 | 69062765 | 69062816 |
| SEQ ID NO: | 277 | 2687780 | CD47 | NM_001777 | chr3 | 107769425 | 107769449 |
| SEQ ID NO: | 278 | 2719502 | CC2D2A | NM_001080522 | chr4 | 15504114 | 15504140 |
| SEQ ID NO: | 279 | 2852783 | C1QTNF3 | NM_030945 | chr5 | 34033484 | 34033517 |
| SEQ ID NO: | 280 | 2881766 | ANXA6 | NM_001155 | chr5 | 150496698 | 150496722 |
| SEQ ID NO: | 281 | 2842463 | C5orf25 | AK126204 | chr5 | 175721931 | 175722032 |
| SEQ ID NO: | 282 | 2878396 | APBB3 | AK125244 | chr5 | 139943698 | 139943736 |
| SEQ ID NO: | 283 | 4047621 | BTNL8 | NM_024850 | chr5 | 180375920 | 180375946 |
| SEQ ID NO: | 284 | 2901692 | ABCF1 | NM_001025091 | chr6 | 30545599 | 30545665 |
| SEQ ID NO: | 285 | 2973284 | C6orf174 | NM_001012279 | chr6 | 127837554 | 127837578 |
| SEQ ID NO: | 286 | 2937603 | C6orf70 | NM_018341 | chr6 | 170175406 | 170175442 |
| SEQ ID NO: | 287 | 2999777 | AEBP1 | NM_001129 | chr7 | 44148891 | 44148940 |
| SEQ ID NO: | 288 | 3001005 | ABCA13 | NM_152701 | chr7 | 48285460 | 48285484 |
| SEQ ID NO: | 289 | 3017084 | ARMC10 | NM_031905 | chr7 | 102716226 | 102716250 |
| SEQ ID NO: | 290 | 3006668 | AUTS2 | NM_015570 | chr7 | 69599533 | 69599557 |
| SEQ ID NO: | 291 | 3158462 | C8ORFK29 | NR_015428 | chr8 | 145577092 | 145577180 |
| SEQ ID NO: | 292 | 3121027 | C8orf33 | NM_023080 | chr8 | 146278059 | 146278089 |
| SEQ ID NO: | 293 | 3105606 | CA2 | ENST00000285379 | chr8 | 86376123 | 86376148 |

-continued

| SEQ ID NO: | # | Probeset ID | Gene Symbol | RefSeq (Accession) | Seqname | start | stop |
|---|---|---|---|---|---|---|---|
| SEQ ID NO: | 294 | 3204670 | CD72 | ENST00000396759 | chr9 | 35618756 | 35618861 |
| SEQ ID NO: | 295 | 3221925 | AKNA | NM_030767 | chr9 | 117103978 | 117104002 |
| SEQ ID NO: | 296 | 3223849 | C5 | NM_001735 | chr9 | 123812463 | 123812487 |
| SEQ ID NO: | 297 | 3190991 | C9orf106 | NM_001012715 | chr9 | 132083295 | 132083325 |
| SEQ ID NO: | 298 | 3222599 | ASTN2 | NM_198186 | chr9 | 119449350 | 119449382 |
| SEQ ID NO: | 299 | 3229062 | BRD3 | NM_007371 | chr9 | 136905156 | 136905186 |
| SEQ ID NO: | 300 | 3986675 | ATG4A | ENST00000457035 | chrX | 107335082 | 107335109 |

An investigation was conducted to determine whether or not specific miRNA could be PTB biomarkers. The same total RNA extracted from the 26-28 week samples, described above, were run on the Affymetrix GeneChip non-coding small RNA array (e.g., 847 human non-coding small RNAs including miRNA, siRNA, snRNA, snoRNA, etc), and only miRNA altered in women destined for PTB were identified by fold change (e.g., ≥1.5×) and p value from control (p<0.01). The miRNA were ordered by narrowness of distribution (e.g., Affymetrix miRNA QC Tool and Ingenuity Systems Pathway Analysis). Of the 847 non-coding small RNA, only 14 were altered at 26 weeks in women destined for PTB; 3 CFP miRNA increased or were up-regulated (e.g., miRNA-548 L (SEQ ID NO: 5), miRNA-99a (SEQ ID NO: 6), and miRNA-99b (SEQ ID NO: 7)); and 10 CFP miRNA decreased or were down-regulated (e.g., miRNA-382 (SEQ ID NO:8), miRNA-491 (SEQ ID NO: 9), miNRA-214 (SEQ ID NO: 10), miRNA-31 (SEQ ID NO: 11), miRNA-342 (SEQ ID NO: 12), miRNA-let-7 g (SEQ ID NO: 13), miRNA-194-1 (SEQ ID NO: 14), miRNA-194-2 (SEQ ID NO: 15), miRNA 92b (SEQ ID NO: 16), miRNA 320b-1 (SEQ ID NO: 17), and miRNA 320b-2 (SEQ ID NO: 18). Genomic mapping revealed the PTB marker miRNAs were associated with cell regulation, muscle dysfunction, contractility and inflammation.

None are previously described in pregnancy and only a few previously associated with reproductive tissues. As miRNA reduce transcription and/or translation and 11 of 14 affected miRNAs are reduced, the findings may explain the activation process of myometrial activation which must precede PTB. That the pattern of miRNA change varied among PTB women suggests the patterns may reflect the underlying mechanism that causes PTB.

In one embodiment, the CFP miRNA PTB biomarkers can include a biomarker that increases in order to indicate susceptibility to PTB. These increasing CFP miRNA PTB biomarkers can include: miRNA-548 L (SEQ ID NO: 5), see accession number NR_031630; miRNA-99a (SEQ ID NO: 6), see accession number NR_029514; and miRNA-99b (SEQ ID NO: 7), see accession number NR_029843, which accession numbers and information associated therewith are incorporated herein by specific reference.

In one embodiment, the CFP miRNA PTB biomarkers can include biomarker that decrease in order to indicate susceptibility to PTB. These decreasing CFP miRNA PTB biomarkers can include: miRNA-382 (SEQ ID NO:8), accession number NR_029874; miRNA-491 (SEQ ID NO: 9), accession number NR_030166; miNRA-214 (SEQ ID NO: 10), accession number NR_029627; miRNA-31 (SEQ ID NO: 11), accession number NR_029505; miRNA-342 (SEQ ID NO: 12), accession number NR_029888; miRNA-let-7 g (SEQ ID NO: 13), accession number NR_029660; miRNA-194-1 (SEQ ID NO: 14), accession number NR_029711; miRNA-194-2 (SEQ ID NO: 15), accession number NR_029829; miRNA 92b (SEQ ID NO: 16), accession number NR_030281; miRNA 320b-1 (SEQ ID NO: 17), accession number NR_031564; and miRNA 320b-2 (SEQ ID NO: 18), accession number NR_031574, which accession numbers and information associated therewith are incorporated herein by specific reference.

Figure 3:
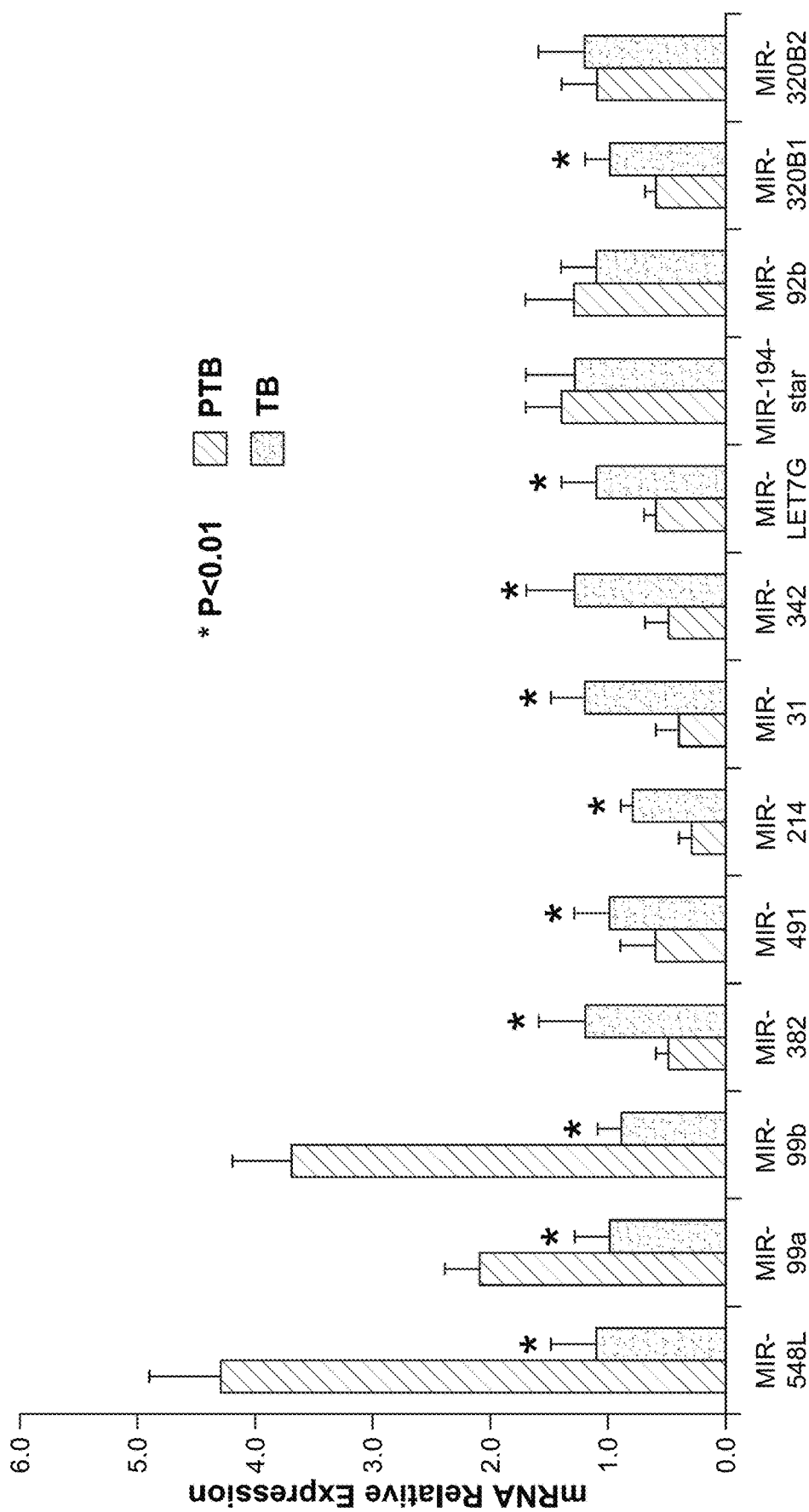
FIG. 3 illustrates results of a high through-put gene Real-time PCR platform validated microarray selected CFP miRNA as PTB biomarkers.
Figure 4A:
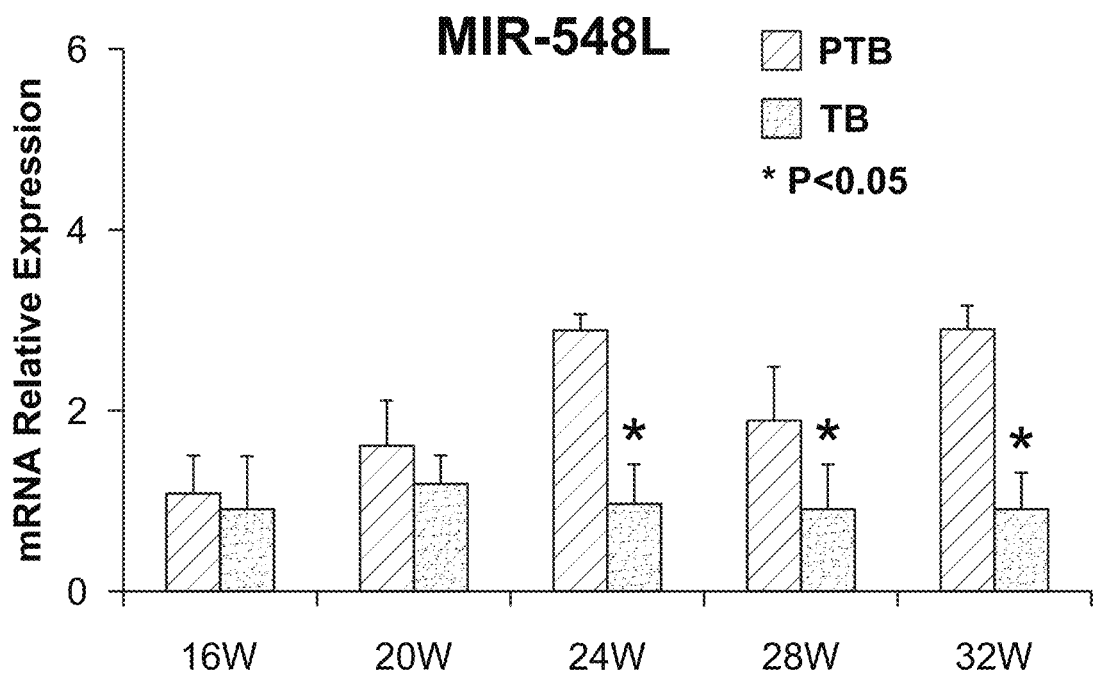
FIGS. 4A-4B illustrates that CFP miRNA PTB biomarkers can be altered by gestation, MIR-99a can be triggered as early as 16 weeks.
Figure 4B:
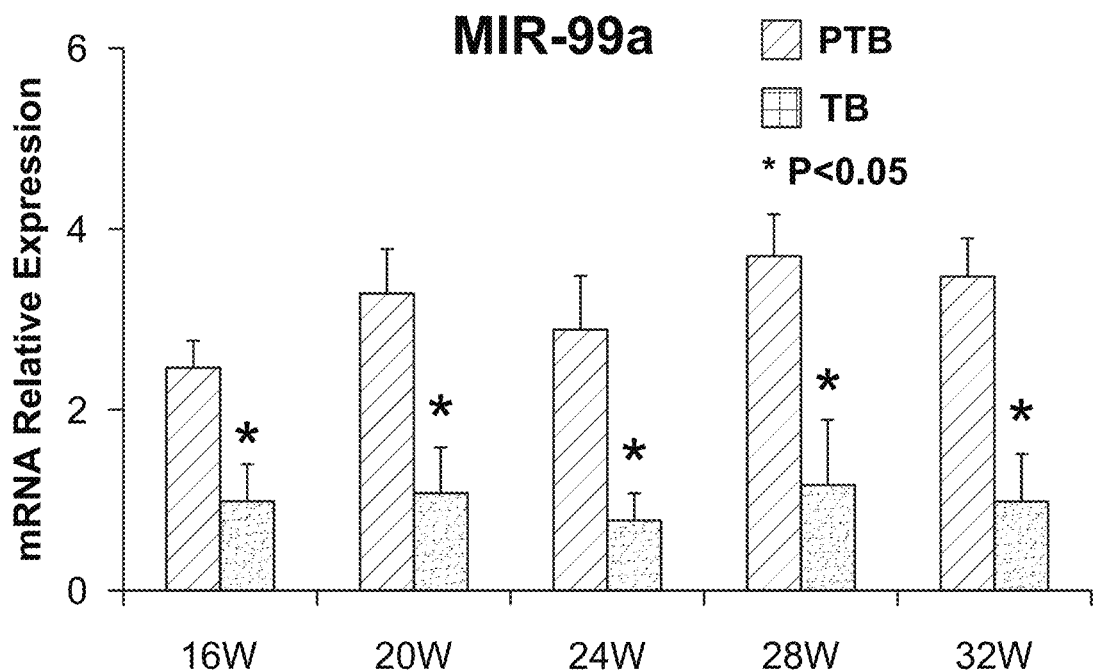

An investigation was also conducted to determine the pattern of miRNA that are altered as early as at 16 weeks in women destined for PTB. Validation of the array results was conducted by high-through put Real-time PCR. Briefly, 3 miRNA that were increased, 7 miRNA that were decreased, respectively at 26 weeks in women destined for spontaneous PTB, and Q-rtPCR was conducted and the miRNA were normalized with the normalization sequences described herein. FIG. 3 confirms the 10/14 of miRNA array findings were significant altered in the miRNA PTB biomarker cell free plasma levels at 26 weeks in women destined for PTB. We also found that gestational age impact on CFP miRNA level. PCR studies were expanded to all biweekly samples available for these same pregnancies, and the PCR were normalized result with the normalization sequences (e.g., miRNA normalization sequence). FIG. 4A indicates that the levels of miRNA-548 L is altered only in early $2^{nd}$ trimester, and FIG. 4B illustrates that miRNA-99a are actually significantly increased by 16 weeks gestation raising the possibility of a late $1^{st}$ testing window. This indicates that testing can be as early as 12 weeks, 10 weeks, and possibly even earlier. That is, the diagnostic testing can be implemented as early as the CFP RNA PTB biomarkers are modulated within the pregnant woman.

To simultaneously complete the validation of the about 296 CFP RNA PTB biomarkers and quantitate their levels across gestation, a PCR card was designed with custom designed primers to amplify the CFP miRNA PTB biomarkers and miRNA normalization sequences (e.g., an Applied Biosciences Taqman card preloaded with custom designed primers for the identified CFP miRNA PTB biomarkers and normalization miRNA sequences, wherein the primers can be readily determined from the sequences of the sequence listing by convention techniques, and may encompass low stringency, medium stringency and high stringency primers, and thereby the primer sequences that are useful can be changed within the sequences provided in the Sequence Listing). This PCR card utilizes high throughput microfluidic technology and allows for up to 384 Q-rtPCR wells with custom designed nested primers such as the CFP miRNA PTB biomarkers and normalization sequences. It is assumed commercialization will lead to the manufacture of large cards and the present invention is not limited to the existing dimensions. Each card requires only 50 ng of total miRNA. The cards were designed to accommodate multiple samples. Isolated CFP RNA was then applied to the custom PTB miRNA card in order to validate the miRNA array. That result is shown in FIG. 3. With a sample size of 6 per group, the microarray results were validated for 10 of the 14 miRNA PTB markers. The miRNA symbols are shown as in FIG. 3.

In one embodiment, the present invention includes a method of determining a primer or a probe for a CFP RNA PTB biomarker. Such a method can include analyzing one or more of the sequences of the Sequence Listing having SEQ ID NO: 5-300 and 304-307 and determining a unique or sufficiently unique specific target sequence that is useful as a primer or a probe therefore. The primers can be readily determined from the sequences of the sequence listing by convention techniques, and may encompass low stringency, medium stringency and high stringency primers, and thereby the primer sequences that are useful can be changed within the sequences provided in the Sequence Listing While all of these CFP RNA PTB biomarkers are from humans, other biomarkers from other animals may also be found and used in veterinary practices.

In one embodiment, the CFP RNA PTB biomarkers can be used to predict whether or not a woman is destined for or susceptible to PTB. This determination can be performed by a blood test at least as early as 12 or 16 weeks gestation. Also, this same process can be applied to women with a multiple gestation with same markers. However, a newly derived set of unique markers applicable only to twins may be identified. Accordingly, the CFP RNA biomarkers identified herein can be combined in a mathematical algorithm that can predict likelihood of preterm birth. As there appears to be multiple pathways that lead to preterm birth. The algorithm may also be used to determine the mechanism causing the PTB in a given woman. The mathematics to create the algorithm is well known and not proprietary. Such an algorithm for predicting PTB can be run on a computing system, and may be configured as software and/or or hardware. Data can be input into the computing system in order to operate and optimize the PTB prediction algorithm.

In one embodiment, the present invention can include a method for predicting PTB in a woman pregnant with one fetus. Such a method can include determining a change in the CFP RNA transcriptome of a pregnant mother, wherein the change is predictive of preterm birth by the pregnant mother. Such a prediction of PTB can include extracting and isolating RNA from a body fluid of the pregnant mother at less than 32 weeks (e.g., 26-28 weeks, or as low as 12 weeks) of pregnancy. The isolated RNA can be used for determining a change in the RNA amount (e.g., at least a fold change, such as ≥1.5×) in the CFP RNA transcriptome of the pregnant mother, wherein the change is predictive of preterm birth by the pregnant mother.

In one embodiment, the present invention provides a method for predicting preterm birth in a woman pregnant with twins. Such a method of predicting PTB of twins can include determining a change in the pregnant woman's CFP RNA transcriptome, where the change is predictive of preterm birth by the pregnant mother. This method can include extracting and isolating RNA from a body fluid of the pregnant mother at less than 32 weeks (e.g., 26-28 weeks, or as low as 12 weeks) of pregnancy. The isolated RNA can be used for determining a change (e.g., at least a fold change, such as ≥1.5×) in the CFP RNA transcriptome of the pregnant mother, wherein the change is predictive of preterm birth by the pregnant mother.

In one embodiment, the present invention can include a method for predicting a pregnancy disease state. Such a method can include determining a change in the CFP RNA transcriptome of a pregnant mother, wherein the change is predictive of a pregnancy disease state. The method can include extracting and isolating RNA from a body fluid of the pregnant mother at less than 32 weeks (e.g., 26-28 weeks, or as low as 12 weeks) of pregnancy. The isolated RNA can then be used for determining a change (e.g., at least a fold change, such as ≥1.5×) in the CFP RNA transcriptome of the pregnant mother, wherein the change is predictive of a pregnancy disease state. For example, the pregnancy disease state can be poor placentation, fetal growth restriction, preeclampsia, or fetal anomalies.

In one embodiment, a method for predicting preterm birth can be performed by using the CFP RNA PTB biomarkers. Such a method can include determining a change in a CFP RNA transcriptome of a pregnant mother, wherein the change is predictive of preterm birth by the pregnant mother. Also, the method can include extracting and isolating CFP RNA from a body fluid of a pregnant mother at less than 32 weeks (e.g., 26-28 weeks, or as low as 12 weeks) of pregnancy. The method can also include determining a change, such as at least a fold change (e.g., ≥1.5×), in the CFP RNA transcriptome of the pregnant mother. The change in the CFP RNA transcriptome is predictive of preterm birth by the pregnant mother. In one aspect, the pregnant mother can be selected to be pregnant at less than 32 weeks of pregnancy and lacking preterm, premature rupture of membranes.

In one aspect, the extracted RNA from the pregnant mother can be processed through a whole-transcript expression array. In another aspect, the method can include identifying one or more RNA sequences that are predictive of preterm birth. For example, the pregnant mother can have one or more altered levels of RNA sequences selected from CFP RNA PTB biomarker sequences that are associated with expression, cell growth, cell proliferation, cell cycle, cell death, and cellular assembly and organization. The CFP RNA can be any type of CFP RNA, such as miRNA or mRNA. The RNA can be associated with cell regulation, muscle dysfunction, contractility and inflammation, and/or can be associated with myometrial quiescence and/or activation, and/or associated with expression, cell growth, cell proliferation, cell cycle, cell death, and cellular assembly and organization.

In one embodiment, the present invention can include a method of predicting preterm birth before 32 weeks of pregnancy. Such a method can include obtaining data regarding levels of biomarkers and gestation age and optionally other health factors. The data can then be input into a machine, which can process the data by computing the data in a mathematic model having parameters of levels of markers and gestation age and optionally other health factors. Such computing can be used for determining patient specific risk to preterm birth. In this method, the mathematical model can include parameters related to change in a preterm birth RNA biomarker amount, whether becoming present, increasing, or decreasing. The preterm birth RNA biomarker can be any of the RNA PTB biomarkers as described herein.

In one embodiment, the present invention can include a method of inhibiting, preventing, or treating PTB. Such a method would reflect identification of the mechanism causing the PTB in the individual woman based on the profile of the predictive PTB markers. The method can include various drug screening protocols that can impact or regulate a particular PTB biomarker, where such regulation can result in a reduced onset of PTB. The method can include obtaining a substance that blocks a message from one of the PTB RNA described herein. This can include blocking a biological signal of a PTB small RNA, mRNA, non-coding RNA, and/or miRNA. Once obtained, the substance can be administering to a pregnant woman prior to 32 weeks of pregnancy in order to block the effect of the PTB marker on the uterus and its contents. For example, the blocked RNA can be one or more of the CFP RNA PTB biomarker described herein, where blocking the RNA can interrupt one or more myometrial preterm birth initiator genes. Also, the CFP RNA PTB biomarker being blocked can be one or more PTB biomarker miRNA, where blocking the miRNA blocks a preterm birth initiator gene.

In one embodiment, the CFP RNA PTB biomarker isolated from the pregnant mother can be normalized against a normalization sequence. If a CFP mRNA PTB biomarker, the isolated RNA can be normalized against the peptidyl-prolyl isomerase normalization sequence (SEQ ID NO: 1). If a CFP miRNA PTB biomarker, the isolated RNA can be normalized against one or more of normalization sequences snRNA:U6:96Aa (SEQ ID NO: 2), snRNA:U6:96Ab (SEQ ID NO: 3), and/or snRNA:U6:96Ac (SEQ ID NO: 4).

The methods described herein can also include any method of isolating RNA from blood components. This can include isolation from whole blood or blood plasma.

In one embodiment, a diagnostic kit can be provided that includes sequences to identify one or more of these CFP miRNA PTB biomarkers and/or one or more of these CFP mRNA PTB biomarkers. These sequences can be the sequences of the Sequence Listing having SEQ ID NOs: 5-300 and 304-307 and/or primers and/or probes thereof. The primers and probes can be at least substantially unique for these CFP RNA PTB biomarker sequences with adequate hybridization thereto for the methods and protocols described herein. The primers and/or probes of the CFP RNA PTB biomarkers recited in the Sequence Listing can also be considered to be CFP RNA PTB biomarkers for the purpose of the invention as these primers and/or probes target to and hybridize with select specific sequences within the CFP RNA PTB biomarkers of the Sequence Listing. The RNA biomarkers can be configured to be in nucleic acid format, such as RNA, DNA, or RNA/DNA hybrid. The diagnostic kit can include individual compositions that each have a single CFP RNA PTB biomarker, or a single composition can include one or more of these CFP miRNA PTB biomarkers and/or one or more of these CFP mRNA PTB biomarkers. The CFP RNA PTB biomarkers can be provided with or without a label, such as a visual label or radiolabel. The CFP RNA PTB biomarker can be provided on a chip or a card configured for use in nucleic acid detection and/or quantification and/or qualification, which chip or card can be configured as a microarray. One or more sample spots on a microarray can one or more of these CFP miRNA PTB biomarkers and/or one or more of these CFP mRNA PTB biomarkers and/or the primers and/or probes thereof. For example, the microarray can have one spot with one of the primer and/or probe CFP miRNA PTB biomarkers and/or one of the primer and/or probe CFP mRNA PTB biomarkers. Such a microarray can have one or more CFP RNA PTB biomarker spots, which spots can be reaction wells or the like. For example, the microarray can be configured as an Affymetrix microarray card or any advancement in technology reasonably related thereto. The incorporation of these CFP RNA PTB biomarkers in the various microarray products allows them to be more readily used for plasma-derived samples, and in repeated measures of CFP RNA PTB biomarkers.

In one embodiment, a CFP RNA PTB biomarker can be a nucleic acid that contains or consists of the sequence which defines the CFP RNA PTB biomarker target or complement thereof. The CFP RNA PTB biomarker can be identical to one of SEQ ID NOs: 5-18 and/or 5-106 and/or 19-106 and/or 5-300 and/or 107-300 and/or 107-142 and/or 143-300 and/or 304-307, or can be a complement thereof, sense or antisense, as well as a sequence that hybridizes therewith under suitable conditions as well as primers and/or probes therefore. For the purposes of this invention, the primers and/or probes of the recited sequences can be considered to be CFP RNA PTB biomarkers as they are used to target the particular RNA produced within a subject. The primers and probes will be complementary to the sequences of SEQ ID NOs: 5-300 and 304-307, as these sequences are the targets. The CFP RNA PTB biomarker can have perfect complementarity or greater than or about 95% complementarity, greater than or about 90% complementarity, greater than or about 85% complementarity, or greater than or about 80% complementarity with the sequences recited or the probes and/or primers thereof. The CFP RNA PTB biomarker can be continuous or it can have one or more bulges or mismatches upon hybridization. The CFP RNA PTB biomarker can also include one or more chemical modifications, such as a 2' carbon modification. The CFP RNA PTB biomarker may or may not form an overhang upon hybridization. The CFP RNA PTB biomarker can include a sequence from about 15 nucleotides to the full sequence, from about 16 nucleotides to about 100 nucleotides, from about 17 nucleotides to about 50 nucleotides, from about 18 nucleotides to about 30 nucleotides, from about 19 nucleotides to about 25 nucleotides, or from about 20 to about 22 nucleotides in sequence of or complement to one of SEQ ID NOs: 5-18 and/or 5-106 and/or 19-106 and/or 5-300 and/or 107-300 and/or 107-142 and/or 143-300 and/or 304-307. The CFP RNA PTB biomarker can include a unique sequence segment of the full sequence having a length as described.

In one embodiment, the methods described herein can be performed with exon and miRNA microarrays, and can quantitate their levels using high throughput PCR. The RNA can be obtained from one or more pregnant women at least by 12 weeks of pregnancy until delivery. The RNA biomarkers can be validated using a high throughput, customized PCR card having the PTB biomarkers as described herein. The PTB biomarkers from one group of women can be validated against a second group of randomly selected women with PTB and or control women that do not have PTB or that have a term birth.

In one embodiment, the CFP mRNA/miRNA PTB biomarkers can be manipulated in presence or amount in order to modify myometrial $Ca^{2+}$ flux that is mediated by myometrial PTB genes. It has now been found that CFP RNA PTB biomarkers that were significantly increased or decreased in women destined for PTB may be manipulated to modify myometrial $Ca^{2+}$ flux which in turn regulates myometrial contractility. For example, the expression of the CFP mRNA APOA-4 ((SEQ ID NO: 66) Homo sapiens apolipoprotein A-IV (APOA4), mRNA, accession number NM_000482) increased myometrial intracellular $Ca^{2+}$ flux. Other CFP RNA PTB biomarkers may be similarly used for manipulation of myometrial function.

RNA Purification

Existing RNA isolation techniques can yield enough CFP RNA for an array, but not for the needed PCR validation of the hundreds of genes identified by the array unless the plasma volume is high. This explains the common practice of using solid tissues (e.g. placenta, myometrium, cervix) to identify candidates and then hope to individually quantitate them in plasma using Q-rtPCR.

Accordingly, the present invention provides a method that in one process separates intact RNA, including mRNA and miRNA, DNA and protein. The process is based on a phenol/guanidium isothiocyanate/glycerol phase separation and results in large quantities of high quality CFP nucleic acid with total RNA yields of 1.5-30 ug or more from only 2 mL of plasma. This amount is more than enough for array technology and the performance of numerous PCR reactions using a clinically practical, single patient sample.

The RNA isolation method described herein allows for the isolation of 1.5 micrograms to 70 micrograms of CFP RNA from a 2 mL sample, which is more than enough for both array use and PCR validation. The method can include obtaining: 2 mL or more of sample from a subject, such as plasma; DEPC-treated Water (Ambion); Ethanol (Sigma); Chloroform (Sigma); 3 M, pH: 5.5 Sodium Acetate (Ambion); Phonel (Sigma); Guanidium isothiocyanate (Sigma); Glycerol (Sigma); Aliquot 2 mL of sample (e.g., plasma) from one patient sample into 8 tubes, 250 uL plasma in each tube. The RNA purification is conducted as follows: spin plasma at 200×g for 5 minutes at 4° C.; add 750 uL phenol/guanidium isothiocyanate/glycerol lysis buffer per 2 mL sample, and vortex samples vigorously for 15 seconds and incubate them for 5 min; add 200 uL chloroform per sample and vortex sample vigorously and incubate at room temperature for 10 min; centrifuge the samples at 10,000×g for 15 minutes at 4° C., and obtain upper aqueous phase for RNA isolation, and lower red/phenol/chloroform phase can be used for DNA and Protein isolation; transfer 300 uL upper aqueous phase carefully without disturbing the interphase into a fresh tube, and add 1/10 volume of 3 M Sodium acetate (pH: 5.5) (30 uI) plus 3 volumes of 100% iced cold ethanol at 900 uL to each tube (note: 2 mL plasma from one patient sample can result in 13-14 tubes); incubate the tubes overnight at −20° C.; centrifuge at 12,000×g for 75 minute (e.g., 4° C.), and remove all liquid; add 50 uL ice cold 80% ethanol to each tube, and then wash the pellet, then transfer all of the sample tubes into one tube, add then add 300-350 mL ice cold ethanol to make the ethanol an amount of about 1 mL; centrifuge at 12,000×g for 60 minutes at 4° C.; remove all liquid, and set at 37° C. to dry for 40 minutes; re-suspend the pellet in about 20-40 uL DEPC water, and incubate at 56° C. for 10 minutes to dissolve RNA, and then put the RNA sample in ice for 30 minutes; and using 2 uL RNA, take OD at 260 nm and 280 nm to determine sample concentration and purity.

Modulating PTB Genes

Figure 5A:
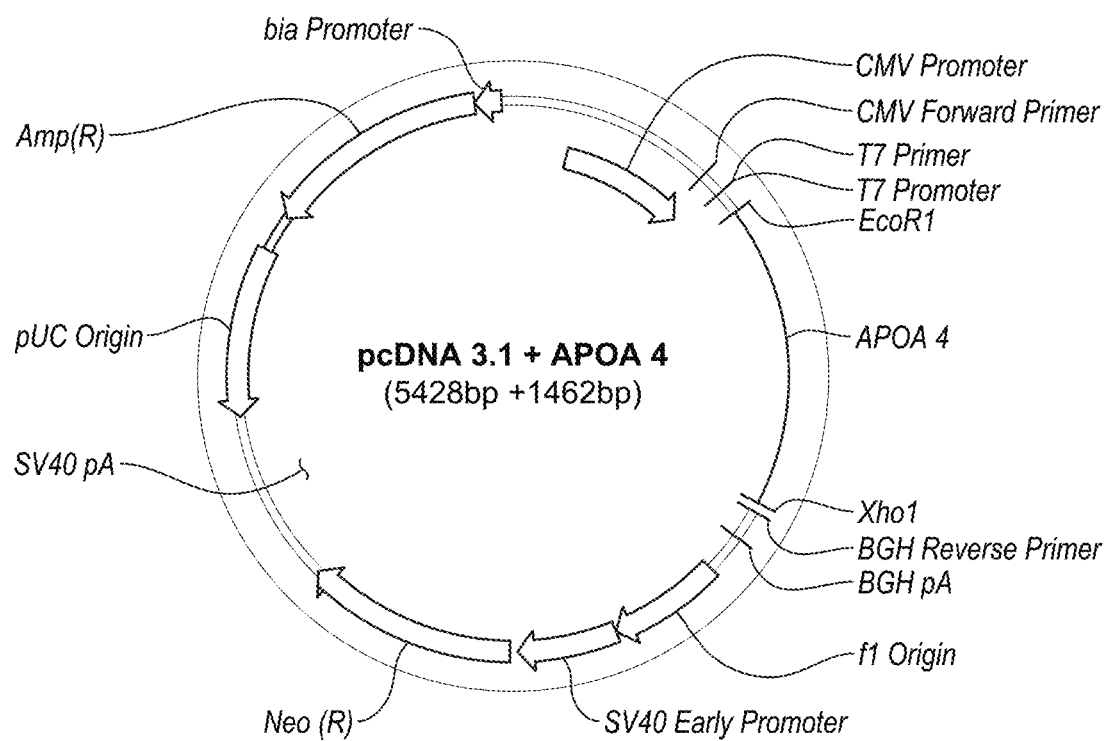
FIG. 5A includes a plasmid DNA reconstruction containing one of the CFP mRNA-APOA4.
Figure 5B:
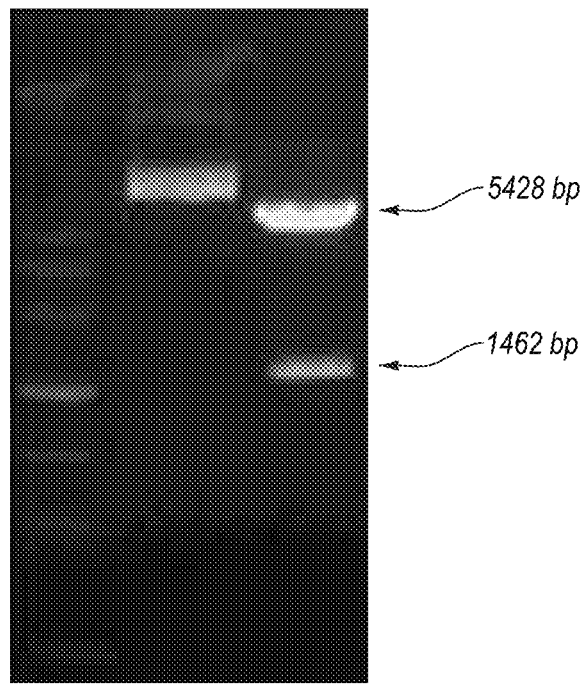
FIG. 5B includes an image of a gel electrophoresis illustrates that the APOA4 Vector reconstruction is successful.
Figure 5C:
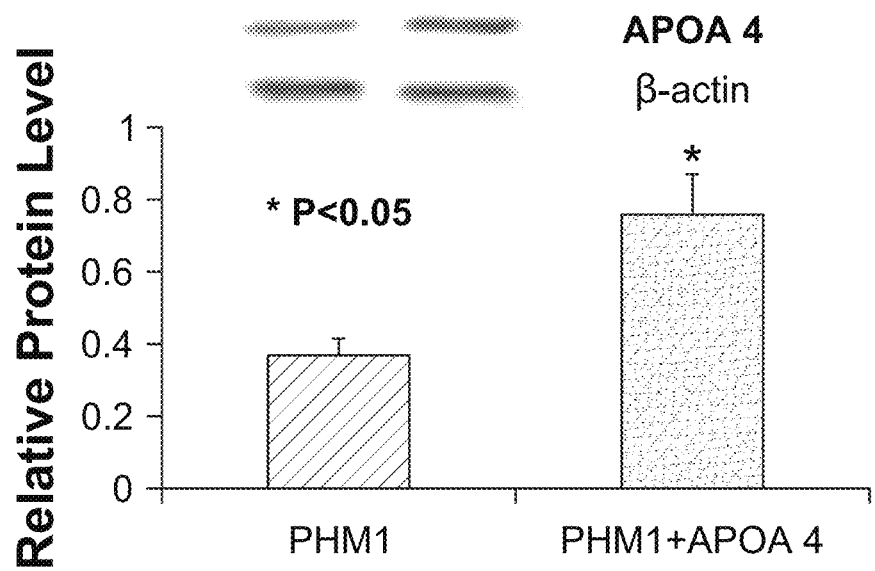
FIG. 5C illustrates that myometrium cell APOA4 protein can be up-regulated by APOA4 plasmid DNA.
Figure 5D:
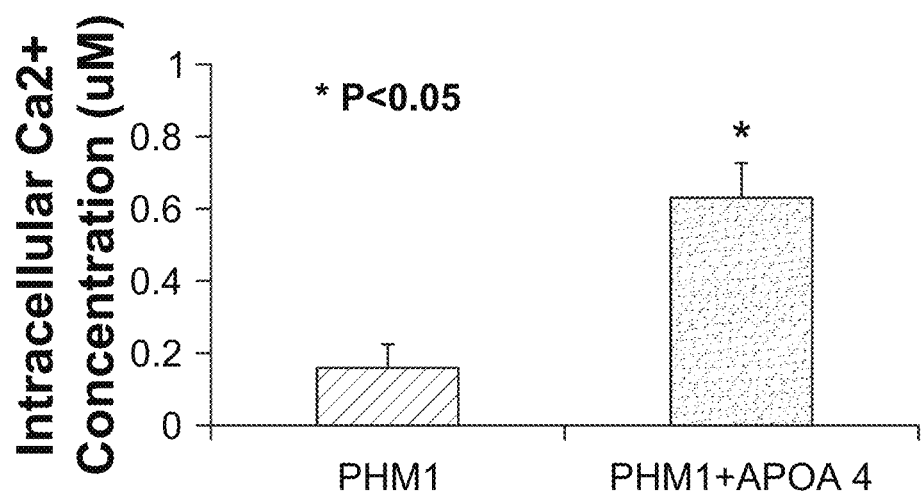
FIG. 5D illustrates that CFP mRNA biomarker-APOA4 can trigger intracellular $Ca^{2+}$ concentration in myometrium cell consistent with enhanced contractility.

In one embodiment, the present invention can modulate CFP RNA in order to regulate intracellular $Ca^{2+}$ flux via their effect on myometrial preterm initiator genes. For example, the CFP RNA can be used to regulate myometrial contractility. It was determined that there was an interaction between 4 CFP mRNA PTB biomarkers (e.g., PSME2, NAMPT, APOA1 and APOA4) and 6 myometrial PTB initiator genes (e.g., IFNG, CD3E, HLA-DOA, NDRG4, VPS33A and ABCA7), and between 1 PTB marker CFP miRNA (miRLET7 G) and 1 PTB Initiator gene (SORCS). This finding supports the possibility CFP mRNA and/or miRNA PTB biomarkers could be used to alter the transcription and/or translation of myometrial preterm initiator genes. It was found that 7 PTB initiator genes that were identified to be associated with these markers could all directly or indirectly be linked to $Ca^{2+}$ flux. A pcDNA 3.1 vector was constructed with the full length of the APOA4 mRNA (FIG. 5A). Successful gene vector cloning was confirmed by EcoR1 and Xho1 restriction enzyme digests (FIG. 5B). The vector was transferred into immortalized pregnant human myometrial cells PHM1, and the APOA4 was overexpressed in the PHM1 cells (FIG. 5C). Over expression of the APOA4 protein dramatically increased intracellular $Ca^{2+}$ as shown in FIG. 5D. Since APOA4 is not normally expressed in cultured myometrial cells, it is conceived that the APOA4 effect on intracellular $Ca^{2+}$ is mediated by local myometrium initiator genes. Accordingly, it is conceived that $Ca^{2+}$ flux can be modulated with the other CFP mRNA PTB biomarkers (e.g., PSME2, NAMPT, APOA1), and the CFP miRNA PTB biomarker (e.g., miR-LET7 G). This approach could be used to identify drugs that target and modulate the CFP RNA PTB biomarkers described herein or later developed. This approach can therefore be used in methods of treating women in need of labor induction, but resistant to existing methods. Also, a similar approach can be used in methods of treating women in need of labor inhibition or prevention, but resistant to existing methods.

Methods

Maternal Plasma: isolated in EDTA as previously described; aliquoted and stored at −80° C.

Plasma RNA Isolation: Plasma RNA is isolated by a proprietary method developed this past year. The plasma sample is lysed by phenol/guanidium isothiocyanate/glycerol buffer, and RNA, DNA and protein isolated from different aqueous phases, then precipitated using a series of proprietary chemical solutions, the pellets cleaned and resuspended in 20-40 uL DEPC water, incubated at 56° C. for 10 min to dissolve RNA, and stored at −80° C. RNA yield, purity and integrity are identified by Nanospectrometer and Aligent Bioanalyzer.

Affymetrix Microarray: Affymetrix whole genome transcript and miRNA microarrays are run. Microarray QC evaluation can be performed. Each protocol is as instructed by the manufacturer.

High-throughput miRNA/mRNA Gene Validation: The ABI VIIA™ 7 is used for high-throughput mRNA/miRNA gene quantification using an ABI customized array card system. The system allows for 384 Real-time PCR reactions in 2 hours using one PCR array card (picture insert). In general, the TagMan microRNA/RNA reverse transcription kit is used to create the cDNA pool. A megaplex RT primers pool is generated based on each validated gene, and cDNA synthesized under the following thermal cycling conditions: 16° C. for 2 minutes, 42° C. for 1 minute, 50° C. for 1 second for 40 cycles, then hold 85° C. for 5 minutes. A preamplification reaction is used to enlarge gene signals. PreAmp primer pools are prepared for each validated gene. TaqMan PreAmp Master Mix will be used. PreAmplification reactions are performed under the following conditions: 95° C. or 10 minutes, 55° C. for 2 minutes, 72° C. for 2 minutes, then 12 cycle of 95° C. for 15 seconds and 60° C. for 4 minutes, then 99.9° C. for final denaturing step. PreAmplified cDNAs are used as the template. Validation parameters are designed and selected based on customized gene sequences.

Myometrial Cell Culture: Primary myometrial cell culture and immortalized pregnant myometrial cell are cultured using standard procedures. All primary cell lines can be derived from a large fundal myometrial biopsy from a single patient at term prior to labor.

Construction of recombinant plasmid pcDNA-CFP genes: Vector construction is used for CFP marker gene over expression. The target genes are selected from the array and IPA analyses (Preliminary Results). The purified CFP gene products and plasmid eukaryotic expression vector (pcDNA 3.1) are digested with EcoR1 and Xho1. The ligation reaction is conducted according to the manufacturer's protocol (Invitrogen). The final plasmid pcDNA-CFP genes are then transformed into *E. coli* JM 2163. The ligation products are cultured with LB medium containing ampicillin (100 ug/ml) overnight. Afterward, the recombinant plasmid is extracted from colony transformants prior to being identified by digesting with EcoR1 and Xho1, and confirmed by agarose gel electrophoresis. Lipofectamine will be used for transfection. Over expression of CFP marker genes will be proven by Western blot and Real-time PCR. The technique is established in our laboratory (FIG. 6A).

$Ca^{2+}$ Flux Measurement: myometrial cells are suspended in 2 mL of DMEM media consisting of 10% fetal bovine serum, 30 μg fungizone, 1% penicillin-streptomycin, 0.5% L-glutamine in DMEM (all ingredients from GIBCO Life Technologies), warmed to 37° C., and then plated on 25-mm glass coverslips. Cells are incubated in fura 2-AM ($2\times10^6$ mol/L) for 40 minutes at room temperature in the dark. Coverslips are inserted into an open microincubator (PDMI-2, Medical Systems) and attached to the stage of an inverted microscope (Nikon EclipseTE2000, Nikon; Melville, NY). The microincubator is maintained at 37° C. with a bipolar temperature controller (TC-202, Medical Systems). Images are collected using Nikon EZ-C1 software and processed with Volocity imaging software (Improvision Inc., Lexington, MA). Data are expressed as a ratio of emitted fluorescence at 510 nm in cells excited at 340 and 380 nm. Responses to genes or their respective vehicles (DMSO, ethanol) are analyzed by directly transfected siRNA or gene expression vector. Changes in the 340/380 nm emission ratios are recorded. $Ca^{2+}$ influx rate is calculated based on previous reports. Data are expressed as a ratio of emitted fluorescence at 510 nm in cells excited at 340 and 380 nm. Responses to genes or their respective vehicles (DMSO, ethanol) are analyzed by directly transfected siRNA or gene expression vector. Changes in the 340/380 nm emission ratios are recorded and $Ca^{2+}$ influx rate is calculated.

Combinations of Nucleic Acid Biomarkers

In some embodiments, a method of detecting a combination of nucleic acid biomarkers in a human subject can include: obtaining a nucleic acid sample from the human subject; selecting the combination of nucleic acid biomarkers; analyzing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from a transcription standard, wherein the combination of nucleic acid biomarkers includes at least two of: miRNA-let-7 g having a nucleotide sequence of or complementary to SEQ ID NO: 13 with a variation less than the transcription standard; PSME2 having a nucleotide sequence of or complementary to SEQ ID NO: 68 with a variation less than the transcription standard; APOA1 having a nucleotide sequence of or complementary to SEQ ID NO: 53 with a variation less than the transcription standard; and NAMPT having a nucleotide sequence of or complementary to SEQ ID NO: 71 with a variation less than the transcription standard. In some aspects: the variation for miRNA-let-7 g is about −1.8 fold change; the variation for PSME2 is about −5.6 fold change; the variation for APOA1 is about −1.9 fold change; and/or the variation for NAMPT is −2.3 fold change. In some aspects, the analyzing includes hybridizing each nucleic acid biomarker in the nucleic acid sample with a complementary nucleic acid configured as a primer or a probe, the method comprising detecting the hybridizing.

In some embodiments, the combination of nucleic acid biomarkers includes one of: PSME2 and APOA1; PSME2 and miRNA-let-7 g; NAMPT and APOA1; or miRNA-let-7 g, PSME2, APOA1, and NAMPT. In some aspects, the combination of nucleic acid biomarkers includes all of miRNA-let-7 g, PSME2, APOA1, and NAMPT, and further includes: APOA4 having a nucleotide sequence of or complementary to SEQ ID NO: 71, wherein the variation for APOA4 is less than the transcription standard. In some aspects, the variation for APA4 is about −1.5 fold change.

In some embodiments, the combination of nucleic acid biomarkers includes at least one of: miRNA-99b having a nucleotide sequence of or complementary to SEQ ID NO: 7 with a variation greater than the transcription standard; miRNA-99a having a nucleotide sequence of or complementary to SEQ ID NO: 6 with a variation greater than the transcription standard; and miRNA-548 L having a nucleotide sequence of or complementary to SEQ ID NO: 5 with a variation greater than the transcription standard.

In some embodiments, the combination of nucleic acid biomarkers includes at least one of: miRNA-99b having a nucleotide sequence of or complementary to SEQ ID NO: 7 with about a 1.7 fold change variation greater than the transcription standard; miRNA-99a having a nucleotide sequence of or complementary to SEQ ID NO: 6 with about a 1.6 fold change variation greater than the transcription standard; and miRNA-548 L having a nucleotide sequence of or complementary to SEQ ID NO: 5 with about a 1.5 variation greater than the transcription standard.

In some embodiments, the combination of nucleic acid biomarkers includes at least one of: miRNA-490 having a nucleotide sequence of or complementary to SEQ ID NO: 304 with a variation less than the transcription standard; miRNA-491 having a nucleotide sequence of or complementary to SEQ ID NO: 9 with a variation less than the transcription standard; miRNA-31 having a nucleotide sequence of or complementary to SEQ ID NO: 11 with a variation less than the transcription standard; miRNA-382 having a nucleotide sequence of or complementary to SEQ ID NO: 8 with a variation less than the transcription standard; miRNA-342 having a nucleotide sequence of or complementary to SEQ ID NO: 12 with a variation less than the transcription standard; miRNA-194 having a nucleotide sequence of or complementary to SEQ ID NO: 305 with a variation less than the transcription standard; miRNA-214 having a nucleotide sequence of or complementary to SEQ ID NO: 10 with a variation less than the transcription standard; miRNA-371 having a nucleotide sequence of or complementary to SEQ ID NO: 306 with a variation less than the transcription standard; and/or miRNA-519c having a nucleotide sequence of or complementary to SEQ ID NO: 307 with a variation less than the transcription standard.

In some embodiments, the combination of nucleic acid biomarkers includes at least one of: miRNA-490 having a nucleotide sequence of or complementary to SEQ ID NO: 304 with about a −4.7 fold change variation less than the transcription standard; miRNA-491 having a nucleotide sequence of or complementary to SEQ ID NO: 9 with about a −2.2 fold change variation less than the transcription standard; miRNA-31 having a nucleotide sequence of or complementary to SEQ ID NO: 11 with about a −1.9 fold change variation less than the transcription standard; miRNA-382 having a nucleotide sequence of or complementary to SEQ ID NO: 8 with about a −1.8 fold change variation less than the transcription standard; miRNA-342 having a nucleotide sequence of or complementary to SEQ ID NO: 12 with about a −1.5 fold change variation less than the transcription standard; miRNA-194 having a nucleotide sequence of or complementary to SEQ ID NO: 305 with about a −1.5 fold change variation less than the transcription standard; miRNA-214 having a nucleotide sequence of or complementary to SEQ ID NO: 10 with about a −1.5 fold change variation less than the transcription standard; miRNA-371 having a nucleotide sequence of or complementary to SEQ ID NO: 306 with about a −1.4 fold change variation less than the transcription standard; and/or miRNA-519c having a nucleotide sequence of or complementary to SEQ ID NO: 307 with about a −1.3 fold change variation less than the transcription standard.

In some embodiments, the combination of nucleic acid biomarkers includes at least one of: SF3A3 having a nucleotide sequence of or complementary to SEQ ID NO: 25 with a variation greater than the transcription standard; FLJ16171 having a nucleotide sequence of or complementary to SEQ ID NO: 21 with a variation greater than the transcription standard; REG3G having a nucleotide sequence of or complementary to SEQ ID NO: 22 with a variation greater than the transcription standard; NDUFA2 having a nucleotide sequence of or complementary to SEQ ID NO: 24 with a variation greater than the transcription standard; LCE2A having a nucleotide sequence of or complementary to SEQ ID NO: 26 with a variation greater than the transcription standard KRTAP6-2 having a nucleotide sequence of or complementary to SEQ ID NO: 42 with a variation less than the transcription standard; CHCHD10 having a nucleotide sequence of or complementary to SEQ ID NO: 50 with a variation less than the transcription standard; OR4D1 having a nucleotide sequence of or complementary to SEQ ID NO: 62 with a variation less than the transcription standard; BLOC1S1 having a nucleotide sequence of or complementary to SEQ ID NO: 52 with a variation less than the transcription standard; PDZK1 having a nucleotide sequence of or complementary to SEQ ID NO: 56 with a variation less than the transcription standard; KRT17 having a nucleotide sequence of or complementary to SEQ ID NO: 58 with a variation less than the transcription standard; CSRP2 having a nucleotide sequence of or complementary to SEQ ID NO: 61 with a variation less than the transcription standard; PSG9 having a nucleotide sequence of or complementary to SEQ ID NO: 46 with a variation less than the transcription standard; ARMC10 having a nucleotide sequence of or complementary to SEQ ID NO: 48 with a variation less than the transcription standard; CD3E having a nucleotide sequence of or complementary to SEQ ID NO: 54 with a variation less than the transcription standard; GUCA2B having a nucleotide sequence of or complementary to SEQ ID NO: 47 with a variation less than the transcription standard; TNFRSF13C having a nucleotide sequence of or complementary to SEQ ID NO: 64 with a variation less than the transcription standard; LOC643008 having a nucleotide sequence of or complementary to SEQ ID NO: 41 with a variation less than the transcription standard; MRPS21 having a nucleotide sequence of or complementary to SEQ ID NO: 65 with a variation less than the transcription standard; NAT14 having a nucleotide sequence of or complementary to SEQ ID NO: 57 with a variation less than the transcription standard; PRTN3 having a nucleotide sequence of or complementary to SEQ ID NO: 45 with a variation less than the transcription standard; OR2A2 having a nucleotide sequence of or complementary to SEQ ID NO: 44 with a variation less than the transcription standard; RPL8 having a nucleotide sequence of or complementary to SEQ ID NO: 63 with a variation less than the transcription standard; TMEM188 having a nucleotide sequence of or complementary to SEQ ID NO: 60 with a variation less than the transcription standard; RPS19BP1 having a nucleotide sequence of or complementary to SEQ ID NO: 59 with a variation less than the transcription standard; and/or JSRP1 having a nucleotide sequence of or complementary to SEQ ID NO: 67 with a variation less than the transcription standard.

In some embodiments, the combination of nucleic acid biomarkers includes at least one of: SF3A3 having a nucleotide sequence of or complementary to SEQ ID NO: 25 with about a 2.7 fold change variation greater than the transcription standard; FLJ16171 having a nucleotide sequence of or complementary to SEQ ID NO: 21 with about a 2.6 fold change variation greater than the transcription standard; REG3G having a nucleotide sequence of or complementary to SEQ ID NO: 22 with about a 1.9 fold change variation greater than the transcription standard; NDUFA2 having a nucleotide sequence of or complementary to SEQ ID NO: 24 with about a 1.6 fold change variation greater than the transcription standard; LCE2A having a nucleotide sequence of or complementary to SEQ ID NO: 26 with about a 2.3 fold change variation greater than the transcription standard KRTAP6-2 having a nucleotide sequence of or complementary to SEQ ID NO: 42 with about a −2.1 fold change variation less than the transcription standard; CHCHD10 having a nucleotide sequence of or complementary to SEQ ID NO: 50 with about a −2.6 fold change variation less than the transcription standard; OR4D1 having a nucleotide sequence of or complementary to SEQ ID NO: 62 with about a −2.3 fold change variation less than the transcription standard; BLOC1S1 having a nucleotide sequence of or complementary to SEQ ID NO: 52 with about a −2.2 fold change variation less than the transcription standard; PDZK1 having a nucleotide sequence of or complementary to SEQ ID NO: 56 with about a −2.0 fold change variation less than the transcription standard; KRT17 having a nucleotide sequence of or complementary to SEQ ID NO: 58 with about a −2.0 fold change variation less than the transcription standard; CSRP2 having a nucleotide sequence of or complementary to SEQ ID NO: 61 with about a −1.8 fold change variation less than the transcription standard; PSG9 having a nucleotide sequence of or complementary to SEQ ID NO: 46 with about a −1.8 fold change variation less than the transcription standard; ARMC10 having a nucleotide sequence of or complementary to SEQ ID NO: 48 with about a −1.7 fold change variation less than the transcription standard; CD3E having a nucleotide sequence of or complementary to SEQ ID NO: 54 with about a −1.7 fold change variation less than the transcription standard; GUCA2B having a nucleotide sequence of or complementary to SEQ ID NO: 47 with about a −1.7 fold change variation less than the transcription standard; TNFRSF13C having a nucleotide sequence of or complementary to SEQ ID NO: 64 with about a −1.6 fold change variation less than the transcription standard; LOC643008 having a nucleotide sequence of or complementary to SEQ ID NO: 41 with about a −1.6 fold change variation less than the transcription standard; MRPS21 having a nucleotide sequence of or complementary to SEQ ID NO: 65 with about a −1.6 fold change variation less than the transcription standard; NAT14 having a nucleotide sequence of or complementary to SEQ ID NO: 57 with about a −1.6 fold change variation less than the transcription standard; PRTN3 having a nucleotide sequence of or complementary to SEQ ID NO: 45 with about a −1.6 fold change variation less than the transcription standard;

OR2A2 having a nucleotide sequence of or complementary to SEQ ID NO: 44 with about a −1.6 fold change variation less than the transcription standard; RPL8 having a nucleotide sequence of or complementary to SEQ ID NO: 63 with about a −1.5 fold change variation less than the transcription standard; TMEM188 having a nucleotide sequence of or complementary to SEQ ID NO: 60 with about a −1.5 fold change variation less than the transcription standard; RPS19BP1 having a nucleotide sequence of or complementary to SEQ ID NO: 59 with about a −1.5 fold change variation less than the transcription standard; and/or JSRP1 having a nucleotide sequence of or complementary to SEQ ID NO: 67 with about a −1.5 fold change variation less than the transcription standard.

In some embodiments, the method includes providing the transcription standard for each nucleic acid biomarker for the combination of nucleic acid biomarkers.

In some embodiments, the method includes providing the combination of nucleic acid biomarkers as a set of primers and/or probes.

In some embodiments, the method includes obtaining cell free plasma RNA as the nucleic acid sample. In some embodiments, the nucleic acid biomarkers are RNA.

In some embodiments, the method can include: selecting a normalization nucleic acid; analyzing the transcriptome of the human subject for the normalization nucleic acid in the nucleic acid sample from the human subject; and detecting in the nucleic acid sample the presence of the normalization nucleic acid, wherein normalization nucleic acid has a variation from a transcription standard, wherein the normalization nucleic acid has a nucleotide sequence of or complementary to one of SEQ ID NOs: 1-4 and 301-303.

In some embodiments, the method can include generating a report, the report reciting the presence of the combination of nucleic acid biomarkers being present in the nucleic acid sample of the human subject being present in a biomarker amount that is varied from the transcription standard.

In some embodiments, a method of detecting a combination of nucleic acid biomarkers in a human subject can include: obtaining a nucleic acid sample from the human subject; selecting the combination of nucleic acid biomarkers; providing a transcription standard for each nucleic acid biomarker for the combination of nucleic acid biomarkers; analyzing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from the transcription standard, wherein the combination of nucleic acid biomarkers includes: miRNA-let-7 g having a nucleotide sequence of or complementary to SEQ ID NO: 13 with a variation less than the transcription standard; miRNA-99b having a nucleotide sequence of or complementary to SEQ ID NO: 7 with a variation greater than the transcription standard; miRNA-99a having a nucleotide sequence of or complementary to SEQ ID NO: 6 with a variation greater than the transcription standard; and miRNA-548 L having a nucleotide sequence of or complementary to SEQ ID NO: 5 with a variation greater than the transcription standard.

In some embodiments, a method of detecting a combination of nucleic acid biomarkers in a human subject can include: obtaining a nucleic acid sample from the human subject; selecting the combination of nucleic acid biomarkers; providing a transcription standard for each nucleic acid biomarker for the combination of nucleic acid biomarkers; analyzing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from the transcription standard, wherein the combination of nucleic acid biomarkers includes: miRNA-let-7 g having a nucleotide sequence of or complementary to SEQ ID NO: 13 with a variation less than the transcription standard; miRNA-490 having a nucleotide sequence of or complementary to SEQ ID NO: 304 with a variation less than the transcription standard; miRNA-491 having a nucleotide sequence of or complementary to SEQ ID NO: 9 with a variation less than the transcription standard; miRNA-31 having a nucleotide sequence of or complementary to SEQ ID NO: 11 with a variation less than the transcription standard; miRNA-382 having a nucleotide sequence of or complementary to SEQ ID NO: 8 with a variation less than the transcription standard; miRNA-342 having a nucleotide sequence of or complementary to SEQ ID NO: 12 with a variation less than the transcription standard; miRNA-194 having a nucleotide sequence of or complementary to SEQ ID NO: 305 with a variation less than the transcription standard; miRNA-214 having a nucleotide sequence of or complementary to SEQ ID NO: 10 with a variation less than the transcription standard; miRNA-371 having a nucleotide sequence of or complementary to SEQ ID NO: 306 with a variation less than the transcription standard; and/or miRNA-519c having a nucleotide sequence of or complementary to SEQ ID NO: 307 with a variation less than the transcription standard.

In one embodiment, a kit includes purified or isolated nucleic acids, wherein the nucleic acids have the sequences of each of the nucleic acid biomarkers in the combination of biomarkers. As such, each recited combination can be uniquely included in a kit. In some aspects, the nucleic acid biomarkers are attached to a substrate of a biochip, where each nucleic acid biomarker can be in a unique position or a position can include one or more of the nucleic acid biomarkers of the combination.

As used herein, "nucleic acid biomarker" or "biomarker" is defined to be a nucleic acid, such as an RNA, that is present in an abnormal amount compared to a standard or normal amount. The biomarker thereby then serves as a tool to look for changes in the transcription thereof. For example, a biomarker can be present at a normal or standard level when there is no disease state or susceptibility of a disease state, but the biomarker is present at a changed level or a variation from the standard or normal amount. While SNPs may be detected by merely identifying the presence, the nucleic acid biomarkers described herein may always be present, but the change in the transcription thereof or change in the amount or concentration in blood or plasma provides the indication that the subject may have a condition that is marked by the biomarker. Thus, by using the term "biomarker" it is clear that the transcription thereof, amount thereof or concentration thereof is not normal, such that it is changed. Such a changed condition can be compared to subject (e.g., pregnant woman) prior to pregnancy or in early pregnancy (e.g., earlier than 12 weeks (PTB) or between 16-20 weeks (pre-eclampsia). Thus, by being defined as a biomarker, it is defined that the transcription thereof, amount thereof or concentration thereof is detectably different from a standard or normal person without the condition or the same subject prior to onset of the condition. In some aspects, a biomarker requires at least a fold change relative to the normal or standard amount or concentration or transcription, or at least a 1.3 fold change, or at least a 1.4 fold change, or at last a 1.5 fold change, or at least a 1.6 fold change, or at least a 1.7 fold change, whether the change is up regulation (increased transcription, amount or concentration) or down regulation (decreased transcription, amount or concentration) compared to a standard or normal amount or compared to that of the subject prior to being pregnant or prior to 10 weeks or prior to 12 weeks of gestation.

As used herein, "combination of biomarkers" or "combination of nucleic biomarkers" defines a unique combination of nucleic acids that are biomarkers under the definition of a biomarker provided herein. The combination of biomarkers provides an indication of a disease state in a pregnant woman or susceptibility thereto. In some instances, the disease state is preterm birth. In other instances the disease state is pre-eclampsia. The presence of the combination of biomarkers provides the indication of the disease state or susceptibility thereto.

In one embodiment, Group 1 is a combination of biomarkers that includes: miRNA-let-7 g (SEQ ID NO: 13), accession number NR_029660; (SEQ ID NO: 68) *Homo sapiens* proteasome (prosome, macropain) activator subunit 2 (PA28 beta) (PSME2), mRNA, accession number NM_002818; (SEQ ID NO: 53) *Homo sapiens* apolipoprotein A-I (APOA1), mRNA, accession number NM_000039; (SEQ ID NO: 66) *Homo sapiens* apolipoprotein A-IV (APOA4), mRNA, accession number NM_000482; and (SEQ ID NO: 71) *Homo sapiens* nicotinamide phosphoribosyltransferase (NAMPT), mRNA, accession number NM_005746. This combination of biomarkers can be used for PTB and pre-eclampsia when detected to be present in a biomarker amount (e.g., not normal or not standard)

In one embodiment, Sub Group 1A can be used for sPTB less than 33 weeks: SEQ ID NO: 68) *Homo sapiens* proteasome (prosome, macropain) activator subunit 2 (PA28 beta) (PSME2), mRNA, accession number NM_002818; and (SEQ ID NO: 53) *Homo sapiens* apolipoprotein A-I (APOA1), mRNA, accession number NM_000039. Sub Group 1A is used for samples at about 12 weeks pregnancy, or from 10 to 15 weeks, or earlier than 16 weeks.

In one embodiment, Sub Group 1B can be used for sPTB less than 33 weeks; SEQ ID NO: 68) *Homo sapiens* proteasome (prosome, macropain) activator subunit 2 (PA28 beta) (PSME2), mRNA, accession number NM_002818; and miRNA-let-7 g (SEQ ID NO: 13), accession number NR_029660. Sub Group 1B is used for samples at about 16 weeks pregnancy, or from 16 to 20 weeks, or earlier than 20 weeks.

In one embodiment, Sub Group 1C can be used for Early Onset Preeclampsia at less than 34 weeks: SEQ ID NO: 71) *Homo sapiens* nicotinamide phosphoribosyltransferase (NAMPT), mRNA, accession number NM_005746; and (SEQ ID NO: 53) *Homo sapiens* apolipoprotein A-I (APOA1), mRNA, accession number NM_000039. Sub Group 1C is used for samples less than 34 weeks.

In one embodiment, Sub Group 1D can be used for all PTB, spontaneous and iatrogenic: miRNA-let-7 g (SEQ ID NO: 13), accession number NR_029660; (SEQ ID NO: 68) *Homo sapiens* proteasome (prosome, macropain) activator subunit 2 (PA28 beta) (PSME2), mRNA, accession number NM_002818; (SEQ ID NO: 53) *Homo sapiens* apolipoprotein A-I (APOA1), mRNA, accession number NM_000039; and (SEQ ID NO: 71) *Homo sapiens* nicotinamide phosphoribosyltransferase (NAMPT), mRNA, accession number NM_005746.

In one embodiment, Group 2 can be used for PTB or pre-eclampsia: miRNA-let-7 g (SEQ ID NO: 13), accession number NR_029660; miRNA-99b (SEQ ID NO: 7), see accession number NR_029843; miRNA-99a (SEQ ID NO: 6), see accession number NR_029514; and miRNA-548 L (SEQ ID NO: 5), see accession number NR_031630.

In one embodiment, Group 3 can be used for PTB or pre-eclampsia: miRNA-let-7 g (SEQ ID NO: 13), accession number NR_029660; miRNA-490 (SEQ ID NO: 304) miRNA-491 (SEQ ID NO: 9), accession number NR_030166; miRNA-31 (SEQ ID NO: 11), accession number NR_029505; miRNA-382 (SEQ ID NO:8), accession number NR_029874; miRNA-342 (SEQ ID NO: 12), accession number NR_029888; miRNA-194 (SEQ ID NO: 305); miNRA-214 (SEQ ID NO: 10), accession number NR_029627; miRNA-371 (SEQ ID NO: 306); and miRNA-519c (SEQ ID NO: 307).

In one embodiment, Group 4 can be used for PTB or pre-eclampsia: (SEQ ID NO: 42) *Homo sapiens* keratin associated protein 6-2 (KRTAP6-2), mRNA, accession number NM_181604; (SEQ ID NO: 25) *Homo sapiens* splicing factor 3a, subunit 3, 60 kDa (SF3A3), mRNA, accession number NM_006802; (SEQ ID NO: 21) *Homo sapiens* cDNA FLJ16171 fis, clone BRHIP2003272, accession number AK131247; (SEQ ID NO: 22) *Homo sapiens* regenerating islet-derived 3 gamma (REG3G), transcript variant 1, mRNA, accession number NM_001008387; (SEQ ID NO: 24) *Homo sapiens* NADH dehydrogenase (ubiquinone) 1 alpha subcomplex, 2, 8 kDa (NDUFA2), nuclear gene encoding mitochondrial protein, transcript variant 1, mRNA, accession number NM_002488; (SEQ ID NO: 50) *Homo sapiens* coiled-coil-helix-coiled-coil-helix domain containing 10, (CHCHD10), mRNA, accession number NM_213720; (SEQ ID NO: 62) *Homo sapiens* olfactory receptor, family 4, subfamily D, member 1 (OR4D1), mRNA, accession numbers NM_012374 and XM_292627; (SEQ ID NO: 52) *Homo sapiens* biogenesis of lysosomal organelles complex-1, subunit 1 (BLOC1S1), mRNA, accession number NM_001487; (SEQ ID NO: 56) *Homo sapiens* PDZ domain containing 1 (PDZK1), mRNA, accession numbers NM_002614, XM_936907, XM_943050, XM_943061, and XM_943068; (SEQ ID NO: 58) *Homo sapiens* keratin 17 (KRT17), mRNA, accession number NM_000422; (SEQ ID NO: 61) *Homo sapiens* cysteine and glycine-rich protein 2 (CSRP2), mRNA, accession number NM_001321; (SEQ ID NO: 46) *Homo sapiens* pregnancy specific beta-1-glycoprotein 9 (PSG9), mRNA, accession number NM_002784; (SEQ ID NO: 48) *Homo sapiens* armadillo repeat containing 10 (ARMC10), transcript variant A, mRNA, accession number NM_031905; (SEQ ID NO: 54) *Homo sapiens* CD3e molecule, epsilon (CD3-TCR complex) (CD3E), mRNA, accession number NM_000733; (SEQ ID NO: 47) *Homo sapiens* guanylate cyclase activator 2B (uroguanylin) (GUCA2B), mRNA, accession number NM_007102; (SEQ ID NO: 64) *Homo sapiens* tumor necrosis factor receptor superfamily, member 13C (TNFRSF13C), mRNA, accession number NM_052945; (SEQ ID NO: 41) *Homo sapiens* hypothetical protein LOC643008 (LOC643008), transcript variant 1, mRNA, accession numbers NM_001162995 and NR_024379; (SEQ ID NO: 65) *Homo sapiens* mitochondrial ribosomal protein S21 (MRPS21), nuclear gene encoding mitochondrial protein, transcript variant 2, mRNA, accession number NM_018997; (SEQ ID NO: 57) *Homo sapiens* N-acetyltransferase 14 (GCN5-related, putative) (NAT14), mRNA, accession number NM_020378; (SEQ ID NO: 45) *Homo sapiens* proteinase 3 (PRTN3), mRNA, accession number NM_002777; (SEQ ID NO: 44) *Homo sapiens* olfactory receptor, family 2, subfamily A, member 2 (OR2A2), mRNA, accession number NM_001005480 and XM_498253; (SEQ ID NO: 63) *Homo sapiens* ribosomal protein L8 (RPL8), transcript variant 1, mRNA, accession number NM_000973; (SEQ ID NO: 60) *Homo sapiens* transmembrane protein 188 (TMEM188), mRNA, accession number NM_153261; (SEQ ID NO: 59) *Homo sapiens* ribosomal protein S19 binding protein 1 (RPS19BP1), mRNA, accession numbers NM_194326 and XM_039373; (SEQ ID NO: 67) *Homo sapiens* junctional sarcoplasmic reticulum protein 1 (JSRP1), mRNA, accession number NM_144616; and (SEQ ID NO: 26) *Homo sapiens* late cornified envelope 2A (LCE2A), mRNA, accession number NM_178428.

The following are combinations of biomarkers:

| Group 1 | | | | |
|---|---|---|---|---|
| Gene Name | p-value | Sequence | Fold Change | Up or Down Regulation |
| hsa-let-7g | 0.00713887 | SEQ ID NO: 13 | −1.8 | Down Regulation |
| PSME2 | 0.00992433 | SEQ ID NO: 68 | −5.6 | Down Regulation |

| Group 1 | | | | |
|---|---|---|---|---|
| Gene Name | p-value | Sequence | Fold Change | Up or Down Regulation |
| APOA1 | 0.00146359 | SEQ ID NO: 53 | −1.9 | Down Regulation |
| APOA4 | 0.00924241 | SEQ ID NO: 66 | −1.5 | Down Regulation |
| NAMPT | 0.00139273 | SEQ ID NO: 71 | −2.3 | Down Regulation |

| Group 2 | | | | |
|---|---|---|---|---|
| Gene Name | p-value | Sequence | Fold Change | Up or Down Regulation |
| hsa-let-7g | 0.00713887 | SEQ ID NO: 13 | −1.8 | Down Regulation |
| hsa-mir-99b | 0.0457254 | SEQ ID NO: 7 | 1.7 | Up Regulation |
| hsa-mir-99a | 0.00464255 | SEQ ID NO: 6 | 1.6 | Up Regulation |
| hsa-mir-548l | 0.00160527 | SEQ ID NO: 5 | 1.5 | Up Regulation |

| Group 3 | | | | |
|---|---|---|---|---|
| Gene Name | p-value | Sequence | Fold Change | Up or Down Regulation |
| hsa-let-7g | 0.00713887 | SEQ ID NO: 13 | −1.8 | Down Regulation |
| hsa-r-490 | 0.00840327 | SEQ ID NO: 304 | −4.7 | Down Regulation |
| hsa-mir-491 | 0.000234436 | SEQ ID NO: 9 | −2.2 | Down Regulation |
| hsa-mir-31 | 0.0013245 | SEQ ID NO: 11 | −1.9 | Down Regulation |
| hsa-mir-382 | 9.49E-05 | SEQ ID NO: 8 | −1.8 | Down Regulation |
| hsa-mir-342 | 0.00601943 | SEQ ID NO: 12 | −1.5 | Down Regulation |
| hsa-mir-194 | 0.0079514 | SEQ ID NO: 305 | −1.5 | Down Regulation |
| hsa-mir-214 | 0.000512653 | SEQ ID NO: 10 | −1.5 | Down Regulation |
| hsa-mir-371 | 0.00779123 | SEQ ID NO: 306 | −1.4 | Down Regulation |
| hsa-mir-519c | 0.00510367 | SEQ ID NO: 307 | −1.3 | Down Regulation |

| Group 4 | | | | |
|---|---|---|---|---|
| Gene Name | p-value | Sequence | Fold Change | Up or Down Regulation |
| KRTAP6-2 | 0.00046104 | SEQ ID NO: 42 | −2.1 | Down Regulation |
| SF3A3 | 0.00910645 | SEQ ID NO: 25 | 2.7 | Up Regulation |
| FLJ16171 | 0.00133126 | SEQ ID NO: 21 | 2.6 | Up Regulation |
| REG3G | 0.00207211 | SEQ ID NO: 22 | 1.9 | Up Regulation |
| NDUFA2 | 0.00749296 | SEQ ID NO: 24 | 1.6 | Up Regulation |
| CHCHD10 | 0.00106558 | SEQ ID NO: 50 | −2.6 | Down Regulation |
| OR4D1 | 0.00698767 | SEQ ID NO: 62 | −2.3 | Down Regulation |
| BLOC1S1 | 0.00118782 | SEQ ID NO: 52 | −2.2 | Down Regulation |
| PDZK1 | 0.00190269 | SEQ ID NO: 56 | −2.0 | Down Regulation |
| KRT17 | 0.00298912 | SEQ ID NO: 58 | −2.0 | Down Regulation |
| CSRP2 | 0.00626579 | SEQ ID NO: 61 | −1.8 | Down Regulation |
| PSG9 | 0.00064014 | SEQ ID NO: 46 | −1.8 | Down Regulation |
| ARMC10 | 0.00098666 | SEQ ID NO: 48 | −1.7 | Down Regulation |
| CD3E | 0.00152925 | SEQ ID NO: 54 | −1.7 | Down Regulation |
| GUCA2B | 0.00076153 | SEQ ID NO: 47 | −1.7 | Down Regulation |
| TNFRSF13C | 0.00814341 | SEQ ID NO: 64 | −1.6 | Down Regulation |
| LOC643008 | 0.00010597 | SEQ ID NO: 41 | −1.6 | Down Regulation |
| MRPS21 | 0.00911331 | SEQ ID NO: 65 | −1.6 | Down Regulation |
| NAT14 | 0.00231347 | SEQ ID NO: 57 | −1.6 | Down Regulation |
| PRTN3 | 0.00060814 | SEQ ID NO: 45 | −1.6 | Down Regulation |
| OR2A2 | 0.00059257 | SEQ ID NO: 44 | −1.6 | Down Regulation |
| RPL8 | 0.00750065 | SEQ ID NO: 63 | −1.5 | Down Regulation |
| TMEM188 | 0.00622275 | SEQ ID NO: 60 | −1.5 | Down Regulation |
| RPS19BP1 | 0.00571346 | SEQ ID NO: 59 | −1.5 | Down Regulation |
| JSRP1 | 0.0092973 | SEQ ID NO: 67 | −1.5 | Down Regulation |
| LCE2A | 0.012785 | SEQ ID NO: 26 | 2.3 | Up Regulation |

The combination of biomarkers can be detected to be present in a biomarker amount by hybridizing the biomarker with a biomarker primer (PCR) or biomarker probe (biochip). The combination of biomarkers can be qualitied or quantitated with a normalization nucleic acid during the detection of the biomarker amount thereof. The combination of biomarkers can be tied to a disease state. Once the disease state is identified for the combination of biomarkers, a treatment regimen can be provided to the subject, such as pregnant woman, that has the biomarker amount. The treatment regimen can then be implemented on the pregnant woman in an attempt to inhibit onset or progression of the disease state. The combination of biomarkers can be present as a kit in the combination. The kit may include instructions identifying the combination of biomarkers and the indication of the disease state thereof.

Transcriptome-typing can be performed with the combination of biomarkers. Transcriptome-typing is equivalent to genotyping for transcribed RNA.

In some embodiments, a method of detecting a combination of nucleic acid biomarkers in a human subject can include: obtaining a nucleic acid sample from the human subject; selecting the combination of nucleic acid biomarkers; transcriptome-typing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from a transcription standard, wherein the combination of nucleic acid biomarkers includes at least two of: miRNA-let-7 g having a nucleotide sequence of or complementary to SEQ ID NO: 13 with a variation less than the transcription standard; PSME2 having a nucleotide sequence of or complementary to SEQ ID NO: 68 with a variation less than the transcription standard; APOA1 having a nucleotide sequence of or complementary to SEQ ID NO: 53 with a variation less than the transcription standard; and NAMPT having a nucleotide sequence of or complementary to SEQ ID NO: 71 with a variation less than the transcription standard. In some aspects: the variation for miRNA-let-7 g is about −1.8 fold change; the variation for PSME2 is about −5.6 fold change; the variation for APOA1 is about −1.9 fold change; and/or the variation for NAMPT is −2.3 fold change. In some aspects, the analyzing includes hybridizing each nucleic acid biomarker in the nucleic acid sample with a complementary nucleic acid configured as a primer or a probe, the method comprising detecting the hybridizing.

Combination Example 1 for sPTB Less than 33 Weeks

The nucleic acid biomarkers of Group 1 were used in a validation study with 40 subjects, 20 being susceptible to PTB or having had a PTB, and 20 being controls without PTB or susceptibility thereto. The samples were obtained between 16-20 weeks gestation. The sensitivity was found to be 100%. The specificity was found to be 100%. The PPV was found to be 100%. The NPV was found to be 100%.

Combination Example 2 for sPTB Less than 33 Weeks

The PSME2 and APOA1 nucleic acid biomarkers of Group 1 were used in a validation study with 60 subjects, 20 being susceptible to PTB or having had a PTB, and 40 being controls without PTB or susceptibility thereto. All subjects being G1P0 (first pregnancy). The samples were obtained at 12 weeks gestation. The APOA1 biomarker (MoM; multiple of the median) plus MA resulted in an AUC of 0.79, a P of 0.001, a FPR (false positive rate) 10% of 52, a FPR 20% of 61 and a FPR 30% being 75. The APOA1 biomarker and PSME2 biomarker combination resulted in an AUC of 0.796, a P of 0.05, a FPR 10% of 48, a FPR 20% of 66 and a FPR 30% being 72. The APOA1 biomarker and PSME2 biomarker (MoMs) combination resulted in an AUC of 0.793, a P of 0.04, a FPR 10% of 41, a FPR 20% of 61 and a FPR 30% being 78.

Combination Example 3 for sPTB Less than 33 Weeks

The PSME2 and has-let-7 g nucleic acid biomarkers of Group 1 were used in a validation study. The samples were obtained at 16-20 weeks gestation. The has-let-7 g biomarker and PSME2 biomarker (MoMs) combination resulted in an AUC of 0.761, a P of less than 0.001, a FPR 10% of 50, a FPR 20% of 57 and a FPR 30% being 70. The has-let-7 g biomarker and PSME2 biomarker (MoMs) combination resulted in an AUC of 0.841, a P of less than 0.001, a FPR 10% of 62, a FPR 20% of 76 and a FPR 30% being 79.

Combination Example 4 for Early Onset Preeclampsia Less than 34 Weeks

The NAMPT and APOA1 nucleic acid biomarkers of Group 1 were used in a validation study. The samples were obtained at 16-20 weeks gestation. The NAMPT biomarker and APOA1 biomarker combination resulted in an AUC of 0.882, a P of less than 0.001, a FPR 10% of 67, a FPR 20% of 67 and a FPR 30% being 100.

Combination Example 5 for all PTB (Spontaneous and Iatrogenic Less than 33 Weeks The PSME2, has-let-7 g, NAMPT and APOA1 nucleic acid biomarkers of Group 1 were used in a validation study. The samples were obtained at 16-20 weeks gestation. The PSME2, has-let-7 g, NAMPT and APOA1 nucleic acid biomarker combination resulted in an AUC of 0.883, a P of less than 0.001, a FPR 10% of 58, a FPR 20% of 78 and a FPR 30% being 83.

Combination Example 6

The APOA4 nucleic acid biomarker was used in combinations with PSME2, has-let-7 g, NAMPT and APOA1 nucleic acid biomarkers in studies of Combination Examples 1-5. The combination of biomarkers with APOA4 produced data comparable with the data of Combination Examples 1-5. It has been found that APOA4 can also beneficially provide information regarding PTB and preeclampsia.

A method of quantification of cell free plasma (CFP) RNA can include: providing one or more normalization nucleic acids, each normalization nucleic acid having a CFP RNA normalization sequence; obtaining a biological sample from a subject; extracting biological sample CFP RNA from the biological sample, wherein the biological sample is cell free plasma RNA; introducing the biological sample CFP RNA to the one or more normalization nucleic acids; performing a polymerase chain reaction (PCR) with the biological sample CFP RNA in the presence of the one or more normalization nucleic acids; measuring the amount of the one or more normalization nucleic acids present in the biological sample CFP RNA; and determining the amount of biological sample CFP RNA based on the amount of the one or more normalization nucleic acids in the biological sample, wherein the CFP RNA normalization sequence and sample CFP RNA are miRNA or mRNA, wherein the CFP RNA normalization sequences have a continuous normalization sequence including or complementary to a continuous sequence of one or more of SEQ ID NOs: 1-4 and 301-303. This normalization can be done with a combination of nucleic acid biomarkers, which can be the nucleic acids having a continuous sequence of one or more of SEQ ID NOS: 5-300 and 304-307 or complement thereof.

A method for determining an amount of a biomarker nucleic acid in a cell free plasma (CFP) RNA transcriptome of a pregnant woman can include: providing one or more normalization nucleic acids, each normalization nucleic acid having a CFP RNA normalization sequence; providing one or more biomarker nucleic acids, each biomarker nucleic acid having a biomarker nucleic acid sequence; obtaining a biological sample from a subject; extracting biological sample CFP RNA from the biological sample; introducing the biological sample CFP RNA to the one or more normalization nucleic acids; performing a polymerase chain reaction (PCR) with the biological sample CFP RNA in the presence of the one or more normalization nucleic acids; measuring the amount of the one or more normalization nucleic acids present in the biological sample CFP RNA; determining the amount of biological sample CFP RNA based on the amount of the one or more normalization nucleic acids in the biological sample; determining an amount of each biomarker nucleic acid in the biological sample CFP RNA of the pregnant woman based on the amount of the one or more normalization nucleic acids in the biological sample, wherein the one or more biomarker nucleic acids each includes a continuous sequence of one or more continuous sequences of SEQ ID NOS: 5-300 and 304-307 or complement thereof as well as a combination of biomarkers as defined herein, wherein the CFP RNA normalization sequence and sample CFP RNA are miRNA or mRNA, wherein the CFP RNA normalization sequences have a continuous normalization sequence including or complementary to a continuous sequence of one or more of SEQ ID NOs: 1-4 and 301-303.

The methods may also include one or more of: extracting and isolating the CFP RNA from a body fluid of the pregnant woman at less than 32 weeks of pregnancy; extracting and isolating the CFP RNA at about 12 weeks to about 32 weeks of pregnancy; one or more biomarker nucleic acids includes a biomarker consisting of one or more sequences from one or more of SEQ ID NOs: 5-18 of complement thereof; the one or more biomarker nucleic acids includes a biomarker consisting of one or more sequences from one or more of SEQ ID NOs: 19-106 or complement thereof; the CFP RNA transcriptome includes a CFP miRNA PTB biomarker that is up-regulated in order to indicate susceptibility of PTB, the CFP miRNA PTB biomarker having a sequence of one or more of SEQ ID NOs: 5-7 or complement thereof; one or more biomarker nucleic acids includes a biomarker that is present in an amount less than a standard, the biomarker consisting of a sequence of one or more of SEQ ID NOs: 8-18 or complement thereof; the CFP RNA transcriptome includes a CFP small RNA PTB biomarker that is up-regulated in order to indicate susceptibility of PTB, the CFP small RNA PTB biomarker having a sequence of one or more of SEQ ID NOs: 19-41 and/or 107-142 or complement thereof; one or more biomarker nucleic acids includes a biomarker that is present in an amount less than a standard, the biomarker consisting of a sequence of one or more of SEQ ID NOs: 42-106 and/or 143-300 or complement thereof; using a primer or a probe that hybridizes with each of the biomarkers of the combination of biomarkers; extracting and isolating a first sample of the one or more CFP RNA PTB biomarkers of the CFP RNA transcriptome prior to 12 weeks of pregnancy and a second sample of the one or more CFP RNA biomarkers after 12 weeks of pregnancy, and comparing the amount of one or more CFP RNA PTB biomarkers from the first sample and second sample, wherein a change in amount indicates susceptibility to PTB.

A method for detecting spontaneous preterm birth in an asymptomatic subject comprising: (a) subjecting a sample from the subject to a procedure to detect polynucleotides (biomarkers); (b) detecting spontaneous preterm birth by comparing the amount of polynucleotides to the amount of such polynucleotides obtained from a control who does not suffer from preterm birth wherein the polynucleotides comprise at least one of, or are selected from Group 1, 2, 3, 4, or sub groups thereof, or any other combination group described herein.

A method where the procedure comprises detecting one or more polynucleotides in the sample by contacting the sample with oligonucleotides that hybridize to the polynucleotides (biomarkers); and detecting in the sample levels of nucleic acids that hybridize to the polynucleotides relative to a control, wherein a change or significant difference in the amount or status of the polynucleotides in the sample compared with the amount or status in the control is indicative of spontaneous preterm birth.

A method wherein the procedure comprises: contacting the sample with biomarkers that specifically bind to the polynucleotides under conditions effective to bind the biomarkers and form complexes; measuring the amount or status of the polynucleotides present in the sample by quantitating the amount of the complexes; and wherein a change or significant difference in the amount or status of polynucleotides in the sample compared with the amount or status obtained from a control subject who does not suffer from preterm birth is indicative of spontaneous preterm birth.

In any of the embodiments, the subject may be asymptomatic for a pregnancy complication, such as PTB or early onset preeclampsia.

The invention further relates to a method of assessing the efficacy of a therapy for preventing, inhibiting, or reducing spontaneous preterm birth in a patient. A method of the invention comprises comparing: (a) levels of a combination of biomarkers in a sample from the patient obtained from the patient prior to providing at least a portion of a therapy to the patient; and (b) levels of combinations of biomarkers in a second sample obtained from the patient following therapy. A significant difference between the levels of biomarkers in the second sample relative to the first sample is an indication that the therapy may be efficacious for inhibiting spontaneous preterm birth. In an embodiment, the method is used to assess the efficacy of a therapy for inhibiting spontaneous preterm birth where changes in amounts of biomarkers relative to the first sample, is an indication that the therapy may be efficacious for inhibiting the condition. In an embodiment, the method is used to assess the efficacy of a therapy for inhibiting spontaneous preterm birth where different levels of the combination of biomarkers relative to the first sample, is an indication that the therapy may be efficacious for inhibiting spontaneous preterm birth. A "therapy" may be any therapy for treating spontaneous preterm birth, in particular, including but not limited to therapeutics, procedures and interventions such as progesterone, cervical cerclage and pessary. A method of the invention can be used to evaluate a patient before, during, and after therapy.

Methods for diagnosing, detecting or monitoring spontaneous preterm birth are contemplated comprising detecting combinations of biomarkers associated with preterm birth. Thus, the present invention relates to a method for diagnosing and monitoring spontaneous preterm birth in a sample from a subject comprising isolating polynucleotides, in particular mRNA, from the sample; and detecting combinations of biomarkers in the sample. The presence of different levels of combinations of biomarkers in the sample compared to a standard or control may be indicative of spontaneous preterm birth and/or a positive prognosis.

The invention provides methods for determining the presence or absence of spontaneous preterm birth in a subject comprising detecting in the sample levels of polynucleotides that hybridize to one or more combinations of biomarkers, comparing the levels with a predetermined standard or cut-off value, and therefrom determining the presence or absence of spontaneous preterm birth in the subject. In an embodiment, the invention provides methods for determining the presence or absence of spontaneous preterm birth in a subject comprising (a) contacting a sample obtained from the subject with oligonucleotides that hybridize to one or more combinations of biomarkers; and (b) detecting in the sample a level of polynucleotides that hybridize to the combinations of biomarkers relative to a predetermined cut-off value, and therefrom determining the presence or absence of spontaneous preterm birth in the subject.

Within certain embodiments, the amount of polynucleotides that are mRNA are detected via polymerase chain reaction using, for example, oligonucleotide primers that hybridize to one or more combinations of biomarkers, or complements of such combinations of biomarkers. Within other embodiments, the amount of mRNA is detected using a hybridization technique, employing oligonucleotide probes that hybridize to one or more combinations of biomarkers, or complements thereof.

The invention contemplates the methods, compositions, and kits described herein comprising assessing one or more additional clinical factor or prognostic factor associated with spontaneous preterm birth. The additional factor may be additional markers of spontaneous preterm birth and/or clinical blood data. In an aspect the additional marker is fetal fibronectin or phosphorylated insulin-like growth factor binding protein-1. The additional factor may be clinical factors comprising or chosen from or selected from the group consisting of history of abortion, history of PTB, alcohol consumption, anaemia, antepartum haemorrhage and urinary tract infection. The additional factor may be clinical factors comprising or chosen from or selected from the group consisting of history of abortion, history of PTB, alcohol consumption and urinary tract infection. Accordingly, the methods of this invention may be used in combination with other methods of preterm birth diagnosis or clinical factors including without limitation, clinical blood data, fetal fibronectin, phosphorylated insulin-like growth factor binding protein-1, and at least one of history of abortion, history of PTB, alcohol consumption, anaemia, antepartum haemorrhage and urinary tract infection, in particular history of abortion, history of PTB, alcohol consumption, and anaemia. Methods including additional markers can include reagents to detect the additional markers. In an aspect, the methods of this invention are used in combination with the clinical factors history of PTB, history of abortion, and anaemia. In an aspect, the methods of this invention are used in combination with the clinical factors history of PTB and history of abortion. In an aspect, the methods of this invention are used in combination with the clinical factors history of PTB, history of abortion, alcohol consumption, urinary tract infections and anaemia. In an aspect, the methods of this invention are used in combination with the clinical factors history of PTB, history of abortion and urinary tract infections, and optionally anaemia. In an aspect, the methods of this invention are used in combination with the clinical factors history of PTB, history of abortion and alcohol consumption. In an aspect, the methods of this invention are used in combination with the clinical factors history of abortion and anaemia.

The terms "sample", "biological sample", and the like mean a material known or suspected of expressing or containing one or more combinations of biomarkers. A test sample can be used directly as obtained from the source or following a pretreatment to modify the character of the sample. A sample can be derived from any biological source, such as tissues, extracts, or cell cultures, including cells, cell lysates, and physiological fluids, such as, for example, whole blood, plasma, serum, saliva, ocular lens fluid, cerebral spinal fluid, sputum, sweat, urine, milk, ascites fluid, synovial fluid, peritoneal fluid, and the like. A sample can be obtained from animals, preferably mammals, most preferably humans. A sample can be treated prior to use, such as preparing plasma from blood, diluting viscous fluids, and the like. Methods of treatment can involve filtration, distillation, extraction, concentration, inactivation of interfering components, the addition of reagents, and the like.

"Spontaneous preterm birth" or "SPTB" refers to birth at <37 weeks of gestation.

"Spontaneous preterm labor (SPTL)" is defined as spontaneous onset of labor <37 weeks of gestation resulting in preterm delivery.

The terms "subject", "individual" or "patient" refer to a warm-blooded animal such as a mammal. In particular, the terms refer to a human A subject, individual or patient may be afflicted with or suspected of having or being predisposed to spontaneous preterm birth. The present invention may be particularly useful for determining spontaneous preterm birth development potential in at-risk patients suffering from particular spontaneous preterm birth predisposing conditions. Spontaneous preterm birth predisposing conditions include without limitation a previous history of preterm birth, previous history of abortion, anaemia, uterine factors such as uterine volume increase, uterine anomalies, trauma and infection. In aspects of the invention the predisposing conditions are history of preterm birth and history of abortion. In other aspects of the invention the predisposing conditions are history of abortion and anaemia. In embodiments of the invention "history of PTB" refers to any previous premature delivery, any type i.e. spontaneous or induced or medically instigated. In embodiments of the invention "history of abortion" refers to any previous abortion, any type i.e. spontaneous or induced. In embodiments of the invention "anaemia" refers to <120 g/L of haemoglobin occurring anytime during a current pregnancy prior to sampling (e.g., prior to 27-33 weeks).

The results of a subject's diagnosis, screening, prognosis or monitoring is typically displayed or provided to a user such as a clinician, health care worker or other caregiver, laboratory personnel or the patient. The results may be quantitative information (e.g. the level or amount of a marker compared to a control) or qualitative information (e.g. diagnosis of spontaneous preterm birth). The output can comprise guidelines or instructions for interpreting the results, for example, numerical or other limits that indicate the presence or absence of spontaneous preterm birth. The guidelines may also specify the diagnosis, for example whether there is a high risk of spontaneous preterm birth. The output can include tools for interpreting the results to arrive at a diagnosis, prognosis or treatment plan, for example, an output may include ranges or cut-offs for abnormal or normal status to arrive at a diagnosis, prognosis, or treatment plan. The output can also provide a recommended therapeutic plan, and it may include other clinical information and guidelines and instructions for interpreting the information.

Devices known in the art can be used to transmit the results of a method of the invention. Examples of output devices include without limitation, a visual output device (e.g. a computer screen or a printed paper), an auditory output device (e.g., a speaker), a printer or a patient s electronic medical record. The format of the output providing the results and related information may be a visual output (e.g., paper or a display on a screen), a diagram such as a graph, chart or voltammetric trace, an audible output (e.g. a speaker) or, a numerical value. In an aspect, the output is a numerical value, in particular the amount or relative amount of at least one marker in a subject's sample compared to a control. In an aspect, the output is a graph that indicates a value, such as an amount or relative amount, of the at least one marker in the sample from the subject on a standard curve. In an embodiment, the output (such as a graphical output) shows or provides a cut-off value or level that indicates the presence of high risk of spontaneous preterm birth. An output may be communicated to a user by physical, audible or electronic means, including mail, telephone, facsimile transmission, email or an electronic medical record.

The analytic methods described herein can be implemented by use of computer systems and methods described below and known in the art. Thus the invention provides computer readable media comprising one or more combinations of biomarkers, and optionally other markers (e.g. markers of preterm birth). "Computer readable media" refers to any medium that can be read and accessed directly by a computer. Thus, the invention contemplates computer readable medium having recorded thereon markers identified for patients and controls. "Recorded" refers to a process for storing information on computer readable medium. The skilled artisan can readily adopt any of the presently known methods for recording information on computer readable medium to generate manufactures comprising information on one or more combinations of biomarkers.

A variety of data processor programs and formats can be used to store information on one or more combinations of biomarkers, and other markers on computer readable medium. Any number of dataprocessor structuring formats (e.g., text file or database) may be adapted in order to obtain computer readable medium having recorded thereon the marker information.

By providing the combination of biomarker information in computer readable form, one can routinely access the information for a variety of purposes. For example, one skilled in the art can use the information in computer readable form to compare marker information obtained during or following therapy with the information stored within the data storage means.

The invention also provides in an electronic system and/or in a network, a method for determining whether a subject has spontaneous preterm birth or is at risk of spontaneous preterm birth, comprising determining the presence or absence of one or more combinations of biomarkers, and based on the presence or absence of the one or more combinations of biomarkers, determining whether the subject has a pre-disposition to spontaneous preterm birth and optionally recommending a procedure or treatment.

The invention further provides in a network, a method for determining whether a subject has a pre-disposition to spontaneous preterm birth comprising: (a) receiving phenotypic and/or clinical information on the subject and information on one or more combinations of biomarkers associated with samples from the subject; (b) acquiring information from the network corresponding to the one or more combinations of biomarkers; and (c) based on the phenotypic information and information on the one or more combinations of biomarkers, determining whether the subject has a pre-disposition to spontaneous preterm birth; and (d) optionally recommending a procedure or treatment.

The invention still further provides a system for identifying selected records that identify spontaneous preterm birth. A system of the invention generally comprises a computer; a database server coupled to the computer; a database coupled to the database server having data stored therein, the data comprising records of data comprising one or more combinations of biomarkers, and a code mechanism for applying queries based upon a desired selection criteria to the data file in the database to produce reports of records which match the desired selection criteria.

In an aspect of the invention a method is provided for detecting cells or tissues associated with spontaneous preterm birth using a computer having a processor, memory, display, and input/output devices, the method comprising the steps of: (a) creating records of one or more combinations of biomarkers, identified in a sample suspected of containing biomarkers associated with spontaneous preterm birth; (b) providing a database comprising records of data comprising one or more combinations of biomarkers of spontaneous preterm birth; and (c) using a code mechanism for applying queries based upon a desired selection criteria to the data file in the database to produce reports of records of step (a) which provide a match of the desired selection criteria of the database of step (b) the presence of a match being a positive indication that the markers of step (a) have been isolated from cells or tissue that are associated with spontaneous preterm birth.

The invention contemplates a method for determining whether a subject has a pre-disposition to spontaneous preterm birth comprising: (a) receiving phenotypic and/or clinical information on the subject and information on one or more combinations of biomarkers, associated with samples from the subject; (b) acquiring information from a network corresponding to one or more biomarkers; and (c) based on the phenotypic information, information on one or more combinations of biomarkers, and optionally other markers, and acquired information, determining whether the subject has a pre-disposition to spontaneous preterm birth; and (d) optionally recommending a procedure or treatment.

In an aspect of the invention, the computer systems, components, and methods described herein are used to monitor preterm birth or determine the stage or type of spontaneous preterm birth. The computer systems, components and methods may also include clinical variables, in particular history of PTB, history of abortion, consumption of alcohol, antepartum haemorrhage in first and/or second trimester, presence of Group B *streptococcus*, urinary tract infection and anaemia, more particularly history of PTB, history of abortion and anaemia.

In some instances, it may be important to determine whether or not an asymptomatic pregnant woman is susceptible to having preterm labor (PTL) or PTB. If the pregnant woman is asymptomatic, it is because there are no indications, physical or biochemical that have been diagnosed or detected that would lead a medical professional to believe she is at risk of PTL or PTB. However, such an asymptomatic pregnant woman indeed may be susceptible to PTL or PTB without them knowing or having any indication of such susceptibility. As such, the asymptomatic pregnant woman may need to be screened to determine whether or not she may have a susceptibility to PTL or PTB. If the asymptomatic pregnant woman is susceptible to PTL or PTB, then medical therapy can be performed to inhibit the PTL or PTB. If the asymptomatic pregnant woman is not susceptible to PTL or PTB, then normal care can be provided. However, determining whether an asymptomatic pregnant woman is susceptible to PTL or PTB may be difficult because there are no obvious symptoms.

In one aspect, the method includes defining the asymptomatic pregnant woman as being asymptomatic when having no physical indication of being susceptible to PTL or PTB. In one aspect, the method includes prior to obtaining the vaginal fluid sample: screening the asymptomatic pregnant woman for physical and/or biochemical indications of being susceptible to preterm labor; and determining the asymptomatic pregnant woman to be not susceptible to preterm labor. In one aspect, the asymptomatic pregnant woman has not previously had: a preterm birth; a complicated pregnancy; diagnosed physical abnormalities; diagnosed aneuploidy; or diagnosed genetic syndromes associated with preterm birth or complicated pregnancy. In one embodiment, when the asymptomatic pregnant woman is determined to be susceptible to PTB, providing instructions for the asymptomatic pregnant women to receive treatment to prevent the PTB. In one aspect, the method can include performing treatment on the asymptomatic pregnant woman to prevent the PTB. Such a treatment can include administering progesterone to the asymptomatic pregnant woman.

In some embodiments, the combination of isolated nucleic acid biomarkers comprises: miRNA-let-7 g having a nucleotide sequence of or complementary to SEQ ID NO: 13; PSME2 having a nucleotide sequence of or complementary to SEQ ID NO: 68; APOA1 having a nucleotide sequence of or complementary to SEQ ID NO: 53; NAMPT having a nucleotide sequence of or complementary to SEQ ID NO: 71; and APOA4 having the nucleotide sequence of or complementary to SEQ ID NO: 71. Wherein this combination of isolated nucleic acid biomarkers can be combined with any other combination of isolated nucleic acid biomarkers, such as any combination of biomarkers recited herein.

In some embodiments, the transcriptional standard can be an amount of the target nucleic acid biomarker that is present in a biological sample from one or more control women that do not have PTB or that have a term birth. That is, the transcriptional standard is for a non-PTB sample or a sample from a pregnant female without a PTB or that has a term birth. The biological sample can be taken from the one or more control women during pregnancy, and then can be labeled as the control once it is determined the one or more control women do not have a PTB or that have a term birth.

The methods can be performed to include measuring an amount of each target nucleic acid biomarker in the biological sample. The methods can include: obtaining a control biological sample from at least one control pregnant female, wherein the at least one control pregnant female has a term birth or does not have a preterm birth; detecting whether the combination of isolated nucleic acid biomarkers is present in the control biological sample by contacting the control biological sample with the combination of complementary nucleic acids; and detecting binding between each complementary nucleic acid with the respective target isolated nucleic acid of the combination of isolated nucleic acids. The methods can include measuring a control amount of each target nucleic acid biomarker in the control biological sample from the at least one control pregnant female. The methods can include: comparing the amount of each target nucleic acid biomarker in the biological sample with the control amount of each target nucleic acid biomarker in the control biological sample; and determining whether or not there is a variance between the amount of each target nucleic acid biomarker in the biological sample and the control amount of each target nucleic acid biomarker in the control biological sample. The methods can include: normalizing the amount of each target nucleic acid biomarker in the biological sample; and normalizing the control amount of each target nucleic acid biomarker in the control biological sample.

We developed a novel technique to maximize the amount of cell free RNA isolated from blood. Past investigators were limited to small quantities of cell free RNA extractable from a blood sample. As a result, scientists were compromised and had to adjust their research with several workarounds. In some instances, investigators obtained larger samples of blood-20 mL or more, volumes that preclude clinical utility. In other instances, they pooled samples from multiple patients to increase the quantity of RNA they could harvest, but at the same time lost the ability to determine patient variation. In other instances they were able to extract enough RNA to run a discovery microarray to search for candidate sequences, but then had inadequate RNA remaining to validate the array results. As a result of these limitations, RNA sequences of interests were more often sought first in solid tissue where the amount extracted was much greater, and sequences rather arbitrarily selected for Q-rtPCR in plasma. Q-rtPCR is the gold standard for the quantification of RNA in a given sample (blood or solid tissue). It requires the measurements be normalized to correct for internal assay variable. The method described herein allows for the isolation of 1.5 micrograms to 7 micrograms of cell free RNA from 2 mL plasma, more than enough for both array use and PCR validation.

A tissue sample of 2 mL plasma was obtained. The following Reagents (source used but not required) were used: DEPC-treated Water (Ambion); Ethanol (Sigma); Chloroform (Sigma); 3 M, pH: 5.5 Sodium Acetate (Ambion); Phonel (Sigma); and Guanidium isothiocyanate (Sigma); Glycerol (Sigma). Equipment and supplies used in RNA isolation include: Refrigerated centrifuge; Microcentrifuge; Micropipettors; Aerosol-barrier tips; Vortex mixer; Powder-free gloves; and 1.5 mL Centrifuge tubes.

The protocol for RNA isolation included: (1) Aliquot 2 mL plasma from one patient sample into 8 tubes, 250 uL plasma in each tube; (12) Spin plasma at 200×g for 5 min at 4° C.; (3) Add 750 uL phenol/guanidium isothiocyanate/glycerol lysis buffer per plasma tube, and cap them securely, vortex samples vigorously for 15 seconds and incubate them for 5 min; (4) Add 200 uL Chloroform per tube, vortex sample vigorously and incubate at room temperature for 10 min; (5) Centrifuge the samples at 10,000×g for 15 min at 4° C., and upper aqueous phase will be used for RNA isolation, and lower red/phenol/chloroform phase will be used for DNA and Protein isolation; (6) Transfer 300 uL upper aqueous phase carefully without disturbing the interphase into fresh tube, add ⅒ volume of 3 M Sodium acetate (pH: 5.5) (30 ul)+3 volumes of 100% iced cold EtOH 900 uL to each tube, and 2 mL plasma from one patient sample eventually will get 13-14 tubes; (7) Incubate step 6 tubes overnight at −20° C.; (8) Centrifuge at 12,000×g for 75 min (4° C.), remove all liquid; (9) Add 50 uL ice cold 80% EtOH to each tube, wash the pellet, then transfer all 13-14 tubes EtOH to one tube, add 300-350 ml ice cold EtOH to make the EtOH 1 mL; (10) Spin at 12,000×g for 60 min at 4° C.; (11) Remove all liquid, 37° C. dry for 40 min; (12) Resuspend the pellet in 20-40 uL DEPC water, incubate at 56° C. for 10 min to dissolve RNA, then put RNA sample in ice for 30 min; (13) Using 2 uL RNA, take OD at 260 nm and 280 nm to determine sample concentration and purity. The amount of total cell free RNA obtained by this RNA isolation procedure includes the following amounts: (1) 1.3 ug; (2) 1.19 ug; (3) 6.11 ug; (4) 1.49 ug; (5) 2.69 ug; (6) 5.86 ug; (7) 4.67 ug; (8) 3.71 ug; (9) 1.76 ug; and (10) 4.85 ug. This data documents from 10 consecutive subjects the actual yield per plasma sample confirming plenty of RNA in a single specimen to perform multiple arrays followed by Q-rtPCR validation of 100s of genes in a single 2 mL sample.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

A unique segment of a sequence in a sequence listing is a specific sequence segment that is found within the recited sequence of the SEQ ID NO, and substantially absent in the rest of the RNA transcriptome. That is, the unique segment of the sequence in the Sequence Listing identified by the SEQ ID NO can be used as a probe or a primer that is specific for that SEQ ID NO. The techniques available for identifying a primer or a probe available to one of ordinary skill in the art can be used to identify one or more unique segments of each SEQ ID NO recited in the Sequence Listing.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A method of detecting a combination of cell free ribonucleic acid (RNA) biomarkers in a pregnant human subject, the method comprising:
   obtaining a plasma sample of cell free ribonucleic acids (RNA) from a pregnant human subject, wherein the pregnant human subject is pregnant less than 32 weeks when the plasma sample is obtained;
   providing a combination of primers or probes having individual nucleotide sequences that have complementarity with and hybridize with individual cell free RNA biomarkers of the combination of cell free RNA biomarkers; and
   detecting in the cell free RNA a presence of the combination of cell free RNA biomarkers, wherein detection comprises contacting the cell free RNA with the combination of primers or probes that hybridize to each of the combination of cell free RNA biomarkers, and detecting hybridization between the combination of primers or probes and the combination of cell free RNA biomarkers,
   wherein the combination of cell free RNA biomarkers consists of:
   miRNA-99b, miRNA-99a, miRNA-548 L, miRNA-let-7 g, PSME2, APOA1, APOA4, and NAMPT.

2. A method of detecting a combination of cell free ribonucleic acid (RNA) biomarkers in a pregnant human subject, the method comprising:
- obtaining a plasma sample of cell free ribonucleic acids (RNA) from pregnant human subject, wherein the pregnant human subject is pregnant less than 32 weeks when the plasma sample is obtained;
- providing a combination of primers or probes having individual nucleotide sequences that have complementarity with and hybridize with individual cell free RNA biomarkers of the combination of cell free RNA biomarkers; and
- detecting in the cell free RNA a presence of the combination of cell free RNA biomarkers, wherein detection comprises contacting the cell free RNA with the combinations of primers or probes that hybridize to each of the combination of cell free RNA biomarkers, and detecting hybridization between the combination of primers or probes and the combination of cell free RNA biomarkers,
- wherein the combination of cell free RNA biomarkers consists of:
- miRNA-99b, miRNA-99a, miRNA-548 L, miRNA-let-7 g, PSME2, APOA1, and NAMPT.

3. A method of detecting a combination of cell free ribonucleic acid (RNA) biomarkers in a pregnant human subject, the method comprising:
- obtaining a plasma sample of cell free nucleic acids (RNA) from the pregnant human subject, wherein the pregnant human subject is pregnant less than 32 weeks when the plasma sample is obtained;
- providing a combination of primers or probes having individual nucleotide sequences that have complementarity with and hybridize with individual cell free RNA biomarkers of the combination of cell free RNA biomarkers; and
- detecting in the cell free RNA a presence of the combination of cell free RNA biomarkers, wherein detection comprises contacting the cell free RNA with the combination of primers or probes that hybridize to each of the combination of cell free RNA biomarkers, and detecting hybridization between the combination of primers or probes and the combination of cell free RNA biomarkers,
- wherein the combination of cell free RNA biomarkers consists of:
- miRNA-let-7 g, PSME2, APOA1, and NAMPT.

* * * * *